United States Patent
Becares et al.

(10) Patent No.: US 11,492,672 B2
(45) Date of Patent: Nov. 8, 2022

(54) MICROBIOME BASED IDENTIFICATION, MONITORING AND ENHANCEMENT OF FERMENTATION PROCESSES AND PRODUCTS

(71) Applicant: Biome Makers Inc., San Francisco, CA (US)

(72) Inventors: Alberto A. Becares, Valladolid (ES); Adrian F. Fernandez, San Francisco, CA (US)

( * ) Notice: Subject to any disclaimer, the term of this patent is extended or adjusted under 35 U.S.C. 154(b) by 1200 days.

(21) Appl. No.: 15/779,531

(22) PCT Filed: Dec. 5, 2016

(86) PCT No.: PCT/US2016/064984
§ 371 (c)(1),
(2) Date: May 28, 2018

(87) PCT Pub. No.: WO2017/096385
PCT Pub. Date: Jun. 8, 2017

(65) Prior Publication Data
US 2018/0363031 A1 Dec. 20, 2018

Related U.S. Application Data

(60) Provisional application No. 62/263,488, filed on Dec. 4, 2015.

(51) Int. Cl.
| | | |
|---|---|---|
| *C12Q 1/689* | (2018.01) | |
| *G16B 30/00* | (2019.01) | |
| *G16B 40/00* | (2019.01) | |
| *C12Q 1/6888* | (2018.01) | |
| *G16B 20/00* | (2019.01) | |
| *G16B 10/00* | (2019.01) | |
| *G16B 40/20* | (2019.01) | |
| *G16B 30/10* | (2019.01) | |

(52) U.S. Cl.
CPC .......... *C12Q 1/689* (2013.01); *C12Q 1/6888* (2013.01); *G16B 10/00* (2019.02); *G16B 20/00* (2019.02); *G16B 30/00* (2019.02); *G16B 30/10* (2019.02); *G16B 40/00* (2019.02); *G16B 40/20* (2019.02)

(58) Field of Classification Search
CPC .... C12Q 1/689; C12Q 1/6888; C12Q 1/6893; C12Q 1/6895; G16B 20/00; G16B 40/00; G16B 10/00; G16B 5/00; G16B 20/20; G16B 5/20; G16B 45/00; G16B 30/10; G16B 30/00; G16B 30/20; G16B 40/30; G16B 40/20; G16B 50/00; G16B 35/00; G16B 50/20; G16B 50/30; G01N 33/56911; G01N 33/56961; G01N 33/56905; G01N 33/569; G16H 50/20; G16H 10/40; G16H 10/60; G16H 50/70; G06N 20/20; G06N 3/02; G06N 3/08; G06N 5/003; G06N 20/00; G06N 20/10; G06N 5/025; G06F 16/35; G16C 20/60
See application file for complete search history.

(56) References Cited

U.S. PATENT DOCUMENTS

| | | |
|---|---|---|
| 6,180,339 B1 | 1/2001 | Sandhu et al. |
| 2010/0129816 A1 | 5/2010 | Savelkoul et al. |
| 2016/0376627 A1* | 12/2016 | Zengler ................. C12Q 1/689 424/93.3 |

FOREIGN PATENT DOCUMENTS

| | | | | |
|---|---|---|---|---|
| CA | 2906921 A1 * | 9/2014 | ........... | A61K 35/742 |
| WO | WO-2015103165 A1 * | 7/2015 | ............. | C12Q 1/689 |
| WO | 2015170979 A1 | 11/2015 | | |

OTHER PUBLICATIONS

Das, S. et al. (2014) Understanding molecular identification and polyphasic taxonomic approaches for genetic relatedness and phylogenetic relationships of microorganisms. Journal of Microbiological Methods 103:80-100. (Year: 2014).*
Schoch, C. L. et al. 2012 Nuclear ribosomal internal transcribed spacer (ITS) region as a universal DNA barcode marker for Fungi. PNAS 109:16 6241-6246. (Year: 2012).*
Santamaria, M. et al. (2013) Reference databases for taxonomic assignment in metagenomics. Briefings in Bioinformatics 13:6 682-695. (Year: 2013).*
Gweon et al (2015) PIPITS: an automated pipeline for analyses of fungal internal spacer sequences from the Illumina sequencing platform. Methods in Ecology and Evolution 6: 973-980. (Year: 2015).*
Hirose, N. et al. (2013) Ribosomal Internal Transcribed Spacer of Prototheca wickerhamii Has Characteristic Structure Useful for Identification and Genotyping. PLOS One 8:11 e81223 (8 pages). (Year: 2013).*
Singh et al. (2014) Phylogenetic relationship of Trichoderma asperellum Tasp/8940 using Internal Transcribed Spacer (ITS) sequences. International Journal of Advanced Research 2:3 979-986. (Year: 2014).*

(Continued)

*Primary Examiner* — Mary K Zeman
(74) *Attorney, Agent, or Firm* — Ivan J. Wong

(57) ABSTRACT

Monitoring, analysis and control of fermentation activities includes methods and corresponding systems directed toward agriculture, biofuels, and food production. Complex methods and corresponding systems are provided for classifying a microorganism; profiling a microbiome; sequencing multiple libraries in a single sequencing run; determining a microbiome profile in a sample; and analyzing a material from a location associated with a fermentation process. Additional implementations are directed to methods and corresponding systems for obtaining, deriving, predicting and evaluating microbiome information; control, analysis and direction of fermentation operations; and evaluating, analyzing and displaying microbiome related information in two and three dimensional plots. Yet additional methods and corresponding systems permit identification and analysis of microorganisms capable of imparting beneficial properties to phases of fermentation processes.

12 Claims, 4 Drawing Sheets

Specification includes a Sequence Listing.

(56) References Cited

OTHER PUBLICATIONS

Stern (2012) Evaluating the Ribosomal Internal Transcribed Spacer (ITS) as a Candidate Dinoflagellate Barcode Marker. PLOS One 7:8 e42780 (12 pages). (Year: 2012).*
Stoddard, S. et al. (2015) rrnDB: improved tools for interpreting rRNA gene abundance in bacteria and archaea and a new foundation for future development. Nucleic Acids Research 43: Database Issue D593-D598. (Year: 2015).*
Tai, V. et al. (2013) Single-Cell DNA Barcoding Using Sequences from the Small Subunit rRNA and Internal Transcribed Spacer Region Identifies New Species of Trichonympha and Trichomitopsis from the Hindgut of the Termite Zootermopsis angusticollis. Plos One 8:3 e58728 (12 pages). (Year: 2013).*
"Accuracy and precision"—Wikipedia, downloaded Jan. 11, 2022. (Year: 2022).*
Microbiome definition NIH NHGRI website downloaded Jan. 11, 2022. (Year: 2022).*
Microbiome Profiling—CD Genomics website. Downloaded Jan. 11, 2022. (Year: 2022).*
Sunagawa et al. "Metagenomic species profiling using universal phylogenetic marker genes," Nature Methods, Dec. 31, 2013, vol. 10, No. 12, pp. 1196-1199.
Alkema et al. "Microbial bioinformatics for food safety and production," Briefings in Bioinformatics, Jun. 16, 2015, vol. 71, No. 2, pp. 283-292.
Sharon et al. "Accurate, multi-kb reads resolve complex populations and detect rare microorganisms," Genome Research, Feb. 9, 2015, vol. 25, No. 4, pp. 534-543.
Segata et al. "Metagenomic Microbial community profiling using unique clade-specific marker genes." Nature Methods, Feb. 1, 2013, vol. 9, No. 8, pp. 811-814.
Spencer et al. "Massively parallel sequencing of single cells by epicPCR links functional genes with phylogenetic markers." The ISME Journal, Sep. 22, 2015, vol. 10, pp. 427-436.
International Search Report for International Application No. PCT/US2016/064984, dated Feb. 8, 2017.
Hellmark B et al: "Simultaneous species identification and detection of rifampicin resistance in staphylococci by sequencing of the rpoB gene", European Journal of Clinical Microbiology & Infectious Diseases, Springer, Berlin, DE, vol. 28, No. 2, Aug. 21, 2008 (Aug. 21, 2008), pp. 183-190.
Pernille Johansen et al: "Development of quantitative PCR and metagenomics-based approaches for strain quantification of a defined mixed-strain starter culture", Systematic and Applied Microbiology, vol. 37, No. 3, Feb. 28, 2014 (Feb. 28, 2014), pp. 186-193.

* cited by examiner

SEQUENCE LISTING

<160> NUMBER OF SEQ ID NOS: 50

<210> SEQ ID NO 1
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatgatacgg cgaccaccga gatctacaca tcgtacggaa tagttgggag tgycagcmgc    60
cgcggtaa                                                            68

<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aatgatacgg cgaccaccga gatctacaca ctatctggaa tagttgggag tgycagcmgc    60
cgcggtaa                                                            68

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatgatacgg cgaccaccga gatctacact agcgagtgaa tagttgggag tgycagcmgc    60
cgcggtaa                                                            68

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aatgatacgg cgaccaccga gatctacacc tgcgtgtgaa tagttgggag tgycagcmgc    60
cgcggtaa                                                            68

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatgatacgg cgaccaccga gatctacact catcgaggaa tagttgggag tgycagcmgc    60
cgcggtaa                                                            68

<210> SEQ ID NO 6

<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatgatacgg cgaccaccga gatctacacc gtgagtggaa tagttgggag tgycagcmgc    60
cgcggtaa                                                             68

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgatacgg cgaccaccga gatctacacg gatatctgaa tagttgggag tgycagcmgc    60
cgcggtaa                                                             68

<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatgatacgg cgaccaccga gatctacacg acaccgtgaa tagttgggag tgycagcmgc    60
cgcggtaa                                                             68

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagcagaag acggcatacg agataactct cgcgccagtc agccggacta chvgggtwtc    60
taat                                                                 64

<210> SEQ ID NO 10
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caagcagaag acggcatacg agatactatg tccgccagtc agccggacta chvgggtwtc    60
taat                                                                 64

<210> SEQ ID NO 11
<211> LENGTH: 64
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 11
caagcagaag acggcatacg agatagtagc gtcgccagtc agccggacta chvgggtwtc    60
taat                                                                64

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caagcagaag acggcatacg agatcagtga gtcgccagtc agccggacta chvgggtwtc    60
taat                                                                64

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caagcagaag acggcatacg agatcgtact cacgccagtc agccggacta chvgggtwtc    60
taat                                                                64

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caagcagaag acggcatacg agatctacgc agcgccagtc agccggacta chvgggtwtc    60
taat                                                                64

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caagcagaag acggcatacg agatggagac tacgccagtc agccggacta chvgggtwtc    60
taat                                                                64

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
```
caagcagaag acggcatacg agatgtcgct cgcgccagtc agccggacta chvgggtwtc    60
taat    64

<210> SEQ ID NO 17
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caagcagaag acggcatacg agatgtcgta gtcgccagtc agccggacta chvgggtwtc    60
taat    64

<210> SEQ ID NO 18
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caagcagaag acggcatacg agattagcag accgccagtc agccggacta chvgggtwtc    60
taat    64

<210> SEQ ID NO 19
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagcagaag acggcatacg agattcatag accgccagtc agccggacta chvgggtwtc    60
taat    64

<210> SEQ ID NO 20
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caagcagaag acggcatacg agattcgcta tacgccagtc agccggacta chvgggtwtc    60
taat    64

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcaagtgtt cttcgga    17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggctcaaccc tggacag                                                  17

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aatgatacgg cgaccaccga gatctacaca cgacgtgact caggcaaaca cctgcggarg   60
gatca                                                               65

<210> SEQ ID NO 24
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aatgatacgg cgaccaccga gatctacaca tatacacact caggcaaaca cctgcggarg   60
gatca                                                               65

<210> SEQ ID NO 25
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatgatacgg cgaccaccga gatctacacc gtcgctaact caggcaaaca cctgcggarg   60
gatca                                                               65

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aatgatacgg cgaccaccga gatctacacc tagagctact caggcaaaca cctgcggarg   60
gatca                                                               65

<210> SEQ ID NO 27
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
aatgatacgg cgaccaccga gatctacacg ctctagtact caggcaaaca cctgcggarg    60
gatca    65

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aatgatacgg cgaccaccga gatctacacg acactgaact caggcaaaca cctgcggarg    60
gatca    65

<210> SEQ ID NO 29
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aatgatacgg cgaccaccga gatctacact gcgtacgact caggcaaaca cctgcggarg    60
gatca    65

<210> SEQ ID NO 30
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aatgatacgg cgaccaccga gatctacact agtgtagact caggcaaaca cctgcggarg    60
gatca    65

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caagcagaag acggcatacg agatacctac tgccatcccc ggctgagatc crttgytraa    60
agtt    64

<210> SEQ ID NO 32
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
caagcagaag acggcatacg agatagcgct atccatcccc ggctgagatc crttgytraa      60
agtt                                                                  64

<210> SEQ ID NO 33
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caagcagaag acggcatacg agatagtcta gaccatcccc ggctgagatc crttgytraa      60
agtt                                                                  64

<210> SEQ ID NO 34
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caagcagaag acggcatacg agatcatgag gaccatcccc ggctgagatc crttgytraa      60
agtt                                                                  64

<210> SEQ ID NO 35
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caagcagaag acggcatacg agatctagct cgccatcccc ggctgagatc crttgytraa      60
agtt                                                                  64

<210> SEQ ID NO 36
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caagcagaag acggcatacg agatctctag agccatcccc ggctgagatc crttgytraa      60
agtt                                                                  64

<210> SEQ ID NO 37
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caagcagaag acggcatacg agatgagctc atccatcccc ggctgagatc crttgytraa      60
agtt                                                                  64
```

<210> SEQ ID NO 38
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caagcagaag acggcatacg agatggtatg ctccatcccc ggctgagatc crttgytraa      60
agtt                                                                  64

<210> SEQ ID NO 39
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caagcagaag acggcatacg agatgtatga cgccatcccc ggctgagatc crttgytraa      60
agtt                                                                  64

<210> SEQ ID NO 40
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caagcagaag acggcatacg agattagact gaccatcccc ggctgagatc crttgytraa      60
agtt                                                                  64

<210> SEQ ID NO 41
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caagcagaag acggcatacg agattcacga tgccatcccc ggctgagatc crttgytraa      60
agtt                                                                  64

<210> SEQ ID NO 42
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caagcagaag acggcatacg agattcgagc tccatcccc ggctgagatc crttgytraa       60
agtt                                                                  64

<210> SEQ ID NO 43
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 43
tccgtaggtg aacctgcgg                                                  19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcctccgctt attgatatgc                                                 20

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gaatagttgg gagtgycagc mgccgcggta a                                    31

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgccagtcag ccggactach vgggtwtcta at                                   32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
attagawacc cbdgtagtcc ggctgactgg cg                                   32

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
actcaggcaa cacctgcgg arggatca                                         28

<210> SEQ ID NO 49
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 49
ccatccccgg ctgagatccr ttgytraaag tt                                  32

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aactttyarc aayggatctc agccggggat gg                                  32
```

MICROBIOME BASED IDENTIFICATION, MONITORING AND ENHANCEMENT OF FERMENTATION PROCESSES AND PRODUCTS

SEQUENCE LISTING

The instant application contains a Sequence Listing which has been submitted electronically in ASCII format and is hereby incorporated by reference in its entirety. Said ASCII copy, created on Jun. 4, 2018, is named 0339-00003_SL.txt and is 14,802 bytes in size.

BACKGROUND OF THE INVENTION

Technical Field

The embodiments described herein relate to novel and unique methods, systems and processes for identifying, analyzing, monitoring, and controlling activities. Fermentation activities entail a wide range of endeavors directed toward agriculture, manufacturing, chemical processing.

The herein described process includes systems and methods for determining and characterizing the microbiome of a fermentation operation or setting, obtaining microbiome information, converting such information such that it is useful for controlling, enhancing, monitoring, detecting deviations, and predicting performance of the fermentation process.

Related Art

Fermentation is a process in which an agent causes transformation of a raw material into a finished product. During fermentation organic matter is decomposed in the absence or presence of air (oxygen) producing an accumulation of resulting fermentation product. Some of these products (for example, alcohol and lactic acid) are of importance to humans, and fermentation has therefore been used for their manufacture on an industrial scale.

Microorganisms like yeast, molds, and bacteria play an important role in the alcohol fermentation process for creating beer and wine, and the formation of acetic acid (vinegar). Lactic fermentation is driven by lactic-acid bacteria which break down monosaccharides into lactic acid. Lactic fermentation is used in the preparation of various sour milk products, yogurt, cheese, and bread. Many mold fungi (for example, *Aspergillus niger*) ferment sugar, resulting in the formation of citric acid. A large proportion of the citric acid used in the food-processing industry is obtained by microbiological means. Ethanol fuel is produced from the fermentation by yeast of common crops such as sugar cane, potato, cassava and corn to produce ethanol which is further processed to become fuel. The production of butyl alcohol and acetone industrially is important for the paint and lacquer industries. In the process of sewage treatment, sewage is digested by enzymes secreted by bacteria, to produce liquid and solid fertilizers, and biogas. Fungi have been employed to break down cellulosic wastes to increase protein content and improve in vitro digestibility. A wide variety of agroindustrial waste products can be fermented to use as food for animals, especially ruminants.

The processes described herein are useful for enhancing any fermentation process. The advantages of the herein described processes are shown for vinification, the process whereby fermentation changes grape juice into wine. However, it is understood that these methods can be applied for enhancement of other fermentation processes.

Winemaking or vinification, is the production of wine by fermentation of raw material, and for grape wine, that starts with the grapes. Factors affecting grape quality, known as the grape's terroir, include the variety of grapes, the weather during growing season, soil, time of harvest, and methods of pruning.

After harvesting the grapes, the fruit is crushed to produce juice, called must. The primary fermentation can be done with natural yeast normally already present on the grapes, visible as a powdery substance, or cultured yeast is added to the must. The sugar content of the grapes is monitored during fermentation and can be adjusted (by addition of sugar) since it affects both the taste and end product, as well as the speed of the fermentation.

During or after the primary fermentation, a secondary, or malolactic fermentation can be initiated by inoculation of desired bacteria which convert malic acid into lactic acid. This fermentation step can improve the taste of wine. During this secondary fermentation and aging process, fermentation continues very slowly in either stainless steel vessels or oak barrels.

Prior to bottling, the wine is usually filtered. Filtration results in clarification and microbial stabilization. In clarification, large particles that affect the visual appearance of the wine are removed. In microbial stabilization, the amount of yeast and bacteria are adjusted to prevent the likelihood of refermentation or spoilage.

As is evident from the winemaking steps described above, byproducts of fermentation by the microbial population or microbiome panel present in the soil, on the fruit, or during the winemaking process, contribute to the taste and quality of the wine.

Therefore, understanding the microbiome, and how it changes along each stage of vinification or wine production, would be advantageous and necessary for influencing the quality of the wine at every level. Using the herein described novel and unique sequencing methods, it is now possible to generate a unique identity for the wine, a genetic footprint, based on its microbiome. Such a footprint would allow winemakers to differentiate wines according to the microbiome panel, and detect and solve problems using bio-based controls such as Brettanomyces contamination, refermentation, mousiness, ropiness, mannitol, granium taint, diacetyl level, to name a few. These problems can be solved by bioremediation and/or changing the physical parameters, e.g. temperature, pH, enzymes, in the vinification process and influencing the microbiome community.

SUMMARY OF THE INVENTION

The present invention addresses the long-standing and unfulfilled need for better monitoring, analysis and control of fermentation activities, including, among others, those directed toward agriculture, biofuels, and food production.

The terms microbiome, microbiome information, microbiome data, microbiome population, microbiome panel and similar terms are used in the broadest possible sense, unless expressly stated otherwise, and would include: a census of currently present microorganisms, both living and nonliving, which may have been present months, years, millennia or longer; a census of components of the microbiome other than bacteria and archea, e.g. viruses and microbial eukaryotes; population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms real-time microbiome data or information includes microbiome information that is collected or obtained at a particular setting during the fermentation process, for example soil, plant/fruit samples taken during a planting or harvesting, must, sampling of wine during alcoholic fermentation (beginning, middle and end, or depending on parameters such as alcoholic graduation, amount of sugar, density), sampling during malolactic fermentation (beginning, middle and end, or depending on amount of malic and acetic acid), barrel (beginning, middle and end, or months) and bottling.

As used herein, the terms derived microbiome information and derived microbiome data are to be given their broadest possible meaning, unless specified otherwise, and includes any real-time, microbiome information that has been computationally linked or used to create a relationship such as for example evaluating the microbiome of milk before, during, and after fermentation, or evaluating the microbiome between planting and harvesting of grapes. Thus, derived microbiome information provides information about the fermentation process setting or activity that may not be readily ascertained from non-derived information.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence. Thus, by way of example, predictive microbiome information would include: a determination and comparison of real-time microbiome information and the derived microbiome information of quality of wine, i.e. abundance of a specific microorganism in a sample and possible positive or negative effect on the fermentation process; a comparison of real-time microbiome information collected during the fermentation of cheese and the quality of cheese.

Real time, derived, and predicted data can be collected and stored, and thus, become historic data for ongoing or future decision-making for a process, setting, or application.

In one embodiment of the invention is provided a method of classifying a microorganism, comprising: obtaining a nucleic acid sequence of a 16S ribosomal subunit, an ITS, internal transcribed spacer, and optionally, a single copy marker gene, of a first microbe; and comparing said nucleic acid sequence of a first microbe to a reference; and identifying the first microbe at the strain level or sub-strain level based on the comparing.

In another embodiment is provided a novel method of profiling a microbiome in a sample, comprising: obtaining nucleic acids sequences of a 16S ribosomal subunit, an ITS, and a marker gene, from at least one microorganism in a sample; analyzing said at least one microorganism within said sample based upon the nucleic acids sequences obtained; and determining a profile of the microbiome based on said analyzing. Using 16S rDNA in combination with another single-copy marker gene provides prokaryotic species boundaries at higher resolution and allows identification of microbial diversity at the strain level. The novelty of this method is in the fact that unlike what is currently taught and used in the art, instead of combining the measurement of 16S region with a functional gene as is taught in the art, we combine the 16S region with single-copy marker genes (described in Sunagawa et al., 2013, Nature Methods 10, 1196-1199). This methodology required sequencing all the DNA in a sample in order to get a high filogenetic resolution level. The method described herein, reduces the amount of sequencing data needed to identify species at high filogenetic resolution because the 16S amplicons and the single-copy marker genes produce an alignment rate below 7% and a false discovery rate below 10%.

In another embodiment is provided a novel method for sequencing two libraries in one sequencing run, by pooling the prepared 16S and ITS libraries, and providing appropriate primers for sequencing both 16S and ITS in a sequencing method.

In some embodiments, determining a profile of the microbiome in said sample can be based on 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, 100 or fewer microbes, 200 or fewer microbes, 300 or fewer microbes, 400 or fewer microbe, 500 or fewer microbes, 600 or fewer microbes, 700 or fewer microbes, or 800 or fewer microbes. In some embodiments determining a profile of the microbiome in said sample has an accuracy greater than 70% based on the measurements. In some embodiments, analyzing uses long read sequencing platforms.

In yet another embodiment is provided a process including: analyzing a material from a location associated with a fermentation process; obtaining microbiome information, selected from real time microbiome information, derived microbiome information and predictive microbiome information; and performing an evaluation on the microbiome information, the evaluation including: a relationship based processing including a related genetic material component and a fermentation setting component; and a bioinformatics stage; whereby the evaluation provides information to direct the fermentation process.

In a further embodiment is provided operations and methods having one or more of the following features: wherein the real time microbiome information is selected from material selected from the group consisting of soil samples, soil sample taken during a planting, soil sample taken during growth, soil sample taken during harvesting, fermentation sample taken at the beginning of a fermentation process, in the middle of a fermentation process, at the end of a fermentation process, any time during a fermentation process; wherein the bioinformatics stage has one or more of the following: submitting the raw DNA sequencing data to bioinformatics pipeline for performing microbiome analysis, including demultiplexing and quality filtering, OTU picking, taxonomic assignment, phylogenetic reconstruction, compiling metadata, diversity analysis, and visualization.

Still in another embodiment is provided a method of controlling a fermentation operation including: analyzing a material from a location associated with an fermentation operation to provide a first microbiome information; associating the first microbiome information with a condition of the operation; obtaining a second microbiome information; associating the second microbiome information with the first microbiome information; and, evaluating the first microbiome information, the associated condition, and the second microbiome information, the evaluation including bioinformatics pipeline for performing microbiome analysis including demultiplexing and quality filtering, OTU picking, taxonomic assignment, plytogenetic reconstruction, compiling metadata, diversity analysis, and visualization; whereby the evaluation identifies a characteristic of the operation; and, directing the fermentation operation based in part on the identified characteristic of operation; whereby the fermentation operation is based upon the evaluation of microbiome information.

Yet still in another embodiment is provided a method for directing a fermentation operation including: analyzing a sample from a location associated with a fermentation operation; obtaining microbiome information; and, performing an evaluation on the microbiome information, whereby the evaluation provides information to direct the fermentation operation.

In another embodiment is provided operations and methods having one or more of the following features: wherein, the microbiome information has real time microbiome information; wherein, the microbiome information has derived microbiome information; wherein, the microbiome information has predictive microbiome information; wherein the analysis has selection and sequencing of the material; wherein the analysis has extracting genetic material from the material; wherein the analysis has preparation of libraries; wherein the analysis has extracting material including genetic material selected from the group consisting of a rRNA gene 16S, Internal transcribed spacer (ITS); wherein the analysis has providing a phylogenetic tree; wherein the analysis has a correction step; wherein the analysis has an extraction procedure selected from the group consisting of beating, sonicating, freezing and thawing, and chemical disruption; wherein the analysis has amplification of at least a portion of the material; wherein the analysis has providing a genetic barcode to a sample of the material; wherein the microbiome information defines a phylogenetic tree; wherein the microbiome information has a OTU; wherein the microbiome information defines an OTU; wherein the microbiome information defines a biogeographical pattern; wherein the microbiome information has information obtained from the 16S rRNA and another marker gene; wherein the another marker gene is metal-dependent proteases with possible chaperone activity; wherein the evaluation has forming an n-dimensional plot, where n is selected from the group of integers consisting of 3, 4, 5, 6, 8, 9, 10, 11, 12, 13, and 14; wherein the evaluation has measuring a change in gene sequences; wherein the evaluation has measuring a change in gene sequences and using the measured change as a molecular clock in the evaluation to determine the related nature of material; and wherein the material is selected from the group consisting of soil, agricultural material, material from dairy processing, a material from a fermentation operation.

There is further provided systems, operations and methods having one or more of the following features: wherein at least a portion of the information resulting from the evaluation is displayed in a two dimensional plot; wherein at least a portion of the information resulting from the evaluation is displayed in a three dimensional plot; wherein at least a portion of the information resulting from the evaluation is displayed in a plot including colors associated with microbiome information; wherein at least a portion of the information resulting from the evaluation is displayed in a plot including colors associated with a type of information selected from the group consisting of microbiome information and non-genetic information; each type of information including a different color; wherein at least a portion of the information resulting from the evaluation is displayed in a plot including colors associated with a type of information selected from the group consisting of microbiome information and non-genetic information; each type of information including a different color; and the non-genetic information selected from the group consisting of temperature, geographical location, climate; wherein at least a portion of the information resulting from the evaluation is transmitted to a memory storage device; wherein at least a portion of the information resulting from the evaluation is communicated to a controller; wherein at least a portion of the information resulting from the evaluation is displayed in a two dimensional plot; and, wherein at least a portion of the information resulting from the evaluation is displayed in a three dimensional plot. In some embodiments, the system can further comprise a user interface configured to communicate or display a report to a user.

In one aspect, the methods of the invention allow the identification of microorganisms capable of imparting one or more beneficial property to one or more phases of a fermentation process. The variability in the microbial populations present in the sample can be used to support a directed process of selection of one or more microorganisms for use in a phase of a fermentation process and for identifying particular combinations and abundances of microorganisms which are of benefit for a particular purpose, and which may never have been recognized using conventional techniques.

The methods of the invention may be used as a part of a plant breeding program. The methods may allow for, or at least assist with, the selection of plants which have a particular genotype/phenotype which is influenced by the microbial flora, in addition to identifying microorganisms and/or compositions that are capable of imparting one or more property to one or more plants.

In one aspect the invention relates to a method for the selection of one or more microorganism(s) which are capable of imparting one or more beneficial property to a plant to be used as raw material in a fermentation process. In other words, the process will allow for enrichment of suitable microorganisms within the plant microbiome. Such microorganism(s) may be contained within a plant, on a plant, and/or within the plant's growing soil or water. It should be appreciated that as referred to herein a "beneficial property to a plant" should be interpreted broadly to mean any property which is beneficial for any particular purpose including properties which may be beneficial to human beings, other animals, the environment, a habitat, an ecosystem, the economy, of commercial benefit, or of any other benefit to any entity or system. Accordingly, the term should be taken to include properties which may suppress, decrease or block one or more characteristic of a plant, including suppressing, decreasing or inhibiting the growth or growth rate of a plant. The invention may be described herein, by way of example only, in terms of identifying positive benefits to one or more plants or improving plants. However, it should be appreciated that the invention is equally applicable to identifying negative benefits that can be conferred to plants.

Such beneficial properties include, but are not limited to, for example: improved growth, health and/or survival characteristics, suitability or quality of the plant for a particular purpose, structure, color, chemical composition or profile, taste, smell, improved quality. In other embodiments, beneficial properties include, but are not limited to, for example: decreasing, suppressing or inhibiting the growth of a plant; constraining the height and width of a plant to a desirable size; regulate production of and/or response to plant pheromones (resulting in increased tannin production in surrounding plant community and decreased appeal to foraging species).

As used herein, "improved" should be taken broadly to encompass improvement of a characteristic of a plant or a fermentation process which may already exist in a plant or process prior to application of the invention, or the presence of a characteristic which did not exist in a plant or process prior to application of the invention. By way of example, "improved" growth should be taken to include growth of a plant where the plant was not previously known to grow under the relevant conditions.

As used herein, "inhibiting and suppressing" and like terms should be taken broadly and should not be construed to require complete inhibition or suppression, although this may be desired in some embodiments.

The term "microbes", "microorganisms" as used herein should be taken broadly. It refers to any single-celled organisms, bacteria, archaea, protozoa, and unicellular fungi and protists. By way of example, the microorganisms may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobium, Sinorhizobium* and *Halomonas*), Firmicutes (such as *Bacillus, Paenibacillus, Lactobacillus, Mycoplasma*, and *Acetobacterium*), Actinobacteria (such as *Streptomyces, Rhodococcus, Microbacterium*, and *Curtobacterium*), and the fungi Ascomycota (such as *Trichoderma, Ampelomyces, Coniothyrium, Paecoelomyces, Penicillium, Cladosporium, Hypocrea, Beauveria, Metarhizium, Verticullium, Cordyceps, Pichea*, and *Candida*, Basidiomycota (such as *Coprinus, Corticium*, and *Agaricus*) and Oomycota (such as *Pythium, Mucor*, and *Mortierella*).

In yet another embodiment, the present disclosure provides a method for detecting contamination in a fermentation sample, comprising determining the microbiome from a fermentation sample, wherein the method comprises detecting at least one marker of a microorganism and preferably two markers of a microorganism; and a computer system for determining a microbiome profile in a sample, the computer system comprising: a memory unit for receiving data comprising measurement of a microbiome panel from a sample; computer-executable instructions for analyzing the measurement data according to a method of described herein; and computer-executable instructions for determining potential microbial contamination in the sample or fermentation process based upon said analyzing. In some embodiments, the computer system further comprises computer-executable instructions to generate a report of the presence or absence of the at least one contamination microorganism in the sample. In some embodiments, computer system can further comprises a user interface configured to communicate or display said report to a user.

The present disclosure provides a computer readable medium comprising: computer-executable instructions for analyzing data comprising measurement of a microbiome profile from a fermentation sample obtained from a fermentation process or environment, wherein the microbiome profile comprises at least one marker and preferably two markers selected from at least one microbe; and computer-executable instructions for determining a presence or absence of a contamination in the fermentation process based upon the analyzing.

Examples of machine learning algorithms that can be used include, but are not limited to: elastic networks, random forests, support vector machines, and logistic regression.

The algorithms provided herein can aid in selection of important microbes and transform the underlying measurements into a score or probability relating to, for example, grape quality, wine quality, presence or absence of contamination, treatment response, and/or classification of organic soil status.

The present disclosure provides a kit, comprising: one or more compositions for use in measuring a microbiome profile in a fermentation sample obtained from fermentation process or environment thereof, wherein the microbiome profile comprises at least one marker and preferably two markers to at least one microbe; and instructions for performing any of the preceding methods. In some embodiments, a kit can further comprises a computer readable medium.

Kit reagents may in one embodiment comprise at least one contiguous oligonucleotide that hybridizes to a fragment of the genome of a microorganism. In another embodiment, the kit comprises at least one pair of oligonucleotides that hybridizes to opposite strands of a genomic segment of a microorganism, wherein each oligonucleotide primer pair is designed to selectively amplify a fragment of the 16S, ITS, and/or marker gene of the organism present in the sample. In one embodiment, the oligonucleotide is completely complementary to the genome of the individual. In another embodiment, the kit further contains buffer and enzyme for amplifying said segment. In another embodiment, the reagents further comprise a label for detecting said fragment.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other features and advantages of the invention will be apparent from the following, more particular description of various exemplary embodiments including a preferred embodiment of the invention, as illustrated in the accompanying drawings.

DETAILED DESCRIPTION OF THE PREFERRED EMBODIMENTS

Figure 1:
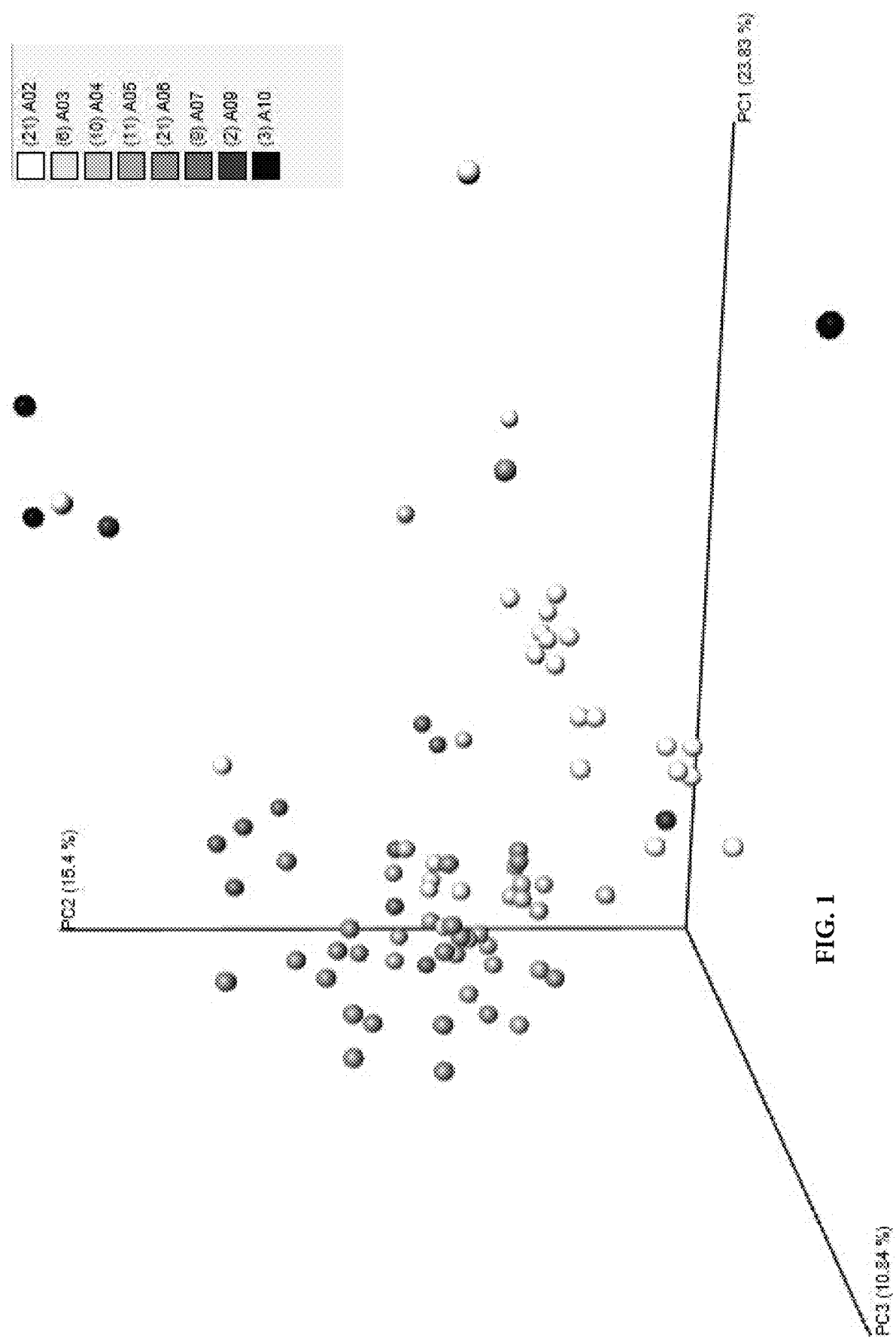
FIG. 1 is a 3-dimensional illustration providing a comparative representations of microbiome profiles of bacterias for differing soil samples.

In the description that follows, a number of terms used are extensively utilized. In order to provide a clearer and consistent understanding of the specification and claims, including the scope to be given such terms, the following definitions are provided.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

"Contacting" refers to the process of bringing into contact at least two distinct species such that they can react. It should be appreciated, however, the resulting reaction product can be produced directly from a reaction between the added reagents or from an intermediate from one or more of the added reagent which can be produced in the reaction mixture.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "microbiome", as used herein, refers to the ecological community of commensal, symbiotic, or pathogenic microorganisms in a sample.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations between the actual nucleic acid sequences may exist between different bacterial strains. The present invention should therefore be understood to extend to all forms of DNA which arise from any other mutation, polymorphic or allelic variation.

The term "sequencing" as used herein refers to sequencing methods for determining the order of the nucleotide bases—adenine, guanine, cytosine, and thymine—in a nucleic acid molecule (e.g., a DNA or RNA nucleic acid molecule.

The term "barcode" as used herein, refers to any unique, non-naturally occurring, nucleic acid sequence that may be used to identify the originating genome of a nucleic acid fragment.

The term "biochip" or "array" can refer to a solid substrate having a generally planar surface to which an adsorbent is attached. A surface of the biochip can comprise a plurality of addressable locations, each of which location may have the adsorbent bound there. Biochips can be adapted to engage a probe interface, and therefore, function as probes. Protein biochips are adapted for the capture of polypeptides and can be comprise surfaces having chromatographic or biospecific adsorbents attached thereto at addressable locations. Microarray chips are generally used for DNA and RNA gene expression detection. Microbiome profiling can further comprise of use of a biochip.

Biochips can be used to screen a large number of macromolecules. Biochips can be designed with immobilized nucleic acid molecules, full-length proteins, antibodies, affibodies (small molecules engineered to mimic monoclonal antibodies), aptamers (nucleic acid-based ligands) or chemical compounds. A chip could be designed to detect multiple macromolecule types on one chip. For example, a chip could be designed to detect nucleic acid molecules, proteins and metabolites on one chip. The biochip can be used to and designed to simultaneously analyze a panel microbes in a single sample.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Any microbiome profile described herein can include one or more, but are not limited to the following microbes:

*Abiotrophia, Abiotrophia defectiva, Abiotrophia, Acetanaerobacterium, Acetanaerobacterium elongatum, Acetanaerobacterium, Acetivibrio, Acetivibrio bacterium, Acetivibrio, Acetobacterium, Acetobacterium, Acetobacterium woodii, Acholeplasma, Acholeplasma, Acidaminococcus, Acidaminococcus fermentans, Acidaminococcus, Acidianus, Acidianus brierleyi, Acidianus, Acidovorax, Acidovorax, Acinetobacter, Acinetobacter guillouiae, Acinetobacter junii, Acinetobacter, Actinobacillus, Actinobacillus M1933/96/1, Actinomyces, Actinomyces ICM34, Actinomyces ICM41, Actinomyces ICM54, Actinomyces lingnae, Actinomyces odontolyticus, Actinomyces oral, Actinomyces ph3, Actinomyces, Adlercreutzia, Adlercreutzia equolifaciens, Adlercreutzia intestinal, Adlercreutzia, Aerococcus, Aerococcus, Aeromonas, Aeromonas 165C, Aeromonas hydrophila, Aeromonas RC50, Aeromonas, Aeropyrum, Aeropyrum pernix, Aeropyrum, Aggregatibacter, Aggregatibacter, Agreia, Agreia bicolorata, Agreia, Agromonas, Agromonas CS30, Akkermansia, Akkermansia muciniphila, Akkermansia, Alistipes, Alistipes ANH, Alistipes AP11, Alistipes bacterium, Alistipes CCUG, Alistipes DJF_B185, Alistipes DSM, Alistipes EBA6-25c12, Alistipes finegoldii, Alistipes indistinctus, Alistipes JC136, Alistipes NML05A004, Alistipes onderdonkii, Alistipes putredinis, Alistipes RMA, Alistipes senegalensis, Alistipes shahii, Alistipes Smarlab, Alistipes, Alkalibaculum, Alkalibaculum, Alkaliflexus, Alkaliflexus, Allisonella, Allisonella histaminiformans, Allisonella, Alloscardovia, Alloscardovia omnicolens, Anaerofilum, Anaerofilum, Anaerofustis, Anaerofustis stercorihominis, Anaerofustis, Anaeroplasma, Anaeroplasma, Anaerostipes, Anaerostipes 08964, Anaerostipes 1y-2, Anaerostipes 494a, Anaerostipes 5.sub.-1.sub.-63FAA, Anaerostipes AIP, Anaerostipes bacterium, Anaerostipes butyraticus, Anaerostipes caccae, Anaerostipes hadrum, Anaerostipes 1E4, Anaerostipes indolis, Anaerostipes, Anaerotruncus, Anaerotruncus colihominis, Anaerotruncus NML, Anaerotruncus, Aquincola, Aquincola, Arcobacter, Arcobacter, Arthrobacter, Arthrobacter FV1-1, Asaccharobacter, Asaccharobacter celatus, Asaccharobacter, Asteroleplasma, Asteroleplasma, Atopobacter, Atopobacter phocae, Atopobium, Atopobium parvulum, Atopobium rimae, Atopobium, Bacteriovorax, Bacteriovorax, Bacteroides, Bacteroides 31SF18, Bacteroides 326-8, Bacteroides 35AE31, Bacteroides 35AE37, Bacteroides 35BE34, Bacteroides 4072, Bacteroides 7853, Bacteroides acidifaciens, Bacteroides AP1, Bacteroides AR20, Bacteroides AR29, Bacteroides B2, Bacteroides bacterium, Bacteroides barnesiae, Bacteroides BLBE-6, Bacteroides BV-1, Bacteroides caccae, Bacteroides CannelCatfish9, Bacteroides cellulosilyticus, Bacteroides chinchillae, Bacteroides CIP103040, Bacteroides clarus, Bacteroides coprocola, Bacteroides coprophilus, Bacteroides D8, Bacteroides DJF_B097, Bacteroides dnLKV2, Bacteroides dnLKV7, Bacteroides dnLKV9, Bacteroides dorei, Bacteroides EBA5-17, Bacteroides eggerthii, Bacteroides enrichment, Bacteroides F-4, Bacteroides faecichinchillae, Bacteroides faecis, Bacteroides fecal, Bacteroides finegoldii, Bacteroides fragilis, Bacteroides gallinarum, Bacteroides helcogenes, Bacteroides ic1292, Bacteroides intestinalis, Bacteroides massiliensis, Bacteroides mpnisolate, Bacteroides NB-8, Bacteroides new, Bacteroides nlaezlc13, Bacteroides nlaezlc158, Bacteroides nlaezlc159, Bacteroides nlaezlc161, Bacteroides nlaezlc163, Bacteroides nlaezlc167, Bacteroides nlaezlc172, Bacteroides nlaezlc18, Bacteroides nlaezlc182, Bacteroides nlaezlc190, Bacteroides nlaezlc198, Bacteroides nlaezlc204, Bacteroides nlaezlc205, Bacteroides nlaezlc206, Bacteroides nlaezlc207, Bacteroides nlaezlc211, Bacteroides nlaezlc218, Bacteroides nlaezlc257, Bacteroides nlaezlc260, Bacteroides nlaezlc261, Bacteroides nlaezlc263, Bacteroides nlaezlc308, Bacteroides nlaezlc315, Bacteroides nlaezlc322, Bacteroides nlaezlc324, Bacteroides nlaezlc331, Bacteroides nlaezlc339, Bacteroides nlaezlc36, Bacteroides nlaezlc367, Bacteroides nlaezlc375, Bacteroides nlaezlc376, Bacteroides nlaezlc380, Bacteroides nlaezlc391, Bacteroides nlaezlc459, Bacteroides nlaezlc484, Bacteroides nlaezlc501, Bacteroides nlaezlc504, Bacteroides nlaezlc515, Bacteroides nlaezlc519, Bacteroides nlaezlc532, Bacteroides nlaezlc557, Bacteroides nlaezlc57, Bacteroides nlaezlc574, Bacteroides nlaezlc592, Bacteroides nlaezlg105, Bacteroides nlaezlg117, Bacteroides nlaezlg127, Bacteroides nlaezlg136, Bacteroides nlaezlg143, Bacteroides nlaezlg157, Bacteroides nlaezlg167, Bacteroides nlaezlg171, Bacteroides nlaezlg187, Bacteroides nlaezlg194, Bacteroides nlaezlg195, Bacteroides nlaezlg199, Bacteroides nlaezlg209, Bacteroides nlaezlg212, Bacteroides nlaezlg213, Bacteroides nlaezlg218, Bacteroides nlaezlg221, Bacteroides nlaezlg228, Bacteroides nlaezlg234, Bacteroides nlaezlg237, Bacteroides nlaezlg24, Bacteroides nlaezlg245, Bacteroides nlaezlg257, Bacteroides nlaezlg27, Bacteroides nlaezlg285, Bacteroides nlaezlg288, Bacteroides nlaezlg295, Bacteroides nlaezlg296, Bacteroides nlaezlg303, Bacteroides nlaezlg310, Bacteroides nlaezlg312, Bacteroides nlaezlg327, Bacteroides nlaezlg329, Bacteroides nlaezlg336, Bacteroides nlaezlg338, Bacteroides nlaezlg347, Bacteroides nlaezlg356, Bacteroides nlaezlg373, Bacteroides nlaezlg376, Bacteroides nlaezlg380, Bacteroides nlaezlg382, Bacteroides nlaezlg385, Bacteroides nlaezlg4, Bacteroides nlaezlg422, Bacteroides nlaezlg437, Bacteroides nlaezlg454, Bacteroides nlaezlg455, Bacteroides nlaezlg456, Bacteroides nlaezlg458, Bacteroides nlaezlg459, Bacteroides nlaezlg46, Bacteroides nlaezlg461, Bacteroides nlaezlg475, Bacteroides nlaezlg481, Bacteroides nlaezlg484, Bacteroides nlaezlg5, Bacteroides nlaezlg502, Bacteroides nlaezlg515, Bacteroides nlaezlg518, Bacteroides nlaezlg521, Bacteroides nlaezlg54, Bacteroides nlaezlg6, Bacteroides nlaezlg8, Bacteroides nlaezlg80, Bacteroides nlaezlg98, Bacteroides nlaezlh120, Bacteroides nlaezlh15, Bacteroides nlaezlh162, Bacteroides nlaezlh17, Bacteroides nlaezlh174, Bacteroides nlaezlh18, Bacteroides nlaezlh188, Bacteroides nlaezlh192, Bacteroides nlaezlh194, Bacteroides nlaezlh195, Bacteroides nlaezlh207, Bacteroides nlaezlh22, Bacteroides nlaezlh250, Bacteroides nlaezlh251, Bacteroides nlaezlh28, Bacteroides nlaezlh313, Bacteroides nlaezlh319, Bacteroides nlaezlh321, Bacteroides nlaezlh328, Bacteroides nlaezlh334, Bacteroides nlaezlh390, Bacteroides nlaezlh391, Bacteroides nlaezlh414, Bacteroides nlaezlh416, Bacteroides nlaezlh419, Bacteroides nlaezlh429, Bacteroides nlaezlh439, Bacteroides nlaezlh444, Bacteroides nlaezlh45, Bacteroides nlaezlh46, Bacteroides nlaezlh462, Bacteroides nlaezlh463, Bacteroides nlaezlh465, Bacteroides nlaezlh468, Bacteroides nlaezlh471, Bacteroides nlaezlh472, Bacteroides nlaezlh474, Bacteroides nlaezlh479, Bacteroides nlaezlh482, Bacteroides nlaezlh49, Bacteroides nlaezlh493, Bacteroides nlaezlh496, Bacteroides nlaezlh497, Bacteroides nlaezlh499, Bacteroides nlaezlh50, Bacteroides nlaezlh531, Bacteroides nlaezlh535, Bacteroides nlaezlh8, Bacteroides nlaezlp104, Bacteroides nlaezlp105, Bacteroi-* des nlaezlp108, Bacteroides nlaezlp132, Bacteroides nlaezlp133, Bacteroides nlaezlp151, Bacteroides nlaezlp157, Bacteroides nlaezlp166, Bacteroides nlaezlp167, Bacteroides nlaezlp171, Bacteroides nlaezlp178, Bacteroides nlaezlp187, Bacteroides nlaezlp191, Bacteroides nlaezlp196, Bacteroides nlaezlp208, Bacteroides nlaezlp213, Bacteroides nlaezlp228, Bacteroides nlaezlp233, Bacteroides nlaezlp267, Bacteroides nlaezlp278, Bacteroides nlaezlp282, Bacteroides nlaezlp286, Bacteroides nlaezlp295, Bacteroides nlaezlp299, Bacteroides nlaezlp301, Bacteroides nlaezlp302, Bacteroides nlaezlp304, Bacteroides nlaezlp317, Bacteroides nlaezlp319, Bacteroides nlaezlp32, Bacteroides nlaezlp332, Bacteroides nlaezlp349, Bacteroides nlaezlp35, Bacteroides nlaezlp356, Bacteroides nlaezlp370, Bacteroides nlaezlp371, Bacteroides nlaezlp376, Bacteroides nlaezlp395, Bacteroides nlaezlp402, Bacteroides nlaezlp403, Bacteroides nlaezlp409, Bacteroides nlaezlp412, Bacteroides nlaezlp436, Bacteroides nlaezlp438, Bacteroides nlaezlp440, Bacteroides nlaezlp447, Bacteroides nlaezlp448, Bacteroides nlaezlp451, Bacteroides nlaezlp476, Bacteroides nlaezlp478, Bacteroides nlaezlp483, Bacteroides nlaezlp489, Bacteroides nlaezlp493, Bacteroides nlaezlp557, Bacteroides nlaezlp559, Bacteroides nlaezlp564, Bacteroides nlaezlp565, Bacteroides nlaezlp572, Bacteroides nlaezlp573, Bacteroides nlaezlp576, Bacteroides nlaezlp591, Bacteroides nlaezlp592, Bacteroides nlaezlp631, Bacteroides nlaezlp633, Bacteroides nlaezlp696, Bacteroides nlaezlp7, Bacteroides nlaezlp720, Bacteroides nlaezlp730, Bacteroides nlaezlp736, Bacteroides nlaezlp737, Bacteroides nlaezlp754, Bacteroides nlaezlp759, Bacteroides nlaezlp774, Bacteroides nlaezlp828, Bacteroides nlaezlp854, Bacteroides nlaezlp860, Bacteroides nlaezlp886, Bacteroides nlaezlp887, Bacteroides nlaezlp900, Bacteroides nlaezlp909, Bacteroides nlaezlp913, Bacteroides nlaezlp916, Bacteroides nlaezlp920, Bacteroides nlaezlp96, Bacteroides nordii, Bacteroides oleiciplenus, Bacteroides ovatus, Bacteroides paurosaccharolyticus, Bacteroides plebeius, Bacteroides R6, Bacteroides rodentium, Bacteroides S-17, Bacteroides S-18, Bacteroides salyersiae, Bacteroides SLC1-38, Bacteroides Smarlab, Bacteroides 'Smarlab, Bacteroides stercorirosoris, Bacteroides stercoris, Bacteroides str, Bacteroides thetaiotaomicron, Bacteroides TP-5, Bacteroides, Bacteroides uniformis, Bacteroides vulgatus, Bacteroides WA1, Bacteroides WH2, Bacteroides WH302, Bacteroides WH305, Bacteroides XB12B, Bacteroides XB44A, Bacteroides X077B42, Bacteroides xylanisolvens, Barnesiella, Barnesiella intestinihominis, Barnesiella NSB1, Barnesiella, Barnesiella viscericola, Bavariicoccus, Bavariicoccus, Bdellovibrio, Bdellovibrio oral, Bergeriella, Bergeriella, Bifidobacterium, Bifidobacterium 103, Bifidobacterium 108, Bifidobacterium 113, Bifidobacterium 120, Bifidobacterium 138, Bifidobacterium 33, Bifidobacterium Acbbto5, Bifidobacterium adolescentis, Bifidobacterium Amsbbt12, Bifidobacterium angulatum, Bifidobacterium animalis, Bifidobacterium bacterium, Bifidobacterium bifidum, Bifidobacterium Bisn6, Bifidobacterium Bma6, Bifidobacterium breve, Bifidobacterium catenulatum, Bifidobacterium choerinum, Bifidobacterium coryneforme, Bifidobacterium dentium, Bifidobacterium DJF_WC44, Bifidobacterium F-10, Bifidobacterium F-11, Bifidobacterium group, Bifidobacterium h12, Bifidobacterium HMLN1, Bifidobacterium HMLN12, Bifidobacterium HMLN5, Bifidobacterium iarfr2341d, Bifidobacterium iarfr642d48, Bifidobacterium ic1332, Bifidobacterium indicum, Bifidobacterium kashiwanohense, Bifidobacterium LISLUCIII-2, Bifidobacterium longum, Bifidobacterium M45, Bifidobacterium merycicum, Bifidobacterium minimum, Bifidobacterium MSX5B, Bifidobacterium oral, Bifidobacterium PG12A, Bifidobacterium PL1, Bifidobacterium pseudocatenulatum, Bifidobacterium pseudolongum, Bifidobacterium pullorum, Bifidobacterium ruminantium, Bifidobacterium S-10, Bifidobacterium saeculare, Bifidobacterium saguini, Bifidobacterium scardovii, Bifidobacterium simiae, Bifidobacterium SLPYG-1, Bifidobacterium stellenboschense, Bifidobacterium stercoris, Bifidobacterium TM-7, Bifidobacterium Trm9, Bifidobacterium, Bilophila, Bilophila nlaezlh528, Bilophila, Bilophila wadsworthia, Blautia, Blautia bacterium, Blautia CE2, Blautia CE6, Blautia coccoides, Blautia DJF_VR52, Blautia DJF_VR67, Blautia DJF_VR70k1, Blautia formate, Blautia glucerasea, Blautia hansenii, Blautia ic1272, Blautia 1E5, Blautia K-1, Blautia luti, Blautia M-1, Blautia mpnisolate, Blautia nlaezlc25, Blautia nlaezlc259, Blautia nlaezlc51, Blautia nlaezlc520, Blautia nlaezlc542, Blautia nlaezlc544, Blautia nlaezlh27, Blautia nlaezlh316, Blautia nlaezlh317, Blautia obeum, Blautia producta, Blautia productus, Blautia schinkii, Blautia Ser5, Blautia Ser8, Blautia, Blautia WAL, Blautia wexlerae, Blautia YHC-4, Brenneria, Brenneria, Brevibacterium, Brevibacterium, Brochothrix, Brochothrix thermosphacta, Buttiauxella, Buttiauxella 57916, Buttiauxella gaviniae, Butyricicoccus, Butyricicoccus bacterium, Butyricicoccus, Butyricimonas, Butyricimonas 180-3, Butyricimonas 214-4, Butyricimonas bacterium, Butyricimonas GD2, Butyricimonas synergistica, Butyricimonas, Butyricimonas virosa, Butyrivibrio, Butyrivibrio fibrisolvens, Butyrivibrio hungatei, Butyrivibrio, Caldimicrobium, Caldimicrobium, Caldisericum, Caldisericum, Campylobacter, Campylobacter coli, Campylobacter hominis, Campylobacter, Capnocytophaga, Capnocytophaga, Carnobacterium, Carnobacterium alterfunditum, Carnobacterium, Caryophanon, Caryophanon, Catenibacterium, Catenibacterium mitsuokai, Catenibacterium, Catonella, Catonella, Caulobacter, Caulobacter, Cellulophaga, Cellulophaga, Cellulosilyticum, Cellulosilyticum, Cetobacterium, Cetobacterium, Chelatococcus, Chelatococcus, Chlorobium, Chlorobium, Chryseobacterium, Chryseobacterium A1005, Chryseobacterium KJ9C8, Chryseobacterium, Citrobacter, Citrobacter 1, Citrobacter agglomerans, Citrobacter amalonaticus, Citrobacter ascorbata, Citrobacter bacterium, Citrobacter BinzhouCLT, Citrobacter braakii, Citrobacter enrichment, Citrobacter F24, Citrobacter F96, Citrobacter farmeri, Citrobacter freundii, Citrobacter gillenii, Citrobacter HBKC_SR1, Citrobacter HD4.9, Citrobacter hormaechei, Citrobacter 191-3, Citrobacter ka55, Citrobacter lapagei, Citrobacter LAR-1, Citrobacter ludwigii, Citrobacter MEB5, Citrobacter MS36, Citrobacter murliniae, Citrobacter nlaezlc269, Citrobacter P014, Citrobacter PO42bN, Citrobacter PO46a, Citrobacter P073, Citrobacter SR3, Citrobacter T1, Citrobacter tnt4, Citrobacter tnt5, Citrobacter trout, Citrobacter TSA-1, Citrobacter, Citrobacter werkmanii, Cloacibacillus, Cloacibacillus adv66, Cloacibacillus nlaezlp702, Cloacibacillus NMLO5A017, Cloacibacillus, Cloacibacterium, Cloacibacterium, Collinsella, Collinsella A-1, Collinsella aerofaciens, Collinsella AUH-Julong21, Collinsella bacterium, Collinsella CCUG, Collinsella, Comamonas, Comamonas straminea, Comamonas testosteroni, Conexibacter, Conexibacter, Coprobacillus, Coprobacillus bacterium, Coprobacillus cateniformis, Coprobacillus TM-40, Coprobacillus, Coprococcus, Coprococcus 14505, Coprococcus bacterium, Coprococcus catus,

*Coprococcus comes, Coprococcus eutactus, Coprococcus nexile, Coprococcus, Coraliomargarita, Coraliomargarita fucoidanolyticus, Coraliomargarita marisflavi, Coraliomargarita, Corynebacterium, Corynebacterium amy°colatum, Corynebacterium durum, Coxiella, Coxiella, Cronobacter, Cronobacter dublinensis, Cronobacter sakazakii, Cronobacter turicensis, Cryptobacterium, Cryptobacterium curtum, Cupriavidus, Cupriavidus eutropha, Dechloromonas, Dechloromonas,* HZ, *Desulfobacterium, Desulfobacterium, Desulfobulbus, Desulfobulbus, Desulfopila, Desulfopila* La4.1, *Desulfovibrio, Desulfovibrio* D4, *Desulfovibrio desulfuricans, Desulfovibrio* DSM12803, *Desulfovibrio enrichment, Desulfovibrio fairfieldensis, Desulfovibrio* LNB1, *Desulfovibrio piger, Desulfovibrio, Dialister, Dialister* E2.sub.-20, *Dialister* GBA27, *Dialister invisus, Dialister oral, Dialister succinatiphilus, Dialister, Dorea, Dorea* auhjulong64, *Dorea bacterium, Dorea formicigenerans, Dorea longicatena, Dorea mpnisolate, Dorea, Dysgonomonas, Dysgonomonas gadei, Dysgonomonas, Edwardsiella, Edwardsiella tarda, Eggerthella, Eggerthella El, Eggerthella lenta, Eggerthella* MLGO43, *Eggerthella* MVA1, *Eggerthella* S6-C1, *Eggerthella* SDG-2, *Eggerthella sinensis, Eggerthella str, Eggerthella, Enhydrobacter, Enhydrobacter, Enterobacter, Enterobacter* 1050, *Enterobacter* 1122, *Enterobacter* 77000, *Enterobacter* 82353, *Enterobacter* 9C, *Enterobacter* ASC, *Enterobacter adecarboxylata, Enterobacter aerogenes, Enterobacter agglomerans, Enterobacter* AJAR-A2, *Enterobacter amnigenus, Enterobacter asburiae, Enterobacter* B1(2012), *Enterobacter* B363, *Enterobacter* B509, *Enterobacter bacterium, Enterobacter* Badong3, *Enterobacter* BEC441, *Enterobacter* C8, *Enterobacter cancerogenus, Enterobacter cloacae, Enterobacter* CO, *Enterobacter* core2, *Enterobacter cowanii, Enterobacter* dc6, *Enterobacter* DRSBII, *Enterobacter enrichment, Enterobacter* FL13-2-1, *Enterobacter* GIST-NKst10, *Enterobacter* GIST-NKst9, *Enterobacter* GJ1-11, *Enterobacter* gx-148, *Enterobacter hormaechei, Enterobacter* I-Bh20-21, *Enterobacter* ICB 113, *Enterobacter kobei, Enterobacter* KW 14, *Enterobacter* 112, *Enterobacter ludwigii, Enterobacter* M10.sub.-1B, *Enterobacter* M1R3, *Enterobacter marine, Enterobacter* NCCP-167, *Enterobacter of, Enterobacter oryzae, Enterobacter oxytoca, Enterobacter* P101, *Enterobacter* S11, *Enterobacter* SEL2, *Enterobacter* SPh, *Enterobacter* SSASP5, *Enterobacter terrigena, Enterobacter* TNT3, *Enterobacter* TP2MC, *Enterobacter* TS4, *Enterobacter* TSSAS2-48, i *Enterobacter, Enterobacter* ZYXCA1, *Enterococcus, Enterococcus* 020824/02-A, *Enterococcus* 1275b, *Enterococcus* 16C, *Enterococcus* 48, *Enterococcus* 6114, *Enterococcus* ABRIINW-H61, *Enterococcus asini, Enterococcus avium, Enterococcus azikeevi, Enterococcus bacterium, Enterococcus* BBDP57, *Enterococcus* BPH34, *Enterococcus* Bt, *Enterococcus canis, Enterococcus casseliflavus, Enterococcus* CmNA2, *Enterococcus* Da-20, *Enterococcus devriesei, Enterococcus dispar, Enterococcus* DJF_O30, *Enterococcus* DMB4, *Enterococcus durans, Enterococcus* enrichment, *Enterococcus* F81, *Enterococcus faecalis, Enterococcus faecium, Enterococcus* fcc9, *Enterococcus fecal, Enterococcus flavescens, Enterococcus fluvialis, Enterococcus* FR-3, *Enterococcus* FUA3374, *Enterococcus gallinarum, Enterococcus* GHAPRB1, *Enterococcus* GSC-2, *Enterococcus* GYPB01, *Enterococcus hermanniensis, Enterococcus hirae, Enterococcus lactis, Enterococcus malodoratus, Enterococcus manure, Enterococcus marine, Enterococcus* MNC1, *Enterococcus moraviensis, Enterococcus* MS2, *Enterococcus mundtii, Enterococcus* NAB 15, *Enterococcus* NBRC, *Enterococcus* nlaezlc434, *Enterococcus* nlaezlg106, *Enterococcus* nlaezlg87, *Enterococcus* nlaezlh339, *Enterococcus* nlaezlh375, *Enterococcus* nlaezlh381, *Enterococcus* nlaezlh383, *Enterococcus* nlaezlh405, *Enterococcus* nlaezlp116, *Enterococcus* nlaezlp148, *Enterococcus* nlaezlp401, *Enterococcus* nlaezlp650, *Enterococcus pseudoavium, Enterococcus* R-25205, *Enterococcus raffinosus, Enterococcus rottae, Enterococcus* RU07, *Enterococcus saccharolyticus, Enterococcus saccharominimus, Enterococcus sanguinicola, Enterococcus* SCA16, *Enterococcus* SCA2, *Enterococcus* SE138, *Enterococcus* SF-1, *Enterococcus sulfureus, Enterococcus* SV6, *Enterococcus tela, Enterococcus* te32a, *Enterococcus* te42a, *Enterococcus* te45r, *Enterococcus* te49a, *Enterococcus* te51a, *Enterococcus* te58r, *Enterococcus* te59r, *Enterococcus* te61r, *Enterococcus* te93r, *Enterococcus* te95a, *Enterococcus, Enterorhabdus, Enterorhabdus caecimuris, Enterorhabdus, Erwinia, Erwinia agglomerans, Erwinia enterica, Erwinia rhapontici, Erwinia tasmaniensis, Erwinia,* Erysipelotrichaceae_incertae_sedis, Erysipelotrichaceae_incertae_sedis aff, Erysipelotrichaceae_incertae_sedis bacterium, Erysipelotrichaceae_incertae_sedis biforme, Erysipelotrichaceae_incertae_sedis C-1, Erysipelotrichaceae_incertae_sedis cylindroides, Erysipelotrichaceae_incertae_sedis GK12, Erysipelotrichaceae_incertae_sedis innocuum, Erysipelotrichaceae_incertae_sedis nlaezlc332, Erysipelotrichaceae_incertae_sedis nlaezlc340, Erysipelotrichaceae_incertae_sedis nlaezlg420, Erysipelotrichaceae_incertae_sedis nlaezlg425, Erysipelotrichaceae_incertae_sedis nlaezlg440, Erysipelotrichaceae_incertae_sedis nlaezlg463, Erysipelotrichaceae_incertae_sedis nlaezlh340, Erysipelotrichaceae_incertae_sedis nlaezlh354, Erysipelotrichaceae_incertae_sedis nlaezlh379, Erysipelotrichaceae_incertae_sedis nlaezlh380, Erysipelotrichaceae_incertae_sedis nlaezlh385, Erysipelotrichaceae_incertae_sedis nlaezlh410, Erysipelotrichaceae_incertae_sedis tortuosum, Erysipelotrichaceae_incertae_sedis, *Escherichia/Shigella, Escherichia/Shigella* 29(2010), *Escherichia/Shigella* 4091, *Escherichia/Shigella* 4104, *Escherichia/Shigella* 8gw18, *Escherichia/Shigella* A94, *Escherichia/Shigella albertii, Escherichia/Shigella* B-1012, *Escherichia/Shigella* B4, *Escherichia/Shigella bacterium, Escherichia/Shigella* BBDP15, *Escherichia/Shigella* BBDP80, *Escherichia/Shigella boydii, Escherichia/Shigella carotovorum, Escherichia/Shigella* CERAR, *Escherichia/Shigella coli, Escherichia/Shigella* DBC-1, *Escherichia/Shigella* dc262011, *Escherichia/Shigella dysenteriae, Escherichia/Shigella* enrichment, *Escherichia/Shigella escherichia, Escherichia/Shigella fecal, Escherichia/Shigella fergusonii, Escherichia/Shigella flexneri, Escherichia/Shigella* GDR05, *Escherichia/Shigella* GDR07, *Escherichia/Shigella* H7, *Escherichia/Shigella marine, Escherichia/Shigella* ML2-46, *Escherichia/Shigella mpnisolate, Escherichia/Shigella* NA, *Escherichia/Shigella* nlaezlg330, *Escherichia/Shigella* nlaezlg400, *Escherichia/Shigella* nlaezlg441, *Escherichia/Shigella* nlaezlg506, *Escherichia/Shigella* nlaezlh204, *Escherichia/Shigella* nlaezlh208, *Escherichia/Shigella* nlaezlh209, *Escherichia/Shigella* nlaezlh213, *Escherichia/Shigella* nlaezlh214, *Escherichia/Shigella* nlaezlh4, *Escherichia/Shigella* nlaezlh435, *Escherichia/Shigella* nlaezlh81, *Escherichia/Shigella* nlaezlp126, *Escherichia/Shigella* nlaezlp198, *Escherichia/Shigella* nlaezlp21, *Escherichia/Shigella* nlaezlp235, *Escherichia/Shigella* nlaezlp237, *Escherichia/Shigella* nlaezlp239, *Escherichia/Shigella* nlaezlp25, *Escherichia/Shigella* nlaezlp252, *Escherichia/Shigella* nlaezlp275, *Escherichia/Shigella* nlaezlp280, *Escherichia/Shigella* nlaezlp51, *Escherichia/*

*Shigella* nlaezlp53, *Escherichia/Shigella* nlaezlp669, *Escherichia/Shigella* nlaezlp676, *Escherichia/Shigella* nlaezlp717, *Escherichia/Shigella* nlaezlp731, *Escherichia/Shigella* nlaezlp826, *Escherichia/Shigella* nlaezlp877, *Escherichia/Shigella* nlaezlp884, *Escherichia/Shigella* NMU-ST2, *Escherichia/Shigella* oc182011, *Escherichia/Shigella* of, *Escherichia/Shigella* proteobacterium, *Escherichia/Shigella* Q1, *Escherichia/Shigella* sakazakii, *Escherichia/Shigella* SF6, *Escherichia/Shigella* sm1719, *Escherichia/Shigella* SOD-7317, *Escherichia/Shigella* sonnei, *Escherichia/Shigella* SW86, *Escherichia/Shigella*, *Escherichia/Shigella* vulneris, *Ethanoligenens*, *Ethanoligenens harbinense*, *Ethanoligenens*, *Eubacterium*, *Eubacterium* ARC-2, *Eubacterium callanderi*, *Eubacterium* E-1, *Eubacterium* G3(2011), *Eubacterium infirmum*, *Eubacterium limosum*, *Eubacterium methylotrophicum*, *Eubacterium* nlaezlp439, *Eubacterium* nlaezlp457, *Eubacterium* nlaezlp458, *Eubacterium* nlaezlp469, *Eubacterium* nlaezlp474, *Eubacterium oral*, *Eubacterium saphenum*, *Eubacterium sulci*, *Eubacterium*, *Eubacterium* WAL, *Euglenida*, *Euglenida longa*, *Faecalibacterium*, *Faecalibacterium bacterium*, *Faecalibacterium canine*, *Faecalibacterium* DJF_VR20, *Faecalibacterium* ic1379, *Faecalibacterium prausnitzii*, *Faecalibacterium*, *Filibacter*, *Filibacter globispora*, *Flavobacterium*, *Flavobacterium* SSL03, *Flavobacterium*, *Flavonifractor*, *Flavonifractor* AUH-JLC235, *Flavonifractor* enrichment, *Flavonifractor* nlaezlc354, *Flavonifractor orbiscindens*, *Flavonifractor plautii*, *Flavonifractor*, *Francisella*, *Francisella piscicida*, *Fusobacterium*, *Fusobacterium nucleatum*, *Fusobacterium*, *Gardnerella*, *Gardnerella*, *Gardnerella vaginalis*, *Gemmiger*, *Gemmiger* DJF_VR33k2, *Gemmiger formicilis*, *Gemmiger*, *Geobacter*, *Geobacter*, *Gordonibacter*, *Gordonibacter bacterium*, *Gordonibacter intestinal*, *Gordonibacter pamelaeae*, *Gordonibacter*, Gp2, Gp2, Gp21, Gp21, Gp4, Gp4, Gp6, Gp6, *Granulicatella*, *Granulicatella adiacens*, *Granulicatella* enrichment, *Granulicatella oral*, *Granulicatella paraadiacens*, *Granulicatella*, *Haemophilus*, *Haemophilus*, *Hafnia*, *Hafnia* 3-12(2010), *Hafnia alvei*, *Hafnia* CC16, *Hafnia proteus*, *Hafnia*, *Haliea*, *Haliea*, *Hallella*, *Hallella seregens*, *Hallella*, *Herbaspirillum*, *Herbaspirillum* 022S4-11, *Herbaspirillum seropedicae*, *Hespellia*, *Hespellia porcina*, *Hespellia stercorisuis*, *Hespellia*, *Holdemania*, *Holdemania* AP2, *Holdemania filiformis*, *Holdemania*, *Howardella*, *Howardella*, *Howardella ureilytica*, *Hydrogenoanaerobacterium*, *Hydrogenoanaerobacterium saccharovorans*, *Hydrogenophaga*, *Hydrogenophaga bacterium*, *Ilumatobacter*, *Ilumatobacter*, *Janthinobacterium*, *Janthinobacterium* C30An7, *Janthinobacterium*, *Jeotgalicoccus*, *Jeotgalicoccus*, *Klebsiella*, *Klebsiella aerogenes*, *Klebsiella bacterium*, *Klebsiella* E1L1, *Klebsiella* EB2-THQ, *Klebsiella* enrichment, *Klebsiella* F83, *Klebsiella* G1-6, *Klebsiella* gg160e, *Klebsiella granulomatis*, *Klebsiella* HaNA20, *Klebsiella* HF2, *Klebsiella* ii.sub.-3 chl.sub.-1, *Klebsiella* KALAICIBA17, *Klebsiella* kpu, *Klebsiella* M3, *Klebsiella* MB45, *Klebsiella milletis*, *Klebsiella* NCCP-138, *Klebsiella* ok1.sub.-1.sub.-9_S16, *Klebsiella* ok1.sub.-1.sub.-9_S54, *Klebsiella planticola*, *Klebsiella pneumoniae*, *Klebsiella poinarii*, *Klebsiella* PSB26, *Klebsiella* RS, *Klebsiella* Se14, *Klebsiella* SRC_DSD12, *Klebsiella* td153s, *Klebsiella* TG-1, *Klebsiella* TPS5, *Klebsiella*, *Klebsiella variicola*, *Klebsiella* WB-2, *Klebsiella* Y9, *Klebsiella* zlmy, *Kluyvera*, *Kluyvera* An5-1, *Kluyvera cryocrescens*, *Kluyvera*, *Kocuria*, *Kocuria* 2216.35.31, *Kurthia*, *Kurthia*, *Lachnobacterium*, *Lachnobacterium* C12b, *Lachnobacterium*, Lachnospiracea_*incertae_sedis*, Lachnospiracea_*incertae_sedis bacterium*, Lachnospiracea_*incertae_sedis contortum*, Lachnospiracea_*incertae_sedis* Eg2, Lachnospiracea_*incertae_sedis eligens*, Lachnospiracea_*incertae_sedis ethanolgignens*, Lachnospiracea_*incertae_sedis galacturonicus*, Lachnospiracea_*incertae_sedis gnavus*, Lachnospiracea_*incertae_sedis hallii*, Lachnospiracea_*incertae_sedis hydrogenotrophica*, Lachnospiracea_*incertae_sedis* ID5, Lachnospiracea_*incertae_sedis intestinal*, Lachnospiracea_*incertae_sedis mpnisolate*, Lachnospiracea_*incertae_sedis pectinoschiza*, Lachnospiracea_*incertae_sedis ramulus*, Lachnospiracea_*incertae_sedis rectale*, Lachnospiracea_*incertae_sedis* RLB1, Lachnospiracea_*incertae_sedis rumen*, Lachnospiracea_*incertae_sedis* SY8519, Lachnospiracea_*incertae_sedis torques*, Lachnospiracea_*incertae_sedis*, Lachnospiracea_*incertae_sedis uniforme*, Lachnospiracea_*incertae_sedis ventriosum*, Lachnospiracea_*incertae_sedis xylanophilum*, Lachnospiracea_*incertae_sedis* ye62, *Lactobacillus*, *Lactobacillus* 5-1-2, *Lactobacillus* 66c, *Lactobacillus acidophilus*, *Lactobacillus arizonensis*, *Lactobacillus* B5406, *Lactobacillus brevis*, *Lactobacillus casei*, *Lactobacillus crispatus*, *Lactobacillus curvatus*, *Lactobacillus delbrueckii*, *Lactobacillus fermentum*, *Lactobacillus gasseri*, *Lactobacillus helveticus*, *Lactobacillus hominis*, *Lactobacillus* ID9203, *Lactobacillus* IDSAc, *Lactobacillus intestinal*, *Lactobacillus johnsonii*, *Lactobacillus lactis*, *Lactobacillus manihotivorans*, *Lactobacillus mucosae*, *Lactobacillus* NA, *Lactobacillus oris*, *Lactobacillus* P23, *Lactobacillus* P8, *Lactobacillus paracasei*, *Lactobacillus paraplantarum*, *Lactobacillus pentosus*, *Lactobacillus plantarum*, *Lactobacillus pontis*, *Lactobacillus* rennanqilfy10, *Lactobacillus* rennanqilfy14, *Lactobacillus* rennanqilyf9, *Lactobacillus reuteri*, *Lactobacillus rhamnosus*, *Lactobacillus salivarius*, *Lactobacillus sanfranciscensis*, *Lactobacillus suntoryeus*, *Lactobacillus* T3R1C1, *Lactobacillus*, *Lactobacillus vaginalis*, *Lactobacillus zeae*, *Lactococcus*, *Lactococcus* 56, *Lactococcus* CR-317S, *Lactococcus* CW-1, *Lactococcus* D8, *Lactococcus* Da-18, *Lactococcus* DAP39, *Lactococcus delbrueckii*, *Lactococcus* F116, *Lactococcus fujiensis*, *Lactococcus* G22, *Lactococcus garvieae*, *Lactococcus lactis*, *Lactococcus manure*, *Lactococcus* RTS, *Lactococcus* SXVIII1(2011), *Lactococcus* TP2MJ, *Lactococcus* TP2ML, *Lactococcus* TP2MN, *Lactococcus* U5-1, *Lactococcus*, *Lactonifactor*, *Lactonifactor bacterium*, *Lactonifactor longoviformis*, *Lactonifactor* nlaezlc533, *Lactonifactor*, *Leclercia*, *Leclercia*, *Lentisphaera*, *Lentisphaera*, *Leuconostoc*, *Leuconostoc carnosum*, *Leuconostoc citreum*, *Leuconostoc garlicum*, *Leuconostoc gasicomitatum*, *Leuconostoc gelidum*, *Leuconostoc inhae*, *Leuconostoc lactis*, *Leuconostoc* MEBE2, *Leuconostoc mesenteroides*, *Leuconostoc pseudomesenteroides*, *Leuconostoc*, *Limnobacter*, *Limnobacter* spf3, *Luteolibacter*, *Luteolibacter bacterium*, *Lutispora*, *Lutispora*, *Marinifilum*, *Marinifilum*, *Marinobacter*, *Marinobacter arcticus*, *Mariprofundus*, *Mariprofundus*, *Marvinbryantia*, *Marvinbryantia*, *Megamonas*, *Megamonas*, *Megasphaera*, *Megasphaera*, *Melissococcus*, *Melissococcus faecalis*, *Methanobacterium*, *Methanobacterium subterraneum*, *Methanobrevibacter*, *Methanobrevibacter arboriphilus*, *Methanobrevibacter millerae*, *Methanobrevibacter olleyae*, *Methanobrevibacter oralis*, *Methanobrevibacter* SM9, *Methanobrevibacter smithii*, *Methanobrevibacter*, *Methanosphaera*, *Methanosphaera stadtmanae*, *Methanosphaera*, *Methylobacterium*, *Methylobacterium adhaesivum*, *Methylobacterium bacterium*, *Methylobacterium* iEII3, *Methylobacterium* MP3, *Methylobacterium oryzae*, *Methylobacterium* PB132, *Methylobacterium* PB20, *Methylobacterium* PB280, *Methylobacterium* PDD-23b-14, *Methylobacterium* radiotolerans, Methylobacterium SKJH-1, Methylobacterium, Mitsuokella, Mitsuokella jalaludinii, Mitsuokella, Morganella, Morganella morganii, Morganella, Moritella, Moritella 2D2, Moryella, Moryella indoligenes, Moryella naviforme, Moryella, Mycobacterium, Mycobacterium tuberculosis, Mycobacterium, Negativicoccus, Negativicoccus, Nitrosomonas, Nitrosomonas eutropha, Novosphingobium, Novosphingobium, Odoribacter, Odoribacter laneus, Odoribacter splanchnicus, Odoribacter, Olsenella, Olsenella 1832, Olsenella F0206, Olsenella, Orbus, Orbus gilliamella, Oribacterium, Oribacterium, Oscillibacter, Oscillibacter bacterium, Oscillibacter enrichment, Oscillibacter, Owenweeksia, Owenweeksia, Oxalobacter, Oxalobacter formigenes, Oxalobacter, Paludibacter, Paludibacter, Pantoea, Pantoea agglomerans, Pantoea eucalypti, Pantoea, Papillibacter, Papillibacter cinnamivorans, Papillibacter, Parabacteroides, Parabacteroides ASF519, Parabacteroides CR-34, Parabacteroides distasonis, Parabacteroides DJF_B084, Parabacteroides DJF_B086, Parabacteroides dnLKV8, Parabacteroides enrichment, Parabacteroides fecal, Parabacteroides goldsteinii, Parabacteroides gordonii, Parabacteroides johnsonii, Parabacteroides merdae, Parabacteroides mpnisolate, Parabacteroides nlaezlp340, Parabacteroides, Paraeggerthella, Paraeggerthella hongkongensis, Paraeggerthella nlaezlp797, Paraeggerthella nlaezlp896, Paraprevotella, Paraprevotella clara, Paraprevotella, Paraprevotella xylaniphila, Parasutterella, Parasutterella excrementihominis, Parasutterella, Pectobacterium, Pectobacterium carotovorum, Pectobacterium wasabiae, Pediococcus, Pediococcus te2r, Pediococcus, Pedobacter, Pedobacter b3N1b-b5, Pedobacter daechungensis, Pedobacter, Peptostreptococcus, Peptostreptococcus anaerobius, Peptostreptococcus stomatis, Peptostreptococcus, Phascolarctobacterium, Phascolarctobacterium faecium, Phascolarctobacterium, Photobacterium, Photobacterium MIE, Pilibacter, Pilibacter, Planctomyces, Planctomyces, Planococcaceae_incertae_sedis, Planococcaceae_incertae_sedis, Planomicrobium, Planomicrobium, Plesiomonas, Plesiomonas, Porphyrobacter, Porphyrobacter KK348, Porphyromonas, Porphyromonas asaccharolytica, Porphyromonas bennonis, Porphyromonas canine, Porphyromonas somerae, Porphyromonas, Prevotella, Prevotella bacterium, Prevotella BI-42, Prevotella bivia, Prevotella buccalis, Prevotella copri, Prevotella DJF_B112, Prevotella mpnisolate, Prevotella oral, Prevotella, Propionibacterium, Propionibacterium acnes, Propionibacterium freudenreichii, Propionibacterium LG, Propionibacterium, Proteiniborus, Proteiniborus, Proteiniphilum, Proteiniphilum, Proteus, Proteus HS7514, Providencia, Providencia, Pseudobutyrivibrio, Pseudobutyrivibrio bacterium, Pseudobutyrivibrio fibrisolvens, Pseudobutyrivibrio ruminis, Pseudobutyrivibrio, Pseudochrobactrum, Pseudochrobactrum, Pseudoflavonifractor, Pseudoflavonifractor asf500, Pseudoflavonifractor bacterium, Pseudoflavonifractor capillosus, Pseudoflavonifractor NML, Pseudoflavonifractor, Pseudomonas, Pseudomonas 1043, Pseudomonas 10569, Pseudomonas 127(39-zx), Pseudomonas 12A.sub.-19, Pseudomonas 145(38zx), Pseudomonas 22010, Pseudomonas 32010, Pseudomonas 34t20, Pseudomonas 3C.sub.-10, Pseudomonas 4-5(2010), Pseudomonas 4-9(2010), Pseudomonas 6-13.J, Pseudomonas 63596, Pseudomonas 82010, Pseudomonas a001-142L, Pseudomonas a101-18-2, Pseudomonas a111-5, Pseudomonas aeruginosa, Pseudomonas agarici, Pseudomonas amspl, Pseudomonas AU2390, Pseudomonas AZ18R1, Pseudomonas azotoformans, Pseudomonas B122, Pseudomonas B65(2012), Pseudomonas bacterium, Pseudomonas BJSX, Pseudomonas BLH-8D5, Pseudomonas BWDY-29, Pseudomonas CA18, Pseudomonas Cantas12, Pseudomonas CB 11, Pseudomonas CBZ-4, Pseudomonas cedrina, Pseudomonas CGMCC, Pseudomonas CL16, Pseudomonas CNE, Pseudomonas corrugata, Pseudomonas cuatrocienegasensis, Pseudomonas CYEB-7, Pseudomonas D5, Pseudomonas DAP37, Pseudomonas DB48, Pseudomonas deceptionensis, Pseudomonas Den-05, Pseudomonas DF7EH1, Pseudomonas DhA-91, Pseudomonas DVS14a, Pseudomonas DYJK4-9, Pseudomonas DZQS, Pseudomonas E11_ICE19B, Pseudomonas E2.2, Pseudomonas e2-CDC-TB4D2, Pseudomonas EM189, Pseudomonas enrichment, Pseudomonas extremorientalis, Pseudomonas FAIR/BE/F/GH37, Pseudomonas FAIR/BE/F/GH39, Pseudomonas FAIR/BE/F/GH94, Pseudomonas FLM05-3, Pseudomonas fluorescens, Pseudomonas fragi, Pseudomonas 'FSL, Pseudomonas G1013, Pseudomonas gingeri, Pseudomonas HC2-2, Pseudomonas HC2-4, Pseudomonas HC2-5, Pseudomonas HC4-8, Pseudomonas HC6-6, Pseudomonas Hg4-06, Pseudomonas HLB8-2, Pseudomonas HLS12-1, Pseudomonas HSF20-13, Pseudomonas HW08, Pseudomonas 11-44, Pseudomonas IpA-92, Pseudomonas IV, Pseudomonas JCM, Pseudomonas jessenii, Pseudomonas JSPBS, Pseudomonas K3R3.1A, Pseudomonas KB40, Pseudomonas KB42, Pseudomonas KB44, Pseudomonas KB63, Pseudomonas KB73, Pseudomonas KK-21-4, Pseudomonas KOPRI, Pseudomonas L1R3.5, Pseudomonas LAB-27, Pseudomonas LAB-44, Pseudomonas Lc10-2, Pseudomonas libanensis, Pseudomonas Ln5C.7, Pseudomonas LS197, Pseudomonas lundensis, Pseudomonas marginalis, Pseudomonas MFY143, Pseudomonas MFY146, Pseudomonas MY1404, Pseudomonas MY1412, Pseudomonas MY1416, Pseudomonas MY1420, Pseudomonas N14zhy, Pseudomonas NBRC, Pseudomonas NCCP-506, Pseudomonas NFU20-14, Pseudomonas NJ-22, Pseudomonas NJ-24, Pseudomonas Nj-3, Pseudomonas Nj-55, Pseudomonas Nj-56, Pseudomonas Nj-59, Pseudomonas Nj-60, Pseudomonas Nj-62, Pseudomonas Nj-70, Pseudomonas NP41, Pseudomonas OCW4, Pseudomonas OW3-15-3-2, Pseudomonas P1(2010), Pseudomonas P2(2010), Pseudomonas P3(2010), Pseudomonas P4(2010), Pseudomonas PD, Pseudomonas PF1B4, Pseudomonas PF2M10, Pseudomonas PILH1, Pseudomonas poae, Pseudomonas proteobacterium, Pseudomonas ps4-12, Pseudomonas ps4-2, Pseudomonas xps4-28, Pseudomonas ps4-34, Pseudomonas ps4-4, Pseudomonas psychrophila, Pseudomonas putida, Pseudomonas R-35721, Pseudomonas R-37257, Pseudomonas R-37265, Pseudomonas R-37908, Pseudomonas RBE1CD-48, Pseudomonas RBE2CD-42, Pseudomonas regd9, Pseudomonas RKS7-3, Pseudomonas S2, Pseudomonas seawater, Pseudomonas SGb08, Pseudomonas SGb 120, Pseudomonas SGb396, Pseudomonas sgn, Pseudomonas 'Shk, Pseudomonas stutzeri, Pseudomonas syringae, Pseudomonas taetrolens, Pseudomonas tolaasii, Pseudomonas trivialis, Pseudomonas TUT1023, Pseudomonas, Pseudomonas W15Feb26, Pseudomonas W15Feb4, Pseudomonas W15Feb6, Pseudomonas WD-3, Pseudomonas WR4-13, Pseudomonas WR7#2, Pseudomonas Y1000, Pseudomonas ZS29-8, Psychrobacter, Psychrobacter umb13d, Psychrobacter, Pyramidobacter, Pyramidobacter piscolens, Pyramidobacter, Rahnella, Rahnella aquatilis, Rahnella carotovorum, Rahnella GIST-WP4w 1, Rahnella LR113, Rahnella, Rahnella Z2-S 1, Ralstonia, Ralstonia bacterium, Ralstonia, Raoultella, Raoultella B 19, Raoultella enrichment, Raoultella planticola, Raoultella sv6xvii, Raoultella SZ015, Raoultella, Renibacterium, Renibacterium G20, Rhizobium, Rhizobium leguminosarum, Rhodococcus, Rhodococcus erythropolis, Rhodopirellula, Rhodopirellula, Riemerella, Riemerella anatipestifer, Rikenella, Rikenella, Robinsoniella, Robinsoniella peoriensis, Robinsoniella, Roseburia, Roseburia 11SE37, Roseburia bacterium, Roseburia cecicola, Roseburia DJF_VR77, Roseburia faecis, Roseburia fibrisolvens, Roseburia hominis, Roseburia intestinalis, Roseburia inulinivorans, Roseburia, Roseibacillus, Roseibacillus, Rothia, Rothia, Rubritalea, Rubritalea, Ruminococcus, Ruminococcus 25F6, Ruminococcus albus, Ruminococcus bacterium, Ruminococcus bromii, Ruminococcus callidus, Ruminococcus champanellensis, Ruminococcus DJF_VR87, Ruminococcus flavefaciens, Ruminococcus gauvreauii, Ruminococcus lactaris, Ruminococcus NK3A76, Ruminococcus, Ruminococcus YE71, Saccharofermentans, Saccharofermentans, Salinicoccus, Salinicoccus, Salinimicrobium, Salinimicrobium, Salmonella, Salmonella agglomerans, Salmonella bacterium, Salmonella enterica, Salmonella freundii, Salmonella hermannii, Salmonella paratyphi, Salmonella SL0604, Salmonella subterranea, Salmonella, Scardovia, Scardovia oral, Schwartzia, Schwartzia, Sedimenticola, Sedimenticola, Sediminibacter, Sediminibacter, Selenomonas, Selenomonas fecal, Selenomonas, Serpens, Serpens, Serratia, Serratia 1135, Serratia 136-2, Serratia 5.1R, Serratia AC-CS-1B, Serratia AC-CS-B2, Serratia aquatilis, Serratia bacterium, Serratia BS26, Serratia carotovorum, Serratia DAP6, Serratia enrichment, Serratia F2, Serratia ficaria, Serratia fonticola, Serratia grimesii, Serratia J145, Serratia JM983, Serratia liquefaciens, Serratia marcescens, Serratia plymuthica, Serratia proteamaculans, Serratia proteolyticus, Serratia ptz-16s, Serratia quinivorans, Serratia SBS, Serratia SS22, Serratia trout, Serratia UA-G004, Serratia, Serratia White, Serratia yellow, Shewanella, Shewanella baltica, Shewanella, Slackia, Slackia intestinal, Slackia isoflavoniconvertens, Slackia NATTS, Slackia, Solibacillus, Solibacillus, Solobacterium, Solobacterium moorei, Solobacterium, Spartobacteria_genera_incertae_sedis, Spartobacteria_genera_incertae_sedis, Sphingobium, Sphingobium, Sphingomonas, Sphingomonas, Sporacetigenium, Sporacetigenium, Sporobacter, Sporobacter, Sporobacterium, Sporobacterium olearium, Staphylococcus, Staphylococcus epidermidis, Staphylococcus PCA17, Staphylococcus, Stenotrophomonas, Stenotrophomonas, Streptococcus, Streptococcus 1606-02B, Streptococcus agalactiae, Streptococcus alactolyticus, Streptococcus anginosus, Streptococcus bacterium, Streptococcus bovis, Streptococcus ChDC, Streptococcus constellatus, Streptococcus CR-3145, Streptococcus criceti, Streptococcus cristatus, Streptococcus downei, Streptococcus dysgalactiae, Streptococcus enrichment, Streptococcus equi, Streptococcus equinus, Streptococcus ES11, Streptococcus eubacterium, Streptococcus fecal, Streptococcus gallinaceus, Streptococcus gallolyticus, Streptococcus gastrococcus, Streptococcus genomosp, Streptococcus gordonii, Streptococcus 15, Streptococcus infantarius, Streptococcus intermedius, Streptococcus Je2, Streptococcus JS-CD2, Streptococcus LRC, Streptococcus luteciae, Streptococcus lutetiensis, Streptococcus M09-11185, Streptococcus mitis, Streptococcus mutans, Streptococcus NA, Streptococcus nlaezlc353, Streptococcus nlaezlp68, Streptococcus nlaezlp758, Streptococcus nlaezlp807, Streptococcus oral, Streptococcus oralis, Streptococcus parasanguinis, Streptococcus phocae, Streptococcus pneumoniae, Streptococcus porcinus, Streptococcus pyogenes, Streptococcus S 16-08, Streptococcus salivarius, Streptococcus sanguinis, Streptococcus sobrinus, Streptococcus suis, Streptococcus symbiont, Streptococcus thermophilus, Streptococcus TW1, Streptococcus, Streptococcus vestibularis, Streptococcus warneri, Streptococcus XJ-RY-3, Streptomyces, Streptomyces malaysiensis, Streptomyces MVCS6, Streptophyta, Streptophyta cordifolium, Streptophyta ginseng, Streptophyta hirsutum, Streptophyta oleracea, Streptophyta sativa, Streptophyta sativum, Streptophyta sativus, Streptophyta tabacum, Streptophyta, Subdivision3_genera_incertae_sedis, Subdivision3_ genera_incertae_sedis, Subdoligranulum, Subdoligranulum bacterium, Subdoligranulum ic1393, Subdoligranulum ic1395, Subdoligranulum, Subdoligranulum variabile, Succiniclasticum, Succiniclasticum, Sulfuricella, Sulfuricella, Sulfurospirillum, Sulfurospirillum, Sutterella, Sutterella, Sutterella wadsworthensis, Syntrophococcus, Syntrophococcus, Syntrophomonas, Syntrophomonas bryantii, Syntrophomonas, Syntrophus, Syntrophus, Tannerella, Tannerella, Tatumella, Tatumella, Thermofilum, Thermofilum, Thermogymnomonas, Thermogymnomonas, Thermovirga, Thermovirga, Thiomonas, Thiomonas ML1-46, Thorsellia, Thorsellia carsonella, TM7 genera_incertae_sedis, TM7 genera_incertae_sedis, Trichococcus, Trichococcus, Turicibacter, Turicibacter sanguinis, Turicibacter, Vagococcus, Vagococcus bfsll-15, Vagococcus, Vampirovibrio, Vampirovibrio, Varibaculum, Varibaculum, Variovorax, Variovorax KS2D-23, Veillonella, Veillonella dispar, Veillonella MSA12, Veillonella OK8, Veillonella oral, Veillonella parvula, Veillonella tobetsuensis, Veillonella, Vibrio, Vibrio 3C1, Vibrio, Victivallis, Victivallis, Victivallis vadensis, Vitellibacter, Vitellibacter, Wandonia, Wandonia haliotis, Weissella, Weissella cibaria, Weissella confusa, Weissella oryzae, Weissella, Yersinia, Yersinia 9gw38, Yersinia A125, Yersinia aldovae, Yersinia aleksiciae, Yersinia b702011, Yersinia bacterium, Yersinia bercovieri, Yersinia enterocolitica, Yersinia entomophaga, Yersinia frederiksenii, Yersinia intermedia, Yersinia kristensenii, Yersinia MAC, Yersinia massiliensis, Yersinia mollaretii, Yersinia nurmii, Yersinia pekkanenii, Yersinia pestis, Yersinia pseudotuberculosis, Yersinia rohdei, Yersinia ruckeri, Yersinia s1Ofe31, Yersinia s17fe31, Yersinia s4fe31, Yersinia, Yersinia YEM17B.

Figure 2:
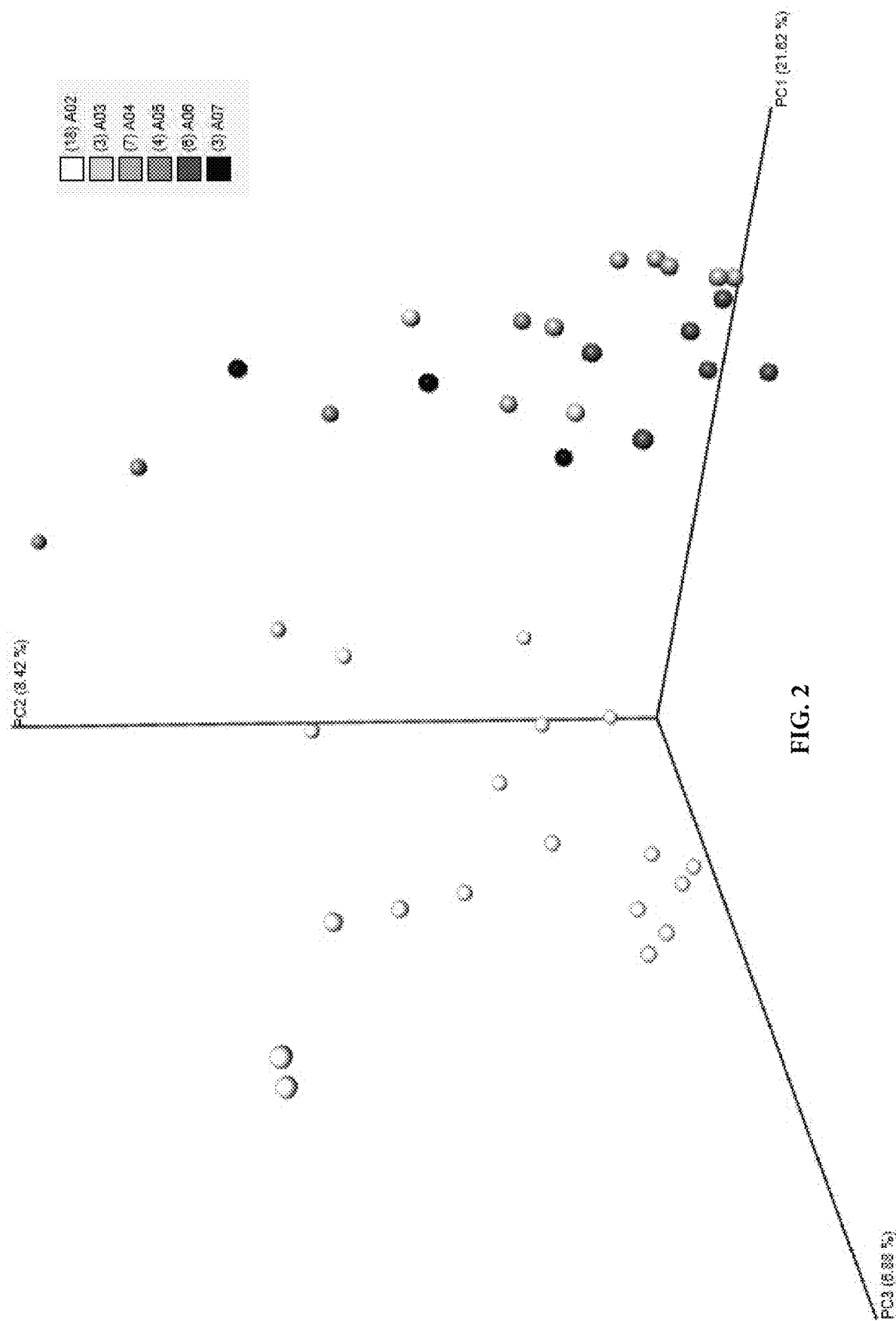
FIG. 2 is a 3-dimensional illustration providing a comparative representations of microbiome profiles of yeast species for differing soil samples.

Additional microbes are listed in Appendix A and Appendix B hereinbelow. 3D images description:

FIGS. 1 and 2 are 3-dimensional illustrations providing comparative representations of microbiome profiles. These microbiomes were found in differing soil samples coming from exemplary vineyards in California, United States, and Spain, in accordance with certain embodiments. FIG. 1 is the profile for bacterias, whereas FIG. 2 is the profile for yeast species. Each winery is represented by a greyscale color on the respective legends as shown. The legends provide the number of samples for each winery, along with a code assigned to each winery.

It was found that the samples coming from the same winery are have greater similarities among themselves as compared to other samples. Additionally the samples coming from wineries from the same region have greater similarities as compared to samples coming from other wine regions. The samples illustrate clustering, for both bacterias and yeast species, demonstrating that applying the methodologies herein provides a scientific-based identity to the terroir concept in winemaking and provides validation to certain assumptions concerning the existence of bio-wine regions upon observation of microbiome profiles of soil.

Figure 3:
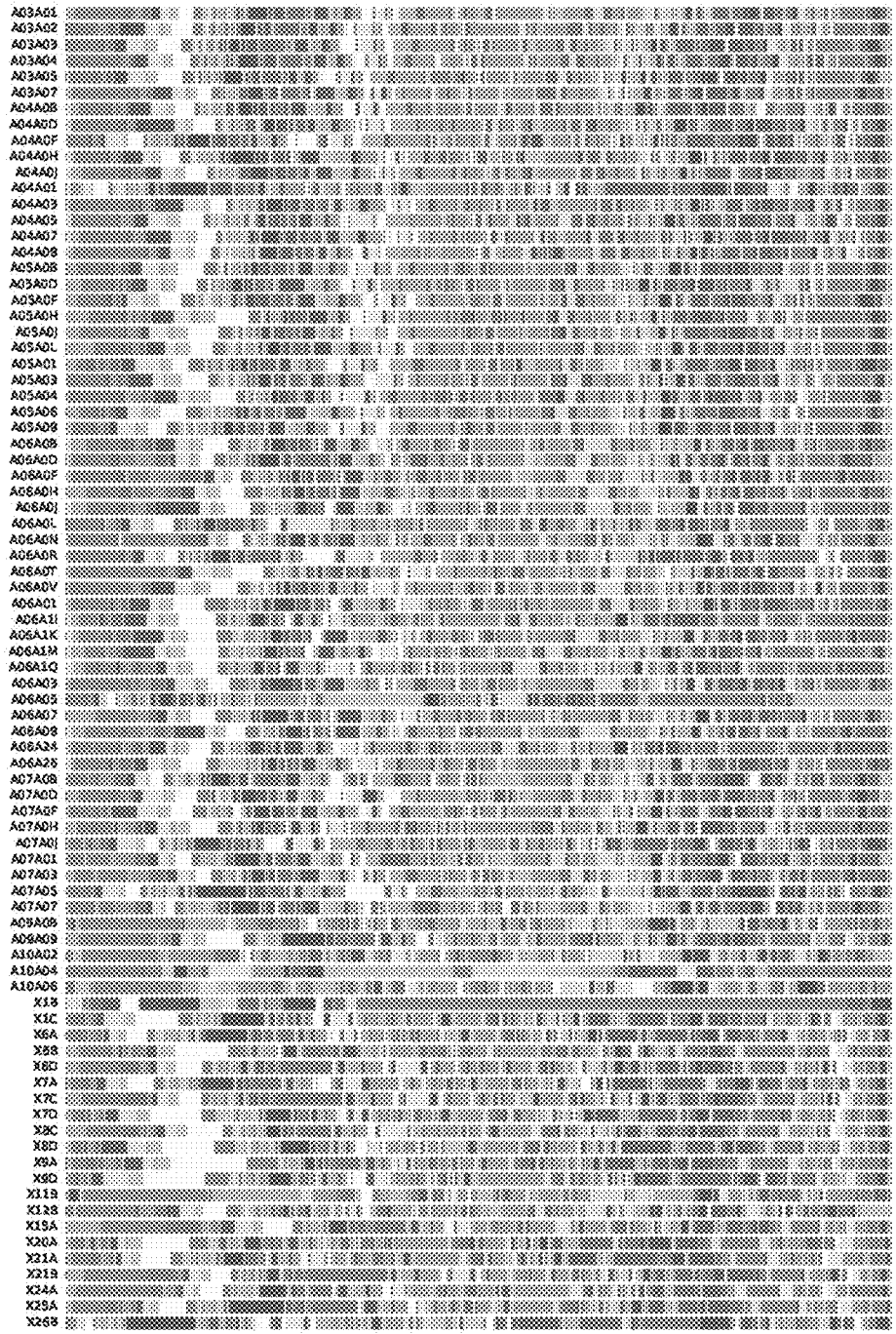
FIG. 3 is a bar chart illustration of the visual comparative representations of microbiome profiles of bacterias found in different soil samples.
Figure 4:
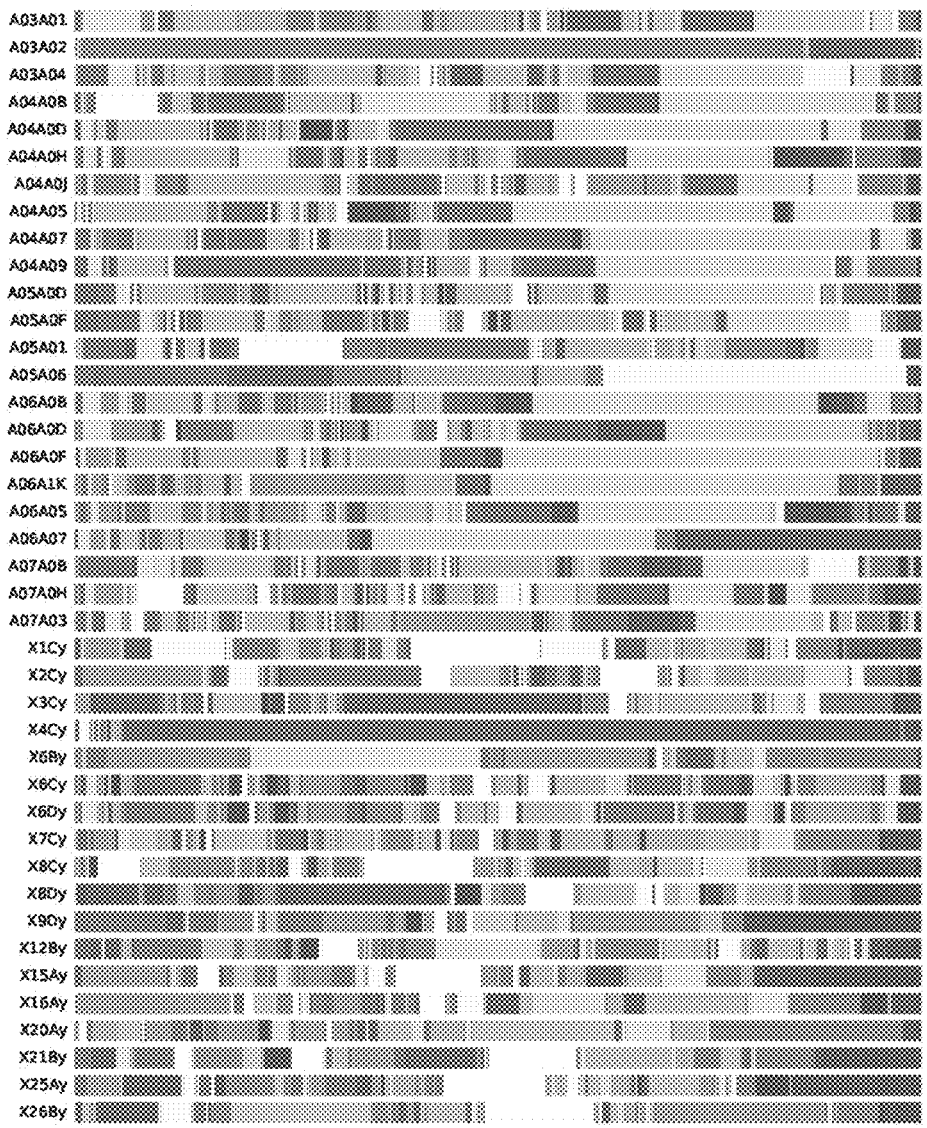
FIG. 4 is a bar chart illustration of the visual comparative representations of microbiome profiles of yeast species found in different soil samples.

FIGS. 3 and 4 are bar charts providing visual comparative representations of the microbiome profiles found in different soil samples. FIG. 3 is a bar chart profile for bacterias, whereas FIG. 4 is a bar chart profile for yeast species. For each of these charts, the x-axis provides sample identification codes, namely codes assigned to the different soil samples from vineyards. In the study, there were 83 samples in the bacteria chart of FIG. 3 and 41 samples in yeast chart of FIG. 4. The y-axis provides the respective abundancies of the microbial species for each given vineyard sample, with each greyscale color representing a different microbiological specie.

Accordingly, illustrated in FIGS. 3 and 4 are visual comparative representations of respective microbiome profiles found in the differing soil samples, with one bar profile per sample, derived from the exemplary vineyards. The vertical distribution of these species, shown in greyscale, is the same along the samples to allow the visual comparison of similarities among the microbiome profiles of the sample.

This representation, for both bacterias and yeast species, demonstrates that we are able to generate and compare microbiome profiles of samples applying the methodology described herein and serves to validate the assumptions of the existence of large microbial diversity for both yeast and bacteria in the vineyard samples.

The methods provided herein can provide strain classification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods provided herein can provide strain quantification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%.

In general, the present inventions further relates to systems and methods for determining and characterizing the microbiomes of fermentation settings, and in particular determining through relationship-based processing, which include custom and unique analytics tools and algorithms, data management, cleansing, filtering, and quality control, which in turn provide information about the fermentation setting. Such characterized information, for example, can have, and be used for, predictive, historical, analytic, development, control and monitoring purposes.

This information, data, processing algorithms support software, such as human machine interface (HMI) programs and graphic programs, and databases, may be cloud-based, locally-based, hosted on remote systems other than cloud-based systems, and combinations and variations of these.

The current disclosure provides computer systems for implementing any of the methods described herein. A computer system may be used to implement one or more steps including, sample collection, sample processing, detecting, quantifying one or more microbes, generating a profile data, comparing said data to a reference, generating a subject-specific microbiome profile, comparing the sample-specific profile to a reference profile, receiving sample-related data, receiving and storing data obtained by one or more methods described herein, analyzing said data, generating a report, and reporting results to a receiver.

Thus, real-time, derived, and predicted data may be collected and stored and thus become historic data for an ongoing process, setting, or application. In this manner, the collection, use, and computational links can create a real-time situation in which machine learning can be applied to further enhance and refine the fermentation activities or processes. Further, real-time, derived, predictive, and historic data can be, and preferably is, associated with other data and information. Thus, the microbiome information can be associated with GPS data; location data, e.g., particular components and subsystems in an fermentation process such as for example a particular barrel type for wine storage; processing stage or step such as filtration of fermentation broth; geological parameters including formation permeability and porosity; soil moisture, nutrient, and rainfall conditions in agricultural processes; chemicals in wine, for example, sulfur acid.

Thus, real-time, derived, historic, and predictive microbiome information may be further combined or processed with these other sources of information and data regarding the fermentation setting or process to provide combined, derived, and predictive information. In this manner, the microbiome information is used in combination with other data and information to provide for unique and novel ways to conduct fermentation operations, to develop or plan fermentation operations, to refine and enhance existing fermentation operations and combinations of these and other activities.

Preferably, these various types of information and data are combined where one or more may become metadata for the other. In this manner, information may be linked in a manner that provides for rapid, efficient, and accurate processing to provide useful information relating to the fermentation setting. Thus for example, in agricultural setting the soil moisture content, the GPS location down to the square yard of a large farm may be linked as metadata to the real-time microbiome information during planting and compared with similarly linked metadata obtained during harvesting along with crop yield for that acre to refine and enhance the agricultural processing of the field in which the acre is located.

In general, historic microbiome data may be obtained from known databases or it may be obtained from conducting population studies or censuses of the microbiome for the particular fermentation setting. Thus samples of biological materials are collected and characterized. This characterized information is then processed and stored. Preferably, the data is processed and stored in a manner that provides for ready and efficient access and utilization in subsequent steps, often using auxiliary data structures such as indexes or hashes.

In general, real-time microbiome data may be obtained from conducting population studies or censuses of the microbiome as it exists at a particular point in time, or over a timeseries, for the particular fermentation setting. Thus samples of biological materials are collected and characterized. This characterized information is then processed and stored. Preferably, the data is processed and utilized in subsequent steps or may be stored as historic data in a manner that provides for ready and efficient access and utilization in subsequent steps.

Generally, microbiome information may be contained in any type of data file that is utilized by current sequencing systems or that is a universal data format such as for example FASTQ (including quality scores), FASTA (omitting quality scores), GFF (for feature tables), etc. This data or files may then be combined using various software and computational techniques with identifiers or other data, examples of such software and identifiers for the combining of the various types of this information include the BIOM file format and the MI(x)S family of standards developed by the Genomic Standards Consortium. Additionally by way of example, in agricultural settings, data from a harvesting combine regarding yield, microbiome information, and commodities price information may be displayed or stored or used for further processing. The combination and communication of these various systems can be implemented by various data processing techniques, conversions of files, compression techniques, data transfer techniques, and other techniques for the efficient, accurate, combination, signal processing and overlay of large data streams and packets.

In general, real-time, historic, and combinations and variations of this microbiome information is analyzed to provide a census or population distribution of various microbes. Unlike conventional identification of a particular species that is present, the analysis of the present invention determines in an n-dimensional space (a mathematical construct having 2, 3, 5, 12, 1000, or more dimensions), the interrelationship of the various microbes present in the system, and potentially also interrelationship of their genes, transcripts, proteins and/or metabolites. The embodiments of the present invention provide further analysis to this n-dimensional space information, which analysis renders this information to a format which is more readily usable and processable and understandable. Thus, for example, by using the techniques of the present invention, the n-dimensional space information is analyzed and studied for patterns of significance pertinent to a particular fermentation setting and then converted to more readily usable data such as for example a 2-dimensional color-coded plot for presentation through a HMI (Human-Machine Interface).

Additionally, the n-dimensional space information may be related, e.g., transformed or correlated with, physical, environmental, or other data such as the conditions under which a particular plant was grown, either by projection into the same spatial coordinates or by relation of the coordinate systems themselves, or by feature extraction or other machine learning or multivariate statistical techniques. This related n-dimensional space information may then be further processed into a more readily usable format such as a 2-dimensional representation. Further, this 2-dimensional representation and processing may, for example, be based upon particular factors or features that are of significance in a particular fermentation setting. The 2-dimensional information may also be further viewed and analyzed for determining particular factors or features of significance for a system. Yet further, either of these types of 2-dimensional information may be still further processed using for example mathematical transformation functions to return them to an n-dimensional space which mathematical functions which may be based upon known or computationally determined factors or features.

Thus the present inventions provide for derived and predicted information that can be based upon the computational distillation of complex n-dimensional space microbiome information, which may be further combined with other data. This computationally distilled data or information may then be displayed and used for operational purposes in the fermentation setting, it may be combined with additional data and displayed and used for operational purposes in the fermentation setting, it may be alone or in combination with additional information subjected to trend, analysis, to determine features or factors of significance, it may be used for planning and operational purposes in combinations and variations of these and other utilizations.

Generally and for example, in ascertaining microbiome information the selection and sequencing of particular regions or portions of genetic materials may be used, including for example, the SSU rRNA gene (16S or 18S), the LSU rRNA gene (23S or 28S), the ITS in the rRNA operon, cpn60, gene marker regions such as metal-dependent proteases with possible chaperone activity, and various other segments consisting of base pairs, peptides or polysaccharides for use in characterizing the microbial community and the relationships among its constituents.

In general, an embodiment of a method of the present invention may include one or more of the following steps which may be conducted in various orders: sample preparation including obtaining the sample at the designated location, and manipulating the sample; extraction of the genetic material and other biomolecules from the microbial communities in the sample; preparation of libraries with identifiers such as an appropriate barcode such as DNA libraries, metabolite libraries, and protein libraries of the material; sequence elucidation of the material (including, for example, DNA, RNA, and protein) of the microbial communities in the sample; processing and analysis of the sequencing and potentially other molecular data; and exploitation of the information for fermentation uses.

For example sampling may be for example from an agricultural, food, surfaces, water. The samples can include for example solid samples such as soil, sediment, rock, and food. The samples can include for example liquid samples such as surface water, and subsurface water, other liquid to be fermented or in a certain stage of fermentation, such as must, barrel fermented wine, yogurt, to name a few. The sample once obtained has the genetic material isolated or obtained from the sample, which for example can be DNA, RNA, proteins and fragments of these.

The accuracy of these analyses depends strongly on the choice of primers. Primers can be prepared by a variety of methods including, but not limited to, cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. In addition, computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. Primers that can be used analyze the 16S ribosomal RNA gene include but are not limited to those described in the Examples below Microbial diversity can be further described by approaches analyzing the intergenic region between 16S ribosomal RNA and 23S ribosomal RNA. Primers can be designed to specifically amplify any identified variable regions in a microbe or similar distinguishing genetic element.

Primers or probes described herein can also include polynucleotides having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 990, or 100% homology to any of the nucleic acid sequences described herein.

A library is prepared from the genetic material. In this stage of the process the library can be prepared by use of amplification, shotgun, whole molecule techniques among others. Additionally, amplification to add adapters for sequencing, and barcoding for sequences can be preformed. Shotgun by sonication, enzymatic cleavage may be performed. Whole molecules can also be used to sequence all DNA in a sample.

Sequencing is performed. Preferably, the sequencing is with a high-throughput system, such as for example 454, Illumina, PacBio, or IonTorrent, Nanopore, to name a few.

Sequence analysis is prepared. This analysis preferably can be performed using tools such as QIIME Analysis Pipeline, Machine learning, and UniFrac. Preferably, there is assigned a sequence to the sample via barcode, for among other things quality control of sequence data.

The analysis is utilized in a fermentation application. The applications can include for example, cheese production, alcoholic and non-alcoholic beverage production, biofuel production, and alternative energy.

Thus as explained in greater detail below, generally, the processing and analysis further involves matching the sequences to the samples, aligning the sequences to each other, and using the aligned sequences to build a phylogenetic tree, further distilling the data to form an n-dimensional plot and then a two or three dimensional plot or other graphical displays, including displays of the results of machine learning and multivariate statistical routines, and using the two or three-dimensional plot or other graphical displays to visualize patterns of the microbial communities in a particular sample over time and geographic space.

Although HMI-type presentation of this information is presently preferred, it should be understood that such plots may be communicated directly to a computational means such as a large computer or computing cluster for performing further analysis to provide predictive information. Thus, the matched sequence samples would be an example of real-time or historic microbiome information, the phylogenetic tree would be an example of derived microbiome information, and portions of the graphical displays which have derived microbial information combined with other data would be an example of predictive microbiome information.

Generally, a phylum is a group of organisms at the formal taxonomic level of Phylum based on sequence identity, physiology, and other such characteristics. There are approximately fifty bacterial phyla, which include Actinobacteria, Proteobacteria, and Firmicutes. Phylum is the classification that is a level below Kingdom, in terms of classifications of organisms. For example, for *E. coli* the taxonomy string is Kingdom: Bacteria; Phylum: Proteobacteria; Class: Gammaproteobacteria; Order: Enterobacteriales; Family: Enterobacteriaceae; Genus: *Escherichia*; and Species: *coli*.

Generally, phylogeny refers to the evolutionary relationship between a set of organisms. This relationship can be based on morphology, biochemical features, and/or nucleic acid (DNA or RNA) sequence. One can measure the changes in gene sequences and use that as a molecular clock to determine how closely or distantly the sequences, and hence the organisms that contain them, are related.

Generally, phylotype (also referred to as operational taxonomic unit ("OTU")) is analogous to "species", although phylotypes can also be defined at other taxonomic levels and these other levels are sometimes critical for identifying microbial community features relevant to a specific analysis. Because short DNA, RNA or protein sequences ("reads") can be used, these sequences may not accurately identify many organisms to the level of species, or even strain (the most detailed level of phylogenetic resolution, which is sometimes important because different strains can have different molecular functions). In cases where a "phylotype" matches a sequence or group of sequences from a known organism in the databases, it can used to say that a particular sequence is from an organism like, for example, *E. coli*.

Generally, a taxon is a group of organisms at any level of taxonomic classification. Here, taxon (plural: taxa) is a catchall term used in order to obviate the usage of the organism names repeatedly and to provide generality across taxonomic levels.

Microbial community diversity and composition may vary considerably across fermentation environments and settings, and the embodiments of the present invention link these changes to biotic or abiotic factors and other factors and conditions in the fermentation environment to create derived and predictive information. Thus these patterns of microbial communities for example geological patterns of microbial communities or patterns of microbial communities in an fermentation system (microbiosystem metrics) which are determined by the present invention can give rise to predictive information for use in the fermentation setting.

Examinations of microbial populations, e.g., a census, may provide insights into the physiologies, environmental tolerances, and ecological strategies of microbial taxa, particularly those taxa which are difficult to culture and that often dominate in natural environments. Thus, this type of derived data is utilized in combination with other data in order to form predictive information.

Microbes are diverse, ubiquitous, and abundant, yet their population patterns and the factors driving these patterns were prior to the present inventions not readily understood in fermentation settings and thus it is believed never effectively used for the purposes for ascertaining predictive information. Microorganisms, just like macroorganisms (i.e., plants and animals), exhibit no single shared population pattern. The specific population patterns shown by microorganisms are variable and depend on a number of factors, including, the degree of phylogenetic resolution at which the communities are examined (e.g., *Escherichia*), the taxonomic group in question, the specific genes and metabolic capabilities that characterize the taxon, and the taxon's interactions with members of other taxa. Thus, such population patterns can be determined in fermentation settings and utilized as derived data for the purposes of ascertaining predictive information.

However, for certain environments, common patterns may emerge if the biogeography (e.g., microbial populations for example as determined from a census), of that particular environment is specifically examined. In particular, the structure and diversity of soil bacterial communities have been found to be closely related to soil environmental characteristics such as soil pH. A comprehensive assessment of the biogeographical patterns of, for example, soil bacterial communities requires 1) surveying individual communities at a reasonable level of phylogenetic detail (depth), and 2) examining a sufficiently large number of samples to assess spatial patterns (breadth). The studies of biogeographical patterns is not limited to soil, and will be extended to other environments, including but not limited to, any part of a living organisms, bodies of water, ice, the atmosphere, energy sources, factories, laboratories, farms, processing plants, hospitals, and other locations, systems and areas.

Sample Collection

Generally, samples will be collected in a manner ensuring that microbes from the target source are the most numerous in the samples while minimizing the contamination of the sample by the storage container, sample collection device, the sample collector, other target or other non-target sources that may introduce microbes into the sample from the target source. Further, samples will be collected in a manner to ensure the target source is accurately represented by single or multiple samples at an appropriate depth (if applicable) to meet the needs of the microbiome analysis, or with known reference controls for possible sources of contamination that can be subtracted by computational analysis. Precautions should be taken to minimize sample degradation during shipping by using commercially available liquids, dry ice or other freezing methods for the duration of transit.

For example, samples can be collected in sterile, DNA/DNase/RNA/RNase-free primary containers with leak resistant caps or lids and placed in a second leak resistant vessel to limit any leakage during transport. Appropriate primary containers can include any plastic container with a tight fitting lid or cap that is suitable for work in microbiology or molecular biology considered to be sterile and free of microbial DNA (or have as little as possible) at minimum. (However, it should be noted that human DNA contamination, depending upon the markers or specific type microbe that is being looked at may not present a problem.) The primary container can also be comprised of metal, clay, earthenware, fabric, wood, etc. So long as the container may be sterilized and tested to ensure that it is ideally DNA/DNase/RNA/RNase-free (or at least contains levels of nucleic acid much lower than the biomass to be studied, and low enough concentration of nuclease that the nucleic acids collected are not degraded) and can be closed with a tight-fitting and leak resistant lid, cap or top, then it can be used as a primary container.

The primary container with the sample can then be placed into a secondary container, if appropriate. Appropriate secondary containers can include plastic screw top vessels with tight fitting lids or caps and plastic bags such as freezer-grade zip-top type bags. The secondary container can also be comprised of metal, clay, earthenware, fabric, wood, etc. So long as the container can be dosed or sealed with a tight-fitting and leak resistant lid, cap or top, then it can be used as a secondary container. The secondary container can also form a seal on itself or it can be fastened shut for leak resistance.

The samples should generally be collected with minimal contact between the target sample and the sample collector to minimize contamination. The sample collector, if human, should generally collect the target sample using gloves or other barrier methods to reduce contamination of the samples with microbes from the skin. The sample can also be collected with instruments that have been cleaned. The sample collector, if machine, should be cleaned and sterilized with UV light and/or by chemical means prior to each sample collection. If the machine sample collector requires any maintenance from a human or another machine, the machine sample collector must be additionally subjected to cleaning prior to collecting any samples.

After the sample is collected and placed in a primary and secondary container, the samples will be preserved. One method of preservation is by freezing on dry ice or liquid nitrogen to between 4° C. to −80° C. Another method of preservation is the addition of preservatives such as RNAstable™, LifeGuard™ or another commercial preservative, and following the respective instructions. So long as the preservation method will allow for the microbial nucleic acid to remain stable upon storage and upon later usage, then the method can be used.

The samples will be shipped in an expedient method to the testing facility. In another embodiment, the testing of the sample can be done on location. The sample testing should be performed within a time period before there is substantial degradation of the microbial material with in the sample. So long as the sample remains preserved and there is no substantial degradation of the microbial material, any method of transport in a reasonable period of time is sufficient.

Tracers will be added to the inflow of a sampling catchment to identify the organisms present in the system that are not from the target source. The tracer can be microorganisms or anything that will allow for analysis of the flow path. For example, in an oil setting, a tracer can be used to calibrate the effectiveness of a flooding operation (water, $CO_2$, chemical, steam, etc.). The tracer will be used to determine factors such as the amount of injection fluid flowing through each zone at the production wellbore and the path of the injection fluid flow from the injection site to the production bore.

DNA/RNA Extraction

The extraction of genetic material will be performed using methods with the ability to separate nucleic acids from other, unwanted cellular and sample matter in a way to make the genetic material suitable for library construction. For example, this can be done with methods including one or more of the following, but not limited to, mechanical disruption such as bead beating, sonicating, freezing and thawing cycles; chemical disruption by detergents, acids, bases, and enzymes; other organic or inorganic chemicals. Isolation of the genetic material can be done through methods including one or more of the following, but not limited to, binding and elution from silica matrices, washing and precipitation by organic or inorganic chemicals, electroelution or electrophoresis or other methods capable of isolating genetic material.

Extractions will be done in an environment suitable to exclude microbes residing in the air or on other surfaces in the work area where the extraction is taking place. Care will be taken to ensure that all work surfaces and instruments are cleaned to remove unwanted microbes, nucleases and genetic material. Cleaning work surfaces and instruments can include, but is not limited to, spraying and/or wiping surfaces with a chlorine bleach solution, commercially available liquids such as DNAse AWAY™ or RNase AWAY™ or similar substances that are acceptable in routine decontamination of molecular biology work areas. Furthermore, aerosol barrier pipette tips used in manual, semi-automated or automated extraction process will be used to limit transfer of genetic material between instruments and samples.

Controls for reagents for extractions and/or primary containers (when appropriate) will be tested to ensure they are free of genetic material. Testing of the reagents includes, but is not limited to performing extraction "blanks" where only the reagents are used in the extraction procedure. When necessary primary collection containers may also be tested for the presence of genetic material serving as one type of 'negative control' in PCR of the genetic material of the sample. In either case, testing the blank or negative control may be accomplished, but not limited to, spectrophotometric, fluorometric, electrophoretic, PCR or other assays capable of detecting genetic material. followed by testing the blank for the presence of genetic material by, but not limited to, spectrophotometric, fluorometric, electrophoretic, PCR or other assays capable of detecting genetic material.

Library Preparation

The methods described in more detail below allow identification of bacteria and fungi present in the fermentation sample. Different biomarkers are used for each kingdom, 16S for bacteria, ITS for fungi. In one improvement of building a library is the use of an additional single-copy marker gene allowing a more precise definition of bacterial strains in the sample.

Genetic material from the samples will be subjected to polymerase chain reaction (PCR) to amplify the gene of interest and encode each copy with barcode unique to the sample. Generally, PCR amplifies a single or a few copies of a piece of DNA across several orders of magnitude, generating thousands to millions, or more, of copies of a particular DNA sequence using a thermostable DNA polymerase. PCR will be used to amplify a portion of specific gene from the genome of the microbes present in the sample. Any method which can amplify genetic material quickly and accurately can be used for library preparation.

The PCR primer will be designed carefully to meet the goals of the sequencing method. The PCR primer will contain a length of nucleotides specific to the target gene, may contain an adapter that will allow the amplicon, also known as the PCR product, to bind and be sequenced on a high-throughput sequencing platform, and additional nucleotides to facilitate sequencing. The portion of the gene with adapters, barcode and necessary additional nucleotides is known as the "amplicon." It being understood that future systems may not use, or need, adaptors. In one embodiment, forward and reverse primers as shown in the examples are used.

The microbial ribosome is made up component proteins and non-coding RNA molecules, one of which is referred to as the 16S ribosomal RNA (or 16S rRNA). The 16S subunit is a component of the small subunit (SSU) of bacterial and archaeal ribosomes. It is 1.542 kb (or 1542 nucleotides) in length. The gene encoding the 16S subunit is referred to as the 16S rRNA gene. The 16S rRNA gene is used for reconstructing phylogenies because it is highly conserved between different species of bacteria and archaea, meaning that all of these organisms encode it in their genomes and it can be easily identified in genomic sequences, but it additionally contains regions that are highly variable, so there is a phylogenetic signature in the sequence of the gene. As a result of these same properties, batch sequencing of all of the 16S rRNA gene sequence in a sample containing many microbial taxa are informative about which microbial taxa are present. These studies are made possible by the remarkable observation that a small fragment of the 16S rRNA gene is sufficient as a proxy for the full-length sequence for many community analyses, including those based on a phylogenetic tree. However, such trees should, at most, be used as a guide to community comparisons and not for inferring true phylogenetic relationships among reads. Advances in sequencing technology, such as the availability of 400-base reads with the Titanium™ kit from Roche; the Illumina™ platforms which can produce 450 Gb per day, and in the course of a 10.8 day run produces 1.6 billion 100-base paired-end reads (HiSeq2000) or for single-day experiments can generate 1.5 Gb per day from 5 million 150-base paired-end reads (MiSeq™), or in the future, the availability of instruments providing 1500-base single-molecule reads, as reported by Pacific Biosciences™, will also improve the accuracy/productivity of existing methods for building phylogenetic trees and classifying functions of metagenomic reads.

Although metagenomics and other alternative techniques provide insight into all of the genes (and potentially gene functions) present in a given community, 16S rRNA-based studies are extremely valuable given that they can be used to discover and record unexplored biodiversity and the ecological characteristics of either whole communities or individual microbial taxa. 16S rRNA phylogenies tend to correspond well to trends in overall gene content. Therefore the ability to relate trends at the species level to host or environmental parameters has proven immensely powerful to understanding the relationships between the microbes and the world.

Alternative microbiome measurement techniques provide important information that is complementary to 16S rRNA or other marker-gene data: shotgun metagenomics provides genome content for the entire microbiome; transcriptomics measures gene expression by microbes, indicating which genes are actually being used by the microbes; proteomics measures actual production of enzymes and other functional proteins in the microbiome; metabolomics directly measures metabolite content in a sample.

Generally, analysis of ribosomal genes (SSU, LSU, ITS) will be used for the determination and characterization of microbes in industrial settings where the only requirement for choosing the particular gene for amplification is that the gene is at least somewhat conserved between different species of microbes. For instance, the amplification, sequencing and analysis of the small subunit ("SSU") of the ribosomal gene (16S rRNA gene) would be used for bacteria and archaea while analysis of the microeukarytotes such as nematodes, ciliates and amoeba would analyze the small subunit ribosomal gene (18S rRNA gene) common in these organisms. Further LSU, ITS and mitochondrial marker such as Cytb or cox1, generally may also be used and could provide enhanced performance. We have found that using 16S rRNA in combination with other single-copy marker genese provided prokaryotic species boundaries at higher resolution than 16S rRNA alone. Fungal populations may also be characterized by the intragenic transcribed spacer gene ("ITS gene") in addition to 18S rRNA gene or other single gene markers. Furthermore, the large subunit ribosomal gene ("LSU") could be analyzed alone or in combination with portions of the SSU in a single amplicon. The genetic material for any analysis could be derived from DNA or cDNA (i.e., complementary DNA) produced from the reverse transcription of RNA isolated from the target sample or samples.

Complete marker genes generally cannot, because of their length, be sequenced using high-throughput methods. However, the use of PacBio, Nanopores, or Moleculo can provide the ability to obtain such a complete sequence. Therefore, a shorter region of the marker gene sequence must be selected to act as proxy. Currently, there is no consensus on a single best region, and consequently different groups are sequencing different or multiple regions. This diversity of methods hinders direct comparisons among studies. Standardization on a single region would be helpful on this front. Of the nine variable regions in the 16S rRNA gene, several of the more popular regions include the regions surrounding V2, V4, and V6. Generally, a combination of variable and moderately conserved regions appears to be optimal for performing analyses at different phylogenetic depths. Both the choice of region and the design of the primers are crucial, and poor design of primers can lead to radically different experimental conclusions. Additionally, primer bias due to differential annealing leads to the over- or underrepresentation of specific taxa can lead to some groups being missed entirely if they match the consensus sequence poorly. Issues of primer bias can be important. Comparisons of relative abundance among different studies should thus be treated with caution. However, meta-analysis of presence/absence data from different studies is particularly useful for revealing broad trends, even when different studies use different primers.

As more sequence data and better taxonomic assignments become available, improved primer sets, with better coverage (including primers for archaea and eukaryotes), will likely provide a substantial advantage over present degenerate primer techniques. Specifically, 16S rRNA and 18s rRNA reads from metagenomic studies provide a source of sequences that is not subject to PCR primer bias (although other biases are present) and therefore covers taxa that are missed by existing but popular primer sets, although in practice exploiting this information has been quite challenging. Another promising approach is the use of miniprimers, which, together with an engineered DNA polymerase, may allow greater coverage of desired groups.

Furthermore, improvements in the ability to produce high quantities of primers (e.g. millions of individual primers) will enable amplification of high quantities of regions (e.g. millions of individual regions), which may be distinct to each microbe or targeted at multiple sites obtained from existing databases or from shotgun sequencing. Such an application could be used to improve discrimination and/or prediction for a particular environment and target parameter.

The primers designed for amplification will be well-suited for the phylogenetic analysis of sequencing reads. Thus, the primer design will be based on the system of sequencing, e.g., chain termination (Sanger) sequencing or high-throughput sequencing. Within the system, there are also many options on the method. For example, for high-throughput sequencing, the sequencing can be performed by, but is not limited to, 454 Life Sciences™ Genome Sequencer FLX (Roche) machine or the Illumina™ platforms (MiSeqm or HiSeqm), IonTorrent, Nanopores or PacBio. These will be described more in the Sequencing section below.

Barcoding

High-throughput sequencing, described below, has revolutionized many sequencing efforts, including studies of microbial community diversity. High-throughput sequencing is advantageous because it eliminates the labor-intensive step of producing clone libraries and generates hundreds of thousands of sequences in a single run. However, two primary factors limit culture-independent marker gene-based analysis of microbial community diversity through high-throughput sequencing: 1) each individual run is high in cost, and 2) separating a single plate across multiple runs is difficult.

A solution to these limitations is barcoding. Double index barcoding protocol is used in the examples below. For barcoding, a unique tag will be added to each primer before PCR amplification. Because each sample will be amplified with a known tagged (barcoded) primer, an equimolar mixture of PCR-amplified DNA can be sequenced from each sample and sequences can be assigned to samples based on these unique barcodes. The presence of these assigned barcodes allow for independent samples to be combined for sequencing, with subsequent bioinformatic separation of the sequencer output. By not relying on physical separators, this procedure maximizes sequence space and multiplexing capabilities. This technique will be used to process many samples (eg 25, 200, 1000, and above) as many as 25 samples in a single high-throughput sequencing run. This number will be increased depending on advances in high-throughput sequencing technology, without limit to the number of samples to be sequenced in a single high-throughput sequencing run.

Barcodes, or unique DNA sequence identifiers, have traditionally been used in different experimental contexts, such as sequence-tagged mutagenesis (STM) screens where a sequence barcode acts as an identifier or type specifier in a heterogeneous cell-pool or organism-pool. However, STM barcodes are usually 20-60 bases (or nt) long, are pre-selected or follow ambiguity codes, and exist as one unit or split into pairs. Such long barcodes are not particularly compatible with available high-throughput sequencing platforms because of restrictions on read length.

Although very short (2- or 4-nt) barcodes can be used with high-throughput sequencing platforms, a more definitive assignment of samples and/or for enhanced multiplexing capabilities can be accomplished by lengthening the barcodes or variations in the fixed forward and reverse linkers used to generate the initial cDNA libraries. Shorter barcodes also have a steeper trade-off between number of possible barcodes and the minimum number of nucleotide variations between individual barcodes.

Existing barcoding methods have limits both in the number of unique barcodes used and in their ability to detect sequencing errors that change sample assignments (this robustness is especially important for sample assignment because the 5' end of the read (sequence for one strand of nucleic acid in a sample) is somewhat more error-prone). Barcodes based on error-correcting codes, which are widely used in devices in other technologies like telecommunications and electronics, will be applied for high-throughput sequencing barcoding purposes. A class of error-correcting codes called Hamming codes, which use a minimum amount of redundancy and will be simple to implement using standard linear algebra techniques. Hamming codes, like all error-correcting codes, employ the principle of redundancy and add redundant parity bits to transmit data over a noisy medium. Sample identifiers will be encoded with redundant parity bits. Then the sample identifiers will be "transmitted" as codewords. Each base (A, T, G, C) will be encoded using 2 bits and using 8 bases for each codeword. Therefore, 16-bit codewords will be transmitted. The codeword and bases is not limited to these numbers, as any number of bits and codewords can be designed by a person of ordinary skill in the art. The design of the barcode is based on the goals of the method. Hamming codes are unique in that they use only a subset of the possible codewords, particularly those that lie at the center of multidimensional spheres (hyperspheres) in a binary subspace. Single bit errors fall within hyperspheres associated with each codeword, and thus they can be corrected. Double bit errors do not fall within hyperspheres associated with each codeword, and thus they can be detected but not corrected.

Another encoding schemes, such as Golay codes, will also be used for barcoding. Golay codes of 12 bases can correct all triple-bit errors and detect all quadruple-bit errors. The extended binary Golay code encodes 12 bits of data in a 24-bit word in such a way that any 3-bit errors can be corrected or any 7-bit errors can be detected. The perfect binary Golay code, has codewords of length 23 and is obtained from the extended binary Golay code by deleting one coordinate position (conversely, the extended binary Golay code is obtained from the perfect binary Golay code by adding a parity bit). In standard code notation the codes have parameters corresponding to the length of the codewords, the dimension of the code, and the minimum Hamming distance between two codewords, respectively.

In general, design for barcoded primers for high-throughput sequencing is as follows. The primer will be designed to include nucleotides specific for the sequencing platform; nucleotides specific for the gene of interest; nucleotides for the barcode chosen; and the nucleotides of the gene. Upon amplification, one contiguous string of nucleotides known as the "forward" primer will be formed from the platform specific sequencing adaptors and the gene specific primer and linker. Additionally formed upon amplification will be one contiguous string of nucleotides known as the "reverse" primer formed from the platform specific sequencing adaptors, the gene specific primer and linker, and the barcode. In general PCR using barcoded primers is known in the art. Other error-correcting codes may be utilized such as Gray codes, low-density parity check codes, etc.

The barcoded high-throughput sequencing technique provides a robust description of the changes in bacterial community structure across the sample set. A high-throughput sequencing run is expensive, and the large number of custom primers required only adds to this cost. However, the barcoding technique allows for thousands of samples to be analyzed simultaneously, with each community analyzed in considerable detail. Although the phylogenetic structure and composition of the surveyed communities can be determined with a high degree of accuracy, the barcoded high-throughput sequencing method may not allow for the identification of bacterial taxa at the finest levels of taxonomic resolution. However, with increasing read lengths in sequencing, this constraint will gradually become less relevant.

Sequencing

The vast majority of life on earth is microbial, and the vast majority of these microbial species has not been, and is not capable of being easily cultured in the laboratory. Consequently, our primary source of information about most microbial species consists of fragments of their DNA sequences. Sequencing a DNA library will be done on a platform capable of producing many sequences for each sample contained in the library. High-throughput sequencing technologies have allowed for new horizons in microbial community analysis by providing a cost-effective method of identifying the microbial OTUs that are present in samples. These studies have drastically changed our understanding of the microbial communities in the human body and on the planet. This development in sequencing technology, combined with more advanced computational tools that employ metadata to relate hundreds of samples to one another in ways that reveal clear biological patterns, has reinvigorated studies of the 16S rRNA and other marker genes. Studies of 16S rRNA genes provide a view of which microbial taxa are present in a given sample because these genes provide an excellent phylogenetic marker. Although alternative techniques, such as metagenomics, provide insight into all of the genes (and potentially gene functions) present in a given community, 16S rRNA-based surveys are extraordinarily valuable given that they can be used to document unexplored biodiversity and the ecological characteristics of either whole communities or individual microbial taxa. Perhaps because 16S rRNA phylogenies tend to correspond well to trends in overall gene content, the ability to relate trends at the species level to host or environmental parameters has proven immensely powerful. The DNA encoding the 16S rRNA gene has been widely used to specify bacterial taxa, since the region can be amplified using PCR primers that bind to conserved sites in most or all species, and large databases are available relating 16S rRNA sequences to bacterial phylogenies. However, as previously discussed, other genes can be used to specify the taxa, such as 18S, LSU, ITS, and SSU (e.g., 16S). For the purposes of bacteria, cpn60 or ftsZ, or other markers, may also be utilized.

New technologies have led to extraordinary decreases in sequencing costs. This rapid increase in sequencing capacity has led to a process in which newer sequencing platforms generate datasets of unprecedented scale that break existing software tools: new software is then developed that exploits these massive datasets to produce new biological insight, but in turn the availability of these software tools prompts new experiments that could not previously have been considered, which lead to the production of the next generation of datasets, starting the process again.

High-Throughput Sequencing

With the advent of high-throughput sequencing, characterization of the nucleic acid world is proceeding at an accelerated pace. Three major high-throughput sequencing platforms are in use today: 1) the Genome Sequencers from Roche/454 Life Sciences™ [GS-20 or GS-FLX]; 2) the 1G Analyzer from Illumina™/Solexa™ which includes the MiSeq™ and the HiSeg™; and 3) the SOLiD™ System from Applied Biosystems™. Comparison across the three platforms reveals a trade-off between average sequence read length and the number of DNA molecules that are sequenced. The Illumina™/Solexa™ and SOLiD systems provide many more sequence reads, but render much shorter read lengths than the 454™/Roche Genome Sequencers. This makes the 454™/Roche platform appealing for use with barcoding technology, as the enhanced read length facilitates the unambiguous identification of both complex barcodes and sequences of interest. However, even reads of less than 100 bases can be used to classify the particular microbe in phylogenetic analysis. Any platform, for example, Illumina™, providing many reads and read lengths of a predetermined necessary length, for example, 150 base pairs or 100 base pairs, is acceptable for this method.

Because the accuracy of phylogenetic reconstruction depends sensitively on the number of informative sites, and tends to be much worse below a few hundred base pairs, the short sequence reads produced from high-throughput sequencing, which are 100 base pairs on average for the GS 20 (Genome Sequencer 20 DNA Sequencing System, 454 Life Sciences™), may be unsuitable for performing phylogenetically based community analysis. However, this limitation can be at least partially overcome by using a reference tree based on full-length sequences, such as the tree from the Greengenes 16S rRNA ARB Database, and then using an algorithm such as parsimony insertion to add the short sequence reads to this reference tree. These procedures are necessarily approximate, and may lead to errors in phylogenetic reconstruction that could affect later conclusions about which communities are more similar or different. One substantial concern is that because different regions of the rRNA sequence differ in variability, conclusions drawn about the similarities between communities from different studies might be affected more by the region of the 16S rRNA that was chosen for sequencing than by the underlying biological reality.

The increase in number of sequences per run from parallel high-throughput sequencing technologies such as the Roche 454 GS FLX™ to Illumina GAIIx™ is on the order of 1,000-fold and greater than the increase in the number of sequences per run from Sanger to 454™. The transition from Sanger sequencing to 454™ sequencing has opened new frontiers in microbial community analysis by making it possible to collect hundreds of thousands of sequences spanning hundreds of samples. A transition to the Illumina™ platform allows for more extensive sequencing than has previously been feasible, with the possibility of detecting even OTUs that are very rare. By using a variant of the barcoding strategy used for 454™ with the Illumina™ platform, thousands of samples could be analyzed in a single run, with each of the samples analyzed in unprecedented depth.

A few sequencing runs using 454™/Roche's pyrosequencing platform can generate sufficient coverage for assembling entire microbial genomes, for the discovery, identification and quantitation of small RNAs, and for the detection of rare variations in cancers, among many other applications. However, as the analytical technology becomes more advanced, the coverage provided by this system becomes unnecessary for phylogenetic classification. For analysis of multiple libraries, the 454/Roche™ pyrosequencers can accommodate a maximum of only 16 independent samples, which have to be physically separated using manifolds on the sequencing medium, drastically limiting is utility in the effort to elucidate the diverse microbial communities in each sample. Relatively speaking, the Illumina™ platforms are experiencing the most growth. However, with the constant improvements in sequencing systems, the different platforms that will be used will change over time. Generally, the method describe herein will be used with any available high-throughput sequencing platform currently available or will be available in the future. For example, the method described herein will be applied to a sequencing method wherein the genetic material will be sequenced without barcoding by simply placing the DNA or RNA directly into a sequencing machine.

In general, high-throughput sequencing technology allows for the characterization of microbial communities orders of magnitude faster and more cheaply than has previously been possible. In addition, the ability to barcode amplicons from individual samples means that hundreds of samples can be sequenced in parallel, further reducing costs and increasing the number of samples that can be analyzed. Though high-throughput sequencing reads tend to be short compared to those produced by the Sanger method, the sequencing effort is best focused on gathering more short sequences (less than 150 base pairs or less than 100 base pairs) rather than fewer longer ones as much of the diversity of microbial communities lies within the "rare biosphere," also known as the "long tail," that traditional culturing and sequencing technologies are slow to detect due to the limited amount of data generated from these techniques.

The length of the read of a sequence describes the number of nucleotides in a row that the sequencer is able to obtain in one read. This length can determine the type of OTU obtained (e.g., family, genus or species). For example, a read length of approximately 300 base pairs will probably provide family information but not a species determination. Depth of coverage in DNA sequencing refers to the number of times a nucleotide is read during the sequencing process. On a genome basis, it means that, on average, each base has been sequenced a certain number of times (10×, 20×, ... ). For a specific nucleotide, it represents the number of sequences that added information about that nucleotide. Coverage is the average number of reads representing a given nucleotide in the reconstructed sequence. Depth can be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy. This parameter also enables estimation of other quantities, such as the percentage of the genome covered by reads (coverage). Sometimes a distinction is made between sequence coverage and physical coverage. Sequence coverage is the average number of times a base is read. Physical coverage is the average number of times a base is read or spanned by mate paired reads.

Organisms of lower abundance rank can be detected if more sequence reads are collected. To verify that these sequences are present, a higher read depth (i.e. more sequences) must be obtained. Analyzing the rare biosphere is attainable because sequencing depth provided by high-throughput sequencing allows for the detection of microbes that would otherwise be detected only occasionally by chance with traditional techniques. Thus high-throughput sequencing will allow for the analysis of the more rare members (low abundance organisms) of any environment which may play critical role in a fermentation process important in food production, agriculture and other industries where microbes are present within a time-frame feasible for industrial settings.

Pyrosequencing

One type of high-throughput sequencing is known as pyrosequencing. Pyrosequencing, based on the "sequencing by synthesis" principle, is a method of DNA sequencing widely used in microbial sequencing studies. Pyrosequencing involves taking a single strand of the DNA to be sequenced and then synthesizing its complementary strand enzymatically. The pyrosequencing method is based on observing the activity of DNA polymerase, which is a DNA synthesizing enzyme, with another chemiluminescent enzyme. The single stranded DNA template is hybridized to a sequencing primer and incubated with the enzymes DNA polymerase, ATP sulfurylase, luciferase and apyrase, and with the substrates adenosine 5' phosphosulfate (APS) and luciferin. Synthesis of the complementary strand along the template DNA allows for sequencing of a single strand of DNA, one base pair at a time, by the detection of which base was actually added at each step.

The template DNA is immobile, and solutions of A, C, G, and T nucleotides are sequentially added and removed from the reaction. The templates for pyrosequencing can be made both by solid phase template preparation (streptavidin-coated magnetic beads) and enzymatic template preparation (apyrase+exonuclease). Specifically, the addition of one of the four deoxynucleoside triphosphates (dNTPs) (dATPalphaS, which is not a substrate for a luciferase, is added instead of dATP) initiates the next step. DNA polymerase incorporates the correct, complementary dNTPs onto the template. This base incorporation releases pyrophosphate (PPi) stoichiometrically. Then, ATP sulfurylase quantitatively converts PPi to ATP in the presence of adenosine 5' phosphosulfate. This ATP acts to catalyze the luciferase-mediated conversion of luciferin to oxyluciferin that generates visible light in amounts that are proportional to the amount of ATP. Light is produced only when the nucleotide solution complements the particular unpaired base of the template. The light output in the luciferase-catalyzed reaction is detected by a camera and analyzed in a program. The sequence of solutions which produce chemiluminescent signals allows the sequence determination of the template. Unincorporated nucleotides and ATP are degraded by the apyrase, and the reaction can restart with another nucleotide.

Illumina's™ sequencing by synthesis (SBS) technology with TruSeq technology supports massively parallel sequencing using a proprietary reversible terminator-based method that enables detection of single bases as they are incorporated into growing DNA strands.

A fluorescently labeled terminator is imaged as each dNTP is added and then cleaved to allow incorporation of the next base. Since all four reversible terminator-bound dNTPs are present during each sequencing cycle, natural competition minimizes incorporation bias. The end result is true base-by-base. Although this is similar to pyrosequencing, the differences between the platforms are noteworthy. The method described herein can be applied to any high-throughput sequencing technology, past, present or future. Pyrosequencing and SBS are merely examples and do not limit the application of the method in terms of sequencing.

Analysis of Sequencing Data

Generally, as the expense of sequencing decreases, the methods for comparing different communities based on the sequences they contain become increasingly important, and are often the bottleneck in obtaining insight from the data. Sequence data can be analyzed in a manner in which sequences are identified and labeled as being from a specific sample using the unique barcode introduced during library preparation, if barcodes are used, or sample identifiers will be associated with each run directly if barcodes are not used. Once sequences have been identified as belonging to a specific sample, the relationship between each pair of samples will be determined based on the distance between the collection of microbes present in each sample. In particular, techniques that allow for the comparison of many microbial samples in terms of the phylogeny of the microbes that live in them ("phylogenetic techniques") are often necessary. Such methods are particularly valuable as the gradients that affect microbial distribution are analyzed, and where there is a need to characterize many communities in an efficient and cost-effective fashion. Gradients of interest include different physical or chemical gradients in natural environments, such as temperature or nutrient gradients in certain industrial settings.

When comparing microbial communities, researchers often begin by determining whether groups of similar community types are significantly different. However, to gain a broad understanding of how and why communities differ, it is essential to move beyond pairwise significance tests. For example, determining whether differences between communities stem primarily from particular lineages of the phylogenetic tree, or whether there are environmental factors (such as temperature, salinity, or acidity) that group multiple communities together is pivotal to an analysis. The analysis systems described herein are merely examples and are not limiting. Any methods which will distill massive data sets from raw sequences to human-interpretable formats, for example, 2-D or 3-D ordination plots, supervised learning for predictive modeling, or more traditional statistical significance testing, allowing for pattern elucidation and recognition, will be used.

QIIME

After DNA sequence data is obtained the bioinformatics stages begin. This includes barcode decoding, sequence quality control, "upstream" analysis steps (including clustering of closely related sequences and phylogenetic tree construction), and "downstream" diversity analyses, visualization, and statistics. All of these steps are currently facilitated by the Quantitative Insights Into Microbial Ecology (QIIME) open source software package, which is the most widely used software for the analysis of microbial community data generated on high-throughput sequencing platforms. QIIME was initially designed to support the analysis of marker gene sequence data, but is also generally applicable to "comparative-omics" data (including but not limited to metabolomics, metatranscriptomics, and comparative human genomics).

QIIME is designed to take users from raw sequencing data (for example, as generated on the Illumina™ and 454™ platforms) though the processing steps mentioned above, leading to quality statistics and visualizations used for interpretation of the data. Because QIIME scales to billions of sequences and runs on systems ranging from laptops to high-performance computer clusters, it will continue to keep pace with advances in sequencing technologies to facilitate characterization of microbial community patterns ranging from normal variations to pathological disturbances in many human, animal and environmental ecosystems.

For microbiome data analysis, the following steps will be taken. Unless otherwise noted, the steps will be performed with QIIME. However, other such systems may be used and the scope of protection afforded to the present inventions is not in anyway limited to, or dependent upon, the use of QIIME.

Compiling the Sample Metadata Mapping File

The first step in the bioinformatics stage of a microbial community analysis study is to consolidate the sample metadata in a spreadsheet. The sample metadata is all per-sample information, including technical information such as the barcode assigned to each sample, and "environmental" metadata. This environmental metadata will differ depending on the types of samples that are being analyzed. If, for example, the study is of microbial communities in soils, the pH and latitude where the soil was collected will be environment metadata categories. Alternatively, if the samples are of the wine microbiome, environmental metadata may include barrel and/or bottling identifiers and collection times. This spreadsheet will be referred to as the sample metadata mapping file in the following sections.

Barcode Decoding and Quality Control

Next, in a combined analysis step, sequence barcodes will be read to identify the source sample of each sequence, poor quality regions of sequence reads will be trimmed, and poor quality reads will be discarded. These steps will be combined for computational efficiency. The features included in quality filtering include whether the barcode will unambiguously be mapped to a sample barcode, per-base quality scores, and the number of ambiguous (N) base calls. The default settings for all quality control parameters in QIIME will be determined by benchmarking combinations of these parameters on artificial (i.e., "mock") community data, where microbial communities were created in the lab from known concentrations of cultured microbes, and the composition of the communities is thus known in advance.

Sequence Clustering or "OTU Picking"

After mapping sequence reads to samples and performing quality control, sequences will be clustered into OTUs (Operational Taxonomic Units). This is typically the most computationally expensive step in microbiome data analysis, and will be performed to reduce the computational complexity at subsequent steps. The assumption made at this stage is that organisms that are closely related, as determined by the similarity of their marker gene sequences, are functionally similar. Highly similar sequences (e.g., those that are greater than 97% identical to one another) will be clustered, the count of sequences that are contained in each cluster will be retained, and then a single representative sequence from that cluster for use in downstream analysis steps such as taxonomic assignment and phylogenetic tree construction will be chosen. This process of clustering sequences is referred to as OTU picking, where the OTUs (i.e., the clusters of sequences) are considered to represent taxonomic units such as species. SILVA, a comprehensive on-line resource for quality checked and aligned ribosomal RNA sequence data, provides regularly updated datasets of aligned small (16S/18S, SSU) and large subunit (23S/28S, LSU) ribosomal RNA (rRNA) sequences for all three domains of life (Bacteria, Archaea and Eukarya).

There are three high-level strategies for OTU picking, each of which is implemented in QIIME. In a de novo OTU picking process, reads will be clustered against one another without any external reference sequence collection. pick_de_novo_otus.py is the primary interface for de novo OTU picking in QIIME, and includes taxonomy assignment, sequence alignment, and tree-building steps. A benefit of de novo OTU picking is that all reads are clustered. A drawback is that there is no existing support for running this in parallel, so it can be too slow to apply to large datasets (e.g., more than 10 million reads). De novo OTU picking must be used if there is no reference sequence collection to cluster against, for example because an infrequently used marker gene is being used. De novo OTU picking cannot be used if the comparison is between non-overlapping amplicons, such as the V2 and the V4 regions of the 16S rRNA gene or for very large data sets, like a full HiSeq™ 2000 run. Although technically, de novo OTU picking can be used for very large data sets, the program would take too long to run to be practical.

In a closed-reference OTU picking process, reads will be clustered against a reference sequence collection and any reads that do not hit a sequence in the reference sequence collection are excluded from downstream analyses. pick_closed_reference_otus.py is the primary interface for dosed-reference OTU picking in QIIME. If the user provides taxonomic assignments for sequences in the reference database, those are assigned to OTUs. Closed-reference OTU picking must be used if non-overlapping amplicons, such as the V2 and the V4 regions of the 16S rRNA, will be compared to each other. The reference sequences must span both of the regions being sequenced. Closed-reference OTU picking cannot be used if there is no reference sequence collection to cluster against, for example because an infrequently used marker gene is being used. A benefit of closed-reference OTU picking is speed in that the picking is fully parallelizable, and therefore useful for extremely large data sets. Another benefit is that because all OTUs are already defined in the reference sequence collection, a trusted tree and taxonomy for those OTUs may already exist. There is the option of using those, or building a tree and taxonomy from the sequence data. A drawback to reference-based OTU picking is that there is an inability to detect novel diversity with respect to the reference sequence collection. Because reads that do not hit the reference sequence collection are discarded, the analyses only focus on the diversity that is already known. Also, depending on how well-characterized the environment is, a small fraction of the reads (e.g., discarding 1-10% of the reads is common for 16S-based human microbiome studies, where databases like Greengenes cover most of the organisms that are typically present) or a large fraction of your reads (e.g., discarding 50-80% of the reads has been observed for "unusual" environments like the Guerrero Negro microbial mats) may be discarded.

In an open-reference OTU picking process, reads will be clustered against a reference sequence collection and any reads which do not hit the reference sequence collection are subsequently clustered de novo. pick_open_reference_otus.py is the primary interface for open-reference OTU picking in QIIME, and includes taxonomy assignment, sequence alignment, and tree-building steps. Open-reference OTU picking with pick_open_reference_otus.py is the preferred strategy for OTU picking. Open-reference OTU picking cannot be used for comparing non-overlapping amplicons, such as the V2 and the V4 regions of the 16S rRNA, or when there is no reference sequence collection to cluster against, for example because an infrequently used marker gene is being used. A benefit of open-reference OTU picking is that all reads are clustered. Another benefit is speed. Open-reference OTU picking is partially run in parallel. In particular, the subsampled open reference OTU picking process implemented in pick_open_reference_otus.py is much faster than pick_de_novo_otus.py as some strategies are applied to run several pieces of the workflow in parallel. However, a drawback of open-reference OTU picking is also speed. Some steps of this workflow run serially. For data sets with a lot of novel diversity with respect to the reference sequence collection, this can still take days to run.

Generally, uclust is the preferred method for performing OTU picking. QIIME's uclust-based open reference OTU picking protocol will be used when circumstances allow (i.e., when none of the cases above, where open reference OTU picking is not possible, apply).

The OTU-picking protocol described above is used for processing taxonomic marker gene sequences such as those from the 16S rRNA, ITS and LSU genes as well as other marker genes. In that case, the sequences themselves are not used to identify biological functions performed by members of the microbial community; they are instead used to identify which kinds of organisms are present. In the case of shotgun metagenomic sequencing, the data obtained are random fragments of all genomic DNA present in a given microbiome. These can be compared to reference genomes to identify the types of organisms present in a manner similar to marker gene sequences, but they may also be used to infer biological functions encoded by the genomes of microbes in the community. Typically this is done by comparing them to reference genomes and/or individual genes or genetic fragments that have been annotated for functional content. In the case of shotgun metatranscriptomic sequencing, the data obtained are similar to that for shotgun metatranscroptomic sequencing except that the RNA rather than the DNA is used, and physical or chemical steps to deplete particular classes of sequence such as eukaryotic messenger RNA or ribosomal RNA are often used prior to library construction for sequencing. In the case of shotgun metaproteomics, protein fragments are obtained and matched to reference databases. In the case of shotgun metabolomics, metabolites are obtained by biophysical methods including nuclear magnetic resonance or mass spectrometry. In all of these cases, some type of coarse-graining of the original data equivalent to OTU picking to identify biologically relevant features is employed, and a biological observation matrix as described in relating either the raw or coarse-grained observations to samples is obtained. The steps downstream from the Biological Observation Matrix, including the construction of distance matrices, taxon or functional tables, and industry-specific, actionable models from such data, are conceptually equivalent for each of these datatypes and are within the scope of the present Invention.

Choosing OTU Representative Sequences, Assigning Taxonomy, Aligning Sequences, and Constructing Phylogenetic Trees Next, the centroid sequence in each OTU will be selected as the representative sequence for that OTU. The centroid sequence will be chosen so that all sequences are within the similarity threshold to their representative sequence, and the centroid sequences are specifically chosen to be the most abundant sequence in each OTU.

The OTU representative sequences will next be aligned using an alignment algorithm such as the PyNAST software package. PyNAST is a reference-based alignment approach, and is chosen because it achieves similar quality alignments to non-reference-based alignment approaches (e.g., muscle), where quality is defined as the effect of the alignment algorithm choice on the results of phylogenetic diversity analyses, but is easily run in parallel, which is not the case for non-reference-based alignment algorithms.

Once a PyNAST alignment is obtained, positions that mostly contain gaps, or too high or too low variability, will be stripped to create a position-filtered alignment. This position-filtered alignment will be used to construct a phylogenetic tree using FastTree. This tree relates the OTUs to one another, will be used in phylogenetic diversity calculations (discussed below), and is referred to below as the OTU phylogenetic tree.

In addition to being aligned, all OTU representative sequences will have taxonomy assigned to them. This can be performed using a variety of techniques, though our currently preferred approach is the uclust-based consensus taxonomy assigner implemented in QIIME. Here, all representative sequences (the "query" sequences) are queried against a reference database (e.g., Greengenes, which contains near-full length 16S rRNA gene sequences with human-curated taxonomic assignments; UNITE database for ITS; SILVA for 18S rRNA) with uclust. The taxonomy assignments of the three best database hits for each query sequences are then compared, and a consensus of those assignments is assigned to the query sequence.

Constructing a Biological Observation Matrix (BIOM) Table

The last of the "upstream" processing steps is to create a Biological Observation Matrix (BIOM) table, which contains counts of OTUs on a per-sample basis and the taxonomic assignment for each OTU. This table, which will be referred to as the BIOM table, the OTU phylogenetic tree constructed above, and the sample metadata mapping file will be the data required for computing phylogenetic diversity metrics in the next steps, and for doing visual and statistical analysis based on these diversity metrics. Although the BIOM is a specific file format for the table with OTU counts on a per-table basis, other file formats, e.g. xls, txt, or csv are also possible.

Analysis of Microbial Communities

Once a BIOM table, an OTU phylogenetic tree, and a sample metadata mapping file (n-dimensional plot) are compiled, the microbial communities present in each sample will be analyzed and compared. These analyses include, but are not limited to, summarizing the taxonomic composition of the samples, understanding the "richness" and "evenness" of samples (defined below), understanding the relative similarity of communities, and identifying organisms or groups of organisms that are significantly different across community types. The different types of analysis on soil microbial community data will be illustrated in the Examples below.

Taxonomic Composition of Samples

The taxonomic composition of samples is often something that researchers are most immediately interested in. This can be studied at various taxonomic levels (e.g., phylum, class, species) by collapsing OTUs in the BIOM table based on their taxonomic assignments. The abundance of each taxon on a per-sample basis is then typically presented in bar charts, area charts or pie charts, though this list is not comprehensive.

Within-Sample Diversity (Richness and Evenness):

Alpha diversity refers to diversity of single samples (i.e., within-sample diversity), including features such as taxonomic richness and evenness. The species richness is a measure of the number of different species of microbes in a given sample. Species evenness refers to how close in numbers the abundance of each species in an environment is.

Measures of alpha diversity (or, within-sample diversity) have a long history in ecology. Alpha diversity scores have been shown to differ in different types of communities, for example, from different human body habitats. For instance, skin-surface bacterial communities have been found to be significantly more rich (i.e., containing more species) in females than in males, and at dry sites rather than sebaceous sites, and the gut microbiome of lean individuals have been found to be significantly more rich than those of obese individuals. One way of viewing alpha diversity in the context of environmental metadata, for example, the degree of phylogenetic diversity in a sample (a phylogeny-aware measure of richness) changes with soil pH, ranging from pH around 6.5 through 9.5, with a peak in richness around neutral pH of 7. In some cases alpha diversity will be useful input features for building predictive models via supervised classifiers.

Between-Sample Diversity (UniFrac and Principal Coordinates Analysis)

Generally the primary question of interest when beginning a survey of new microbial community types is what environmental features are associated with differences in the composition of microbial communities? This is a question of between-sample (or "beta") diversity. Beta diversity metrics provide a measure of community dissimilarity, allowing investigators to determine the relative similarity of microbial communities. Metrics of beta diversity are pairwise, operating on two samples at a time.

The difference in overall community composition between each pair of samples can be determined using the phylogenetically-aware UniFrac distance metric, which allows researchers to address many of these broader questions about the composition of microbial communities. UniFrac calculates the fraction of branch length unique to a sample across a phylogenetic tree constructed from each pair of samples. In other words, the UniFrac metric measures the distance between communities as the percentage of branch length that leads to descendants from only one of a pair of samples represented in a single phylogenetic tree, or the fraction of evolution that is unique to one of the microbial communities. Phylogenetic techniques for comparing microbial communities, such as UniFrac, avoid some of the pitfalls associated with comparing communities at only a single level of taxonomic resolution and provide a more robust index of community distances than traditional taxon-based methods, such as the Jaccard and Sorenson indices. Unlike phylogenetic techniques, species-based methods that measure the distance between communities based solely on the number of shared taxa do not consider the amount of evolutionary divergence between taxa, which can vary widely in diverse microbial populations. Among the first applications of phylogenetic information to comparisons of microbial communities were the Phylogenetic (P)-test and the Fst test. Pairwise significance tests are limited because they cannot be used to relate many samples simultaneously. Although phylogenetically-aware techniques such as UniFrac offer significant benefits, techniques lacking phylogenetic awareness can also be implemented with success: after an alternative distance metric (e.g. Bray-Curtis, Jensen-Shannon divergence) has been applied, the resulting inter-sample distance matrix is processed in the same way as a UniFrac distance matrix as described below.

QIIME implements the UniFrac metric and uses multivariate statistical techniques to determine whether groups of microbial communities are significantly different. When studying a set of n microbial communities, the UniFrac distances between all pairs of communities are computed to derive a distance matrix (using UniFrac or other distances) for all samples. This will be an n×n matrix, which is symmetric (because the distance between sample A and sample B is always equal to the distance between sample B and sample A) and will have zeros on the diagonal (because the distance between any sample and itself is always zero). For any reasonably larger value of n (e.g., n>5) it becomes difficult to interpret patterns of beta diversity from a distance matrix directly.

Ordination techniques, such as principal coordinates analysis (PCoA) and non-metric multidimensional scaling (NMDS), together with approximations to these techniques that reduce computational cost or improve parallelism, will be used to summarize these patterns in two or three dimensional scatter plots. The patterns can also be represented in two dimensions using, for example, line graph, bar graphs, pie charts, Venn diagrams, etc. This is a non-exhaustive list. The patterns can also be represented in three dimensions using, for example, wire frame, ball and stick models, 3-D monitors, etc. This list is also non-exhaustive and does not limit the 2-D or 3-D forms by which the data can be represented.

PCoA is a multivariate statistical technique for finding the most important orthogonal axes along which samples vary. Distances are converted into points in a space with a number of dimensions one less than the number of samples. The principal components, in descending order, describe how much of the variation (technically, the inertia) each of the axes in this new space explains. The first principal component separates the data as much as possible; the second principal component provides the next most separation along an orthogonal axis, and so forth. QIIME returns information on all principal component axes in a data table. It also allows easy visualization of that data in interactive scatter plots that allow users to choose which principal components to display. The points (each representing a single sample) are typically marked with colored symbols, and users can interactively change the colors of the points to detect associations between sample microbial composition and sample metadata. PCoA often reveals patterns of similarity that are difficult to see in a distance matrix, and the axes along which variation occurs can sometimes be correlated with environmental variables such as pH or temperature. Industrial variables, or control data, can include presence of oil, pressure, viscosity, etc. These control data can be filtered or removed in order to observe other control data factors to visualize possible patterns.

New ways of exploring and visualizing results and identifying meaningful patterns are increasingly important as the size and complexity of microbial datasets rapidly increase. QIIME 1.8.0 (released in December 2013) introduces several powerful tools to assist in visualizations of the results of PCoA, primarily the Emperor 3D scatter plot viewer. This includes (i) the ability to color large collections of samples using different user-defined subcategories (for example, coloring environmental samples according to temperature or pH), (ii) automatic scaled/unscaled views, which accentuate dimensions that explain more variance, (iii) the ability to interactively explore tens of thousands of points (and user-configurable labels) in 3D, and (iv) parallel coordinates displays that allow the dimensions that separate particular groups of environments to be readily identified.

The significance of patterns identified in PCoA can be tested with a variety of methods. The significance of the clusters identified by UniFrac can be established using Monte Carlo based t-tests, where samples are grouped into categories based on their metadata, and distributions of distances within and between categories are compared. For example, if microbial communities are being compared between soils from a vineyard and soils unassociated with a vineyard, the distribution of UniFrac distances between soils from the same group can be compared to those between soils from different groups by computing a t-score (the actual t-score). The sample labels (vineyard, non-vineyard) can then be randomly shuffled 10,000 times, and a t-score calculated for each of these randomized data sets (the randomized t-scores). If the vineyard soils and non-vineyard soils are significantly different from one another in composition, the actual t-score should higher than the vast majority of the randomized t-scores. A p-value will be computed by dividing the number of randomized t-scores that are better than the actual t-score by 9999. The Monte Carlo simulations described here will be run in parallel, and are not limited to pairs of sample categories, so they support analysis of many different sample types.

If the samples fall along a gradient that is correlated with some environmental metadata (e.g., pH, salinity), rather than clustering into discrete groups (as described above), there are alternative approaches to testing for statistical significance. For example, if pH appears to be correlated with the principal coordinate 1 (PC1) values in a PCoA plot, a Monte Carlo-based Pearson or Spearman correlation test will be performed. Here, pH and PC1 will be tested to, for example, compute a Spearman rho value. The labels of the samples will again be shuffled 10,000 times and rho computed for each randomized data set. The p-value for the pH versus PC1 correlation will then be the number of randomized rho values that are higher than the actual rho value divided by 9999.

Identifying Features that are Predictive of Environment Characteristics (i.e., Sample Metadata)

Supervised classification is a machine learning approach for developing predictive models from training data. Each training data point consists of a set of input features, for example, the relative abundance of taxa, and a qualitative dependent variable giving the correct classification of that data point. In microbiome analysis, such classifications might include soil nutrients, predominant weather patterns, disease states, therapeutic results, or forensic identification. The goal of supervised classification is to derive some function from the training data that can be used to assign the correct class or category labels to novel inputs (e.g. new samples), and to learn which features, for example, taxa, discriminate between classes. Common applications of supervised learning include text classification, microarray analysis, and other bioinformatics analyses. For example, when microbiologists use the Ribosomal Database Project website to classify 16S rRNA gene sequences taxonomically, a form of supervised classification is used.

The primary goal of supervised learning is to build a model from a set of categorized data points that can predict the appropriate category membership of unlabeled future data. The category labels can be any type of important metadata, such as sugar content, viscosity, pH or temperature. The ability to classify unlabeled data is useful whenever alternative methods for obtaining data labels are difficult or expensive.

This goal of building predictive models is very different from the traditional goal of fitting an explanatory model to one's data set. The concern is less with how well the model fits our particular set of training data, but rather with how well it will generalize to novel input data. Hence, there is a problem of model selection. A model that is too simple or general is undesirable because it will fail to capture subtle, but important information about the independent variables (underfitting). A model that is too complex or specific is also undesirable because it will incorporate idiosyncrasies that are specific only to the particular training data (overfitting). The expected prediction error (EPE) of the model on future data must be optimized.

When the labels for the data are easily obtained, a predictive model is unnecessary. In these cases, supervised learning will still be useful for building descriptive models of the data, especially in data sets where the number of independent variables or the complexity of their interactions diminishes the usefulness of classical univariate hypothesis testing. Examples of this type of model can be seen in the various applications of supervised classification to microarray data, in which the goal is to identify a small, but highly predictive subset of the thousands of genes profiled in an experiment for further investigation. In microbial ecology, the analogous goal is to identify a subset of predictive taxa. In these descriptive models, accurate estimation of the EPE is still important to ensure that the association of the selected taxa with the class labels is not just happenstance or spurious. This process of finding small but predictive subsets of features, called feature selection, is increasingly important as the size and dimensionality of microbial community analyses continue to grow.

A common way to estimate the EPE of a particular model is to fit the model to a subset (e.g., 90%) of the data and then test its predictive accuracy on the other 10% of the data. This can provide an idea of how well the model would perform on future data sets if the goal is to fit it to the entire current data set. To improve the estimate of the EPE, this process will be repeated ten times so that each data point is part of the held-out validation data once. This procedure, known as cross-validation, will allow for the comparison of models that use very different inner machinery or different subsets of input features. Of course if many different models are tried and one provides the lowest cross-validation error for the entire data set is selected, it is likely that the reported EPE will be too optimistic. This is similar to the problem of making multiple comparisons in statistical inference; some models are bound to fortuitously match a particular data set. Hence, whenever possible, an entirely separate test set will be held out for estimating the EPE of the final model, after performing model selection.

Even if the method for selecting the best parameters or degree of complexity for a particular kind of model is determined, there is still a general challenge of picking what general class of models is most appropriate for a particular data set. The core aspect of choosing the right models for microbiome classification is to combine the knowledge of the most relevant constraints (e.g., data sparseness) inherent in the data with the understanding of the strengths and weaknesses of various approaches to supervised classification. If it is understood what structures will be inherent in the data, then models that take advantage of those structures will be chosen. For example, in the classification of microbiome, methods that can model nonlinear effects and complex interactions between organisms will be desired. In another example, the highly diverse nature of many microbial communities on the human body, models designed specifically to perform aggressive feature selection when faced with high-dimensional data will be most appropriate. Specialized generative models will be designed to incorporate prior knowledge about the data as well as the level of certainty about that prior knowledge. Instead of learning to predict class labels based on input features, a generative model will learn to predict the input features themselves. In other words, a generative model will learn what the data "looks like," regardless of the class labels. One potential benefit of generative models such as topic models and deep-layered belief nets will be that they can extract useful information even when the data are unlabeled. The ability to use data from related experiments to help build classifiers for one's own labeled data will be important as the number of publicly available microbial community data sets continues to grow.

Machine learning classification techniques will be applied to many types of microbial community data, for example, to the analysis of soil samples. For the soil samples, the samples will be classified according to environment type using support vector machines (SVMs) and k-nearest neighbors (KNN). Supervised learning will be used extensively in other classification domains with high-dimensional data, such as macroscopic ecology, microarray analysis, and text classification.

The goal of feature selection will be to find the combination of the model parameters and the feature subset that provides the lowest expected error on novel input data. Feature selection will be of utmost importance in the realm of microbiome classification due to the generally large number of features (i.e., constituent species-level taxa, or genes, or transcripts, or metabolites, or some combination of these): in addition to improving predictive accuracy, reducing the number of features leads to the production of more interpretable models. Approaches to feature selection known to people in the art and are typically divided into three categories: filter methods, wrapper methods, and embedded methods.

As the simplest form of feature selection, filter methods are completely agnostic to the choice of learning algorithm being used; that is, they treat the classifier as a black box. Filter methods use a two-step process. First a univariate test (e.g. t-test) or multivariate test (e.g., a linear classifier built with each unique pair of features) will be performed to estimate the relevance of each feature, and (1) all features whose scores exceed a predetermined threshold will be selected or (2) the best n features for inclusion in the model will be selected; then a classifier on the reduced feature set will be run. The choice of n can be determined using a validation data set or cross-validation on the training set.

Filter methods have several benefits, including their low computational complexity, their ease of implementation, and their potential, in the case of multivariate filters, to identify important interactions between features. The fact that the filter has no knowledge about the classifier is advantageous in that it provides modularity, but it can also be disadvantageous, as there is no guarantee that the filter and the classifier will have the same optimal feature subsets. For example, a linear filter (e.g., correlation-based) is unlikely to choose an optimal feature subset for a nonlinear classifier such as an SVM or a random forest (RF).

The purpose of a filter will be to identify features that are generally predictive of the response variable, or to remove features that are noisy or uninformative. Common filters include, but are not limited to, the between-class chi2 test, information gain (decrease in entropy when the feature is removed), various standard classification performance measures such as precision, recall, and the F-measure, and the accuracy of a univariate classifier, and the bi-normal separation (BNS), which treats the univariate true positive rate and the false-positive rate (tpr, fpr, based on document presence/absence in text classification) as though they were cumulative probabilities from the standard normal cumulative distribution function, and the difference between their respective z-scores, F1 (tpr)-F1 (fpr), will be used as a measure of that variable's relevance to the classification task.

Wrapper methods are usually the most computationally intensive and perhaps the least elegant of the feature selection methods. A wrapper method, like a filter method, will treat the classifier as a black box, but instead of using a simple univariate or multivariate test to determine which features are important, a wrapper will use the classifier itself to evaluate subsets of features. This leads to a computationally intensive search: an ideal wrapper will retrain the classifier for all feature subsets, and will choose the one with the lowest validation error. Were this search tractable, wrappers would be superior to filters because they would be able to find the optimal combination of features and classifier parameters. The search will not be tractable for high-dimensional data sets; hence, the wrapper will use heuristics during the search to find the optimal feature subset. The use of a heuristic will limit the wrapper's ability to interact with the classifier for two reasons: the inherent lack of optimality of the search heuristic, and the compounded lack of optimality in cases where the wrapper's optimal feature set differs from that of the classifier. In many cases the main benefit of using wrappers instead of filters, namely that the wrapper can interact with the underlying classifier, is shared by embedded methods, and the additional computational cost incurred by wrappers therefore makes such methods unattractive.

Embedded approaches to feature selection will perform an integrated search over the joint space of model parameters and feature subsets so that feature selection becomes an integral part of the learning process. Embedded feature selection will have the advantage over filters that it has the opportunity to search for the globally optimal parameter-feature combination. This is because feature selection will be performed with knowledge of the parameter selection process, whereas filter and wrapper methods treat the classifier as a "black box." As discussed above, performing the search over the whole joint parameter-feature space is generally intractable, but embedded methods will use knowledge of the classifier structure to inform the search process, while in the other methods the classifier must be built from scratch for every feature set.

Industrial Use Examples

The method described herein will be useful in a plethora of industrial settings. The scope of the information obtained can vary, based on the type of goal to be obtained. For example, the method can be applied on a macro scale, for example, sampling and analysis from all vineyards throughout the world. The method can also be applied on a regional scale, for example, sampling and analysis of vineyards in a region of the United States. Further, the method can be applied on a local scale, for example, sampling and analysis in a vineyard in Virginia. Next, the method can be applied on a run-based scale, for example, sampling and analysis of different harvests in one winery.

Vintners rely heavily on the soil for the growth of their vineyards. With microbiome analysis of particular soil that yielded a successful harvest generally or that was especially resistant to climatic variation, a vintner will use this information to predict a number of things. First, the vintner will use the microbiome information from a successful harvest of the previous season and compare with the soil on his vineyard currently to see if the soil is likely to yield a successful harvest this season. Second, if the soil microbiome is much different, he will use that information to plant a different grape variety that will flourish in the soil. This data will be obtained from previous years' soil analysis. Third, if the vintner is looking to expand his vineyard or purchase a different vineyard, the soil microbiome of the prospective vineyard will be tested to see which grape varieties have growth potential in that particular soil. If the vintner desires to plant a specific grape variety, the analysis of the soil may steer him away from the new land if the microbiome of the soil is more likely to yield a successful season of a different variety. Fourth, a particular high-end variety in which the vintner is interested in cultivating may only grow in certain soil conditions. An analysis of the soil (including the microbiome) where the particular crop has thrived compared to the vintner's current soil will inform the vintner of the feasibility of the new crop. Precision oenology is one of the advantages of the embodiments of this invention. Using the information related to the fermentation species identifies in the soil to provide advice to vintners and winemakers to improve the organoleptic properties of the wine. With the soil being the repository of most of the fermentation species, the value of the soil/harvest could fluctuate depending on a Micro-Wine-Makers index identifying the percentage of fermentation species relevant for the specific winemaking process. The index would provide information on the optimal microbiome community needed in the soil to launch the fermentation process.

In another embodiment the first set of one or more microorganisms are obtained from a source likely to favor the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fibre content, oil content, and the like, or plants displaying desirable colours, taste or smell. The microorganisms may be collected from a plant of interest or any material occurring in the environment of interest, including fungi and other animal and plant biota, soil, water, sediments, and other elements of the environment as referred to previously.

While the invention obviates the need for pre-existing knowledge about a microorganism's desirable properties with respect to a particular plant species, in one embodiment a microorganism or a combination of microorganisms of use in the methods of the invention may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g. rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g. *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilization of resources such as nutrients or space; change the color of one or more part of the plant, or change the chemical profile of the plant, its smell, taste or one or more other quality.

As used herein, "individual isolates" should be taken to mean a composition or culture comprising a predominance of a single genera, species or strain of microorganism, following separation from one or more other microorganisms. The phrase should not be taken to indicate the extent to which the microorganism has been isolated or purified. However, "individual isolates" preferably comprise substantially only one genus, species, or strain of microorganism.

The microorganisms can be isolated from a plant or plant material, surface or growth media associates with a selected plant using any appropriate techniques known in the art, including but not limited to those techniques described herein. For example, whole plant could be obtained and optionally processed, such as mulched or crushed. Alternatively, individual tissues or parts of selected plants (such as leaves, stems, roots, and seeds) may be processed.

The following is a list of non-limiting examples of the types of plants the methods of the invention may be applied to:

Crops grown for the production of non-alcoholic beverages and stimulants (coffee, black and green teas, cocoa, tobacco);

Plants grown for conversion to Energy, biological transformation during the production of biofuels, industrial solvents or chemical products, e.g. ethanol or buranol, propane diols, or other fuel of industrial material including sugar crops (e.g. beet, sugar cane), starch producing crops (e.g. C3 and C4 cereal crops and tuberous crops), cellulosic crops such as forest cellulosic crops such as forest trees (e.g. Pines, Eucalypts) and Graminaceous and Poaceous plants such as bamboo, switch grass, *miscanthus*; crops used in energy, biofuel or industrial chemical production via gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, miscanthus, sugar cane, or hemp or softwoods such as poplars, willows; and, biomass crops used in the production of biochar;

The present invention also provides kits which are useful for carrying out the present invention. The present kits comprise one or more container means containing the above-described assay components. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be •considered to constitute preferred modes for its practice. However, those of skill in the art should, in light of the present disclosure, •appreciate that many changes can be made in the specific embodiments which are disclosed and still obtain a like or similar result without departing from the spirit and scope of the invention. •

All documents cited herein are hereby •incorporated in their entirety by reference thereto.

Example 1

Sample Reception/Order Management

It is necessary to receive samples from their point of origin to the genetic testing laboratory where the samples are processed. We have created a full system to manage orders automatically by using internet based tools similar to ecommerce. That is the way we receive basic client's data information as identification or shipping address.

Example 2

Sample Collection

We have developed a specific methodology to collect samples, concretely from the winemaking process. We can distinguish among seven different stages:
1. Soil,
2. Grape/Fruit,
3. Must,
4. Alcoholic fermentation (beginning, middle and end) Depending on parameters as alcoholic graduation, amount of sugar, density.
5. Malolactic fermentation (beginning, middle and end) Depending on amount of malic and acetic acid.
6. Barrel (Beginning, middle and end) measure in months.
7. Bottle To test the soil, it is enough to collect 200 mg of soil coming from what we call soil unit. In the case of vineyards, a unit is defined as a parcel of land with the same grape variety, type of soil, culture techniques, and climate characteristics. If the vineyard is on the side of a hill, it should be divided into different independent units and different sampling kits used.

To capture most of the fermentative species, samples should be taken at the distance to vine trunk: 30 cm (12 in) and depth: 5-10 cm (2-4 in)

Example 3

Metadata Provision

We have developed specific forms and questionnaires to collect the additional data which will allow the understanding of the influence of microorganisms in the fermentation processes and data comparison.

Most of the forms have been translated to information technology (IT) language and tools. For example, through a mobile application it is possible to register a soil sample by providing: tube ID, grape variety, planting year of the grape, and a picture including: an image of the soil, sampling date and timing, coordinates of the sample (location). With this information, especially the coordinates, it is possible to gather additional information from external databases regarding soil composition, climate, or weather conditions to be included in the sample assessment an evaluation.

Example 4

Sample Shipping

Each kind of sample should be shipped in different ways. Usually freezing the samples is a standard methodology to stabilize the microbial community included in a sample.

Soil: After some experiments with different conservative buffers, we have determined that the best way to ship soil samples is at room temperature. Microbiome is consistent and does not change significantly for at least 14 days.

Liquid samples: We are developing test with different conservative buffers to identify the most ideal additive to inactivate microbial activity in a sample. The ideal buffer should be in form of powder instead of liquid: easier to preserve and easier to deliver.

Example 5

Coding and Traceability

Each sample should be identified with an unique ID in order to provide each sample with its special character so that it can be treated as unique during the workflow. We have designed a database architecture. We have designed our own structure according to the requirement and optimal functionality of data that we request/use/collect. This structure includes tables and fields which create relationships among parameters/data, including some evolutionary fields to be able to track each sample at real time.

Sample ID has been conceived as a combination of six alphanumeric fields. The first three digits identify the client and the last three digits identify the sample number. With this unique code it is possible to create almost 50,000 sample IDs per client. If we run out of sample IDs, a new client ID could be assigned if necessary for the same client.

Samples can pass through the following traceability steps:
1. Order: pending shipping
2. Shipped
3. Received in the lab
4. DNA extraction
5. Quality Control 1
6. Library building
7. Quality Control 2
8. DNA Sequencing
9. Bioinformatics processing
10. See results Example 6

Sample Processing
a) DNA Extraction

When a sample arrives to our genetic facilities the first step is to extract the DNA by breaking the molecular union of cells, releasing the DNA and concentrating it. We apply an improved metagenomic approach.

We are using RNA PowerSoil® Total RNA Isolation Kit, MO BIO Laboratories, Inc. Carlsbad, Calif.) for the metatranscriptome analysis. From 50 ml of wine, must, alcoholic or malolactic fermentation sample, centrifuge at 4000×g during 15 minutes in a 50 ml Falcon tube.
1. Discard the supernatant.
2. Wash step: Dilute the pellet using 1.5 ml of PBS and transfer to a 1.5 ml eppendorf.
3. Centrifuge at maximum speed during 3 minutes.
4. Repeat step 3-4 twice. Note: In this step you have to be aware of the pellet quantity so if you get little pellet avoid repeat the wash step and procedes to step 6. If you are processing must, avoid the wash step.
5. Dilute the pellet using the liquid.
6. The samples that we are dealing with are soil, liquids, fruit. In the following lines we will describe the steps that we have identified as optimal. To do this we use some commercial DNA extraction kits adapted to our necessities.

DNA Extraction for Soil

Based in PowerLyzer® PowerSoil® (MO BIO Laboratories, Inc. Carlsbad, Calif.) DNA Isolation Kit
1. To the PowerLyzer® Glass Bead Tube, 0.1 mm provided, add 0.2 grams of soil sample.
2. Add 750 •l of Guanidine thiocyanate solution to the Glass Bead Tube. Gently vortex to mix.
3. Add 60 ul of surfactant and invert several times or vortex briefly.
4. After adding surfactant solution, incubate 10 minutes at 70° C.
5. Secure PowerBead Tubes into the Precellys device (bead-beating homogenation, Bertin Technologies, Montigny-le-Bretonneux, France). Vortex at 5500 rpm, during 90 seconds. You will have to set up the program at 3 cycles.
6. Make sure the PowerBead Tubes rotate freely in your centrifuge without rubbing. Centrifuge tubes at 10,000×g for 30 seconds at room temperature.
7. Transfer the supernatant to a clean 2 ml Collection Tube (provided).
8. Add 250 ul of Solution protein precipitant and vortex for 5 seconds. Incubate at 4° C. for 5 minutes.
9. Centrifuge the tubes at room temperature for 1 minute at 10,000×g.
10. Avoiding the pellet, transfer up to, but no more than, 600 ul of supernatant to a clean 2 ml Collection Tube (provided).
11. Add 200 ul of Inhibitor removal compound and vortex briefly. Incubate at 4° C. for 5 minutes.
12. Centrifuge the tubes at room temperature for 1 minute at 10,000×g.
13. Avoiding the pellet, transfer up to, but no more than, 750 ul of supernatant into a clean 2 ml Collection Tube (provided).
14. Shake to mix chaotropic agent before use. Add 1200 ul of Solution C4 to the supernatant and vortex for 5 seconds.
15. Load approximately 675 ul onto a Spin Filter and centrifuge at 10,000×g for 1 minute at room temperature. Discard the flow through and add an additional 675 ul of supernatant to the Spin Filter and centrifuge at 10,000×g for 1 minute at room temperature. Load the remaining supernatant onto the Spin Filter and centrifuge at 10,000×g for 1 minute at room temperature. Note: A total of 3-4 loads for each sample processed are required.
16. Add 500 ul of Solution Ethanol 60% and centrifuge at room temperature for 30 seconds at 10,000×g.
17. Discard the flow through.
18. Centrifuge again at room temperature for 1 minute at 10,000×g.
19. Carefully place spin filter in a clean 2 ml Collection Tube (provided). Avoid splashing any Solution C5 onto the Spin Filter.
20. Add 100 ul of 1,3-Propanediol, 2-amino-2-(hydroxymethyl)-, hydrochloride mix with Tris HCl 2-Amino-2-(hydroxymethyl)-1,3-propaneiol to the center of the white filter membrane. Stand the tube for at least 1 minute.

21. Centrifuge at room temperature for 30 seconds at 10,000×g.

22. Discard the Spin Filter. The DNA in the tube is now ready for 16S-ITS library preparation Example 7

DNA Extraction for Fruit (Grapes)
Based in PowerLyzer® PowerSoil® DNA Isolation Kit 1. Add 20 units of grapes previously frozen at −80° C. to a 50 ml falcon tube.
2. Add 20 ml of purified water.
3. Vortex 5 minutes without breaking the grapes.
4. Collect all liquid.
5. Centrifuge at 4000×g during 15 minutes in a 50 ml Falcon tube
6. Discard the supernatant.
7. Wash step: Dilute the pellet using 1.5 ml of PBS and transfer to a 1.5 ml eppendorf.
8. Centrifuge at maximum speed during 3 minutes.
9. Repeat step 3-4 twice. Note: In this step you have to be aware of the pellet quantity so if you get little pellet avoid repeating the wash step and procedes to step 6. If you are processing must, avoid the wash step.

1. Dillute the pellet adding 750 •l of Guanidine thiocyanate solution to the Glass Bead Tube. Gently vortex to mix.
2. Add 60 ul of surfactant Solution and invert several times or vortex briefly.
3. After adding Solution surfactant, incubate 10 minutes at 70° C.
4. Secure PowerBead Tubes into the Precellys device (bead-beating homogenization, Bertin Technologies, Montigny-le-Bretonneux, France). Vortex at 5500 rpm, during 90 seconds. You will have to set up the program at 3 cycles.
5. Make sure the PowerBead Tubes rotate freely in your centrifuge without rubbing. Centrifuge tubes at 10,000×g for 30 seconds at room temperature.
6. Transfer the supernatant to a clean 2 ml Collection Tube (provided).
7. Add 250 ul of protein precipitant Solution and vortex for 5 seconds. Incubate at 4° C. for 5 minutes.
8. Centrifuge the tubes at room temperature for 1 minute at 10,000×g.
9. Avoiding the pellet, transfer up to, but no more than, 600 ul of supernatant to a clean 2 ml Collection Tube.
10. Dilute the pellet adding 750 •l of Guanidine thiocyanate solution to the Glass Bead Tube. Gently vortex to mix.
11. Add 60 ul of surfactant Solution and invert several times or vortex briefly.
12. After adding Solution surfactant, incubate 10 minutes at 70° C.
13. Secure PowerBead Tubes into the Precellys device (bead-beating homogenization, Bertin Technologies, Montigny-le-Bretonneux, France). Vortex at 5500 rpm, during 90 seconds. You will have to set up the program at 3 cycles.
14. Make sure the PowerBead Tubes rotate freely in your centrifuge without rubbing. Centrifuge tubes at 10,000×g for 30 seconds at room temperature.
15. Transfer the supernatant to a clean 2 ml Collection Tube (provided).
16. Add 250 ul of protein precipitant Solution and vortex for 5 seconds. Incubate at 4° C. for 5 minutes.
17. Centrifuge the tubes at room temperature for 1 minute at 10,000×g.
18. Avoiding the pellet, transfer up to, but no more than, 600 ul of supernatant to a clean 2 ml Collection Tube.
19. Add 200 ul of Inhibitor removal compound Solution and vortex briefly. Incubate at 4° C. for 5 minutes.
20. Centrifuge the tubes at room temperature for 1 minute at 10,000×g.
21. Avoiding the pellet, transfer up to, but no more than, 750 ul of supernatant into a clean 2 ml Collection Tube (provided).
22. Shake to mix chaotropic agent Solution before use. Add 1200 ul of Solution C4 to the supernatant and vortex for 5 seconds.
23. Load approximately 675 ul onto a Spin Filter and centrifuge at 10,000×g for 1 minute at room temperature. Discard the flow through and add an additional 675 ul of supernatant to the Spin Filter and centrifuge at 10,000×g for 1 minute at room temperature. Load the remaining supernatant onto the Spin Filter and centrifuge at 10,000×g for 1 minute at room temperature. Note: A total of 3-4 loads for each sample processed are required.
24. Add 500 ul of Solution Ethanol 60% and centrifuge at room temperature for 30 seconds at 10,000×g.
25. Discard the flow through.
26. Centrifuge again at room temperature for 1 minute at 10,000×g.
27. Carefully place spin filter in a clean 2 ml Collection Tube (provided). Avoid splashing any Solution C5 onto the Spin Filter.
28. Add 100 ul of 1,3-Propanediol, 2-amino-2-(hydroxymethyl)-, hydrochloride mix with Tris HCl 2-Amino-2-(hydroxymethyl)-1,3-propanediol to the center of the white filter membrane. Stand the tube for at least 1 minute.
29. Centrifuge at room temperature for 30 seconds at 10,000×g.
30. Discard the Spin Filter. The DNA in the tube is now ready for 16S-ITS library preparation.

Example 8

DNA Extraction from Wine (Liquid)
Based in PowerLyzer® PowerSoil® DNA Isolation Kit 1. From 50 ml of wine, must, alcoholic or malolactic fermentation sample, centrifuge at 4000×g during 15 minutes in a 50 ml Falcon tube
2. Discard the supernatant.
3. Wash step: Dilute the pellet using 1.5 ml of PBS and transfer to a 1.5 ml eppendorf.
4. Centrifuge at maximum speed during 3 minutes.
5. Repeat step 3-4 twice. Note: In this step you have to be aware of the pellet quantity so if you get little pellet avoid repeat the wash step and procedes to step 6. If you are processing must, avoid the wash step.
6. Dillute the pellet adding 750 •l of Guanidine thiocyanate solution to the Glass Bead Tube. Gently vortex to mix.
7. Add 60 ul of surfactant Solution and invert several times or vortex briefly.
8. After adding Solution surfactant, incubate 10 minutes at 70° C.
9. Secure PowerBead Tubes into the Precellys device (bead-beating homogenization, Bertin Technologies, Montigny-le-Bretonneux, France). Vortex at 5500 rpm, during 90 seconds. You will have to set up the program at 3 cycles.
10. Make sure the PowerBead Tubes rotate freely in your centrifuge without rubbing. Centrifuge tubes at 10,000×g for 30 seconds at room temperature.
11. Transfer the supernatant to a clean 2 ml Collection Tube (provided).
12. Add 250 ul of protein precipitant Solution and vortex for 5 seconds. Incubate at 4° C. for 5 minutes.

13. Centrifuge the tubes at room temperature for 1 minute at 10,000×g.

14. Avoiding the pellet, transfer up to, but no more than, 600 ul of supernatant to a clean 2 ml Collection Tube.

15. Add 200 ul of Inhibitor removal compound Solution and vortex briefly. Incubate at 4° C. for 5 minutes.

16. Centrifuge the tubes at room temperature for 1 minute at 10,000×g.

17. Avoiding the pellet, transfer up to, but no more than, 750 ul of supernatant into a clean 2 ml Collection Tube (provided).

18. Shake to mix chaotropic agent Solution before use. Add 1200 ul of Solution C4 to the supernatant and vortex for 5 seconds.

19. Load approximately 675 ul onto a Spin Filter and centrifuge at 10,000×g for 1 minute at room temperature. Discard the flow through and add an additional 675 ul of supernatant to the Spin Filter and centrifuge at 10,000×g for 1 minute at room temperature. Load the remaining supernatant onto the Spin Filter and centrifuge at 10,000×g for 1 minute at room temperature. Note: A total of 3-4 loads for each sample processed are required.

20. Add 500 ul of Solution Ethanol 60% and centrifuge at room temperature for 30 seconds at 10,000×g.

21. Discard the flow through.

22. Centrifuge again at room temperature for 1 minute at 10,000×g.

23. Carefully place spin filter in a clean 2 ml Collection Tube (provided). Avoid splashing any Solution C5 onto the Spin Filter.

24. Add 100 ul of 1,3-Propanediol, 2-amino-2-(hydroxymethyl)-, hydrochloride mix with Tris HCl 2-Amino-2-(hydroxymethyl)-1,3-propanediol to the center of the white filter membrane. Stand the tube for at least 1 minute.

25. Centrifuge at room temperature for 30 seconds at 10,000×g.

Discard the Spin Filter. The DNA in the tube is now ready for 16S-ITS library preparation.

Example 9 b) Library Building 1

Once we have extracted the DNA it is necessary to build the library of genome regions that we want to read.

Our technology identifies the bacteria and the fungi kingdoms present in a biological sample. We use different biomarkers for each kingdom and in the following lines we explain in detail the methodologies to build libraries for:

Bacteria: 16S gene
Fungi: ITS gene
Complex samples (also vegetable species as grape)
Shotgun for samples collected from bottled wine.
Bacteria Kingdom: 16S Prep Workflow 1. Prepare a 96 well plate format with DNA samples previously diluted 1:50

2. Prepare 8 different mixes per each 8 different primer FW and 5 primer hot Master Mix (MM). (0.5 ul×12 wells)+(10 ul of 5 primer hot Master Mix×12 wells)

3. Add each Mix in the different wells in Column 1 of the 96 well plate.

4. Distribute 10.5 ul per well in horizontal direction in the plate.

5. Prepare 12 different mixes per each 12 different primers RV and miliQ water. (0.5 ul×8 wells)+(13 ul of miliQ water×8 wells).

6. Distribute 13.5 ul per well in vertical direction in the plate.

7. With a multichannel distribute 1 ul of DNA in each well in horizontal direction.

Put the plate in the thermocycler
Complete reagent recipe (master mix) for 1×PCR reaction
PCR Grade $H_2O$ (note 1, below) 13.0 μL
5 Primer Hot MM note2) 10.0 μL
Forward primer (5 μM) 0.5 μL
Reverse primer (5 μM) 0.5 μL
Template DNA 1.0 μL
Total reaction volume 25.0 μL
1. Five Prime Hot Master Mix (5 prime: Item #2200410)
2. Final primer concentration of master mix: 0.2 μM
Thermocycler Conditions for 96 well thermocyclers:
1. 94° C. 3 minutes
2. 94° C. 20 seconds
3. 50° C. 20 seconds
4. 72° C. 40 seconds
5. Repeat steps 2-4 35 times
6. 72° C. 10 minutes
7. 4° C. HOLD

TABLE 1

16S Primers FW
(SEQ ID NOS 1-8, respectively, in order of appearance)

| | |
|---|---|
| 15f_SA501 | AATGATACGGCGACCACCGAGATCTACACAT CGTACGGAATAGTTGGGAGTGYCAGCMGCCGCGGTAA |
| 15f_SA502 | AATGATACGGCGACCACCGAGATCTACACAC TATCTGGAATAGTTGGGAGTGYCAGCMGCCGCGGTAA |
| 15f_SA503 | AATGATACGGCGACCACCGAGATCTACACTA GCGAGTGAATAGTTGGGAGTGYCAGCMGCCGCGGTAA |
| 15f_SA504 | AATGATACGGCGACCACCGAGATCTACACCT GCGTGTGAATAGTTGGGAGTGYCAGCMGCCGCGGTAA |
| 15f_SA505 | AATGATACGGCGACCACCGAGATCTACACTC ATCGAGGAATAGTTGGGAGTGYCAGCMGCCGCGGTAA |
| 15f_SA506 | AATGATACGGCGACCACCGAGATCTACACCG TGAGTGGAATAGTTGGGAGTGYCAGCMGCCGCGGTAA |
| 15f_SA507 | AATGATACGGCGACCACCGAGATCTACACGG ATATCTGAATAGTTGGGAGTGYCAGCMGCCGCGGTAA |
| 15f_SA508 | AATGATACGGCGACCACCGAGATCTACACGA CACCGTGAATAGTTGGGAGTGYCAGCMGCCGCGGTAA |

TABLE 2

16S Primers RV
(SEQ ID NOS 9-20, respectively, in order of appearance)

| | |
|---|---|
| 06r_SA701 | CAAGCAGAAGACGGCATACGAGATAACTCTC GCGCCAGTCAGCCGGACTACHVGGGTWTCTAAT |
| 06r_SA702 | CAAGCAGAAGACGGCATACGAGATACTATGT CCGCCAGTCAGCCGGACTACHVGGGTWTCTAAT |
| 06r_SA703 | CAAGCAGAAGACGGCATACGAGATAGTAGCG TCGCCAGTCAGCCGGACTACHVGGGTWTCTAAT |
| 06r_SA704 | CAAGCAGAAGACGGCATACGAGATCAGTGAG TCGCCAGTCAGCCGGACTACHVGGGTWTCTAAT |
| 06r_SA705 | CAAGCAGAAGACGGCATACGAGATCGTACTC ACGCCAGTCAGCCGGACTACHVGGGTWTCTAAT |
| 06r_SA706 | CAAGCAGAAGACGGCATACGAGATCTACGCA GCGCCAGTCAGCCGGACTACHVGGGTWTCTAAT |

TABLE 2-continued

16S Primers RV
(SEQ ID NOS 9-20, respectively, in order of appearance)

| | |
|---|---|
| 06r_SA707 | CAAGCAGAAGACGGCATACGAGATGGAGACT<br>ACGCCAGTCAGCCGGACTACHVGGGTWTCTAAT |
| 06r_SA708 | CAAGCAGAAGACGGCATACGAGATGTCGCTC<br>GCGCCAGTCAGCCGGACTACHVGGGTWTCTAAT |
| 06r_SA709 | CAAGCAGAAGACGGCATACGAGATGTCGTAG<br>TCGCCAGTCAGCCGGACTACHVGGGTWTCTAAT |
| 06r_SA710 | CAAGCAGAAGACGGCATACGAGATTAGCAGA<br>CCGCCAGTCAGCCGGACTACHVGGGTWTCTAAT |
| 06r_SA711 | CAAGCAGAAGACGGCATACGAGATTCATAGA<br>CCGCCAGTCAGCCGGACTACHVGGGTWTCTAAT |
| 06r_SA712 | CAAGCAGAAGACGGCATACGAGATTCGCTAT<br>ACGCCAGTCAGCCGGACTACHVGGGTWTCTAAT |

Note: No Soil Samples include a modification in the complete reagent recipe (master mix) for 1×PCR reaction. It is necessary to add the sequence of mPNA (ggcaagtgttcttcgga (SEQ ID NO: 21)) to block mitochondria contamination, and pPNA (ggctcaaccctggacag (SEQ ID NO: 22)) to block chloroplast contamitation.
PCR Grade H$_2$O (note 1, below) 11.0 µL
5 Primer Hot MM note2) 10.0 µL
Forward primer (5 µM) 0.5 µL
Reverse primer (5 µM) 0.5 µL
Template DNA 1.0 µL
1 ul mPNA blocker (5 µM stock)
1 ul pPNA blocker (5 µM stock)
Total reaction volume 25.0 µL
Fungi: ITS Prep Workflow
1. Prepare a 96 well plate format with DNA samples.
2. Prepare 8 different mixes per each 8 different primer FW and miliQ water. (0.5 ul×12 wells)+(6 ul miliQ water× 12 wells)
3. Add each Mix in the different wells in Column 1 of the 96 well plate.
4. Distribute 6.5 ul per well in horizontal direction in the plate.
5. Prepare 12 different mix per each 12 different primer RV and miliQ water. (0.5 ul×8 wells)+(7 ul of miliQ water×8 wells).
6. Distribute 7.5 ul per well in vertical direction in the plate.
7. With a multichannel distribute 1 ul of DNA in each well in horizontal direction.
8. Put the plate in the thermocycler and start
9. When 5 minutes after start the first cycle, open the thermocycler tap and without remove the plate add 10 ul of Five Prime Hot Master Mix per well.
Complete reagent recipe (master mix) for 1×PCR reaction
PCR Grade H$_2$O (note 1, below) 13.0 µL
5 Primer Hot MM note2) 10.0 µL
Forward primer (5 µM) 0.5 µL
Reverse primer (5 µM) 0.5 µL
Template DNA 1.0 µL
Total reaction volume 25.0 µL
1. Five Prime Hot Master Mix (5 prime)
2. Final primer concentration of master mix: 0.2 µM
Thermocycler Conditions for 96 well thermocyclers:
1. 94° C. 7 minutes
2. 94° C. 20 seconds
3. 55° C. 20 seconds
4. 72° C. 40 seconds
5. Repeat steps 2-4 40 times
6. 72° C. 10 minutes
7. 4° C. HOLD

TABLE 3

ITS primers FW
(SEQ ID NOS 23-30, respectively, in order of appearance)

| | |
|---|---|
| ITSf_SC501 | AATGATACGGCGACCACCGAGATCTACACA<br>CGACGTGACTCAGGCAAACACCTGCGGARGGATCA |
| ITSf_SC502 | AATGATACGGCGACCACCGAGATCTACACA<br>TATACACACTCAGGCAAACACCTGCGGARGGATCA |
| ITSf_SC503 | AATGATACGGCGACCACCGAGATCTACACC<br>GTCGCTAACTCAGGCAAACACCTGCGGARGGATCA |
| ITSf_SC504 | AATGATACGGCGACCACCGAGATCTACACC<br>TAGAGCTACTCAGGCAAACACCTGCGGARGGATCA |
| ITSf_SC505 | AATGATACGGCGACCACCGAGATCTACACG<br>CTCTAGTACTCAGGCAAACACCTGCGGARGGATCA |
| ITSf_SC506 | AATGATACGGCGACCACCGAGATCTACACG<br>ACACTGAACTCAGGCAAACACCTGCGGARGGATCA |
| ITSf_SC507 | AATGATACGGCGACCACCGAGATCTACACT<br>GCGTACGACTCAGGCAAACACCTGCGGARGGATCA |
| ITSf_SC508 | AATGATACGGCGACCACCGAGATCTACACT<br>AGTGTAGACTCAGGCAAACACCTGCGGARGGATCA |

TABLE 4

ITS primers RV
(SEQ ID NOS 31-42, respectively, in order of appearance)

| | |
|---|---|
| 58S3R_5C701 | CAAGCAGAAGACGGCATACGAGATACCTAC<br>TGCCATCCCCGGCTGAGATCCRTTGYTRAAAGTT |
| 58S3R_SC702 | CAAGCAGAAGACGGCATACGAGATAGCGCT<br>ATCCATCCCCGGCTGAGATCCRTTGYTRAAAGTT |
| 58S3R_SC703 | CAAGCAGAAGACGGCATACGAGATAGTCTA<br>GACCATCCCCGGCTGAGATCCRTTGYTRAAAGTT |
| 58S3R_SC704 | CAAGCAGAAGACGGCATACGAGATCATGAG<br>GACCATCCCCGGCTGAGATCCRTTGYTRAAAGTT |
| 58S3R_SC705 | CAAGCAGAAGACGGCATACGAGATCTAGCT<br>CGCCATCCCCGGCTGAGATCCRTTGYTRAAAGTT |
| 58S3R_SC706 | CAAGCAGAAGACGGCATACGAGATCTCTAG<br>AGCCATCCCCGGCTGAGATCCRTTGYTRAAAGTT |
| 58S3R_SC707 | CAAGCAGAAGACGGCATACGAGATGAGCTC<br>ATCCATCCCCGGCTGAGATCCRTTGYTRAAAGTT |
| 58S3R_SC708 | CAAGCAGAAGACGGCATACGAGATGGTATG<br>CTCCATCCCCGGCTGAGATCCRTTGYTRAAAGTT |
| 58S3R_SC709 | CAAGCAGAAGACGGCATACGAGATGTATGA<br>CGCCATCCCCGGCTGAGATCCRTTGYTRAAAGTT |
| 58S3R_SC710 | CAAGCAGAAGACGGCATACGAGATTAGACT<br>GACCATCCCCGGCTGAGATCCRTTGYTRAAAGTT |
| 58S3R_SC711 | CAAGCAGAAGACGGCATACGAGATTCACGA<br>TGCCATCCCCGGCTGAGATCCRTTGYTRAAAGTT |
| 58S3R_SC712 | CAAGCAGAAGACGGCATACGAGATTCGAGC<br>TCCCATCCCCGGCTGAGATCCRTTGYTRAAAGTT |

Complex Samples: ITS Prep Workflow

Complex samples are samples with PCR inhibitors. Wine contains many phenols which cause problems in the PCR procedure depending on their concentration.

Step 1.
1. Prepare a 96 well plate format with DNA samples.
2. Prepare master mix with primers.

TABLE 5

ITS primers
(SEQ ID NOS 43-44,
respectively, in order of
appearance)

| | |
|---|---|
| ITS1Fw | TCCGTAGGTGAACCTGCGG |
| ITS4Rv | TCCTCCGCTTATTGATATGC |

1. Distribute 24 ul per well.
2. With a multichannel distribute 1 ul of DNA in each well.
3. Put the plate in the termocycler and start
Complete reagent recipe (master mix) for 1×PCR reaction
PCR Grade $H_2O$ (note 1, below) 13.0 μL
5 Primer Hot MM note2) 10.0 μL
Forward primer (5 μM) 0.5 μL
Reverse primer (5 μM) 0.5 μL
Template DNA 1.0 μL
Total reaction volume 25.0 μL
1. Five Prime Hot Master Mix (5 prime: Item #2200410)
2. Final primer concentration of master mix: 0.2 μM
Thermocycler Conditions for 96 well thermocyclers:
1. 94° C. 3 minutes
2. 94° C. 20 seconds
3. 55° C. 20 seconds
4. 72° C. 60 seconds
5. Repeat steps 2-4 35 times
6. 72° C. 10 minutes
7. 4° C. HOLD Step 2.
1. Prepare 8 different mix per each 8 different primer FW and miliQ water. (0.5 ul×12 wells)+(6 ul miliQ water×12 wells)
2. Add each Mix in the different wells in Column 1 of the 96 well plate.
3. Distribute 6.5 ul per well in horizontal direction in the plate.
4. Prepare 12 different mix per each 12 different primers R and miliQ water. (0.5 ul×8 wells)+(7 ul of miliQ water×8 wells).
5. Distribute 7.5 ul per well in vertical direction in the plate.
6. With a multichannel distribute 1 ul of PCR product produced in the first step in each well in horizontal direction.
7. Put the plate in the thermocycler and start.
8. When 5 minutes after start the first cycle, open the thermocycler tap and without remove the plate add 10 ul of Five Prime Hot Master Mix per well.

Shotgun Metagenomic: Library Prep Workflow for a Bottled Wine Sample
1. Isolate DNA according to DNA extraction from Wine (liquid) sample Protocol
2. Use TruePrime™ Single Cell WGA (Illumina Inc., San Diego, Calif.) kit according to manufacturer instructions.
3. Use Nextera XT DNA Library Preparation Kit (Illumina, San Diego, Calif.) according to manufacture instructions.

Note 1: 16S and ITS protocol are dual index PCR protocol, with only 20 different primers its possible to sequence 96 samples. The method is adapted from *Development of a Dual-Index Sequencing Strategy and Curation Pipeline for Analyzing Amplicon Sequence Data on the MiSeq Illumina Sequencing Platform publication* (Kozinch, J. J. et al., 2013, Appl. Environ Microbiol 79, 5112-5120) by designing and using different primer sequences.

Note 2: master mix plates can be stablilizated at room temperature using ADN AmpligelMaster Mix plastes (Biotools).

Example 10 c) Library Building 2

In addition to the previous library building methodologies, we have designed and developed a new methodology to build an improved library to detect bacteria and fungi more accurately. We call it "Precision metagenomic protocol applying dual phylogenetic markers with single cell epicPCR (Emulsion, Paired Isolation and Concatenation PCR)."

16S rDNA is a powerful phylogenetic marker commonly used for profiling diversity in microbial samples, yet its use is associated with known problems including biases introduced by copy-number variations, variability in amplification efficiency, inconsistencies when targeting different regions of the gene, and problems with accurately and consistently delineating prokaryotic species. To solve these problems we use 16S rDNA in combination with another single-copy marker gene. This results in prokaryotic species boundaries at higher resolution than 16S rDNA.

Use of both markers guarantees identification of microbial diversity at the strain level. It is a new and powerful tool which can be applied to describe microbial communities in any sample.

The improved protocol is based on the following publication: Spencer et al., 2015, ISME J.

However, most importantly, we do not combine the 16S region with a functional gene, we combine the 16S region with one of the gene markers region described in Sunagawa, S. et al., 2013, Nat Methods 10: 1196-1199.

A selection of genes we are now testing is found in Table 6.

TABLE 6

Phylogenetic makers to combine with 16S gene marker

| COG name | OG | Lean length in 3496 genomes |
|---|---|---|
| Predicted GTPase, probable translation factor | OG0012 | 3099 |
| Phenylalanyl-tRNA synthetase alpha subunit | OG0016 | 3058 |
| Arginyl-tRNA synthetase | OG0018 | 3721 |
| Seryl-tRNA synthetase | OG0172 | 3285 |
| Cysteinyl-tRNA synthetase | OG0215 | 3415 |
| Leucyl-tRNA synthetase | OG0495 | 3571 |
| Valyl-tRNA synthetase | OG0525 | 3722 |
| Metal-dependent proteases with possible chaperone activity | OG0533 | 3054 |
| Signal recognition particle GTPase (Ffh) | OG0541 | 3415 |
| Signal recognition particle GTPase (FtsY) | OG0552 | 3189 |
| RNA polymerase subunit gene (rpoB), | | | d) Pre-Sequencing: Pool Preparation

Most of the described libraries follow the next steps to prepare for sequencing:

Cleanup, Normalization, and Pooling 16S and ITS libraries.

Use the SequalPrep Thermo Fisher Scientific, Waltham, Mass. Normalization Plate Kit 1. Transfer 20 •l of PCR product from PCR plate to corresponding well on the normalization plate.

2. Add 120.1 of Binding Buffer. Mix by pipetting, sealing, vortexing, and spinning briefly.

3. Incubate at room temperature for 60 minutes. Note: can incubate overnight if needed. Extra time does not improve results.

4. Aspirate the liquid from the wells. Do not scrape the sides.

5. Add 50 •l of Wash Buffer and pipette up and down twice, then aspirate immediately. Ensure there is no residual wash buffer in any wells.

6. Add 20 •l of Elution Buffer. Mix by pipetting up and down 5 times. Seal, vortex, and spin briefly.

7. Incubate at room temperature for 5 minutes.

8. Create a pool from each plate. Take 10 •l of each well to pool.

9. Concentrate the pool in a SpeedVac

10. Freeze the remaining sample for later use.

For the Shotgun Metagenomic the Protocol to Properly Prepare for Sequencing Change.

Normalization, and Pooling

1. Measure the samples in a fragment analyzer or Bioanalyzer machine.

2. Dilute the samples to 2 nM concentration.

3. Pool the samples in a equimolar concentration.

4. Sequencing according the Miseq protocol.

Example 11 e) Next-Generation Sequencing (NGS)

The Sequencing can be done with any available technology the unique requirement is add to the original gene marker primer and index sequence the specific adaptor sequence related with the sequencing technology.

In this case we are going to describe the use of the technique with Illumina Miseq. We should follow the Sequencing instructions according with the custom protocol.

1. Place 100 •l of the Read 1 (10 uM) Sequencing Primer(s) into a clean PCR tube. Repeat in separate tubes for the Index Primer(s) and Read 2 Sequencing Primer(s).

TABLE 7

Sequencing 16S primers
(SEQ ID NOS 45-47,
respectively, in order of appearance)

| Read1_515f | GAATAGTTGGGAGTGYCAGCMG CCGCGGTAA |
|---|---|
| Read2_806r | CGCCAGTCAGCCGGACTACHVG GGTWTCTAAT |
| IndexRead_806r | ATTAGAWACCCBDGTAGTCCGG CTGACTGGCG |

TABLE 8

Sequencing ITS primers
(SEQ ID NOS 48-50,
respectively, in order of appearance)

| Read1_BITSf | ACTCAGGCAAACACCTGCGGA RGGATCA |
|---|---|
| Read2_B5S3r | CCATCCCCGGCTGAGATCCRT TGYTRAAAGTT |
| IndexRead_B58SRr | AACTTTYARCAAYGGATCTCA GCCGGGGATGG |

2. Using a 1000 •l pipette tip, break the foil over wells 12, 13, 14, and 17.

3. Use an extra long 100 •l tip with the pipettor set on 75 •l to transfer the 30 •l of Read 1 Sequencing Primer to the bottom of well 12 and pipette 10× to mix. Repeat this process spiking the Index Primer into well 13 and the Read 2 Sequencing Primer into well 14.

4. Prepare a fresh dilution of 0.2N NaOH.

5. To a 1.5 ml tube add 5 •l of library 2 nM, and 5 •l of 0.2N NaOH. Vortex and wait 5 minutes. Add 990 ul of Hybridization Buffer and 200 ul of adapter-ligated control library based in PhiX, previously denatured with 0.2N NaOH to 20% final concentration of PhiX. Add 600 ul in the well sample.

Example 12

One of our greatest discoveries is that it is possible to mix different libraries in the same run of the NGS sequencer. In the following lines we described the step followed to perform this achievement in one of the most common sequencing platforms as Illumina's MySeq, however, can be adapted to other sequencing platforms.

Sequencing 16S and ITS libraries in the same Miseq Run.

1. Pool equimolar (nM) 16S and ITS libraries

2. Place 100 •l of the Read 1 (10 uM) Sequencing Primer(s) into a clean PCR tube. Repeat in separate tubes for the Index Primer(s) and Read 2 Sequencing Primer(s).

3. Mix 30 ul of the read 1 16S primer (10 uM) with 30 ul of the read 1 ITS primer (10 uM)

4. Mix 30 ul of the read 2 16S primer (10 uM) with 30 ul of the read 2 ITS primer (10 uM)

5. Mix 30 ul of the Index 16S primer (10 uM) with 30 ul of the Index ITS primer (10 uM)

6. Using a 1000 •l pipette tip, break the foil over wells 12, 13, 14, and 17.

7. Use an extra-long 100 •l tip with the pipette set on 75 •l to transfer the 60 •l of mix 16S and ITS Read 1 Sequencing Primer to the bottom of well 12 and pipette 10× to mix. Repeat this process. Spiking the Index Mix Primer into well 13 and the Read 2 Mix Sequencing Primer into well 14.

8. Prepare a fresh dilution of 0.2N NaOH.

9. To a 1.5 ml tube add 5 •l of library 2 nM, and 5 •l of 0.2N NaOH. Vortex and wait 5 minutes. Add 990 ul of HT1 and 200 ul of PhiX previously denature with 0.2N NaOH to 20% final concentration of PhiX. Add 600 ul in the well sample.

Example 13

Data Processing

The pipeline is programmed to run on a custom made cloud-based computing platform such as Amazon Machine Image (AMI) on Amazon Web Services, Microsoft Azure Cloud Computing, or Compute Engine on Google Cloud Platform. The instance is able to connect directly to BaseSpace via Illumina's Basemount program The pipeline is a bash script that wraps the following free programs along with custom Unix commands.

We have developed this improved tool to ensure that all the microbiological information is generated under the same standard and it is easily comparable.

In the following paragraphs we will described the steps done by this pipeline in order to process all the genetic information generated by NGS.

a) Quality Filter
1. Remove any reads that align to PhiX with Bowtie2
2. Remove primers and Illumina adapters from reads with Cutadapt
3. Quality filter reads based on Q-scores with QIIME's split_libraries_fastq.py script Cut each read at the first three bases in which the average Q-score is less than 20. If the chopped sequence is at least 75% as long as the original sequence, then keep that read.

b) Linking Pair End Sequencing
It is possible to analyse with and without pairing end reads. We have developed analyses without this pairing. We use Pear.

The pipeline can pick OTUs using two different algorithms: QIIME open reference (free, and minimum entropy decomposition (MED).

d) Database Matching
For QIIME open reference OTU picking with 16S sequences, the initial reference alignment step is against the SILVA database. Taxonomy is assigned to representative sequences for each OTU (QIIME and MED) according to SILVA. For ITS sequences, UNITE database is used.

e) Definition of Data Format for Integration
The pipeline produces two main tables. One table of OTU abundances by sample. The other table has the corresponding taxonomy for each OTU.

f) Database Itself
All the data are storage in servers according the database structure designed by us. All fields are related among them and it is possible the development of big data mining techniques. Our knowledge stack is based in different databases/tables:

DNA sequences coming from the different samples: Raw DNA data extracted from the NGS technology, Filtered and processed Genetic Information: Mainly the phylogenetic track and abundances of the different microbial species found in each sample independently of the kind of sample: soil, fruit, or liquid.

Metatranscriptomic information for each sample: RNA information to identify gene expression.

Client database: information related to client and users.

Sample metadata: non-genetic information related to the different samples as location, grape variety, sampling date and hour, chemical conditions, additives or any other information providing useful inputs to enable comparison and data understanding.

Auxiliary data: different auxiliary information processed and storage digitally which increase the value of the data generated by NGS and facilitate the understanding and comprehension of the information. Different groups have been developed here:

a. Geographical Information System (GIS): as for example wine regions, geography, climate, weather, soil composition, and other similar GIS data layers.

b. Microorganisms' profiles: specific information related to the effect of each microbial species and string to the winemaking process. This information includes assessment (positive/negative) and abundances threshold of the effect in the wine.

c. Microorganisms' genomes: Whole genome database for each of the fermentation species. We are building this specific database to improve the species identification (Database matching, letter d of this section) and increase the understanding of the specific species/string's influence in wine and other food products.

Example 14

Data Intelligence
a) Data Visualization
This technology produces big amount of heterogeneous data which could be used to provide interesting inputs for viticulturist and winemakers. We have developed different visualization tools for the generated data, especially those linked to soil samples.

Some of the visualization tools we developed/coded and specifically designed for the wine industry. Some of the main features are interactivity, utility and design.

b) GIS Information: Map Layers
Keeping in mind that we have geographical information of the samples, we have designed specific tools to use Geographical Information Systems (GIS) to generate understandable knowledge.

These tools use different GIS layers as for example wine regions, geography, climate, weather, soil composition, and other similar GIS data layers. Some of the layers have been developed by us and other are open data.

For instance related to Wine Region GIS layer, we have gathered geographical information of the wine regions worldwide. At this stage we have information for USA, France, Spain, Italy, and Portugal. We plan to start to parameterize the wine regions in other European countries, as well as the rest of the world. At this moment we have identified more than 1,500 wine regions worldwide.

A Geo-map identifying the different wine regions and the microbiome profile, highlighting the presence of the Micro-Wine-Makers is in preparation. This map will also match different grape varieties and microbiome profile worldwide.

c) Knowledge Related to Fermetation Species
This technology helps to identify and quantify all the fermentation species from bacteria and fungi kingdoms for different samples.

In the winemaking process some of these species are completely new/unseen before and for this reason we have generated knowledge about who are the real fermentation species in winemaking, the Micro-Wine-Makers, in form of different species profiles including information about its origin, picture, and influence in wine.

Presently, we have collected information for more than 200 species. Appendix C lists of some species discovered in the different samples and their influence in wine.

We have also developed a methodology to assess if the abundance of the specific species in any kind of sample is appropriate or indicative of a warning/alert.

d) Microbial Profile Report
We have designed a digital report including information structured in different sections which are accessible through a session in our proprietary portal:

Dashboard: listing all the client's data, including general overview of their status, and basic comparison information among all the client sample data specially focus in findings of the microbiome.

Sample information: Specific sample information screened in different ways, focusing in the findings of microbiome in the soil samples and assessing the threshold to determine if the microbiome proportions raise any alerts.

Microbiome profiles: Specific fermentation species information including a picture and descriptions about its influence in wine.

Client profile: user and client basic information as name, address, contact details, company, type of business and other similar information used to identify the client.

e) Data Mining and Big Data Techniques

Some data mining and big data techniques are used to make queries to our databases and get useful information especially interesting to better understand the relevance of the microbiome profile in products as wine. An interesting example of the outcomes of this process is the matching between the composition of the microbiome community in the wine and the organoleptic characteristics (flavours/taste) of the wine.

This allows us to provide prescription/recommendation to industry (Precision enology) and consumers (personalized product prescription)

f) Social Network Based in Microbiological Data

Our users can communicate and create a social network once they log into our client portal. This is going to be a new network around the microorganisms in wine industry.

Example 15

Whole Genome Sequencing

Whole genome high-throughput sequencing and annotation can be used to identify genes and single nucleotide polymorphisms (SNPs) between *Saccharomyces cerevisiae* strains and other non *Saccharomyces* species involved in wine fermentation process.

Yeasts selected provide specific and desirable phenotype with fermentation characteristics knowing and represent 80% of commercial world yeast.

The objective of this work is to connect the phenotype known with the genotype of these strains to provide tools to:

Evaluate the potential fermentation characteristics of wild yeast without use fermentation experiments.

Quality Control of organic wineries.

Provide tools to prevent fraudulent use of commercial yeasts.

Example 16

Detect Grape Variety in Wine Samples Previously to Bottle

Using the same protocol for library building described for analyzing bacteria kingdom (Bacteria Kingdom: 16S Prep Workflow), we can detect chloroplast and mitochondrial DNA from the plant to define the type of grape (variety). Similar primers as described for the bacteria protocol above are used.

We use minimum entropy decomposition analysis protocol to differentiate this reads at SNP level. With this we can group chloroplast and mitochondrial DNA reads and differentiate the type of grape in the sample comparing the reads with our chloroplast and mitochondrial DNA database.

Example 17

Kits/Products

Terroir Identity

A Genomic soil test to identify all the bacteria and yeast unique to a specific terroir. The result is presented in a digital report accessible through a private session at the proprietary portal.

Users will unveil the wine-related fermentation species of bacteria & yeast, and will detect potential biological contamination.

The benefits of this service are:

Identify the native Micro Wine Makers (MWM) or fermentation species in the soil which make your wine unique.

Compare different areas of a vineyard or different vineyards to characterize local scale differences in the microbial terroir.

Compare a soil microbiome to other regions

Estimate the organoleptic potential of a wine

Assess necessity of inoculums and sulfur doses

Anticipate contamination due to unwanted microorganisms

This service will allow collection of data coming from vineyard soils from different part of the world to increase the amount of data and empower a geo-map.

Wine DNA

This methodology defines the Genome of the wine, a genuine genetic DNA footprint, which could be included as a label in the bottle and will provide a new and innovative tool to identify and differentiate wines. The DNA of wine can be used to target consumers and rank wines. It creates a microbiological fingerprint of the wine along the winemaking process, from soil to the bottle, creating a unique identity of the wine which can be labelled as Wine's Genome.

As we understand better the microbiome influence in the wine, conclusions, for example that some specific species are present in quality vineyards, or in a specific wine region can be made. Specific bio-fertilizers to replicate the same conditions of a quality vineyard can be produced and utilized.

Also, bio-based control tools designed to avoid possible problems in a certain phases of vinification process can be applied. For example, depending on our analysis of the soil microbiome, we can state if that soil has organic properties and has been cultivated environmentally sustainable. The "Genetic Friendly Label" is our first labelling product and it is used for soil quality assessment at a certain moment.

Appendix A

| |
|---|
| # Constructed from biom file - Bacteria |
| #OTU ID |
| D_0__Archaea;D_1__Euryarchaeota;D_2__Halobacteria;D_3__Halobacteriales;D_4__Deep Sea Hydrothermal Vent Gp 6(DHVEG-6);D_5__uncultured archaeon |
| D_0__Archaea;D_1__Euryarchaeota;D_2__Halobacteria;D_3__Halobacteriales;D_4__Deep Sea Hydrothermal Vent Gp 6(DHVEG-6);D_5__uncultured euryarchaeote |
| D_0__Archaea;D_1__Euryarchaeota;D_2__Halobacteria;D_3__Halobacteriales;D_4__Halobacteriaceae;D_5__Halorientalis |
| D_0__Archaea;D_1__Euryarchaeota;D_2__Halobacteria;D_3__Halobacteriales;D_4__Halobacteriaceae;D_5__Haloterrigena |
| D_0__Archaea;D_1__Euryarchaeota;D_2__Halobacteria;D_3__Halobacteriales;D_4__Halobacteriaceae;D_5__Natronococcus |
| D_0__Archaea;D_1__Euryarchaeota;D_2__Methanobacteria;D_3__Methanobacteriales;D_4__Methanobacteriaceae;D_5__Methanobacterium |
| D_0__Archaea;D_1__Euryarchaeota;D_2__Methanobacteria;D_3__Methanobacteriales;D_4__Methanobacteriaceae;D_5__Methanobrevibacter |
| D_0__Archaea;D_1__Euryarchaeota;D_2__Methanobacteria;D_3__Methanobacteriales;D_4__Methanobacteriaceae;D_5__Methanosphaera |
| D_0__Archaea;D_1__Euryarchaeota;D_2__Methanobacteria;D_3__Methanobacteriales;D_4__Methanobacteriaceae;D_5__Methanothermobacter |
| D_0__Archaea;D_1__Euryarchaeota;D_2__Methanomicrobia;D_3__Methanocellales;D_4__Methanocellaceae;D_5__Methanocella |
| D_0__Archaea;D_1__Euryarchaeota;D_2__Methanomicrobia;D_3__Methanocellales;D_4__Methanocellaceae;D_5__Rice Cluster I |
| D_0__Archaea;D_1__Euryarchaeota;D_2__Methanomicrobia;D_3__Methanomicrobiales;D_4__Methanomicrobiaceae;D_5__Methanoculleus |
| D_0__Archaea;D_1__Euryarchaeota;D_2__Methanomicrobia;D_3__Methanosarcinales;D_4__Methanosarcinaceae;D_5__Methanosarcina |
| D_0__Archaea;D_1__Euryarchaeota;D_2__Thermoplasmata;D_3__Thermoplasmatales;D_4__ASC21;D_5__uncultured archaeon |
| D_0__Archaea;D_1__Euryarchaeota;D_2__Thermoplasmata;D_3__Thermoplasmatales;D_4__Marine Group II;D_5__uncultured archaeon |
| D_0__Archaea;D_1__Euryarchaeota;D_2__Thermoplasmata;D_3__Thermoplasmatales;D_4__Terrestrial Miscellaneous Gp(TMEG);D_5__uncultured archaeon |
| D_0__Archaea;D_1__Euryarchaeota;D_2__Thermoplasmata;D_3__Thermoplasmatales;D_4__Terrestrial Miscellaneous Gp(TMEG);Other |
| D_0__Archaea;D_1__Euryarchaeota;D_2__Thermoplasmata;D_3__Thermoplasmatales;D_4__Thermoplasmatales Incertae Sedis;D_5__Methanomassiliicoccus |
| D_0__Archaea;D_1__Euryarchaeota;D_2__Thermoplasmata;D_3__Thermoplasmatales;Other;Other |
| D_0__Archaea;D_1__Thaumarchaeota;D_2__Marine Group I;D_3__Unknown Order;D_4__Unknown Family;D_5__Candidatus Nitrosoarchaeum |
| D_0__Archaea;D_1__Thaumarchaeota;D_2__Miscellaneous Crenarchaeotic Group;D_3__uncultured archaeon;D_4__;D_5__ |
| D_0__Archaea;D_1__Thaumarchaeota;D_2__Soil Crenarchaeotic Group(SCG);D_3__Unknown Order;D_4__Unknown Family;D_5__Candidatus Nitrososphaera |
| D_0__Archaea;D_1__Thaumarchaeota;D_2__Soil Crenarchaeotic Group(SCG);D_3__uncultured archaeon;D_4__;D_5__ |
| D_0__Archaea;D_1__Thaumarchaeota;D_2__Soil Crenarchaeotic Group(SCG);D_3__uncultured crenarchaeote;D_4__;D_5__ |
| D_0__Archaea;D_1__Thaumarchaeota;D_2__Soil Crenarchaeotic Group(SCG);Other;Other;Other |
| D_0__Archaea;D_1__Thaumarchaeota;D_2__South African Gold Mine Gp 1(SAGMCG-1);D_3__Unknown Order;D_4__Unknown Family;D_5__Candidatus Nitrosotalea |
| D_0__Archaea;D_1__Thaumarchaeota;D_2__South African Gold Mine Gp 1(SAGMCG-1);D_3__uncultured archaeon;D_4__;D_5__ |

| |
|---|
| D_0__Archaea;D_1__Thaumarchaeota;D_2__South African Gold Mine Gp 1(SAGMCG-1);Other;Other;Other |
| D_0__Archaea;D_1__Thaumarchaeota;D_2__terrestrial group;D_3__uncultured archaeon;D_4__;D_5__ |
| D_0__Archaea;D_1__Thaumarchaeota;D_2__terrestrial group;D_3__uncultured crenarchaeote;D_4__;D_5__ |
| D_0__Bacteria;D_1__Acidobacteria;D_2__Acidobacteria;D_3__AT-s3-28;D_4__uncultured bacterium;D_5__ |
| D_0__Bacteria;D_1__Acidobacteria;D_2__Acidobacteria;D_3__Acidobacteriales;D_4__Acidobacteriaceae (Subgroup 1);D_5__Acidicapsa |
| D_0__Bacteria;D_1__Acidobacteria;D_2__Acidobacteria;D_3__Acidobacteriales;D_4__Acidobacteriaceae (Subgroup 1);D_5__Acidobacterium |
| D_0__Bacteria;D_1__Acidobacteria;D_2__Acidobacteria;D_3__Acidobacteriales;D_4__Acidobacteriaceae (Subgroup 1);D_5__Bryocella |
| D_0__Bacteria;D_1__Acidobacteria;D_2__Acidobacteria;D_3__Acidobacteriales;D_4__Acidobacteriaceae (Subgroup 1);D_5__Candidatus Koribacter |
| D_0__Bacteria;D_1__Acidobacteria;D_2__Acidobacteria;D_3__Acidobacteriales;D_4__Acidobacteriaceae (Subgroup 1);D_5__Edaphobacter |
| D_0__Bacteria;D_1__Acidobacteria;D_2__Acidobacteria;D_3__Acidobacteriales;D_4__Acidobacteriaceae (Subgroup 1);D_5__Granulicella |
| D_0__Bacteria;D_1__Acidobacteria;D_2__Acidobacteria;D_3__Acidobacteriales;D_4__Acidobacteriaceae (Subgroup 1);D_5__Telmatobacter |
| D_0__Bacteria;D_1__Acidobacteria;D_2__Acidobacteria;D_3__Acidobacteriales;D_4__Acidobacteriaceae (Subgroup 1);D_5__Terriglobus |
| D_0__Bacteria;D_1__Acidobacteria;D_2__Acidobacteria;D_3__Acidobacteriales;D_4__Acidobacteriaceae (Subgroup 1);D_5__uncultured |
| D_0__Bacteria;D_1__Acidobacteria;D_2__Acidobacteria;D_3__Acidobacteriales;D_4__Acidobacteriaceae (Subgroup 1);Other |
| D_0__Bacteria;D_1__Acidobacteria;D_2__Acidobacteria;D_3__FFCH5909;D_4__uncultured bacterium;D_5__ |
| D_0__Bacteria;D_1__Acidobacteria;D_2__Acidobacteria;D_3__Subgroup 11;D_4__uncultured Acidobacteria bacterium;D_5__ |
| D_0__Bacteria;D_1__Acidobacteria;D_2__Acidobacteria;D_3__Subgroup 11;D_4__uncultured bacterium;D_5__ |
| D_0__Bacteria;D_1__Acidobacteria;D_2__Acidobacteria;D_3__Subgroup 12;D_4__uncultured bacterium;D_5__ |
| D_0__Bacteria;D_1__Acidobacteria;D_2__Acidobacteria;D_3__Subgroup 13;D_4__uncultured bacterium;D_5__ |
| D_0__Bacteria;D_1__Acidobacteria;D_2__Acidobacteria;D_3__Subgroup 13;Other;Other |
| D_0__Bacteria;D_1__Acidobacteria;D_2__Acidobacteria;D_3__Subgroup 15;D_4__uncultured bacterium;D_5__ |
| D_0__Bacteria;D_1__Acidobacteria;D_2__Acidobacteria;D_3__Subgroup 15;Other;Other |
| D_0__Bacteria;D_1__Acidobacteria;D_2__Acidobacteria;D_3__Subgroup 17;D_4__uncultured Acidobacteria bacterium;D_5__ |
| D_0__Bacteria;D_1__Acidobacteria;D_2__Acidobacteria;D_3__Subgroup 17;D_4__uncultured Acidobacteriales bacterium;D_5__ |
| D_0__Bacteria;D_1__Acidobacteria;D_2__Acidobacteria;D_3__Subgroup 17;D_4__uncultured bacterium;D_5__ |
| D_0__Bacteria;D_1__Acidobacteria;D_2__Acidobacteria;D_3__Subgroup 17;Other;Other |
| D_0__Bacteria;D_1__Acidobacteria;D_2__Acidobacteria;D_3__Subgroup 18;D_4__uncultured bacterium;D_5__ |
| D_0__Bacteria;D_1__Acidobacteria;D_2__Acidobacteria;D_3__Subgroup 19;D_4__uncultured bacterium;D_5__ |
| D_0__Bacteria;D_1__Acidobacteria;D_2__Acidobacteria;D_3__Subgroup 2;D_4__uncultured bacterium;D_5__ |
| D_0__Bacteria;D_1__Acidobacteria;D_2__Acidobacteria;D_3__Subgroup 2;D_4__uncultured forest soil bacterium;D_5__ |
| D_0__Bacteria;D_1__Acidobacteria;D_2__Acidobacteria;D_3__Subgroup 2;Other;Other |
| D_0__Bacteria;D_1__Acidobacteria;D_2__Acidobacteria;D_3__Subgroup 20;D_4__uncultured bacterium;D_5__ |

| |
|---|
| D_0__Bacteria;D_1__Acidobacteria;D_2__Acidobacteria;D_3__Subgroup 25;D_4__uncultured Acidobacteria bacterium;D_5__ |
| D_0__Bacteria;D_1__Acidobacteria;D_2__Acidobacteria;D_3__Subgroup 25;D_4__uncultured bacterium;D_5__ |
| D_0__Bacteria;D_1__Acidobacteria;D_2__Acidobacteria;D_3__Subgroup 3;D_4__AKIW659;D_5__uncultured bacterium |
| D_0__Bacteria;D_1__Acidobacteria;D_2__Acidobacteria;D_3__Subgroup 3;D_4__Elev-16S-1166;D_5__uncultured bacterium |
| D_0__Bacteria;D_1__Acidobacteria;D_2__Acidobacteria;D_3__Subgroup 3;D_4__Elev-16S-1166;D_5__uncultured soil bacterium |
| D_0__Bacteria;D_1__Acidobacteria;D_2__Acidobacteria;D_3__Subgroup 3;D_4__Elev-16S-1166;Other |
| D_0__Bacteria;D_1__Acidobacteria;D_2__Acidobacteria;D_3__Subgroup 3;D_4__PAUC26f;D_5__uncultured bacterium |
| D_0__Bacteria;D_1__Acidobacteria;D_2__Acidobacteria;D_3__Subgroup 3;D_4__PAUC26f;Other |
| D_0__Bacteria;D_1__Acidobacteria;D_2__Acidobacteria;D_3__Subgroup 3;D_4__SJA-149;D_5__uncultured bacterium |
| D_0__Bacteria;D_1__Acidobacteria;D_2__Acidobacteria;D_3__Subgroup 3;D_4__SJA-149;Other |
| D_0__Bacteria;D_1__Acidobacteria;D_2__Acidobacteria;D_3__Subgroup 3;D_4__Unknown Family;D_5__Bryobacter |
| D_0__Bacteria;D_1__Acidobacteria;D_2__Acidobacteria;D_3__Subgroup 3;D_4__Unknown Family;D_5__Candidatus Solibacter |
| D_0__Bacteria;D_1__Acidobacteria;D_2__Acidobacteria;D_3__Subgroup 3;D_4__Unknown Family;Other |
| D_0__Bacteria;D_1__Acidobacteria;D_2__Acidobacteria;D_3__Subgroup 3;Other;Other |
| D_0__Bacteria;D_1__Acidobacteria;D_2__Acidobacteria;D_3__Subgroup 4;D_4__11-24;D_5__uncultured Acidobacteria bacterium |
| D_0__Bacteria;D_1__Acidobacteria;D_2__Acidobacteria;D_3__Subgroup 4;D_4__11-24;D_5__uncultured bacterium |
| D_0__Bacteria;D_1__Acidobacteria;D_2__Acidobacteria;D_3__Subgroup 4;D_4__11-24;D_5__uncultured proteobacterium |
| D_0__Bacteria;D_1__Acidobacteria;D_2__Acidobacteria;D_3__Subgroup 4;D_4__11-24;Other |
| D_0__Bacteria;D_1__Acidobacteria;D_2__Acidobacteria;D_3__Subgroup 4;D_4__DS-100;D_5__uncultured Acidobacteria bacterium |
| D_0__Bacteria;D_1__Acidobacteria;D_2__Acidobacteria;D_3__Subgroup 4;D_4__DS-100;D_5__uncultured Acidobacteriales bacterium |
| D_0__Bacteria;D_1__Acidobacteria;D_2__Acidobacteria;D_3__Subgroup 4;D_4__DS-100;D_5__uncultured bacterium |
| D_0__Bacteria;D_1__Acidobacteria;D_2__Acidobacteria;D_3__Subgroup 4;D_4__DS-100;Other |
| D_0__Bacteria;D_1__Acidobacteria;D_2__Acidobacteria;D_3__Subgroup 4;D_4__Elev-16S-573;D_5__uncultured bacterium |
| D_0__Bacteria;D_1__Acidobacteria;D_2__Acidobacteria;D_3__Subgroup 4;D_4__RB41;D_5__uncultured Acidobacteria bacterium |
| D_0__Bacteria;D_1__Acidobacteria;D_2__Acidobacteria;D_3__Subgroup 4;D_4__RB41;D_5__uncultured bacterium |
| D_0__Bacteria;D_1__Acidobacteria;D_2__Acidobacteria;D_3__Subgroup 4;D_4__RB41;Other |
| D_0__Bacteria;D_1__Acidobacteria;D_2__Acidobacteria;D_3__Subgroup 4;D_4__Unknown Family;D_5__Blastocatella |
| D_0__Bacteria;D_1__Acidobacteria;D_2__Acidobacteria;D_3__Subgroup 5;D_4__uncultured Acidobacteria bacterium;D_5__ |
| D_0__Bacteria;D_1__Acidobacteria;D_2__Acidobacteria;D_3__Subgroup 5;D_4__uncultured bacterium;D_5__ |
| D_0__Bacteria;D_1__Acidobacteria;D_2__Acidobacteria;D_3__Subgroup 5;Other;Other |
| D_0__Bacteria;D_1__Acidobacteria;D_2__Acidobacteria;D_3__Subgroup 6;D_4__uncultured Acidobacteria bacterium;D_5__ |
| D_0__Bacteria;D_1__Acidobacteria;D_2__Acidobacteria;D_3__Subgroup 6;D_4__uncultured Acidobacteriales bacterium;D_5__ |
| D_0__Bacteria;D_1__Acidobacteria;D_2__Acidobacteria;D_3__Subgroup 6;D_4__uncultured |

| |
|---|
| bacterium;D_5__ |
| D_0__Bacteria;D_1__Acidobacteria;D_2__Acidobacteria;D_3__Subgroup 6;D_4__uncultured soil bacterium;D_5__ |
| D_0__Bacteria;D_1__Acidobacteria;D_2__Acidobacteria;D_3__Subgroup 6;Other;Other |
| D_0__Bacteria;D_1__Acidobacteria;D_2__Acidobacteria;D_3__Subgroup 9;D_4__uncultured bacterium;D_5__ |
| D_0__Bacteria;D_1__Acidobacteria;D_2__Holophagae;D_3__Holophagales;D_4__Holophagaceae;D_5__Holophaga |
| D_0__Bacteria;D_1__Acidobacteria;D_2__Holophagae;D_3__Subgroup 10;D_4__ABS-19;D_5__uncultured Acidobacteria bacterium |
| D_0__Bacteria;D_1__Acidobacteria;D_2__Holophagae;D_3__Subgroup 10;D_4__ABS-19;D_5__uncultured bacterium |
| D_0__Bacteria;D_1__Acidobacteria;D_2__Holophagae;D_3__Subgroup 10;D_4__ABS-19;D_5__uncultured soil bacterium |
| D_0__Bacteria;D_1__Acidobacteria;D_2__Holophagae;D_3__Subgroup 10;D_4__ABS-19;Other |
| D_0__Bacteria;D_1__Acidobacteria;D_2__Holophagae;D_3__Subgroup 10;D_4__CA002;D_5__uncultured Acidobacteria bacterium |
| D_0__Bacteria;D_1__Acidobacteria;D_2__Holophagae;D_3__Subgroup 10;D_4__NS72;D_5__uncultured bacterium |
| D_0__Bacteria;D_1__Acidobacteria;D_2__Holophagae;D_3__Subgroup 10;D_4__NS72;Other |
| D_0__Bacteria;D_1__Acidobacteria;D_2__Holophagae;D_3__Subgroup 10;D_4__Sva0725;D_5__uncultured bacterium |
| D_0__Bacteria;D_1__Acidobacteria;D_2__Holophagae;D_3__Subgroup 10;D_4__Sva0725;Other |
| D_0__Bacteria;D_1__Acidobacteria;D_2__Holophagae;D_3__Subgroup 10;Other;Other |
| D_0__Bacteria;D_1__Acidobacteria;D_2__Holophagae;D_3__Subgroup 7;D_4__uncultured Acidobacteria bacterium;D_5__ |
| D_0__Bacteria;D_1__Acidobacteria;D_2__Holophagae;D_3__Subgroup 7;D_4__uncultured Acidobacterium sp.;D_5__ |
| D_0__Bacteria;D_1__Acidobacteria;D_2__Holophagae;D_3__Subgroup 7;D_4__uncultured bacterium;D_5__ |
| D_0__Bacteria;D_1__Acidobacteria;D_2__Holophagae;D_3__Subgroup 7;D_4__uncultured proteobacterium;D_5__ |
| D_0__Bacteria;D_1__Acidobacteria;D_2__Holophagae;D_3__Subgroup 7;Other;Other |
| D_0__Bacteria;D_1__Acidobacteria;D_2__Subgroup 22;D_3__uncultured Acidobacteria bacterium;D_4__;D_5__ |
| D_0__Bacteria;D_1__Acidobacteria;D_2__Subgroup 22;D_3__uncultured bacterium;D_4__;D_5__ |
| D_0__Bacteria;D_1__Acidobacteria;D_2__Subgroup 22;Other;Other;Other |
| D_0__Bacteria;D_1__Acidobacteria;D_2__Subgroup 26;D_3__uncultured bacterium;D_4__;D_5__ |
| D_0__Bacteria;D_1__Acidobacteria;Other;Other;Other;Other |
| D_0__Bacteria;D_1__Actinobacteria;D_2__Acidimicrobiia;D_3__Acidimicrobiales;D_4__Acidimicrobiaceae;D_5__CL500-29 marine group |
| D_0__Bacteria;D_1__Actinobacteria;D_2__Acidimicrobiia;D_3__Acidimicrobiales;D_4__Acidimicrobiaceae;D_5__Ilumatobacter |
| D_0__Bacteria;D_1__Actinobacteria;D_2__Acidimicrobiia;D_3__Acidimicrobiales;D_4__Acidimicrobiaceae;D_5__uncultured |
| D_0__Bacteria;D_1__Actinobacteria;D_2__Acidimicrobiia;D_3__Acidimicrobiales;D_4__Acidimicrobiaceae;Other |
| D_0__Bacteria;D_1__Actinobacteria;D_2__Acidimicrobiia;D_3__Acidimicrobiales;D_4__Acidimicrobiales Incertae Sedis;D_5__Aciditerrimonas |
| D_0__Bacteria;D_1__Actinobacteria;D_2__Acidimicrobiia;D_3__Acidimicrobiales;D_4__Acidimicrobiales Incertae Sedis;D_5__Candidatus Microthrix |
| D_0__Bacteria;D_1__Actinobacteria;D_2__Acidimicrobiia;D_3__Acidimicrobiales;D_4__Iamiaceae;D_5__Iamia |
| D_0__Bacteria;D_1__Actinobacteria;D_2__Acidimicrobiia;D_3__Acidimicrobiales;D_4__OM1 clade;D_5__uncultured bacterium |

| |
|---|
| D_0__Bacteria;D_1__Actinobacteria;D_2__Acidimicrobiia;D_3__Acidimicrobiales;D_4__OM1 clade;D_5__uncultured compost bacterium |
| D_0__Bacteria;D_1__Actinobacteria;D_2__Acidimicrobiia;D_3__Acidimicrobiales;D_4__OM1 clade;Other |
| D_0__Bacteria;D_1__Actinobacteria;D_2__Acidimicrobiia;D_3__Acidimicrobiales;D_4__uncultured;D_5__uncultured Acidimicrobidae bacterium |
| D_0__Bacteria;D_1__Actinobacteria;D_2__Acidimicrobiia;D_3__Acidimicrobiales;D_4__uncultured;D_5__uncultured Actinomycetales bacterium |
| D_0__Bacteria;D_1__Actinobacteria;D_2__Acidimicrobiia;D_3__Acidimicrobiales;D_4__uncultured;D_5__uncultured actinobacterium |
| D_0__Bacteria;D_1__Actinobacteria;D_2__Acidimicrobiia;D_3__Acidimicrobiales;D_4__uncultured;D_5__uncultured bacterium |
| D_0__Bacteria;D_1__Actinobacteria;D_2__Acidimicrobiia;D_3__Acidimicrobiales;D_4__uncultured;Other |
| D_0__Bacteria;D_1__Actinobacteria;D_2__Acidimicrobiia;D_3__Acidimicrobiales;Other;Other |
| D_0__Bacteria;D_1__Actinobacteria;D_2__Actinobacteria;D_3__Actinomycetales;D_4__Actinomycetaceae;D_5__Actinobaculum |
| D_0__Bacteria;D_1__Actinobacteria;D_2__Actinobacteria;D_3__Actinomycetales;D_4__Actinomycetaceae;D_5__Actinomyces |
| D_0__Bacteria;D_1__Actinobacteria;D_2__Actinobacteria;D_3__Actinomycetales;D_4__Actinomycetaceae;D_5__Arcanobacterium |
| D_0__Bacteria;D_1__Actinobacteria;D_2__Actinobacteria;D_3__Actinomycetales;D_4__Actinomycetaceae;D_5__Mobiluncus |
| D_0__Bacteria;D_1__Actinobacteria;D_2__Actinobacteria;D_3__Actinomycetales;D_4__Actinomycetaceae;D_5__Varibaculum |
| D_0__Bacteria;D_1__Actinobacteria;D_2__Actinobacteria;D_3__Actinomycetales;D_4__Actinomycetaceae;D_5__uncultured |
| D_0__Bacteria;D_1__Actinobacteria;D_2__Actinobacteria;D_3__Actinopolysporales;D_4__Actinopolysporaceae;D_5__Actinopolyspora |
| D_0__Bacteria;D_1__Actinobacteria;D_2__Actinobacteria;D_3__Bifidobacteriales;D_4__Bifidobacteriaceae;D_5__Bifidobacterium |
| D_0__Bacteria;D_1__Actinobacteria;D_2__Actinobacteria;D_3__Catenulisporales;D_4__Actinospicaceae;D_5__Actinospica |
| D_0__Bacteria;D_1__Actinobacteria;D_2__Actinobacteria;D_3__Corynebacteriales;D_4__Corynebacteriaceae;D_5__Corynebacterium |
| D_0__Bacteria;D_1__Actinobacteria;D_2__Actinobacteria;D_3__Corynebacteriales;D_4__Corynebacteriaceae;D_5__uncultured |
| D_0__Bacteria;D_1__Actinobacteria;D_2__Actinobacteria;D_3__Corynebacteriales;D_4__Corynebacteriaceae;Other |
| D_0__Bacteria;D_1__Actinobacteria;D_2__Actinobacteria;D_3__Corynebacteriales;D_4__Dietziaceae;D_5__Dietzia |
| D_0__Bacteria;D_1__Actinobacteria;D_2__Actinobacteria;D_3__Corynebacteriales;D_4__Mycobacteriaceae;D_5__Mycobacterium |
| D_0__Bacteria;D_1__Actinobacteria;D_2__Actinobacteria;D_3__Corynebacteriales;D_4__Nocardiaceae;D_5__Gordonia |
| D_0__Bacteria;D_1__Actinobacteria;D_2__Actinobacteria;D_3__Corynebacteriales;D_4__Nocardiaceae;D_5__Nocardia |
| D_0__Bacteria;D_1__Actinobacteria;D_2__Actinobacteria;D_3__Corynebacteriales;D_4__Nocardiaceae;D_5__Rhodococcus |
| D_0__Bacteria;D_1__Actinobacteria;D_2__Actinobacteria;D_3__Corynebacteriales;D_4__Nocardiaceae;D_5__Skermania |
| D_0__Bacteria;D_1__Actinobacteria;D_2__Actinobacteria;D_3__Corynebacteriales;D_4__Nocardiaceae;D_5__Smaragdicoccus |
| D_0__Bacteria;D_1__Actinobacteria;D_2__Actinobacteria;D_3__Corynebacteriales;D_4__Nocardiaceae;D_5__Williamsia |
| D_0__Bacteria;D_1__Actinobacteria;D_2__Actinobacteria;D_3__Corynebacteriales;D_4__uncultured;D_5__uncultured Mycobacteriaceae bacterium |
| D_0__Bacteria;D_1__Actinobacteria;D_2__Actinobacteria;D_3__Corynebacteriales;D_4__uncultured;D_5__uncultured Mycobacterium sp. |
| D_0__Bacteria;D_1__Actinobacteria;D_2__Actinobacteria;D_3__Corynebacteriales;D_4__uncultured;D_5__uncultured bacterium |
| D_0__Bacteria;D_1__Actinobacteria;D_2__Actinobacteria;D_3__Corynebacteriales;D_4__uncultu |

| |
|---|
| red;Other |
| D_0__Bacteria;D_1__Actinobacteria;D_2__Actinobacteria;D_3__Corynebacteriales;Other;Other |
| D_0__Bacteria;D_1__Actinobacteria;D_2__Actinobacteria;D_3__Frankiales;D_4__Acidothermaceae;D_5__Acidothermus |
| D_0__Bacteria;D_1__Actinobacteria;D_2__Actinobacteria;D_3__Frankiales;D_4__Cryptosporangiaceae;D_5__Cryptosporangium |
| D_0__Bacteria;D_1__Actinobacteria;D_2__Actinobacteria;D_3__Frankiales;D_4__Cryptosporangiaccac;D_5__Fodinicola |
| D_0__Bacteria;D_1__Actinobacteria;D_2__Actinobacteria;D_3__Frankiales;D_4__Frankiaceae;D_5__Frankia |
| D_0__Bacteria;D_1__Actinobacteria;D_2__Actinobacteria;D_3__Frankiales;D_4__Frankiaceae;D_5__Jatrophihabitans |
| D_0__Bacteria;D_1__Actinobacteria;D_2__Actinobacteria;D_3__Frankiales;D_4__Frankiaceae;Other |
| D_0__Bacteria;D_1__Actinobacteria;D_2__Actinobacteria;D_3__Frankiales;D_4__Geodermatophilaceae;D_5__Blastococcus |
| D_0__Bacteria;D_1__Actinobacteria;D_2__Actinobacteria;D_3__Frankiales;D_4__Geodermatophilaceae;D_5__Geodermatophilus |
| D_0__Bacteria;D_1__Actinobacteria;D_2__Actinobacteria;D_3__Frankiales;D_4__Geodermatophilaceae;D_5__Modestobacter |
| D_0__Bacteria;D_1__Actinobacteria;D_2__Actinobacteria;D_3__Frankiales;D_4__Geodermatophilaceae;D_5__uncultured |
| D_0__Bacteria;D_1__Actinobacteria;D_2__Actinobacteria;D_3__Frankiales;D_4__Geodermatophilaceae;Other |
| D_0__Bacteria;D_1__Actinobacteria;D_2__Actinobacteria;D_3__Frankiales;D_4__Nakamurellaceae;D_5__Nakamurella |
| D_0__Bacteria;D_1__Actinobacteria;D_2__Actinobacteria;D_3__Frankiales;D_4__Sporichthyaceae;D_5__Sporichthya |
| D_0__Bacteria;D_1__Actinobacteria;D_2__Actinobacteria;D_3__Frankiales;D_4__Sporichthyaceae;D_5__hgcI clade |
| D_0__Bacteria;D_1__Actinobacteria;D_2__Actinobacteria;D_3__Frankiales;D_4__Sporichthyaceae;D_5__uncultured |
| D_0__Bacteria;D_1__Actinobacteria;D_2__Actinobacteria;D_3__Frankiales;D_4__Sporichthyaceae;Other |
| D_0__Bacteria;D_1__Actinobacteria;D_2__Actinobacteria;D_3__Frankiales;D_4__uncultured;D_5__uncultured actinobacterium |
| D_0__Bacteria;D_1__Actinobacteria;D_2__Actinobacteria;D_3__Frankiales;D_4__uncultured;D_5__uncultured bacterium |
| D_0__Bacteria;D_1__Actinobacteria;D_2__Actinobacteria;D_3__Frankiales;D_4__uncultured;Other |
| D_0__Bacteria;D_1__Actinobacteria;D_2__Actinobacteria;D_3__Frankiales;Other;Other |
| D_0__Bacteria;D_1__Actinobacteria;D_2__Actinobacteria;D_3__Glycomycetales;D_4__Glycomycetaceae;D_5__Glycomyces |
| D_0__Bacteria;D_1__Actinobacteria;D_2__Actinobacteria;D_3__Glycomycetales;D_4__Glycomycetaceae;D_5__uncultured |
| D_0__Bacteria;D_1__Actinobacteria;D_2__Actinobacteria;D_3__Glycomycetales;D_4__Glycomycetaceae;D_5__uncultured bacterium |
| D_0__Bacteria;D_1__Actinobacteria;D_2__Actinobacteria;D_3__Kineosporiales;D_4__Kineosporiaceae;D_5__Angustibacter |
| D_0__Bacteria;D_1__Actinobacteria;D_2__Actinobacteria;D_3__Kineosporiales;D_4__Kineosporiaceae;D_5__Kineococcus |
| D_0__Bacteria;D_1__Actinobacteria;D_2__Actinobacteria;D_3__Kineosporiales;D_4__Kineosporiaceae;D_5__Kineosporia |
| D_0__Bacteria;D_1__Actinobacteria;D_2__Actinobacteria;D_3__Kineosporiales;D_4__Kineosporiaceae;D_5__Pseudokineococcus |
| D_0__Bacteria;D_1__Actinobacteria;D_2__Actinobacteria;D_3__Kineosporiales;D_4__Kineosporiaceae;D_5__Quadrisphaera |
| D_0__Bacteria;D_1__Actinobacteria;D_2__Actinobacteria;D_3__Kineosporiales;D_4__Kineosporiaceae;Other |
| D_0__Bacteria;D_1__Actinobacteria;D_2__Actinobacteria;D_3__Micrococcales;D_4__Bogoriellaceae;D_5__Georgenia |

| |
|---|
| D_0__Bacteria;D_1__Actinobacteria;D_2__Actinobacteria;D_3__Micrococcales;D_4__Brevibacteriaceae;D_5__Brevibacterium |
| D_0__Bacteria;D_1__Actinobacteria;D_2__Actinobacteria;D_3__Micrococcales;D_4__Cellulomonadaceae;D_5__Actinotalea |
| D_0__Bacteria;D_1__Actinobacteria;D_2__Actinobacteria;D_3__Micrococcales;D_4__Cellulomonadaceae;D_5__Cellulomonas |
| D_0__Bacteria;D_1__Actinobacteria;D_2__Actinobacteria;D_3__Micrococcales;D_4__Cellulomonadaceae;Other |
| D_0__Bacteria;D_1__Actinobacteria;D_2__Actinobacteria;D_3__Micrococcales;D_4__Dermabacteraceae;D_5__Brachybacterium |
| D_0__Bacteria;D_1__Actinobacteria;D_2__Actinobacteria;D_3__Micrococcales;D_4__Dermabacteraceae;D_5__Dermabacter |
| D_0__Bacteria;D_1__Actinobacteria;D_2__Actinobacteria;D_3__Micrococcales;D_4__Dermacoccaceae;D_5__Branchiibius |
| D_0__Bacteria;D_1__Actinobacteria;D_2__Actinobacteria;D_3__Micrococcales;D_4__Dermacoccaceae;D_5__Dermacoccus |
| D_0__Bacteria;D_1__Actinobacteria;D_2__Actinobacteria;D_3__Micrococcales;D_4__Dermacoccaceae;D_5__Flexivirga |
| D_0__Bacteria;D_1__Actinobacteria;D_2__Actinobacteria;D_3__Micrococcales;D_4__Dermacoccaceae;D_5__Kytococcus |
| D_0__Bacteria;D_1__Actinobacteria;D_2__Actinobacteria;D_3__Micrococcales;D_4__Dermacoccaceae;Other |
| D_0__Bacteria;D_1__Actinobacteria;D_2__Actinobacteria;D_3__Micrococcales;D_4__Dermatophilaceae;D_5__Dermatophilus |
| D_0__Bacteria;D_1__Actinobacteria;D_2__Actinobacteria;D_3__Micrococcales;D_4__Dermatophilaceae;D_5__Kineosphaera |
| D_0__Bacteria;D_1__Actinobacteria;D_2__Actinobacteria;D_3__Micrococcales;D_4__Dermatophilaceae;Other |
| D_0__Bacteria;D_1__Actinobacteria;D_2__Actinobacteria;D_3__Micrococcales;D_4__Intrasporangiaceae;D_5__Arsenicicoccus |
| D_0__Bacteria;D_1__Actinobacteria;D_2__Actinobacteria;D_3__Micrococcales;D_4__Intrasporangiaceae;D_5__Janibacter |
| D_0__Bacteria;D_1__Actinobacteria;D_2__Actinobacteria;D_3__Micrococcales;D_4__Intrasporangiaceae;D_5__Ornithinicoccus |
| D_0__Bacteria;D_1__Actinobacteria;D_2__Actinobacteria;D_3__Micrococcales;D_4__Intrasporangiaceae;D_5__Ornithinimicrobium |
| D_0__Bacteria;D_1__Actinobacteria;D_2__Actinobacteria;D_3__Micrococcales;D_4__Intrasporangiaceae;D_5__Oryzihumus |
| D_0__Bacteria;D_1__Actinobacteria;D_2__Actinobacteria;D_3__Micrococcales;D_4__Intrasporangiaceae;D_5__Phycicoccus |
| D_0__Bacteria;D_1__Actinobacteria;D_2__Actinobacteria;D_3__Micrococcales;D_4__Intrasporangiaceae;D_5__Terrabacter |
| D_0__Bacteria;D_1__Actinobacteria;D_2__Actinobacteria;D_3__Micrococcales;D_4__Intrasporangiaceae;D_5__Tetrasphaera |
| D_0__Bacteria;D_1__Actinobacteria;D_2__Actinobacteria;D_3__Micrococcales;D_4__Intrasporangiaceae;D_5__uncultured |
| D_0__Bacteria;D_1__Actinobacteria;D_2__Actinobacteria;D_3__Micrococcales;D_4__Intrasporangiaceae;Other |
| D_0__Bacteria;D_1__Actinobacteria;D_2__Actinobacteria;D_3__Micrococcales;D_4__Microbacteriaceae;D_5__Agromyces |
| D_0__Bacteria;D_1__Actinobacteria;D_2__Actinobacteria;D_3__Micrococcales;D_4__Microbacteriaceae;D_5__Candidatus Rhodoluna |
| D_0__Bacteria;D_1__Actinobacteria;D_2__Actinobacteria;D_3__Micrococcales;D_4__Microbacteriaceae;D_5__Clavibacter |
| D_0__Bacteria;D_1__Actinobacteria;D_2__Actinobacteria;D_3__Micrococcales;D_4__Microbacteriaceae;D_5__Curtobacterium |
| D_0__Bacteria;D_1__Actinobacteria;D_2__Actinobacteria;D_3__Micrococcales;D_4__Microbacteriaceae;D_5__Frigoribacterium |
| D_0__Bacteria;D_1__Actinobacteria;D_2__Actinobacteria;D_3__Micrococcales;D_4__Microbacteriaceae;D_5__Frondihabitans |
| D_0__Bacteria;D_1__Actinobacteria;D_2__Actinobacteria;D_3__Micrococcales;D_4__Microbacteriaceae;D_5__Gulosibacter |

| |
|---|
| D_0__Bacteria;D_1__Actinobacteria;D_2__Actinobacteria;D_3__Micrococcales;D_4__Microbacteriaceae;D_5__Herbiconiux |
| D_0__Bacteria;D_1__Actinobacteria;D_2__Actinobacteria;D_3__Micrococcales;D_4__Microbacteriaceae;D_5__Leifsonia |
| D_0__Bacteria;D_1__Actinobacteria;D_2__Actinobacteria;D_3__Micrococcales;D_4__Microbacteriaceae;D_5__Leucobacter |
| D_0__Bacteria;D_1__Actinobacteria;D_2__Actinobacteria;D_3__Micrococcales;D_4__Microbacteriaceae;D_5__Lysinimonas |
| D_0__Bacteria;D_1__Actinobacteria;D_2__Actinobacteria;D_3__Micrococcales;D_4__Microbacteriaceae;D_5__Marisediminicola |
| D_0__Bacteria;D_1__Actinobacteria;D_2__Actinobacteria;D_3__Micrococcales;D_4__Microbacteriaceae;D_5__Microbacterium |
| D_0__Bacteria;D_1__Actinobacteria;D_2__Actinobacteria;D_3__Micrococcales;D_4__Microbacteriaceae;D_5__Plantibacter |
| D_0__Bacteria;D_1__Actinobacteria;D_2__Actinobacteria;D_3__Micrococcales;D_4__Microbacteriaceae;D_5__Pseudoclavibacter |
| D_0__Bacteria;D_1__Actinobacteria;D_2__Actinobacteria;D_3__Micrococcales;D_4__Microbacteriaceae;D_5__Rathayibacter |
| D_0__Bacteria;D_1__Actinobacteria;D_2__Actinobacteria;D_3__Micrococcales;D_4__Microbacteriaceae;D_5__uncultured |
| D_0__Bacteria;D_1__Actinobacteria;D_2__Actinobacteria;D_3__Micrococcales;D_4__Microbacteriaceae;Other |
| D_0__Bacteria;D_1__Actinobacteria;D_2__Actinobacteria;D_3__Micrococcales;D_4__Micrococcaceae;D_5__Arthrobacter |
| D_0__Bacteria;D_1__Actinobacteria;D_2__Actinobacteria;D_3__Micrococcales;D_4__Micrococcaceae;D_5__Kocuria |
| D_0__Bacteria;D_1__Actinobacteria;D_2__Actinobacteria;D_3__Micrococcales;D_4__Micrococcaceae;D_5__Micrococcus |
| D_0__Bacteria;D_1__Actinobacteria;D_2__Actinobacteria;D_3__Micrococcales;D_4__Micrococcaceae;D_5__Nesterenkonia |
| D_0__Bacteria;D_1__Actinobacteria;D_2__Actinobacteria;D_3__Micrococcales;D_4__Micrococcacae;D_5__Rothia |
| D_0__Bacteria;D_1__Actinobacteria;D_2__Actinobacteria;D_3__Micrococcales;D_4__Micrococcaceae;D_5__Yaniella |
| D_0__Bacteria;D_1__Actinobacteria;D_2__Actinobacteria;D_3__Micrococcales;D_4__Micrococcaceae;D_5__uncultured |
| D_0__Bacteria;D_1__Actinobacteria;D_2__Actinobacteria;D_3__Micrococcales;D_4__Micrococcaceae;Other |
| D_0__Bacteria;D_1__Actinobacteria;D_2__Actinobacteria;D_3__Micrococcales;D_4__Promicromonosporaceae;D_5__Cellulosimicrobium |
| D_0__Bacteria;D_1__Actinobacteria;D_2__Actinobacteria;D_3__Micrococcales;D_4__Promicromonosporaceae;D_5__Isoptericola |
| D_0__Bacteria;D_1__Actinobacteria;D_2__Actinobacteria;D_3__Micrococcales;D_4__Promicromonosporaceae;D_5__Promicromonospora |
| D_0__Bacteria;D_1__Actinobacteria;D_2__Actinobacteria;D_3__Micrococcales;D_4__Promicromonosporaceae;Other |
| D_0__Bacteria;D_1__Actinobacteria;D_2__Actinobacteria;D_3__Micrococcales;D_4__Sanguibacteraceae;D_5__Sanguibacter |
| D_0__Bacteria;D_1__Actinobacteria;D_2__Actinobacteria;D_3__Micrococcales;Other;Other |
| D_0__Bacteria;D_1__Actinobacteria;D_2__Actinobacteria;D_3__Micromonosporales;D_4__Micromonosporaceae;D_5__Actinocatenispora |
| D_0__Bacteria;D_1__Actinobacteria;D_2__Actinobacteria;D_3__Micromonosporales;D_4__Micromonosporaceae;D_5__Actinoplanes |
| D_0__Bacteria;D_1__Actinobacteria;D_2__Actinobacteria;D_3__Micromonosporales;D_4__Micromonosporaceae;D_5__Allocatelliglobosispora |
| D_0__Bacteria;D_1__Actinobacteria;D_2__Actinobacteria;D_3__Micromonosporales;D_4__Micromonosporaceae;D_5__Asanoa |
| D_0__Bacteria;D_1__Actinobacteria;D_2__Actinobacteria;D_3__Micromonosporales;D_4__Micromonosporaceae;D_5__Catelliglobosispora |
| D_0__Bacteria;D_1__Actinobacteria;D_2__Actinobacteria;D_3__Micromonosporales;D_4__Micromonosporaceae;D_5__Catenuloplanes |
| D_0__Bacteria;D_1__Actinobacteria;D_2__Actinobacteria;D_3__Micromonosporales;D_4__Micromo |

| |
|---|
| nosporaceae;D_5__Dactylosporangium |
| D_0__Bacteria;D_1__Actinobacteria;D_2__Actinobacteria;D_3__Micromonosporales;D_4__Micromonosporaceae;D_5__Krasilnikovia |
| D_0__Bacteria;D_1__Actinobacteria;D_2__Actinobacteria;D_3__Micromonosporales;D_4__Micromonosporaceae;D_5__Longispora |
| D_0__Bacteria;D_1__Actinobacteria;D_2__Actinobacteria;D_3__Micromonosporales;D_4__Micromonosporaceae;D_5__Luedemannella |
| D_0__Bacteria;D_1__Actinobacteria;D_2__Actinobacteria;D_3__Micromonosporales;D_4__Micromonosporaceae;D_5__Micromonospora |
| D_0__Bacteria;D_1__Actinobacteria;D_2__Actinobacteria;D_3__Micromonosporales;D_4__Micromonosporaceae;D_5__Pilimelia |
| D_0__Bacteria;D_1__Actinobacteria;D_2__Actinobacteria;D_3__Micromonosporales;D_4__Micromonosporaceae;D_5__Planosporangium |
| D_0__Bacteria;D_1__Actinobacteria;D_2__Actinobacteria;D_3__Micromonosporales;D_4__Micromonosporaceae;D_5__Stackebrandtia |
| D_0__Bacteria;D_1__Actinobacteria;D_2__Actinobacteria;D_3__Micromonosporales;D_4__Micromonosporaceae;D_5__uncultured |
| D_0__Bacteria;D_1__Actinobacteria;D_2__Actinobacteria;D_3__Micromonosporales;D_4__Micromonosporaceae;Other |
| D_0__Bacteria;D_1__Actinobacteria;D_2__Actinobacteria;D_3__PeM15;D_4__uncultured bacterium;D_5__ |
| D_0__Bacteria;D_1__Actinobacteria;D_2__Actinobacteria;D_3__PeM15;Other;Other |
| D_0__Bacteria;D_1__Actinobacteria;D_2__Actinobacteria;D_3__Propionibacteriales;D_4__Nocardioidaceae;D_5__Actinopolymorpha |
| D_0__Bacteria;D_1__Actinobacteria;D_2__Actinobacteria;D_3__Propionibacteriales;D_4__Nocardioidaceae;D_5__Aeromicrobium |
| D_0__Bacteria;D_1__Actinobacteria;D_2__Actinobacteria;D_3__Propionibacteriales;D_4__Nocardioidaceae;D_5__Kribbella |
| D_0__Bacteria;D_1__Actinobacteria;D_2__Actinobacteria;D_3__Propionibacteriales;D_4__Nocardioidaceae;D_5__Marmoricola |
| D_0__Bacteria;D_1__Actinobacteria;D_2__Actinobacteria;D_3__Propionibacteriales;D_4__Nocardioidaceae;D_5__Nocardioides |
| D_0__Bacteria;D_1__Actinobacteria;D_2__Actinobacteria;D_3__Propionibacteriales;D_4__Nocardioidaceae;Other |
| D_0__Bacteria;D_1__Actinobacteria;D_2__Actinobacteria;D_3__Propionibacteriales;D_4__Propionibacteriaceae;D_5__Friedmanniella |
| D_0__Bacteria;D_1__Actinobacteria;D_2__Actinobacteria;D_3__Propionibacteriales;D_4__Propionibacteriaceae;D_5__Haloactinopolyspora |
| D_0__Bacteria;D_1__Actinobacteria;D_2__Actinobacteria;D_3__Propionibacteriales;D_4__Propionibacteriaceae;D_5__Microlunatus |
| D_0__Bacteria;D_1__Actinobacteria;D_2__Actinobacteria;D_3__Propionibacteriales;D_4__Propionibacteriaceae;D_5__Propionibacterium |
| D_0__Bacteria;D_1__Actinobacteria;D_2__Actinobacteria;D_3__Propionibacteriales;D_4__Propionibacteriaceae;D_5__uncultured |
| D_0__Bacteria;D_1__Actinobacteria;D_2__Actinobacteria;D_3__Propionibacteriales;D_4__Propionibacteriaceae;Other |
| D_0__Bacteria;D_1__Actinobacteria;D_2__Actinobacteria;D_3__Propionibacteriales;Other;Other |
| D_0__Bacteria;D_1__Actinobacteria;D_2__Actinobacteria;D_3__Pseudonocardiales;D_4__Pseudonocardiaceae;D_5__Actinoalloteichus |
| D_0__Bacteria;D_1__Actinobacteria;D_2__Actinobacteria;D_3__Pseudonocardiales;D_4__Pseudonocardiaceae;D_5__Actinokineospora |
| D_0__Bacteria;D_1__Actinobacteria;D_2__Actinobacteria;D_3__Pseudonocardiales;D_4__Pseudonocardiaceae;D_5__Actinomycetospora |
| D_0__Bacteria;D_1__Actinobacteria;D_2__Actinobacteria;D_3__Pseudonocardiales;D_4__Pseudonocardiaceae;D_5__Actinophytocola |
| D_0__Bacteria;D_1__Actinobacteria;D_2__Actinobacteria;D_3__Pseudonocardiales;D_4__Pseudonocardiaceae;D_5__Amycolatopsis |
| D_0__Bacteria;D_1__Actinobacteria;D_2__Actinobacteria;D_3__Pseudonocardiales;D_4__Pseudonocardiaceae;D_5__Crossiella |
| D_0__Bacteria;D_1__Actinobacteria;D_2__Actinobacteria;D_3__Pseudonocardiales;D_4__Pseudonocardiaceae;D_5__Kibdelosporangium |

| |
|---|
| D_0__Bacteria;D_1__Actinobacteria;D_2__Actinobacteria;D_3__Pseudonocardiales;D_4__Pseudonocardiaceae;D_5__Lentzea |
| D_0__Bacteria;D_1__Actinobacteria;D_2__Actinobacteria;D_3__Pseudonocardiales;D_4__Pseudonocardiaceae;D_5__Prauserella |
| D_0__Bacteria;D_1__Actinobacteria;D_2__Actinobacteria;D_3__Pseudonocardiales;D_4__Pseudonocardiaceae;D_5__Pseudonocardia |
| D_0__Bacteria;D_1__Actinobacteria;D_2__Actinobacteria;D_3__Pseudonocardiales;D_4__Pseudonocardiaceae;D_5__Saccharomonospora |
| D_0__Bacteria;D_1__Actinobacteria;D_2__Actinobacteria;D_3__Pseudonocardiales;D_4__Pseudonocardiaceae;D_5__Saccharopolyspora |
| D_0__Bacteria;D_1__Actinobacteria;D_2__Actinobacteria;D_3__Pseudonocardiales;D_4__Pseudonocardiaceae;D_5__Saccharothrix |
| D_0__Bacteria;D_1__Actinobacteria;D_2__Actinobacteria;D_3__Pseudonocardiales;D_4__Pseudonocardiaceae;D_5__Sciscionella |
| D_0__Bacteria;D_1__Actinobacteria;D_2__Actinobacteria;D_3__Pseudonocardiales;D_4__Pseudonocardiaceae;D_5__Thermocrispum |
| D_0__Bacteria;D_1__Actinobacteria;D_2__Actinobacteria;D_3__Pseudonocardiales;D_4__Pseudonocardiaceae;D_5__uncultured |
| D_0__Bacteria;D_1__Actinobacteria;D_2__Actinobacteria;D_3__Pseudonocardiales;D_4__Pseudonocardiaceae;Other |
| D_0__Bacteria;D_1__Actinobacteria;D_2__Actinobacteria;D_3__Streptomycetales;D_4__Streptomycetaceae;D_5__Kitasatospora |
| D_0__Bacteria;D_1__Actinobacteria;D_2__Actinobacteria;D_3__Streptomycetales;D_4__Streptomycetaceae;D_5__Streptacidiphilus |
| D_0__Bacteria;D_1__Actinobacteria;D_2__Actinobacteria;D_3__Streptomycetales;D_4__Streptomycetaceae;D_5__Streptomyces |
| D_0__Bacteria;D_1__Actinobacteria;D_2__Actinobacteria;D_3__Streptomycetales;D_4__Streptomycetaceae;Other |
| D_0__Bacteria;D_1__Actinobacteria;D_2__Actinobacteria;D_3__Streptosporangiales;D_4__Nocardiopsaceae;D_5__Nocardiopsis |
| D_0__Bacteria;D_1__Actinobacteria;D_2__Actinobacteria;D_3__Streptosporangiales;D_4__Nocardiopsaceae;D_5__Thermobifida |
| D_0__Bacteria;D_1__Actinobacteria;D_2__Actinobacteria;D_3__Streptosporangiales;D_4__Nocardiopsaceae;D_5__uncultured |
| D_0__Bacteria;D_1__Actinobacteria;D_2__Actinobacteria;D_3__Streptosporangiales;D_4__Streptosporangiaceae;D_5__Microbispora |
| D_0__Bacteria;D_1__Actinobacteria;D_2__Actinobacteria;D_3__Streptosporangiales;D_4__Streptosporangiaceae;D_5__Nonomuraea |
| D_0__Bacteria;D_1__Actinobacteria;D_2__Actinobacteria;D_3__Streptosporangiales;D_4__Streptosporangiaceae;D_5__Planobispora |
| D_0__Bacteria;D_1__Actinobacteria;D_2__Actinobacteria;D_3__Streptosporangiales;D_4__Streptosporangiaceae;D_5__Planotetraspora |
| D_0__Bacteria;D_1__Actinobacteria;D_2__Actinobacteria;D_3__Streptosporangiales;D_4__Streptosporangiaceae;D_5__Sphaerisporangium |
| D_0__Bacteria;D_1__Actinobacteria;D_2__Actinobacteria;D_3__Streptosporangiales;D_4__Streptosporangiaceae;D_5__Streptosporangium |
| D_0__Bacteria;D_1__Actinobacteria;D_2__Actinobacteria;D_3__Streptosporangiales;D_4__Streptosporangiaceae;Other |
| D_0__Bacteria;D_1__Actinobacteria;D_2__Actinobacteria;D_3__Streptosporangiales;D_4__Streptosporangiales Incertae Sedis;D_5__Motilibacter |
| D_0__Bacteria;D_1__Actinobacteria;D_2__Actinobacteria;D_3__Streptosporangiales;D_4__Thermomonosporaceae;D_5__Actinoallomurus |
| D_0__Bacteria;D_1__Actinobacteria;D_2__Actinobacteria;D_3__Streptosporangiales;D_4__Thermomonosporaceae;D_5__Actinocorallia |
| D_0__Bacteria;D_1__Actinobacteria;D_2__Actinobacteria;D_3__Streptosporangiales;D_4__Thermomonosporaceae;D_5__Actinomadura |
| D_0__Bacteria;D_1__Actinobacteria;D_2__Actinobacteria;D_3__Streptosporangiales;D_4__Thermomonosporaceae;D_5__Thermobispora |
| D_0__Bacteria;D_1__Actinobacteria;D_2__Actinobacteria;D_3__Streptosporangiales;D_4__Thermomonosporaceae;D_5__Thermomonospora |
| D_0__Bacteria;D_1__Actinobacteria;D_2__Actinobacteria;D_3__Streptosporangiales;D_4__Thermomonosporaceae;Other |

| |
|---|
| D_0__Bacteria;D_1__Actinobacteria;D_2__Actinobacteria;Other;Other;Other |
| D_0__Bacteria;D_1__Actinobacteria;D_2__Coriobacteriia;D_3__Coriobacteriales;D_4__Coriobacteriaceae;D_5__Atopobium |
| D_0__Bacteria;D_1__Actinobacteria;D_2__Coriobacteriia;D_3__Coriobacteriales;D_4__Coriobacteriaceae;D_5__Collinsella |
| D_0__Bacteria;D_1__Actinobacteria;D_2__Coriobacteriia;D_3__Coriobacteriales;D_4__Coriobacteriaceae;D_5__uncultured |
| D_0__Bacteria;D_1__Actinobacteria;D_2__Coriobacteriia;D_3__Coriobacteriales;D_4__Coriobacteriaceae;Other |
| D_0__Bacteria;D_1__Actinobacteria;D_2__MB-A2-108;D_3__uncultured Micromonospora sp.;D_4__;D_5__ |
| D_0__Bacteria;D_1__Actinobacteria;D_2__MB-A2-108;D_3__uncultured actinobacterium;D_4__;D_5__ |
| D_0__Bacteria;D_1__Actinobacteria;D_2__MB-A2-108;D_3__uncultured bacterium;D_4__;D_5__ |
| D_0__Bacteria;D_1__Actinobacteria;D_2__MB-A2-108;Other;Other;Other |
| D_0__Bacteria;D_1__Actinobacteria;D_2__Nitriliruptoria;D_3__Euzebyales;D_4__Euzebyaceae;D_5__Euzebya |
| D_0__Bacteria;D_1__Actinobacteria;D_2__Rubrobacteria;D_3__Rubrobacterales;D_4__Rubrobacteriaceae;D_5__Rubrobacter |
| D_0__Bacteria;D_1__Actinobacteria;D_2__TakashiAC-B11;D_3__uncultured actinobacterium;D_4__;D_5__ |
| D_0__Bacteria;D_1__Actinobacteria;D_2__TakashiAC-B11;D_3__uncultured bacterium;D_4__;D_5__ |
| D_0__Bacteria;D_1__Actinobacteria;D_2__TakashiAC-B11;Other;Other;Other |
| D_0__Bacteria;D_1__Actinobacteria;D_2__Thermoleophilia;D_3__Gaiellales;D_4__Gaiellaceae;D_5__Gaiella |
| D_0__Bacteria;D_1__Actinobacteria;D_2__Thermoleophilia;D_3__Gaiellales;D_4__uncultured;D_5__uncultured actinobacterium |
| D_0__Bacteria;D_1__Actinobacteria;D_2__Thermoleophilia;D_3__Gaiellales;D_4__uncultured;D_5__uncultured bacterium |
| D_0__Bacteria;D_1__Actinobacteria;D_2__Thermoleophilia;D_3__Gaiellales;D_4__uncultured;D_5__uncultured microorganism |
| D_0__Bacteria;D_1__Actinobacteria;D_2__Thermoleophilia;D_3__Gaiellales;D_4__uncultured;Other |
| D_0__Bacteria;D_1__Actinobacteria;D_2__Thermoleophilia;D_3__Gaiellales;Other;Other |
| D_0__Bacteria;D_1__Actinobacteria;D_2__Thermoleophilia;D_3__Solirubrobacterales;D_4__0319-6M6;D_5__uncultured actinobacterium |
| D_0__Bacteria;D_1__Actinobacteria;D_2__Thermoleophilia;D_3__Solirubrobacterales;D_4__0319-6M6;D_5__uncultured bacterium |
| D_0__Bacteria;D_1__Actinobacteria;D_2__Thermoleophilia;D_3__Solirubrobacterales;D_4__0319-6M6;D_5__uncultured organism |
| D_0__Bacteria;D_1__Actinobacteria;D_2__Thermoleophilia;D_3__Solirubrobacterales;D_4__0319-6M6;Other |
| D_0__Bacteria;D_1__Actinobacteria;D_2__Thermoleophilia;D_3__Solirubrobacterales;D_4__288-2;D_5__uncultured bacterium |
| D_0__Bacteria;D_1__Actinobacteria;D_2__Thermoleophilia;D_3__Solirubrobacterales;D_4__480-2;D_5__uncultured Gemmatimonadetes bacterium |
| D_0__Bacteria;D_1__Actinobacteria;D_2__Thermoleophilia;D_3__Solirubrobacterales;D_4__480-2;D_5__uncultured actinobacterium |
| D_0__Bacteria;D_1__Actinobacteria;D_2__Thermoleophilia;D_3__Solirubrobacterales;D_4__480-2;D_5__uncultured bacterium |
| D_0__Bacteria;D_1__Actinobacteria;D_2__Thermoleophilia;D_3__Solirubrobacterales;D_4__480-2;Other |
| D_0__Bacteria;D_1__Actinobacteria;D_2__Thermoleophilia;D_3__Solirubrobacterales;D_4__Conexibacteraceae;D_5__Conexibacter |
| D_0__Bacteria;D_1__Actinobacteria;D_2__Thermoleophilia;D_3__Solirubrobacterales;D_4__Elev-16S-1332;D_5__uncultured bacterium |
| D_0__Bacteria;D_1__Actinobacteria;D_2__Thermoleophilia;D_3__Solirubrobacterales;D_4__Elev-16S-1332;Other |

| |
|---|
| D_0__Bacteria;D_1__Actinobacteria;D_2__Thermoleophilia;D_3__Solirubrobacterales;D_4__FCPU744;D_5__uncultured bacterium |
| D_0__Bacteria;D_1__Actinobacteria;D_2__Thermoleophilia;D_3__Solirubrobacterales;D_4__FFCH13075;D_5__uncultured bacterium |
| D_0__Bacteria;D_1__Actinobacteria;D_2__Thermoleophilia;D_3__Solirubrobacterales;D_4__FFCH13075;Other |
| D_0__Bacteria;D_1__Actinobacteria;D_2__Thermoleophilia;D_3__Solirubrobacterales;D_4__Patulibacteraceae;D_5__Patulibacter |
| D_0__Bacteria;D_1__Actinobacteria;D_2__Thermoleophilia;D_3__Solirubrobacterales;D_4__Q3-6C1;D_5__uncultured bacterium |
| D_0__Bacteria;D_1__Actinobacteria;D_2__Thermoleophilia;D_3__Solirubrobacterales;D_4__S1-80;Other |
| D_0__Bacteria;D_1__Actinobacteria;D_2__Thermoleophilia;D_3__Solirubrobacterales;D_4__Solirubrobacteraceae;D_5__Solirubrobacter |
| D_0__Bacteria;D_1__Actinobacteria;D_2__Thermoleophilia;D_3__Solirubrobacterales;D_4__TM146;D_5__uncultured bacterium |
| D_0__Bacteria;D_1__Actinobacteria;D_2__Thermoleophilia;D_3__Solirubrobacterales;D_4__TM146;D_5__uncultured soil bacterium |
| D_0__Bacteria;D_1__Actinobacteria;D_2__Thermoleophilia;D_3__Solirubrobacterales;D_4__TM146;Other |
| D_0__Bacteria;D_1__Actinobacteria;D_2__Thermoleophilia;D_3__Solirubrobacterales;D_4__YNPFFP1;D_5__uncultured bacterium |
| D_0__Bacteria;D_1__Actinobacteria;D_2__Thermoleophilia;D_3__Solirubrobacterales;D_4__YNPFFP1;Other |
| D_0__Bacteria;D_1__Actinobacteria;D_2__Thermoleophilia;D_3__Solirubrobacterales;Other;Other |
| D_0__Bacteria;D_1__Actinobacteria;D_2__Thermoleophilia;Other;Other;Other |
| D_0__Bacteria;D_1__Actinobacteria;Other;Other;Other;Other |
| D_0__Bacteria;D_1__Armatimonadetes;D_2__Armatimonadia;D_3__Armatimonadales;D_4__Armatimonadaceae;D_5__Armatimonas |
| D_0__Bacteria;D_1__Armatimonadetes;D_2__Armatimonadia;D_3__Armatimonadales;D_4__uncultured bacterium;D_5__ |
| D_0__Bacteria;D_1__Armatimonadetes;D_2__Armatimonadia;D_3__Armatimonadales;Other;Other |
| D_0__Bacteria;D_1__Armatimonadetes;D_2__Chthonomonadetes;D_3__Chthonomonadales;D_4__Chthonomonadaceae;D_5__Chthonomonas |
| D_0__Bacteria;D_1__Armatimonadetes;D_2__Chthonomonadetes;D_3__Chthonomonadales;D_4__uncultured bacterium;D_5__ |
| D_0__Bacteria;D_1__Armatimonadetes;D_2__uncultured Armatimonadetes bacterium;D_3__;D_4__;D_5__ |
| D_0__Bacteria;D_1__Armatimonadetes;D_2__uncultured bacterium;D_3__;D_4__;D_5__ |
| D_0__Bacteria;D_1__Armatimonadetes;D_2__uncultured soil bacterium;D_3__;D_4__;D_5__ |
| D_0__Bacteria;D_1__Armatimonadetes;Other;Other;Other;Other |
| D_0__Bacteria;D_1__BD1-5;D_2__uncultured bacterium;D_3__;D_4__;D_5__ |
| D_0__Bacteria;D_1__BD1-5;Other;Other;Other;Other |
| D_0__Bacteria;D_1__BHI80-139;D_2__uncultured bacterium;D_3__;D_4__;D_5__ |
| D_0__Bacteria;D_1__Bacteroidetes;D_2__BSV13;Other;Other;Other |
| D_0__Bacteria;D_1__Bacteroidetes;D_2__Bacteroidia;D_3__Bacteroidales;D_4__BS11 gut group;D_5__uncultured bacterium |
| D_0__Bacteria;D_1__Bacteroidetes;D_2__Bacteroidia;D_3__Bacteroidales;D_4__Bacteroidaceae;D_5__Bacteroides |
| D_0__Bacteria;D_1__Bacteroidetes;D_2__Bacteroidia;D_3__Bacteroidales;D_4__Bacteroidales Incertae Sedis;D_5__Phocaeicola |
| D_0__Bacteria;D_1__Bacteroidetes;D_2__Bacteroidia;D_3__Bacteroidales;D_4__Marinilabiaceae;D_5__Anaerophaga |
| D_0__Bacteria;D_1__Bacteroidetes;D_2__Bacteroidia;D_3__Bacteroidales;D_4__Porphyromonadaceae;D_5__Barnesiella |

| |
|---|
| D_0__Bacteria;D_1__Bacteroidetes;D_2__Bacteroidia;D_3__Bacteroidales;D_4__Porphyromonadaceae;D_5__Dysgonomonas |
| D_0__Bacteria;D_1__Bacteroidetes;D_2__Bacteroidia;D_3__Bacteroidales;D_4__Porphyromonadaceae;D_5__Paludibacter |
| D_0__Bacteria;D_1__Bacteroidetes;D_2__Bacteroidia;D_3__Bacteroidales;D_4__Porphyromonadaceae;D_5__Parabacteroides |
| D_0__Bacteria;D_1__Bacteroidetes;D_2__Bacteroidia;D_3__Bacteroidales;D_4__Porphyromonadaceae;D_5__Porphyromonas |
| D_0__Bacteria;D_1__Bacteroidetes;D_2__Bacteroidia;D_3__Bacteroidales;D_4__Porphyromonadaceae;D_5__Proteiniphilum |
| D_0__Bacteria;D_1__Bacteroidetes;D_2__Bacteroidia;D_3__Bacteroidales;D_4__Porphyromonadaceae;D_5__uncultured |
| D_0__Bacteria;D_1__Bacteroidetes;D_2__Bacteroidia;D_3__Bacteroidales;D_4__Prevotellaceae;D_5__Alloprevotella |
| D_0__Bacteria;D_1__Bacteroidetes;D_2__Bacteroidia;D_3__Bacteroidales;D_4__Prevotellaceae;D_5__Prevotella |
| D_0__Bacteria;D_1__Bacteroidetes;D_2__Bacteroidia;D_3__Bacteroidales;D_4__Prevotellaceae;D_5__uncultured |
| D_0__Bacteria;D_1__Bacteroidetes;D_2__Bacteroidia;D_3__Bacteroidales;D_4__RF16;D_5__uncultured bacterium |
| D_0__Bacteria;D_1__Bacteroidetes;D_2__Bacteroidia;D_3__Bacteroidales;D_4__Rikenellaceae;D_5__Alistipes |
| D_0__Bacteria;D_1__Bacteroidetes;D_2__Bacteroidia;D_3__Bacteroidales;D_4__Rikenellaceae;D_5__RC9 gut group |
| D_0__Bacteria;D_1__Bacteroidetes;D_2__Bacteroidia;D_3__Bacteroidales;D_4__Rikenellaceae;D_5__vadinBC27 wastewater-sludge group |
| D_0__Bacteria;D_1__Bacteroidetes;D_2__Bacteroidia;D_3__Bacteroidales;D_4__S24-7;D_5__uncultured bacterium |
| D_0__Bacteria;D_1__Bacteroidetes;D_2__Cytophagia;D_3__Cytophagales;D_4__Cyclobacteriaceae;D_5__Algoriphagus |
| D_0__Bacteria;D_1__Bacteroidetes;D_2__Cytophagia;D_3__Cytophagales;D_4__Cyclobacteriaceae;D_5__uncultured |
| D_0__Bacteria;D_1__Bacteroidetes;D_2__Cytophagia;D_3__Cytophagales;D_4__Cyclobacteriaceae;Other |
| D_0__Bacteria;D_1__Bacteroidetes;D_2__Cytophagia;D_3__Cytophagales;D_4__Cytophagaceae;D_5__Adhaeribacter |
| D_0__Bacteria;D_1__Bacteroidetes;D_2__Cytophagia;D_3__Cytophagales;D_4__Cytophagaceae;D_5__Chryseolinea |
| D_0__Bacteria;D_1__Bacteroidetes;D_2__Cytophagia;D_3__Cytophagales;D_4__Cytophagaceae;D_5__Cytophaga |
| D_0__Bacteria;D_1__Bacteroidetes;D_2__Cytophagia;D_3__Cytophagales;D_4__Cytophagaceae;D_5__Dyadobacter |
| D_0__Bacteria;D_1__Bacteroidetes;D_2__Cytophagia;D_3__Cytophagales;D_4__Cytophagaceae;D_5__Emticicia |
| D_0__Bacteria;D_1__Bacteroidetes;D_2__Cytophagia;D_3__Cytophagales;D_4__Cytophagaceae;D_5__Flexibacter |
| D_0__Bacteria;D_1__Bacteroidetes;D_2__Cytophagia;D_3__Cytophagales;D_4__Cytophagaceae;D_5__Hymenobacter |
| D_0__Bacteria;D_1__Bacteroidetes;D_2__Cytophagia;D_3__Cytophagales;D_4__Cytophagaceae;D_5__Larkinella |
| D_0__Bacteria;D_1__Bacteroidetes;D_2__Cytophagia;D_3__Cytophagales;D_4__Cytophagaceae;D_5__Leadbetterella |
| D_0__Bacteria;D_1__Bacteroidetes;D_2__Cytophagia;D_3__Cytophagales;D_4__Cytophagaceae;D_5__Ohtaekwangia |
| D_0__Bacteria;D_1__Bacteroidetes;D_2__Cytophagia;D_3__Cytophagales;D_4__Cytophagaceae;D_5__Persicitalea |
| D_0__Bacteria;D_1__Bacteroidetes;D_2__Cytophagia;D_3__Cytophagales;D_4__Cytophagaceae;D_5__Pontibacter |
| D_0__Bacteria;D_1__Bacteroidetes;D_2__Cytophagia;D_3__Cytophagales;D_4__Cytophagaceae;D_5__Pseudarcicella |
| D_0__Bacteria;D_1__Bacteroidetes;D_2__Cytophagia;D_3__Cytophagales;D_4__Cytophagaceae;D_5__Rhodocytophaga |

| |
|---|
| D_0__Bacteria;D_1__Bacteroidetes;D_2__Cytophagia;D_3__Cytophagales;D_4__Cytophagaceae;D_5__Rudanella |
| D_0__Bacteria;D_1__Bacteroidetes;D_2__Cytophagia;D_3__Cytophagales;D_4__Cytophagaceae;D_5__Siphonobacter |
| D_0__Bacteria;D_1__Bacteroidetes;D_2__Cytophagia;D_3__Cytophagales;D_4__Cytophagaceae;D_5__Spirosoma |
| D_0__Bacteria;D_1__Bacteroidetes;D_2__Cytophagia;D_3__Cytophagales;D_4__Cytophagaceae;D_5__Sporocytophaga |
| D_0__Bacteria;D_1__Bacteroidetes;D_2__Cytophagia;D_3__Cytophagales;D_4__Cytophagaceae;D_5__uncultured |
| D_0__Bacteria;D_1__Bacteroidetes;D_2__Cytophagia;D_3__Cytophagales;D_4__Cytophagaceae;Other |
| D_0__Bacteria;D_1__Bacteroidetes;D_2__Cytophagia;D_3__Cytophagales;D_4__Flammeovirgaceae;D_5__Candidatus Amoebophilus |
| D_0__Bacteria;D_1__Bacteroidetes;D_2__Cytophagia;D_3__Cytophagales;D_4__Flammeovirgaceae;D_5__Candidatus Cardinium |
| D_0__Bacteria;D_1__Bacteroidetes;D_2__Cytophagia;D_3__Cytophagales;D_4__Flammeovirgaceae;D_5__Flexithrix |
| D_0__Bacteria;D_1__Bacteroidetes;D_2__Cytophagia;D_3__Cytophagales;D_4__Flammeovirgaceae;D_5__Roseivirga |
| D_0__Bacteria;D_1__Bacteroidetes;D_2__Cytophagia;D_3__Cytophagales;D_4__Flammeovirgaceae;D_5__uncultured |
| D_0__Bacteria;D_1__Bacteroidetes;D_2__Cytophagia;D_3__Cytophagales;D_4__MWH-CFBk5;D_5__uncultured bacterium |
| D_0__Bacteria;D_1__Bacteroidetes;D_2__Cytophagia;D_3__Cytophagales;Other;Other |
| D_0__Bacteria;D_1__Bacteroidetes;D_2__Cytophagia;D_3__Order II;D_4__Rhodothermaceae;D_5__Rubrivirga |
| D_0__Bacteria;D_1__Bacteroidetes;D_2__Cytophagia;D_3__Order II;D_4__Rhodothermaceae;D_5__uncultured |
| D_0__Bacteria;D_1__Bacteroidetes;D_2__Cytophagia;D_3__Order II;D_4__Rhodothermaceae;Other |
| D_0__Bacteria;D_1__Bacteroidetes;D_2__Cytophagia;D_3__Order III;D_4__uncultured;D_5__uncultured organism |
| D_0__Bacteria;D_1__Bacteroidetes;D_2__Flavobacteriia;D_3__Flavobacteriales;D_4__Blattabacteriaceae;D_5__Blattabacterium |
| D_0__Bacteria;D_1__Bacteroidetes;D_2__Flavobacteriia;D_3__Flavobacteriales;D_4__Blattabacteriaceae;D_5__Candidatus Sulcia |
| D_0__Bacteria;D_1__Bacteroidetes;D_2__Flavobacteriia;D_3__Flavobacteriales;D_4__Blattabacteriaceae;D_5__Candidatus Uzinura |
| D_0__Bacteria;D_1__Bacteroidetes;D_2__Flavobacteriia;D_3__Flavobacteriales;D_4__Cryomorphaceae;D_5__Crocinitomix |
| D_0__Bacteria;D_1__Bacteroidetes;D_2__Flavobacteriia;D_3__Flavobacteriales;D_4__Cryomorphaceae;D_5__Fluviicola |
| D_0__Bacteria;D_1__Bacteroidetes;D_2__Flavobacteriia;D_3__Flavobacteriales;D_4__Cryomorphaceae;D_5__Owenweeksia |
| D_0__Bacteria;D_1__Bacteroidetes;D_2__Flavobacteriia;D_3__Flavobacteriales;D_4__Flavobacteriaceae;D_5__Bergeyella |
| D_0__Bacteria;D_1__Bacteroidetes;D_2__Flavobacteriia;D_3__Flavobacteriales;D_4__Flavobacteriaceae;D_5__Capnocytophaga |
| D_0__Bacteria;D_1__Bacteroidetes;D_2__Flavobacteriia;D_3__Flavobacteriales;D_4__Flavobacteriaceae;D_5__Chryseobacterium |
| D_0__Bacteria;D_1__Bacteroidetes;D_2__Flavobacteriia;D_3__Flavobacteriales;D_4__Flavobacteriaceae;D_5__Cloacibacterium |
| D_0__Bacteria;D_1__Bacteroidetes;D_2__Flavobacteriia;D_3__Flavobacteriales;D_4__Flavobacteriaceae;D_5__Epilithonimonas |
| D_0__Bacteria;D_1__Bacteroidetes;D_2__Flavobacteriia;D_3__Flavobacteriales;D_4__Flavobacteriaceae;D_5__Flavobacterium |
| D_0__Bacteria;D_1__Bacteroidetes;D_2__Flavobacteriia;D_3__Flavobacteriales;D_4__Flavobacteriaceae;D_5__Gelidibacter |
| D_0__Bacteria;D_1__Bacteroidetes;D_2__Flavobacteriia;D_3__Flavobacteriales;D_4__Flavobacteriaceae;D_5__Gillisia |
| D_0__Bacteria;D_1__Bacteroidetes;D_2__Flavobacteriia;D_3__Flavobacteriales;D_4__Flavobacteriaceae;D_5__Salinimicrobium |

| |
|---|
| D_0__Bacteria;D_1__Bacteroidetes;D_2__Flavobacteriia;D_3__Flavobacteriales;D_4__Flavobacteriaceae;D_5__Wautersiella |
| D_0__Bacteria;D_1__Bacteroidetes;D_2__Flavobacteriia;D_3__Flavobacteriales;D_4__Flavobacteriaceae;D_5__uncultured |
| D_0__Bacteria;D_1__Bacteroidetes;D_2__Flavobacteriia;D_3__Flavobacteriales;D_4__Flavobacteriaceae;Other |
| D_0__Bacteria;D_1__Bacteroidetes;D_2__Flavobacteriia;D_3__Flavobacteriales;D_4__NS9 marine group;D_5__uncultured Bacteroidetes bacterium |
| D_0__Bacteria;D_1__Bacteroidetes;D_2__Flavobacteriia;D_3__Flavobacteriales;D_4__NS9 marine group;D_5__uncultured bacterium |
| D_0__Bacteria;D_1__Bacteroidetes;D_2__SB-1;D_3__uncultured bacterium;D_4__;D_5__ |
| D_0__Bacteria;D_1__Bacteroidetes;D_2__SB-5;Other;Other;Other |
| D_0__Bacteria;D_1__Bacteroidetes;D_2__Sphingobacteriia;D_3__Sphingobacteriales;D_4__AKYH767;D_5__uncultured bacterium |
| D_0__Bacteria;D_1__Bacteroidetes;D_2__Sphingobacteriia;D_3__Sphingobacteriales;D_4__AKYH767;Other |
| D_0__Bacteria;D_1__Bacteroidetes;D_2__Sphingobacteriia;D_3__Sphingobacteriales;D_4__CWT CU03-E12;D_5__uncultured bacterium |
| D_0__Bacteria;D_1__Bacteroidetes;D_2__Sphingobacteriia;D_3__Sphingobacteriales;D_4__CWT CU03-E12;Other |
| D_0__Bacteria;D_1__Bacteroidetes;D_2__Sphingobacteriia;D_3__Sphingobacteriales;D_4__Chitinophagaceae;D_5__Chitinophaga |
| D_0__Bacteria;D_1__Bacteroidetes;D_2__Sphingobacteriia;D_3__Sphingobacteriales;D_4__Chitinophagaceae;D_5__Ferruginibacter |
| D_0__Bacteria;D_1__Bacteroidetes;D_2__Sphingobacteriia;D_3__Sphingobacteriales;D_4__Chitinophagaceae;D_5__Filimonas |
| D_0__Bacteria;D_1__Bacteroidetes;D_2__Sphingobacteriia;D_3__Sphingobacteriales;D_4__Chitinophagaceae;D_5__Flavihumibacter |
| D_0__Bacteria;D_1__Bacteroidetes;D_2__Sphingobacteriia;D_3__Sphingobacteriales;D_4__Chitinophagaceae;D_5__Flavisolibacter |
| D_0__Bacteria;D_1__Bacteroidetes;D_2__Sphingobacteriia;D_3__Sphingobacteriales;D_4__Chitinophagaceae;D_5__Flavitalea |
| D_0__Bacteria;D_1__Bacteroidetes;D_2__Sphingobacteriia;D_3__Sphingobacteriales;D_4__Chitinophagaceae;D_5__Hydrotalea |
| D_0__Bacteria;D_1__Bacteroidetes;D_2__Sphingobacteriia;D_3__Sphingobacteriales;D_4__Chitinophagaceae;D_5__Lacibacter |
| D_0__Bacteria;D_1__Bacteroidetes;D_2__Sphingobacteriia;D_3__Sphingobacteriales;D_4__Chitinophagaceae;D_5__Niabella |
| D_0__Bacteria;D_1__Bacteroidetes;D_2__Sphingobacteriia;D_3__Sphingobacteriales;D_4__Chitinophagaceae;D_5__Niastella |
| D_0__Bacteria;D_1__Bacteroidetes;D_2__Sphingobacteriia;D_3__Sphingobacteriales;D_4__Chitinophagaceae;D_5__Parasegetibacter |
| D_0__Bacteria;D_1__Bacteroidetes;D_2__Sphingobacteriia;D_3__Sphingobacteriales;D_4__Chitinophagaceae;D_5__Sediminibacterium |
| D_0__Bacteria;D_1__Bacteroidetes;D_2__Sphingobacteriia;D_3__Sphingobacteriales;D_4__Chitinophagaceae;D_5__Segetibacter |
| D_0__Bacteria;D_1__Bacteroidetes;D_2__Sphingobacteriia;D_3__Sphingobacteriales;D_4__Chitinophagaceae;D_5__Taibaiella |
| D_0__Bacteria;D_1__Bacteroidetes;D_2__Sphingobacteriia;D_3__Sphingobacteriales;D_4__Chitinophagaceae;D_5__Terrimonas |
| D_0__Bacteria;D_1__Bacteroidetes;D_2__Sphingobacteriia;D_3__Sphingobacteriales;D_4__Chitinophagaceae;D_5__uncultured |
| D_0__Bacteria;D_1__Bacteroidetes;D_2__Sphingobacteriia;D_3__Sphingobacteriales;D_4__Chitinophagaceae;Other |
| D_0__Bacteria;D_1__Bacteroidetes;D_2__Sphingobacteriia;D_3__Sphingobacteriales;D_4__FFCH9454;D_5__uncultured bacterium |
| D_0__Bacteria;D_1__Bacteroidetes;D_2__Sphingobacteriia;D_3__Sphingobacteriales;D_4__KD3-93;D_5__uncultured bacterium |
| D_0__Bacteria;D_1__Bacteroidetes;D_2__Sphingobacteriia;D_3__Sphingobacteriales;D_4__KD3-93;Other |
| D_0__Bacteria;D_1__Bacteroidetes;D_2__Sphingobacteriia;D_3__Sphingobacteriales;D_4__LiUU-11-161;D_5__uncultured Bacteroidetes bacterium |

| |
|---|
| D_0__Bacteria;D_1__Bacteroidetes;D_2__Sphingobacteriia;D_3__Sphingobacteriales;D_4__LiUU-11-161;Other |
| D_0__Bacteria;D_1__Bacteroidetes;D_2__Sphingobacteriia;D_3__Sphingobacteriales;D_4__NS11-12 marine group;D_5__uncultured Bacteroidetes bacterium |
| D_0__Bacteria;D_1__Bacteroidetes;D_2__Sphingobacteriia;D_3__Sphingobacteriales;D_4__NS11-12 marine group;D_5__uncultured bacterium |
| D_0__Bacteria;D_1__Bacteroidetes;D_2__Sphingobacteriia;D_3__Sphingobacteriales;D_4__NS11-12 marine group;Other |
| D_0__Bacteria;D_1__Bacteroidetes;D_2__Sphingobacteriia;D_3__Sphingobacteriales;D_4__PHOS-HE51;D_5__uncultured bacterium |
| D_0__Bacteria;D_1__Bacteroidetes;D_2__Sphingobacteriia;D_3__Sphingobacteriales;D_4__S15-21;D_5__uncultured bacterium |
| D_0__Bacteria;D_1__Bacteroidetes;D_2__Sphingobacteriia;D_3__Sphingobacteriales;D_4__Saprospiraceae;D_5__Aureispira |
| D_0__Bacteria;D_1__Bacteroidetes;D_2__Sphingobacteriia;D_3__Sphingobacteriales;D_4__Saprospiraceae;D_5__uncultured |
| D_0__Bacteria;D_1__Bacteroidetes;D_2__Sphingobacteriia;D_3__Sphingobacteriales;D_4__Sphingobacteriaceae;D_5__Arcticibacter |
| D_0__Bacteria;D_1__Bacteroidetes;D_2__Sphingobacteriia;D_3__Sphingobacteriales;D_4__Sphingobacteriaceae;D_5__Mucilaginibacter |
| D_0__Bacteria;D_1__Bacteroidetes;D_2__Sphingobacteriia;D_3__Sphingobacteriales;D_4__Sphingobacteriaceae;D_5__Nubsella |
| D_0__Bacteria;D_1__Bacteroidetes;D_2__Sphingobacteriia;D_3__Sphingobacteriales;D_4__Sphingobacteriaceae;D_5__Olivibacter |
| D_0__Bacteria;D_1__Bacteroidetes;D_2__Sphingobacteriia;D_3__Sphingobacteriales;D_4__Sphingobacteriaceae;D_5__Pedobacter |
| D_0__Bacteria;D_1__Bacteroidetes;D_2__Sphingobacteriia;D_3__Sphingobacteriales;D_4__Sphingobacteriaceae;D_5__Pseudosphingobacterium |
| D_0__Bacteria;D_1__Bacteroidetes;D_2__Sphingobacteriia;D_3__Sphingobacteriales;D_4__Sphingobacteriaceae;D_5__Solitalea |
| D_0__Bacteria;D_1__Bacteroidetes;D_2__Sphingobacteriia;D_3__Sphingobacteriales;D_4__Sphingobacteriaceae;D_5__Sphingobacterium |
| D_0__Bacteria;D_1__Bacteroidetes;D_2__Sphingobacteriia;D_3__Sphingobacteriales;D_4__Sphingobacteriaceae;D_5__uncultured |
| D_0__Bacteria;D_1__Bacteroidetes;D_2__Sphingobacteriia;D_3__Sphingobacteriales;D_4__Sphingobacteriaceae;Other |
| D_0__Bacteria;D_1__Bacteroidetes;D_2__Sphingobacteriia;D_3__Sphingobacteriales;D_4__WCHB1-69;D_5__uncultured bacterium |
| D_0__Bacteria;D_1__Bacteroidetes;D_2__Sphingobacteriia;D_3__Sphingobacteriales;D_4__WCHB1-69;Other |
| D_0__Bacteria;D_1__Bacteroidetes;D_2__Sphingobacteriia;D_3__Sphingobacteriales;D_4__env.OPS 17;D_5__uncultured Bacteroidetes bacterium |
| D_0__Bacteria;D_1__Bacteroidetes;D_2__Sphingobacteriia;D_3__Sphingobacteriales;D_4__env.OPS 17;D_5__uncultured bacterium |
| D_0__Bacteria;D_1__Bacteroidetes;D_2__Sphingobacteriia;D_3__Sphingobacteriales;Other;Other |
| D_0__Bacteria;D_1__Bacteroidetes;D_2__VC2.1 Bac22;D_3__uncultured bacterium;D_4__;D_5__ |
| D_0__Bacteria;D_1__Bacteroidetes;D_2__WCHB1-32;D_3__uncultured bacterium;D_4__;D_5__ |
| D_0__Bacteria;D_1__Bacteroidetes;D_2__vadinHA17;D_3__uncultured Bacteroidales bacterium;D_4__;D_5__ |
| D_0__Bacteria;D_1__Bacteroidetes;D_2__vadinHA17;D_3__uncultured bacterium;D_4__;D_5__ |
| D_0__Bacteria;D_1__Bacteroidetes;Other;Other;Other;Other |
| D_0__Bacteria;D_1__Candidate division BRC1;D_2__uncultured bacterium;D_3__;D_4__;D_5__ |
| D_0__Bacteria;D_1__Candidate division BRC1;D_2__uncultured organism;D_3__;D_4__;D_5__ |
| D_0__Bacteria;D_1__Candidate division BRC1;Other;Other;Other;Other |
| D_0__Bacteria;D_1__Candidate division OD1;D_2__uncultured Parcubacteria bacterium;D_3__;D_4__;D_5__ |
| D_0__Bacteria;D_1__Candidate division OD1;D_2__uncultured bacterium;D_3__;D_4__;D_5__ |

| |
|---|
| D_0__Bacteria;D_1__Candidate division OD1;D_2__uncultured soil bacterium;D_3__;D_4__;D_5__ |
| D_0__Bacteria;D_1__Candidate division OD1;Other;Other;Other;Other |
| D_0__Bacteria;D_1__Candidate division OP11;D_2__uncultured bacterium;D_3__;D_4__;D_5__ |
| D_0__Bacteria;D_1__Candidate division OP11;D_2__uncultured candidate division WS6 bacterium;D_3__;D_4__;D_5__ |
| D_0__Bacteria;D_1__Candidate division OP11;Other;Other;Other;Other |
| D_0__Bacteria;D_1__Candidate division OP3;D_2__uncultured Omnitrophica bacterium;D_3__;D_4__;D_5__ |
| D_0__Bacteria;D_1__Candidate division OP3;D_2__uncultured bacterium;D_3__;D_4__;D_5__ |
| D_0__Bacteria;D_1__Candidate division SR1;D_2__uncultured bacterium;D_3__;D_4__;D_5__ |
| D_0__Bacteria;D_1__Candidate division TM7;D_2__uncultured bacterium;D_3__;D_4__;D_5__ |
| D_0__Bacteria;D_1__Candidate division TM7;D_2__uncultured soil bacterium;D_3__;D_4__;D_5__ |
| D_0__Bacteria;D_1__Candidate division TM7;Other;Other;Other;Other |
| D_0__Bacteria;D_1__Candidate division WS3;D_2__uncultured bacterium;D_3__;D_4__;D_5__ |
| D_0__Bacteria;D_1__Candidate division WS3;Other;Other;Other;Other |
| D_0__Bacteria;D_1__Chlamydiae;D_2__Chlamydiae;D_3__Chlamydiales;D_4__Chlamydiaceae;D_5__uncultured Chlamydiales bacterium |
| D_0__Bacteria;D_1__Chlamydiae;D_2__Chlamydiae;D_3__Chlamydiales;D_4__Chlamydiaceae;Other |
| D_0__Bacteria;D_1__Chlamydiae;D_2__Chlamydiae;D_3__Chlamydiales;D_4__Parachlamydiaceae;D_5__Candidatus Metachlamydia |
| D_0__Bacteria;D_1__Chlamydiae;D_2__Chlamydiae;D_3__Chlamydiales;D_4__Parachlamydiaceae;D_5__Candidatus Protochlamydia |
| D_0__Bacteria;D_1__Chlamydiae;D_2__Chlamydiae;D_3__Chlamydiales;D_4__Parachlamydiaceae;D_5__Neochlamydia |
| D_0__Bacteria;D_1__Chlamydiae;D_2__Chlamydiae;D_3__Chlamydiales;D_4__Parachlamydiaceae;D_5__Parachlamydia |
| D_0__Bacteria;D_1__Chlamydiae;D_2__Chlamydiae;D_3__Chlamydiales;D_4__Parachlamydiaceae;Other |
| D_0__Bacteria;D_1__Chlamydiae;D_2__Chlamydiae;D_3__Chlamydiales;D_4__Simkaniaceae;D_5__Candidatus Rhabdochlamydia |
| D_0__Bacteria;D_1__Chlamydiae;D_2__Chlamydiae;D_3__Chlamydiales;D_4__Simkaniaceae;Other |
| D_0__Bacteria;D_1__Chlamydiae;D_2__Chlamydiae;D_3__Chlamydiales;D_4__Waddliaceae;D_5__Waddlia |
| D_0__Bacteria;D_1__Chlamydiae;D_2__Chlamydiae;D_3__Chlamydiales;D_4__cvE6;D_5__uncultured bacterium |
| D_0__Bacteria;D_1__Chlamydiae;D_2__Chlamydiae;D_3__Chlamydiales;D_4__cvE6;Other |
| D_0__Bacteria;D_1__Chlamydiae;D_2__Chlamydiae;D_3__Chlamydiales;Other;Other |
| D_0__Bacteria;D_1__Chlorobi;D_2__Chlorobia;D_3__Chlorobiales;D_4__OPB56;D_5__uncultured bacterium |
| D_0__Bacteria;D_1__Chlorobi;D_2__Chlorobia;D_3__Chlorobiales;D_4__SJA-28;D_5__uncultured bacterium |
| D_0__Bacteria;D_1__Chlorobi;D_2__Ignavibacteria;D_3__Ignavibacteriales;D_4__BSV26;D_5__uncultured bacterium |
| D_0__Bacteria;D_1__Chlorobi;D_2__Ignavibacteria;D_3__Ignavibacteriales;D_4__PHOS-HE36;D_5__uncultured bacterium |
| D_0__Bacteria;D_1__Chloroflexi;D_2__Anaerolineae;D_3__Anaerolineales;D_4__Anaerolineaceae;D_5__Anaerolinea |
| D_0__Bacteria;D_1__Chloroflexi;D_2__Anaerolineae;D_3__Anaerolineales;D_4__Anaerolineaceae;D_5__Longilinea |
| D_0__Bacteria;D_1__Chloroflexi;D_2__Anaerolineae;D_3__Anaerolineales;D_4__Anaerolineaceae;D_5__Ornatilinea |
| D_0__Bacteria;D_1__Chloroflexi;D_2__Anaerolineae;D_3__Anaerolineales;D_4__Anaerolineaceae |

| |
|---|
| ;D_5__uncultured |
| D_0__Bacteria;D_1__Chloroflexi;D_2__Anaerolineae;D_3__Anaerolineales;D_4__Anaerolineaceae;Other |
| D_0__Bacteria;D_1__Chloroflexi;D_2__Ardenticatenia;D_3__Ardenticatenales;D_4__uncultured bacterium;D_5__ |
| D_0__Bacteria;D_1__Chloroflexi;D_2__Ardenticatenia;D_3__Ardenticatenales;Other;Other |
| D_0__Bacteria;D_1__Chloroflexi;D_2__Ardenticatenia;D_3__uncultured;D_4__uncultured Chloroflexi bacterium;D_5__ |
| D_0__Bacteria;D_1__Chloroflexi;D_2__Ardenticatenia;D_3__uncultured;D_4__uncultured bacterium;D_5__ |
| D_0__Bacteria;D_1__Chloroflexi;D_2__Caldilineae;D_3__Caldilineales;D_4__Caldilineaceae;D_5__Litorilinea |
| D_0__Bacteria;D_1__Chloroflexi;D_2__Caldilineae;D_3__Caldilineales;D_4__Caldilineaceae;D_5__uncultured |
| D_0__Bacteria;D_1__Chloroflexi;D_2__Chloroflexia;D_3__AKIW781;D_4__uncultured bacterium;D_5__ |
| D_0__Bacteria;D_1__Chloroflexi;D_2__Chloroflexia;D_3__AKIW781;Other;Other |
| D_0__Bacteria;D_1__Chloroflexi;D_2__Chloroflexia;D_3__Chloroflexales;D_4__Chloroflexaceae;D_5__Chloroflexus |
| D_0__Bacteria;D_1__Chloroflexi;D_2__Chloroflexia;D_3__Chloroflexales;D_4__Chloroflexaceae;D_5__Chloronema |
| D_0__Bacteria;D_1__Chloroflexi;D_2__Chloroflexia;D_3__Chloroflexales;D_4__Chloroflexales Incertae Sedis;D_5__Candidatus Chlorothrix |
| D_0__Bacteria;D_1__Chloroflexi;D_2__Chloroflexia;D_3__Chloroflexales;D_4__FFCH7168;D_5__uncultured bacterium |
| D_0__Bacteria;D_1__Chloroflexi;D_2__Chloroflexia;D_3__Chloroflexales;D_4__Oscillochloridaceae;D_5__Oscillochloris |
| D_0__Bacteria;D_1__Chloroflexi;D_2__Chloroflexia;D_3__Chloroflexales;D_4__Roseiflexaceae;D_5__Roseiflexus |
| D_0__Bacteria;D_1__Chloroflexi;D_2__Chloroflexia;D_3__Herpetosiphonales;D_4__Herpetosiphonaceae;D_5__Herpetosiphon |
| D_0__Bacteria;D_1__Chloroflexi;D_2__Elev-1554;D_3__uncultured bacterium;D_4__;D_5__ |
| D_0__Bacteria;D_1__Chloroflexi;D_2__Gitt-GS-136;D_3__uncultured bacterium;D_4__;D_5__ |
| D_0__Bacteria;D_1__Chloroflexi;D_2__Gitt-GS-136;Other;Other;Other |
| D_0__Bacteria;D_1__Chloroflexi;D_2__JG30-KF-CM66;D_3__uncultured Chloroflexi bacterium;D_4__;D_5__ |
| D_0__Bacteria;D_1__Chloroflexi;D_2__JG30-KF-CM66;D_3__uncultured bacterium;D_4__;D_5__ |
| D_0__Bacteria;D_1__Chloroflexi;D_2__JG30-KF-CM66;D_3__uncultured soil bacterium;D_4__;D_5__ |
| D_0__Bacteria;D_1__Chloroflexi;D_2__JG30-KF-CM66;Other;Other;Other |
| D_0__Bacteria;D_1__Chloroflexi;D_2__JG37-AG-4;D_3__uncultured Chloroflexi bacterium;D_4__;D_5__ |
| D_0__Bacteria;D_1__Chloroflexi;D_2__JG37-AG-4;D_3__uncultured bacterium;D_4__;D_5__ |
| D_0__Bacteria;D_1__Chloroflexi;D_2__JG37-AG-4;Other;Other;Other |
| D_0__Bacteria;D_1__Chloroflexi;D_2__KD4-96;D_3__bacterium Ellin6529;D_4__;D_5__ |
| D_0__Bacteria;D_1__Chloroflexi;D_2__KD4-96;D_3__uncultured Chloroflexi bacterium;D_4__;D_5__ |
| D_0__Bacteria;D_1__Chloroflexi;D_2__KD4-96;D_3__uncultured bacterium;D_4__;D_5__ |
| D_0__Bacteria;D_1__Chloroflexi;D_2__KD4-96;Other;Other;Other |
| D_0__Bacteria;D_1__Chloroflexi;D_2__Ktedonobacteria;D_3__B10-SB3A;D_4__uncultured bacterium;D_5__ |
| D_0__Bacteria;D_1__Chloroflexi;D_2__Ktedonobacteria;D_3__B12-WMSP1;D_4__uncultured bacterium;D_5__ |
| D_0__Bacteria;D_1__Chloroflexi;D_2__Ktedonobacteria;D_3__C0119;D_4__uncultured |

| |
|---|
| Chloroflexi bacterium;D_5__ |
| D_0__Bacteria;D_1__Chloroflexi;D_2__Ktedonobacteria;D_3__C0119;D_4__uncultured bacterium;D_5__ |
| D_0__Bacteria;D_1__Chloroflexi;D_2__Ktedonobacteria;D_3__C0119;D_4__uncultured soil bacterium;D_5__ |
| D_0__Bacteria;D_1__Chloroflexi;D_2__Ktedonobacteria;D_3__C0119;Other;Other |
| D_0__Bacteria;D_1__Chloroflexi;D_2__Ktedonobacteria;D_3__JG30-KF-AS9;D_4__uncultured bacterium;D_5__ |
| D_0__Bacteria;D_1__Chloroflexi;D_2__Ktedonobacteria;D_3__JG30-KF-AS9;Other;Other |
| D_0__Bacteria;D_1__Chloroflexi;D_2__Ktedonobacteria;D_3__Ktedonobacterales;D_4__1921-3;D_5__uncultured bacterium |
| D_0__Bacteria;D_1__Chloroflexi;D_2__Ktedonobacteria;D_3__Ktedonobacterales;D_4__1921-3;Other |
| D_0__Bacteria;D_1__Chloroflexi;D_2__Ktedonobacteria;D_3__Ktedonobacterales;D_4__1959-1;D_5__uncultured bacterium |
| D_0__Bacteria;D_1__Chloroflexi;D_2__Ktedonobacteria;D_3__Ktedonobacterales;D_4__BacC-u-018;D_5__uncultured bacterium |
| D_0__Bacteria;D_1__Chloroflexi;D_2__Ktedonobacteria;D_3__Ktedonobacterales;D_4__FCPS473;D_5__uncultured Ktedonobacter sp. |
| D_0__Bacteria;D_1__Chloroflexi;D_2__Ktedonobacteria;D_3__Ktedonobacterales;D_4__FCPS473;D_5__uncultured bacterium |
| D_0__Bacteria;D_1__Chloroflexi;D_2__Ktedonobacteria;D_3__Ktedonobacterales;D_4__FCPS473;Other |
| D_0__Bacteria;D_1__Chloroflexi;D_2__Ktedonobacteria;D_3__Ktedonobacterales;D_4__G12-WMSP1;D_5__uncultured Chloroflexi bacterium |
| D_0__Bacteria;D_1__Chloroflexi;D_2__Ktedonobacteria;D_3__Ktedonobacterales;D_4__G12-WMSP1;D_5__uncultured bacterium |
| D_0__Bacteria;D_1__Chloroflexi;D_2__Ktedonobacteria;D_3__Ktedonobacterales;D_4__HSB OF53-F07;D_5__uncultured Ktedonobacter sp. |
| D_0__Bacteria;D_1__Chloroflexi;D_2__Ktedonobacteria;D_3__Ktedonobacterales;D_4__HSB OF53-F07;D_5__uncultured bacterium |
| D_0__Bacteria;D_1__Chloroflexi;D_2__Ktedonobacteria;D_3__Ktedonobacterales;D_4__HSB OF53-F07;Other |
| D_0__Bacteria;D_1__Chloroflexi;D_2__Ktedonobacteria;D_3__Ktedonobacterales;D_4__JG30a-KF-32;D_5__uncultured Ktedobacteria bacterium |
| D_0__Bacteria;D_1__Chloroflexi;D_2__Ktedonobacteria;D_3__Ktedonobacterales;D_4__JG30a-KF-32;D_5__uncultured bacterium |
| D_0__Bacteria;D_1__Chloroflexi;D_2__Ktedonobacteria;D_3__Ktedonobacterales;D_4__JG30a-KF-32;Other |
| D_0__Bacteria;D_1__Chloroflexi;D_2__Ktedonobacteria;D_3__Ktedonobacterales;D_4__Ktedonobacteraceae;D_5__Ktedonobacter |
| D_0__Bacteria;D_1__Chloroflexi;D_2__Ktedonobacteria;D_3__Ktedonobacterales;D_4__Ktedonobacteraceae;D_5__uncultured |
| D_0__Bacteria;D_1__Chloroflexi;D_2__Ktedonobacteria;D_3__Ktedonobacterales;D_4__Ktedonobacteraceae;Other |
| D_0__Bacteria;D_1__Chloroflexi;D_2__Ktedonobacteria;D_3__Ktedonobacterales;D_4__Thermosporotrichaceae;D_5__Thermosporothrix |
| D_0__Bacteria;D_1__Chloroflexi;D_2__Ktedonobacteria;D_3__Ktedonobacterales;D_4__Thermosporotrichaceae;D_5__uncultured |
| D_0__Bacteria;D_1__Chloroflexi;D_2__Ktedonobacteria;D_3__Ktedonobacterales;Other;Other |
| D_0__Bacteria;D_1__Chloroflexi;D_2__Ktedonobacteria;D_3__Thermogemmatisporales;D_4__1921-2;D_5__uncultured Ktedobacteria bacterium |
| D_0__Bacteria;D_1__Chloroflexi;D_2__Ktedonobacteria;D_3__Thermogemmatisporales;D_4__1921-2;D_5__uncultured bacterium |
| D_0__Bacteria;D_1__Chloroflexi;D_2__P2-11E;D_3__uncultured bacterium;D_4__;D_5__ |
| D_0__Bacteria;D_1__Chloroflexi;D_2__S085;D_3__uncultured Chloroflexi bacterium;D_4__;D_5__ |
| D_0__Bacteria;D_1__Chloroflexi;D_2__S085;D_3__uncultured bacterium;D_4__;D_5__ |

```
D_0__Bacteria;D_1__Chloroflexi;D_2__SAR202 clade;D_3__uncultured bacterium;D_4__;D_5__
D_0__Bacteria;D_1__Chloroflexi;D_2__SAR202 clade;Other;Other;Other
D_0__Bacteria;D_1__Chloroflexi;D_2__SHA-26;D_3__uncultured bacterium;D_4__;D_5__
D_0__Bacteria;D_1__Chloroflexi;D_2__TK10;D_3__bacterium Ellin6543;D_4__;D_5__
D_0__Bacteria;D_1__Chloroflexi;D_2__TK10;D_3__uncultured Chloroflexi bacterium;D_4__;D_5__
D_0__Bacteria;D_1__Chloroflexi;D_2__TK10;D_3__uncultured bacterium;D_4__;D_5__
D_0__Bacteria;D_1__Chloroflexi;D_2__TK10;D_3__uncultured soil bacterium;D_4__;D_5__
D_0__Bacteria;D_1__Chloroflexi;D_2__TK10;Other;Other;Other
D_0__Bacteria;D_1__Chloroflexi;D_2__Thermomicrobia;D_3__AKYG1722;D_4__uncultured bacterium;D_5__
D_0__Bacteria;D_1__Chloroflexi;D_2__Thermomicrobia;D_3__AKYG1722;Other;Other
D_0__Bacteria;D_1__Chloroflexi;D_2__Thermomicrobia;D_3__JG30-KF-CM45;D_4__uncultured Chloroflexi bacterium;D_5__
D_0__Bacteria;D_1__Chloroflexi;D_2__Thermomicrobia;D_3__JG30-KF-CM45;D_4__uncultured Thermomicrobia bacterium;D_5__
D_0__Bacteria;D_1__Chloroflexi;D_2__Thermomicrobia;D_3__JG30-KF-CM45;D_4__uncultured bacterium;D_5__
D_0__Bacteria;D_1__Chloroflexi;D_2__Thermomicrobia;D_3__JG30-KF-CM45;Other;Other
D_0__Bacteria;D_1__Chloroflexi;D_2__Thermomicrobia;D_3__Sphaerobacterales;D_4__Sphaerobacteraceae;D_5__Nitrolancea
D_0__Bacteria;D_1__Chloroflexi;D_2__Thermomicrobia;D_3__Sphaerobacterales;D_4__Sphaerobacteraceae;Other
D_0__Bacteria;D_1__Chloroflexi;D_2__uncultured;D_3__uncultured Chloroflexi bacterium;D_4__;D_5__
D_0__Bacteria;D_1__Chloroflexi;D_2__uncultured;D_3__uncultured bacterium;D_4__;D_5__
D_0__Bacteria;D_1__Chloroflexi;D_2__uncultured;D_3__uncultured soil bacterium;D_4__;D_5__
D_0__Bacteria;D_1__Chloroflexi;D_2__uncultured Bellilinea sp.;D_3__;D_4__;D_5__
D_0__Bacteria;D_1__Chloroflexi;Other;Other;Other;Other
D_0__Bacteria;D_1__Cyanobacteria;D_2__Cyanobacteria;D_3__SubsectionI;D_4__FamilyI;D_5__Synechococcus
D_0__Bacteria;D_1__Cyanobacteria;D_2__Cyanobacteria;D_3__SubsectionII;D_4__FamilyII;D_5__Chroococcidiopsis
D_0__Bacteria;D_1__Cyanobacteria;D_2__Cyanobacteria;D_3__SubsectionII;D_4__FamilyII;D_5__Pleurocapsa
D_0__Bacteria;D_1__Cyanobacteria;D_2__Cyanobacteria;D_3__SubsectionIII;D_4__FamilyI;D_5__Crinalium
D_0__Bacteria;D_1__Cyanobacteria;D_2__Cyanobacteria;D_3__SubsectionIII;D_4__FamilyI;D_5__Leptolyngbya
D_0__Bacteria;D_1__Cyanobacteria;D_2__Cyanobacteria;D_3__SubsectionIII;D_4__FamilyI;D_5__Microcoleus
D_0__Bacteria;D_1__Cyanobacteria;D_2__Cyanobacteria;D_3__SubsectionIII;D_4__FamilyI;D_5__Phormidium
D_0__Bacteria;D_1__Cyanobacteria;D_2__Cyanobacteria;D_3__SubsectionIII;D_4__FamilyI;D_5__Planktothrix
D_0__Bacteria;D_1__Cyanobacteria;D_2__Cyanobacteria;D_3__SubsectionIII;D_4__FamilyI;D_5__uncultured
D_0__Bacteria;D_1__Cyanobacteria;D_2__Cyanobacteria;D_3__SubsectionIII;D_4__FamilyI;Other
D_0__Bacteria;D_1__Cyanobacteria;D_2__Cyanobacteria;D_3__SubsectionIV;D_4__FamilyI;D_5__Anabaena
D_0__Bacteria;D_1__Cyanobacteria;D_2__Cyanobacteria;D_3__SubsectionIV;D_4__FamilyI;D_5__Gloeotrichia
D_0__Bacteria;D_1__Cyanobacteria;D_2__Cyanobacteria;D_3__SubsectionIV;D_4__FamilyI;D_5__Nodularia
```

| |
|---|
| D_0__Bacteria;D_1__Cyanobacteria;D_2__Cyanobacteria;D_3__SubsectionIV;D_4__FamilyI;D_5__Nostoc |
| D_0__Bacteria;D_1__Cyanobacteria;D_2__Cyanobacteria;D_3__SubsectionIV;D_4__FamilyI;D_5__Trichormus |
| D_0__Bacteria;D_1__Cyanobacteria;D_2__Cyanobacteria;D_3__SubsectionIV;D_4__FamilyI;Other |
| D_0__Bacteria;D_1__Cyanobacteria;D_2__Cyanobacteria;D_3__SubsectionIV;D_4__FamilyII;D_5__Calothrix |
| D_0__Bacteria;D_1__Cyanobacteria;D_2__Cyanobacteria;D_3__uncultured;D_4__uncultured bacterium;D_5__ |
| D_0__Bacteria;D_1__Cyanobacteria;D_2__Cyanobacteria;D_3__uncultured bacterium;D_4__;D_5__ |
| D_0__Bacteria;D_1__Cyanobacteria;D_2__ML635J-21;D_3__uncultured bacterium;D_4__;D_5__ |
| D_0__Bacteria;D_1__Cyanobacteria;D_2__ML635J-21;D_3__uncultured cyanobacterium;D_4__;D_5__ |
| D_0__Bacteria;D_1__Cyanobacteria;D_2__ML635J-21;Other;Other;Other |
| D_0__Bacteria;D_1__Cyanobacteria;D_2__Melainabacteria;D_3__Obscuribacterales;D_4__uncultured Gloeobacter sp.;D_5__ |
| D_0__Bacteria;D_1__Cyanobacteria;D_2__Melainabacteria;D_3__Obscuribacterales;D_4__uncultured bacterium;D_5__ |
| D_0__Bacteria;D_1__Cyanobacteria;D_2__Melainabacteria;D_3__Obscuribacterales;D_4__uncultured cyanobacterium;D_5__ |
| D_0__Bacteria;D_1__Cyanobacteria;D_2__Melainabacteria;D_3__Vampirovibrionales;D_4__uncultured bacterium;D_5__ |
| D_0__Bacteria;D_1__Cyanobacteria;D_2__Melainabacteria;D_3__Vampirovibrionales;Other;Other |
| D_0__Bacteria;D_1__Deferribacteres;D_2__Deferribacteres;D_3__Deferribacterales;D_4__Deferribacterales Incertae Sedis;D_5__Caldithrix |
| D_0__Bacteria;D_1__Deinococcus-Thermus;D_2__Deinococci;D_3__Deinococcales;D_4__Deinococcaceae;D_5__Deinococcus |
| D_0__Bacteria;D_1__Deinococcus-Thermus;D_2__Deinococci;D_3__Deinococcales;D_4__Trueperaceae;D_5__Truepera |
| D_0__Bacteria;D_1__Deinococcus-Thermus;D_2__Deinococci;D_3__KD3-62;D_4__uncultured bacterium;D_5__ |
| D_0__Bacteria;D_1__Deinococcus-Thermus;D_2__Deinococci;D_3__Thermales;D_4__Thermaceae;D_5__Thermus |
| D_0__Bacteria;D_1__Elusimicrobia;D_2__Elusimicrobia;D_3__FCPU453;Other;Other |
| D_0__Bacteria;D_1__Elusimicrobia;D_2__Elusimicrobia;D_3__Lineage IIa;D_4__uncultured bacterium;D_5__ |
| D_0__Bacteria;D_1__Elusimicrobia;D_2__Elusimicrobia;D_3__Lineage IIa;Other;Other |
| D_0__Bacteria;D_1__Elusimicrobia;D_2__Elusimicrobia;D_3__Lineage IIb;D_4__uncultured bacterium;D_5__ |
| D_0__Bacteria;D_1__Elusimicrobia;D_2__Elusimicrobia;D_3__Lineage IIb;Other;Other |
| D_0__Bacteria;D_1__Elusimicrobia;D_2__Elusimicrobia;D_3__Lineage IIc;D_4__uncultured bacterium;D_5__ |
| D_0__Bacteria;D_1__Elusimicrobia;D_2__Elusimicrobia;D_3__Lineage IV;D_4__uncultured bacterium;D_5__ |
| D_0__Bacteria;D_1__Elusimicrobia;D_2__Elusimicrobia;D_3__MVP-88;D_4__uncultured bacterium;D_5__ |
| D_0__Bacteria;D_1__Elusimicrobia;D_2__Elusimicrobia;D_3__MVP-88;Other;Other |
| D_0__Bacteria;D_1__Fibrobacteres;D_2__Fibrobacteria;D_3__Fibrobacterales;D_4__Fibrobacteraceae;D_5__possible genus 04 |
| D_0__Bacteria;D_1__Fibrobacteres;D_2__Fibrobacteria;D_3__Fibrobacterales;D_4__Fibrobacteraceae;D_5__uncultured |
| D_0__Bacteria;D_1__Fibrobacteres;D_2__Fibrobacteria;D_3__Fibrobacterales;D_4__possible family 01;D_5__uncultured bacterium |
| D_0__Bacteria;D_1__Firmicutes;D_2__Bacilli;D_3__Bacillales;D_4__Alicyclobacillaceae;D_5__Alicyclobacillus |
| D_0__Bacteria;D_1__Firmicutes;D_2__Bacilli;D_3__Bacillales;D_4__Alicyclobacillaceae;D_5__Tumebacillus |

| |
|---|
| D_0__Bacteria;D_1__Firmicutes;D_2__Bacilli;D_3__Bacillales;D_4__Alicyclobacillaceae;Other |
| D_0__Bacteria;D_1__Firmicutes;D_2__Bacilli;D_3__Bacillales;D_4__Bacillaceae;D_5__Aeribacillus |
| D_0__Bacteria;D_1__Firmicutes;D_2__Bacilli;D_3__Bacillales;D_4__Bacillaceae;D_5__Amphibacillus |
| D_0__Bacteria;D_1__Firmicutes;D_2__Bacilli;D_3__Bacillales;D_4__Bacillaceae;D_5__Anaerobacillus |
| D_0__Bacteria;D_1__Firmicutes;D_2__Bacilli;D_3__Bacillales;D_4__Bacillaceae;D_5__Anoxybacillus |
| D_0__Bacteria;D_1__Firmicutes;D_2__Bacilli;D_3__Bacillales;D_4__Bacillaceae;D_5__Bacillus |
| D_0__Bacteria;D_1__Firmicutes;D_2__Bacilli;D_3__Bacillales;D_4__Bacillaceae;D_5__Caldalkalibacillus |
| D_0__Bacteria;D_1__Firmicutes;D_2__Bacilli;D_3__Bacillales;D_4__Bacillaceae;D_5__Caldibacillus |
| D_0__Bacteria;D_1__Firmicutes;D_2__Bacilli;D_3__Bacillales;D_4__Bacillaceae;D_5__Cerasibacillus |
| D_0__Bacteria;D_1__Firmicutes;D_2__Bacilli;D_3__Bacillales;D_4__Bacillaceae;D_5__Fictibacillus |
| D_0__Bacteria;D_1__Firmicutes;D_2__Bacilli;D_3__Bacillales;D_4__Bacillaceae;D_5__Geobacillus |
| D_0__Bacteria;D_1__Firmicutes;D_2__Bacilli;D_3__Bacillales;D_4__Bacillaceae;D_5__Gracilibacillus |
| D_0__Bacteria;D_1__Firmicutes;D_2__Bacilli;D_3__Bacillales;D_4__Bacillaceae;D_5__Halobacillus |
| D_0__Bacteria;D_1__Firmicutes;D_2__Bacilli;D_3__Bacillales;D_4__Bacillaceae;D_5__Halolactibacillus |
| D_0__Bacteria;D_1__Firmicutes;D_2__Bacilli;D_3__Bacillales;D_4__Bacillaceae;D_5__Lentibacillus |
| D_0__Bacteria;D_1__Firmicutes;D_2__Bacilli;D_3__Bacillales;D_4__Bacillaceae;D_5__Oceanobacillus |
| D_0__Bacteria;D_1__Firmicutes;D_2__Bacilli;D_3__Bacillales;D_4__Bacillaceae;D_5__Paucisalibacillus |
| D_0__Bacteria;D_1__Firmicutes;D_2__Bacilli;D_3__Bacillales;D_4__Bacillaceae;D_5__Sediminibacillus |
| D_0__Bacteria;D_1__Firmicutes;D_2__Bacilli;D_3__Bacillales;D_4__Bacillaceae;D_5__Terribacillus |
| D_0__Bacteria;D_1__Firmicutes;D_2__Bacilli;D_3__Bacillales;D_4__Bacillaceae;D_5__Ureibacillus |
| D_0__Bacteria;D_1__Firmicutes;D_2__Bacilli;D_3__Bacillales;D_4__Bacillaceae;D_5__Virgibacillus |
| D_0__Bacteria;D_1__Firmicutes;D_2__Bacilli;D_3__Bacillales;D_4__Bacillaceae;D_5__uncultured |
| D_0__Bacteria;D_1__Firmicutes;D_2__Bacilli;D_3__Bacillales;D_4__Bacillaceae;Other |
| D_0__Bacteria;D_1__Firmicutes;D_2__Bacilli;D_3__Bacillales;D_4__Family XI;D_5__Gemella |
| D_0__Bacteria;D_1__Firmicutes;D_2__Bacilli;D_3__Bacillales;D_4__Family XII;D_5__Exiguobacterium |
| D_0__Bacteria;D_1__Firmicutes;D_2__Bacilli;D_3__Bacillales;D_4__Family XII;D_5__Incertae Sedis |
| D_0__Bacteria;D_1__Firmicutes;D_2__Bacilli;D_3__Bacillales;D_4__Family XII;Other |
| D_0__Bacteria;D_1__Firmicutes;D_2__Bacilli;D_3__Bacillales;D_4__Listeriaceae;D_5__Brochothrix |
| D_0__Bacteria;D_1__Firmicutes;D_2__Bacilli;D_3__Bacillales;D_4__Paenibacillaceae;D_5__Aneurinibacillus |
| D_0__Bacteria;D_1__Firmicutes;D_2__Bacilli;D_3__Bacillales;D_4__Paenibacillaceae;D_5__Brevibacillus |
| D_0__Bacteria;D_1__Firmicutes;D_2__Bacilli;D_3__Bacillales;D_4__Paenibacillaceae;D_5__Cohnella |
| D_0__Bacteria;D_1__Firmicutes;D_2__Bacilli;D_3__Bacillales;D_4__Paenibacillaceae;D_5__Oxalophagus |

| |
|---|
| D_0__Bacteria;D_1__Firmicutes;D_2__Bacilli;D_3__Bacillales;D_4__Paenibacillaceae;D_5__Paenibacillus |
| D_0__Bacteria;D_1__Firmicutes;D_2__Bacilli;D_3__Bacillales;D_4__Paenibacillaceae;D_5__Saccharibacillus |
| D_0__Bacteria;D_1__Firmicutes;D_2__Bacilli;D_3__Bacillales;D_4__Paenibacillaceae;D_5__Thermobacillus |
| D_0__Bacteria;D_1__Firmicutes;D_2__Bacilli;D_3__Bacillales;D_4__Paenibacillaceae;D_5__uncultured |
| D_0__Bacteria;D_1__Firmicutes;D_2__Bacilli;D_3__Bacillales;D_4__Paenibacillaceae;D_5__uncultured bacterium |
| D_0__Bacteria;D_1__Firmicutes;D_2__Bacilli;D_3__Bacillales;D_4__Paenibacillaceae;Other |
| D_0__Bacteria;D_1__Firmicutes;D_2__Bacilli;D_3__Bacillales;D_4__Pasteuriaceae;D_5__Pasteuria |
| D_0__Bacteria;D_1__Firmicutes;D_2__Bacilli;D_3__Bacillales;D_4__Planococcaceae;D_5__Chungangia |
| D_0__Bacteria;D_1__Firmicutes;D_2__Bacilli;D_3__Bacillales;D_4__Planococcaceae;D_5__Incertae Sedis |
| D_0__Bacteria;D_1__Firmicutes;D_2__Bacilli;D_3__Bacillales;D_4__Planococcaceae;D_5__Jeotgalibacillus |
| D_0__Bacteria;D_1__Firmicutes;D_2__Bacilli;D_3__Bacillales;D_4__Planococcaceae;D_5__Lysinibacillus |
| D_0__Bacteria;D_1__Firmicutes;D_2__Bacilli;D_3__Bacillales;D_4__Planococcaceae;D_5__Paenisporosarcina |
| D_0__Bacteria;D_1__Firmicutes;D_2__Bacilli;D_3__Bacillales;D_4__Planococcaceae;D_5__Planococcus |
| D_0__Bacteria;D_1__Firmicutes;D_2__Bacilli;D_3__Bacillales;D_4__Planococcaceae;D_5__Planomicrobium |
| D_0__Bacteria;D_1__Firmicutes;D_2__Bacilli;D_3__Bacillales;D_4__Planococcaceae;D_5__Solibacillus |
| D_0__Bacteria;D_1__Firmicutes;D_2__Bacilli;D_3__Bacillales;D_4__Planococcaceae;D_5__Sporosarcina |
| D_0__Bacteria;D_1__Firmicutes;D_2__Bacilli;D_3__Bacillales;D_4__Planococcaceae;D_5__uncultured |
| D_0__Bacteria;D_1__Firmicutes;D_2__Bacilli;D_3__Bacillales;D_4__Planococcaceae;Other |
| D_0__Bacteria;D_1__Firmicutes;D_2__Bacilli;D_3__Bacillales;D_4__Sporolactobacillaceae;D_5__Pullulanibacillus |
| D_0__Bacteria;D_1__Firmicutes;D_2__Bacilli;D_3__Bacillales;D_4__Sporolactobacillaceae;D_5__Sporolactobacillus |
| D_0__Bacteria;D_1__Firmicutes;D_2__Bacilli;D_3__Bacillales;D_4__Sporolactobacillaceae;D_5__Tuberibacillus |
| D_0__Bacteria;D_1__Firmicutes;D_2__Bacilli;D_3__Bacillales;D_4__Staphylococcaceae;D_5__Jeotgalicoccus |
| D_0__Bacteria;D_1__Firmicutes;D_2__Bacilli;D_3__Bacillales;D_4__Staphylococcaceae;D_5__Nosocomiicoccus |
| D_0__Bacteria;D_1__Firmicutes;D_2__Bacilli;D_3__Bacillales;D_4__Staphylococcaceae;D_5__Salinicoccus |
| D_0__Bacteria;D_1__Firmicutes;D_2__Bacilli;D_3__Bacillales;D_4__Staphylococcaceae;D_5__Staphylococcus |
| D_0__Bacteria;D_1__Firmicutes;D_2__Bacilli;D_3__Bacillales;D_4__Staphylococcaceae;D_5__uncultured |
| D_0__Bacteria;D_1__Firmicutes;D_2__Bacilli;D_3__Bacillales;D_4__Staphylococcaceae;Other |
| D_0__Bacteria;D_1__Firmicutes;D_2__Bacilli;D_3__Bacillales;D_4__Thermoactinomycetaceae;D_5__Hazenella |
| D_0__Bacteria;D_1__Firmicutes;D_2__Bacilli;D_3__Bacillales;D_4__Thermoactinomycetaceae;D_5__Kroppenstedtia |
| D_0__Bacteria;D_1__Firmicutes;D_2__Bacilli;D_3__Bacillales;D_4__Thermoactinomycetaceae;D_5__Laceyella |
| D_0__Bacteria;D_1__Firmicutes;D_2__Bacilli;D_3__Bacillales;D_4__Thermoactinomycetaceae;D_5__Marininema |
| D_0__Bacteria;D_1__Firmicutes;D_2__Bacilli;D_3__Bacillales;D_4__Thermoactinomycetaceae;D_5__Melghirimyces |

| |
|---|
| D_0__Bacteria;D_1__Firmicutes;D_2__Bacilli;D_3__Bacillales;D_4__Thermoactinomycetaceae;D_5__Planifilum |
| D_0__Bacteria;D_1__Firmicutes;D_2__Bacilli;D_3__Bacillales;D_4__Thermoactinomycetaceae;D_5__Polycladomyces |
| D_0__Bacteria;D_1__Firmicutes;D_2__Bacilli;D_3__Bacillales;D_4__Thermoactinomycetaceae;D_5__Seinonella |
| D_0__Bacteria;D_1__Firmicutes;D_2__Bacilli;D_3__Bacillales;D_4__Thermoactinomycetaceae;D_5__Shimazuella |
| D_0__Bacteria;D_1__Firmicutes;D_2__Bacilli;D_3__Bacillales;D_4__Thermoactinomycetaceae;D_5__Thermoactinomyces |
| D_0__Bacteria;D_1__Firmicutes;D_2__Bacilli;D_3__Bacillales;D_4__Thermoactinomycetaceae;D_5__Thermoflavimicrobium |
| D_0__Bacteria;D_1__Firmicutes;D_2__Bacilli;D_3__Bacillales;D_4__Thermoactinomycetaceae;D_5__uncultured |
| D_0__Bacteria;D_1__Firmicutes;D_2__Bacilli;D_3__Bacillales;D_4__Thermoactinomycetaceae;Other |
| D_0__Bacteria;D_1__Firmicutes;D_2__Bacilli;D_3__Bacillales;D_4__uncultured;D_5__uncultured bacterium |
| D_0__Bacteria;D_1__Firmicutes;D_2__Bacilli;D_3__Bacillales;Other;Other |
| D_0__Bacteria;D_1__Firmicutes;D_2__Bacilli;D_3__C178B;D_4__uncultured compost bacterium;D_5__ |
| D_0__Bacteria;D_1__Firmicutes;D_2__Bacilli;D_3__C178B;Other;Other |
| D_0__Bacteria;D_1__Firmicutes;D_2__Bacilli;D_3__Lactobacillales;D_4__Aerococcaceae;D_5__Abiotrophia |
| D_0__Bacteria;D_1__Firmicutes;D_2__Bacilli;D_3__Lactobacillales;D_4__Aerococcaceae;D_5__Aerococcus |
| D_0__Bacteria;D_1__Firmicutes;D_2__Bacilli;D_3__Lactobacillales;D_4__Aerococcaceae;D_5__Eremococcus |
| D_0__Bacteria;D_1__Firmicutes;D_2__Bacilli;D_3__Lactobacillales;D_4__Aerococcaceae;D_5__Facklamia |
| D_0__Bacteria;D_1__Firmicutes;D_2__Bacilli;D_3__Lactobacillales;D_4__Aerococcaceae;D_5__Globicatella |
| D_0__Bacteria;D_1__Firmicutes;D_2__Bacilli;D_3__Lactobacillales;D_4__Aerococcaceae;D_5__uncultured |
| D_0__Bacteria;D_1__Firmicutes;D_2__Bacilli;D_3__Lactobacillales;D_4__Carnobacteriaceae;D_5__Alkalibacterium |
| D_0__Bacteria;D_1__Firmicutes;D_2__Bacilli;D_3__Lactobacillales;D_4__Carnobacteriaceae;D_5__Alloiococcus |
| D_0__Bacteria;D_1__Firmicutes;D_2__Bacilli;D_3__Lactobacillales;D_4__Carnobacteriaceae;D_5__Atopostipes |
| D_0__Bacteria;D_1__Firmicutes;D_2__Bacilli;D_3__Lactobacillales;D_4__Carnobacteriaceae;D_5__Carnobacterium |
| D_0__Bacteria;D_1__Firmicutes;D_2__Bacilli;D_3__Lactobacillales;D_4__Carnobacteriaceae;D_5__Desemzia |
| D_0__Bacteria;D_1__Firmicutes;D_2__Bacilli;D_3__Lactobacillales;D_4__Carnobacteriaceae;D_5__Dolosigranulum |
| D_0__Bacteria;D_1__Firmicutes;D_2__Bacilli;D_3__Lactobacillales;D_4__Carnobacteriaceae;D_5__Marinilactibacillus |
| D_0__Bacteria;D_1__Firmicutes;D_2__Bacilli;D_3__Lactobacillales;D_4__Carnobacteriaceae;D_5__Trichococcus |
| D_0__Bacteria;D_1__Firmicutes;D_2__Bacilli;D_3__Lactobacillales;D_4__Carnobacteriaceae;D_5__uncultured |
| D_0__Bacteria;D_1__Firmicutes;D_2__Bacilli;D_3__Lactobacillales;D_4__Carnobacteriaceae;Other |
| D_0__Bacteria;D_1__Firmicutes;D_2__Bacilli;D_3__Lactobacillales;D_4__Enterococcaceae;D_5__Bavariicoccus |
| D_0__Bacteria;D_1__Firmicutes;D_2__Bacilli;D_3__Lactobacillales;D_4__Enterococcaceae;D_5__Enterococcus |
| D_0__Bacteria;D_1__Firmicutes;D_2__Bacilli;D_3__Lactobacillales;D_4__Lactobacillaceae;D_5__Lactobacillus |
| D_0__Bacteria;D_1__Firmicutes;D_2__Bacilli;D_3__Lactobacillales;D_4__Lactobacillaceae;D_5__Pediococcus |

| |
|---|
| D_0__Bacteria;D_1__Firmicutes;D_2__Bacilli;D_3__Lactobacillales;D_4__Lactobacillaceae;Other |
| D_0__Bacteria;D_1__Firmicutes;D_2__Bacilli;D_3__Lactobacillales;D_4__Leuconostocaceae;D_5__Fructobacillus |
| D_0__Bacteria;D_1__Firmicutes;D_2__Bacilli;D_3__Lactobacillales;D_4__Leuconostocaceae;D_5__Leuconostoc |
| D_0__Bacteria;D_1__Firmicutes;D_2__Bacilli;D_3__Lactobacillales;D_4__Leuconostocaceae;D_5__Oenococcus |
| D_0__Bacteria;D_1__Firmicutes;D_2__Bacilli;D_3__Lactobacillales;D_4__Leuconostocaceae;D_5__Weissella |
| D_0__Bacteria;D_1__Firmicutes;D_2__Bacilli;D_3__Lactobacillales;D_4__Leuconostocaceae;Other |
| D_0__Bacteria;D_1__Firmicutes;D_2__Bacilli;D_3__Lactobacillales;D_4__Streptococcaceae;D_5__Lactococcus |
| D_0__Bacteria;D_1__Firmicutes;D_2__Bacilli;D_3__Lactobacillales;D_4__Streptococcaceae;D_5__Streptococcus |
| D_0__Bacteria;D_1__Firmicutes;D_2__Bacilli;D_3__Lactobacillales;Other;Other |
| D_0__Bacteria;D_1__Firmicutes;D_2__Bacilli;D_3__SHBZ1548;D_4__uncultured bacterium;D_5__ |
| D_0__Bacteria;D_1__Firmicutes;D_2__Bacilli;D_3__SHBZ1548;D_4__uncultured compost bacterium;D_5__ |
| D_0__Bacteria;D_1__Firmicutes;D_2__Bacilli;D_3__SHBZ1548;Other;Other |
| D_0__Bacteria;D_1__Firmicutes;D_2__Clostridia;D_3__Clostridia Incertae Sedis;D_4__Unknown Family;D_5__Candidatus Desulforudis |
| D_0__Bacteria;D_1__Firmicutes;D_2__Clostridia;D_3__Clostridiales;D_4__Caldicoprobacteraceae;D_5__Caldicoprobacter |
| D_0__Bacteria;D_1__Firmicutes;D_2__Clostridia;D_3__Clostridiales;D_4__Christensenellaceae;D_5__uncultured |
| D_0__Bacteria;D_1__Firmicutes;D_2__Clostridia;D_3__Clostridiales;D_4__Christensenellaceae;Other |
| D_0__Bacteria;D_1__Firmicutes;D_2__Clostridia;D_3__Clostridiales;D_4__Clostridiaceae 1;D_5__Clostridium sensu stricto 1 |
| D_0__Bacteria;D_1__Firmicutes;D_2__Clostridia;D_3__Clostridiales;D_4__Clostridiaceae 1;D_5__Clostridium sensu stricto 10 |
| D_0__Bacteria;D_1__Firmicutes;D_2__Clostridia;D_3__Clostridiales;D_4__Clostridiaceae 1;D_5__Clostridium sensu stricto 12 |
| D_0__Bacteria;D_1__Firmicutes;D_2__Clostridia;D_3__Clostridiales;D_4__Clostridiaceae 1;D_5__Clostridium sensu stricto 13 |
| D_0__Bacteria;D_1__Firmicutes;D_2__Clostridia;D_3__Clostridiales;D_4__Clostridiaceae 1;D_5__Clostridium sensu stricto 18 |
| D_0__Bacteria;D_1__Firmicutes;D_2__Clostridia;D_3__Clostridiales;D_4__Clostridiaceae 1;D_5__Clostridium sensu stricto 3 |
| D_0__Bacteria;D_1__Firmicutes;D_2__Clostridia;D_3__Clostridiales;D_4__Clostridiaceae 1;D_5__Clostridium sensu stricto 5 |
| D_0__Bacteria;D_1__Firmicutes;D_2__Clostridia;D_3__Clostridiales;D_4__Clostridiaceae 1;D_5__Clostridium sensu stricto 7 |
| D_0__Bacteria;D_1__Firmicutes;D_2__Clostridia;D_3__Clostridiales;D_4__Clostridiaceae 1;D_5__Clostridium sensu stricto 8 |
| D_0__Bacteria;D_1__Firmicutes;D_2__Clostridia;D_3__Clostridiales;D_4__Clostridiaceae 1;D_5__Clostridium sensu stricto 9 |
| D_0__Bacteria;D_1__Firmicutes;D_2__Clostridia;D_3__Clostridiales;D_4__Clostridiaceae 1;D_5__Fonticella |
| D_0__Bacteria;D_1__Firmicutes;D_2__Clostridia;D_3__Clostridiales;D_4__Clostridiaceae 1;D_5__Oxobacter |
| D_0__Bacteria;D_1__Firmicutes;D_2__Clostridia;D_3__Clostridiales;D_4__Clostridiaceae 1;D_5__Proteiniclasticum |
| D_0__Bacteria;D_1__Firmicutes;D_2__Clostridia;D_3__Clostridiales;D_4__Clostridiaceae 1;Other |
| D_0__Bacteria;D_1__Firmicutes;D_2__Clostridia;D_3__Clostridiales;D_4__Clostridiaceae 2;D_5__Alkaliphilus |
| D_0__Bacteria;D_1__Firmicutes;D_2__Clostridia;D_3__Clostridiales;D_4__Clostridiaceae 3;D_5__uncultured |

| |
|---|
| D_0__Bacteria;D_1__Firmicutes;D_2__Clostridia;D_3__Clostridiales;D_4__Clostridiaceae 4;D_5__uncultured |
| D_0__Bacteria;D_1__Firmicutes;D_2__Clostridia;D_3__Clostridiales;D_4__Clostridiaceae 4;Other |
| D_0__Bacteria;D_1__Firmicutes;D_2__Clostridia;D_3__Clostridiales;D_4__Clostridiales Incertae Sedis;D_5__Proteiniborus |
| D_0__Bacteria;D_1__Firmicutes;D_2__Clostridia;D_3__Clostridiales;D_4__Defluviitaleaceae;D_5__Defluviitalea |
| D_0__Bacteria;D_1__Firmicutes;D_2__Clostridia;D_3__Clostridiales;D_4__Defluviitaleaceae;D_5__Incertae Sedis |
| D_0__Bacteria;D_1__Firmicutes;D_2__Clostridia;D_3__Clostridiales;D_4__Defluviitaleaceae;D_5__uncultured |
| D_0__Bacteria;D_1__Firmicutes;D_2__Clostridia;D_3__Clostridiales;D_4__Eubacteriaceae;D_5__Alkalibacter |
| D_0__Bacteria;D_1__Firmicutes;D_2__Clostridia;D_3__Clostridiales;D_4__Eubacteriaceae;D_5__Garciella |
| D_0__Bacteria;D_1__Firmicutes;D_2__Clostridia;D_3__Clostridiales;D_4__Family XI;D_5__Anaerococcus |
| D_0__Bacteria;D_1__Firmicutes;D_2__Clostridia;D_3__Clostridiales;D_4__Family XI;D_5__Anaerosalibacter |
| D_0__Bacteria;D_1__Firmicutes;D_2__Clostridia;D_3__Clostridiales;D_4__Family XI;D_5__Anaerosphaera |
| D_0__Bacteria;D_1__Firmicutes;D_2__Clostridia;D_3__Clostridiales;D_4__Family XI;D_5__Finegoldia |
| D_0__Bacteria;D_1__Firmicutes;D_2__Clostridia;D_3__Clostridiales;D_4__Family XI;D_5__Gallicola |
| D_0__Bacteria;D_1__Firmicutes;D_2__Clostridia;D_3__Clostridiales;D_4__Family XI;D_5__Helcococcus |
| D_0__Bacteria;D_1__Firmicutes;D_2__Clostridia;D_3__Clostridiales;D_4__Family XI;D_5__Parvimonas |
| D_0__Bacteria;D_1__Firmicutes;D_2__Clostridia;D_3__Clostridiales;D_4__Family XI;D_5__Peptoniphilus |
| D_0__Bacteria;D_1__Firmicutes;D_2__Clostridia;D_3__Clostridiales;D_4__Family XI;D_5__Sedimentibacter |
| D_0__Bacteria;D_1__Firmicutes;D_2__Clostridia;D_3__Clostridiales;D_4__Family XI;D_5__Tepidimicrobium |
| D_0__Bacteria;D_1__Firmicutes;D_2__Clostridia;D_3__Clostridiales;D_4__Family XI;D_5__Tissierella |
| D_0__Bacteria;D_1__Firmicutes;D_2__Clostridia;D_3__Clostridiales;D_4__Family XI;D_5__uncultured |
| D_0__Bacteria;D_1__Firmicutes;D_2__Clostridia;D_3__Clostridiales;D_4__Family XI;Other |
| D_0__Bacteria;D_1__Firmicutes;D_2__Clostridia;D_3__Clostridiales;D_4__Family XIII;D_5__Anaerovorax |
| D_0__Bacteria;D_1__Firmicutes;D_2__Clostridia;D_3__Clostridiales;D_4__Family XIII;D_5__Incertae Sedis |
| D_0__Bacteria;D_1__Firmicutes;D_2__Clostridia;D_3__Clostridiales;D_4__Family XIII;D_5__Mogibacterium |
| D_0__Bacteria;D_1__Firmicutes;D_2__Clostridia;D_3__Clostridiales;D_4__Family XIII;D_5__uncultured |
| D_0__Bacteria;D_1__Firmicutes;D_2__Clostridia;D_3__Clostridiales;D_4__Family XIV;D_5__Anaerobranca |
| D_0__Bacteria;D_1__Firmicutes;D_2__Clostridia;D_3__Clostridiales;D_4__Family XVII;D_5__Thermaerobacter |
| D_0__Bacteria;D_1__Firmicutes;D_2__Clostridia;D_3__Clostridiales;D_4__Family XVIII;D_5__Symbiobacterium |
| D_0__Bacteria;D_1__Firmicutes;D_2__Clostridia;D_3__Clostridiales;D_4__Family XVIII;D_5__uncultured |
| D_0__Bacteria;D_1__Firmicutes;D_2__Clostridia;D_3__Clostridiales;D_4__Gracilibacteraceae;D_5__Gracilibacter |
| D_0__Bacteria;D_1__Firmicutes;D_2__Clostridia;D_3__Clostridiales;D_4__Gracilibacteraceae;D_5__Lutispora |
| D_0__Bacteria;D_1__Firmicutes;D_2__Clostridia;D_3__Clostridiales;D_4__Gracilibacteraceae; |

| |
|---|
| D_5__uncultured |
| D_0__Bacteria;D_1__Firmicutes;D_2__Clostridia;D_3__Clostridiales;D_4__Gracilibacteraceae;Other |
| D_0__Bacteria;D_1__Firmicutes;D_2__Clostridia;D_3__Clostridiales;D_4__Heliobacteriaceae;D_5__uncultured |
| D_0__Bacteria;D_1__Firmicutes;D_2__Clostridia;D_3__Clostridiales;D_4__Lachnospiraceae;D_5__Acetitomaculum |
| D_0__Bacteria;D_1__Firmicutes;D_2__Clostridia;D_3__Clostridiales;D_4__Lachnospiraceae;D_5__Anaerosporobacter |
| D_0__Bacteria;D_1__Firmicutes;D_2__Clostridia;D_3__Clostridiales;D_4__Lachnospiraceae;D_5__Blautia |
| D_0__Bacteria;D_1__Firmicutes;D_2__Clostridia;D_3__Clostridiales;D_4__Lachnospiraceae;D_5__Cellulosilyticum |
| D_0__Bacteria;D_1__Firmicutes;D_2__Clostridia;D_3__Clostridiales;D_4__Lachnospiraceae;D_5__Coprococcus |
| D_0__Bacteria;D_1__Firmicutes;D_2__Clostridia;D_3__Clostridiales;D_4__Lachnospiraceae;D_5__Incertae Sedis |
| D_0__Bacteria;D_1__Firmicutes;D_2__Clostridia;D_3__Clostridiales;D_4__Lachnospiraceae;D_5__Lachnoanaerobaculum |
| D_0__Bacteria;D_1__Firmicutes;D_2__Clostridia;D_3__Clostridiales;D_4__Lachnospiraceae;D_5__Marvinbryantia |
| D_0__Bacteria;D_1__Firmicutes;D_2__Clostridia;D_3__Clostridiales;D_4__Lachnospiraceae;D_5__Oribacterium |
| D_0__Bacteria;D_1__Firmicutes;D_2__Clostridia;D_3__Clostridiales;D_4__Lachnospiraceae;D_5__Pseudobutyrivibrio |
| D_0__Bacteria;D_1__Firmicutes;D_2__Clostridia;D_3__Clostridiales;D_4__Lachnospiraceae;D_5__Roseburia |
| D_0__Bacteria;D_1__Firmicutes;D_2__Clostridia;D_3__Clostridiales;D_4__Lachnospiraceae;D_5__Stomatobaculum |
| D_0__Bacteria;D_1__Firmicutes;D_2__Clostridia;D_3__Clostridiales;D_4__Lachnospiraceae;D_5__uncultured |
| D_0__Bacteria;D_1__Firmicutes;D_2__Clostridia;D_3__Clostridiales;D_4__Lachnospiraceae;Other |
| D_0__Bacteria;D_1__Firmicutes;D_2__Clostridia;D_3__Clostridiales;D_4__P. palm C-A 51;D_5__uncultured bacterium |
| D_0__Bacteria;D_1__Firmicutes;D_2__Clostridia;D_3__Clostridiales;D_4__Peptococcaceae;D_5__Dehalobacter |
| D_0__Bacteria;D_1__Firmicutes;D_2__Clostridia;D_3__Clostridiales;D_4__Peptococcaceae;D_5__Desulfitibacter |
| D_0__Bacteria;D_1__Firmicutes;D_2__Clostridia;D_3__Clostridiales;D_4__Peptococcaceae;D_5__Desulfitobacterium |
| D_0__Bacteria;D_1__Firmicutes;D_2__Clostridia;D_3__Clostridiales;D_4__Peptococcaceae;D_5__Desulfosporosinus |
| D_0__Bacteria;D_1__Firmicutes;D_2__Clostridia;D_3__Clostridiales;D_4__Peptococcaceae;D_5__Desulfotomaculum |
| D_0__Bacteria;D_1__Firmicutes;D_2__Clostridia;D_3__Clostridiales;D_4__Peptococcaceae;D_5__Desulfurispora |
| D_0__Bacteria;D_1__Firmicutes;D_2__Clostridia;D_3__Clostridiales;D_4__Peptococcaceae;D_5__Pelotomaculum |
| D_0__Bacteria;D_1__Firmicutes;D_2__Clostridia;D_3__Clostridiales;D_4__Peptococcaceae;D_5__Peptococcus |
| D_0__Bacteria;D_1__Firmicutes;D_2__Clostridia;D_3__Clostridiales;D_4__Peptococcaceae;D_5__Thermincola |
| D_0__Bacteria;D_1__Firmicutes;D_2__Clostridia;D_3__Clostridiales;D_4__Peptococcaceae;D_5__uncultured |
| D_0__Bacteria;D_1__Firmicutes;D_2__Clostridia;D_3__Clostridiales;D_4__Peptococcaceae;Other |
| D_0__Bacteria;D_1__Firmicutes;D_2__Clostridia;D_3__Clostridiales;D_4__Peptostreptococcaceae;D_5__Incertae Sedis |
| D_0__Bacteria;D_1__Firmicutes;D_2__Clostridia;D_3__Clostridiales;D_4__Peptostreptococcaceae;D_5__Peptostreptococcus |
| D_0__Bacteria;D_1__Firmicutes;D_2__Clostridia;D_3__Clostridiales;D_4__Peptostreptococcace |

| |
|---|
| ae;D_5__Tepidibacter |
| D_0__Bacteria;D_1__Firmicutes;D_2__Clostridia;D_3__Clostridiales;D_4__Peptostreptococcaceae;D_5__uncultured |
| D_0__Bacteria;D_1__Firmicutes;D_2__Clostridia;D_3__Clostridiales;D_4__Peptostreptococcaceae;Other |
| D_0__Bacteria;D_1__Firmicutes;D_2__Clostridia;D_3__Clostridiales;D_4__Ruminococcaceae;D_5__Acetivibrio |
| D_0__Bacteria;D_1__Firmicutes;D_2__Clostridia;D_3__Clostridiales;D_4__Ruminococcaceae;D_5__Ethanoligenens |
| D_0__Bacteria;D_1__Firmicutes;D_2__Clostridia;D_3__Clostridiales;D_4__Ruminococcaceae;D_5__Faecalibacterium |
| D_0__Bacteria;D_1__Firmicutes;D_2__Clostridia;D_3__Clostridiales;D_4__Ruminococcaceae;D_5__Fastidiosipila |
| D_0__Bacteria;D_1__Firmicutes;D_2__Clostridia;D_3__Clostridiales;D_4__Ruminococcaceae;D_5__Incertae Sedis |
| D_0__Bacteria;D_1__Firmicutes;D_2__Clostridia;D_3__Clostridiales;D_4__Ruminococcaceae;D_5__Oscillibacter |
| D_0__Bacteria;D_1__Firmicutes;D_2__Clostridia;D_3__Clostridiales;D_4__Ruminococcaceae;D_5__Papillibacter |
| D_0__Bacteria;D_1__Firmicutes;D_2__Clostridia;D_3__Clostridiales;D_4__Ruminococcaceae;D_5__Ruminococcus |
| D_0__Bacteria;D_1__Firmicutes;D_2__Clostridia;D_3__Clostridiales;D_4__Ruminococcaceae;D_5__Saccharofermentans |
| D_0__Bacteria;D_1__Firmicutes;D_2__Clostridia;D_3__Clostridiales;D_4__Ruminococcaceae;D_5__Sporobacter |
| D_0__Bacteria;D_1__Firmicutes;D_2__Clostridia;D_3__Clostridiales;D_4__Ruminococcaceae;D_5__uncultured |
| D_0__Bacteria;D_1__Firmicutes;D_2__Clostridia;D_3__Clostridiales;D_4__Ruminococcaceae;Other |
| D_0__Bacteria;D_1__Firmicutes;D_2__Clostridia;D_3__Clostridiales;D_4__Syntrophomonadaceae;D_5__Dethiobacter |
| D_0__Bacteria;D_1__Firmicutes;D_2__Clostridia;D_3__Clostridiales;D_4__Syntrophomonadaceae;D_5__Syntrophomonas |
| D_0__Bacteria;D_1__Firmicutes;D_2__Clostridia;D_3__Clostridiales;D_4__Syntrophomonadaceae;D_5__uncultured |
| D_0__Bacteria;D_1__Firmicutes;D_2__Clostridia;D_3__Clostridiales;D_4__vadinBB60;D_5__uncultured Clostridiales bacterium |
| D_0__Bacteria;D_1__Firmicutes;D_2__Clostridia;D_3__Clostridiales;D_4__vadinBB60;D_5__uncultured bacterium |
| D_0__Bacteria;D_1__Firmicutes;D_2__Clostridia;D_3__Clostridiales;Other;Other |
| D_0__Bacteria;D_1__Firmicutes;D_2__Clostridia;D_3__D8A-2;D_4__uncultured Thermoanaerobacteraceae bacterium;D_5__ |
| D_0__Bacteria;D_1__Firmicutes;D_2__Clostridia;D_3__D8A-2;D_4__uncultured bacterium;D_5__ |
| D_0__Bacteria;D_1__Firmicutes;D_2__Clostridia;D_3__Halanaerobiales;D_4__Halanaerobiaceae;D_5__Halocella |
| D_0__Bacteria;D_1__Firmicutes;D_2__Clostridia;D_3__Halanaerobiales;D_4__Halobacteroidaceae;D_5__Sporohalobacter |
| D_0__Bacteria;D_1__Firmicutes;D_2__Clostridia;D_3__Halanaerobiales;D_4__Halobacteroidaceae;D_5__uncultured |
| D_0__Bacteria;D_1__Firmicutes;D_2__Clostridia;D_3__Thermoanaerobacterales;D_4__Family III;D_5__Tepidanaerobacter |
| D_0__Bacteria;D_1__Firmicutes;D_2__Clostridia;D_3__Thermoanaerobacterales;D_4__Family III;D_5__Thermoanaerobacterium |
| D_0__Bacteria;D_1__Firmicutes;D_2__Clostridia;D_3__Thermoanaerobacterales;D_4__SRB2;Other |
| D_0__Bacteria;D_1__Firmicutes;D_2__Clostridia;D_3__Thermoanaerobacterales;D_4__Thermoanaerobacteraceae;D_5__Gelria |
| D_0__Bacteria;D_1__Firmicutes;D_2__Clostridia;D_3__Thermoanaerobacterales;D_4__Thermoanaerobacteraceae;D_5__Moorella |
| D_0__Bacteria;D_1__Firmicutes;D_2__Clostridia;D_3__Thermoanaerobacterales;D_4__Thermoanaerobacteraceae;D_5__Syntrophaceticus |

| |
|---|
| D_0__Bacteria;D_1__Firmicutes;D_2__Clostridia;D_3__Thermoanaerobacterales;D_4__Thermoanaerobacteraceae;D_5__Thermacetogenium |
| D_0__Bacteria;D_1__Firmicutes;D_2__Clostridia;D_3__Thermoanaerobacterales;D_4__Thermoanaerobacteraceae;D_5__Thermanaeromonas |
| D_0__Bacteria;D_1__Firmicutes;D_2__Clostridia;D_3__Thermoanaerobacterales;D_4__Thermoanaerobacteraceae;D_5__Thermoanaerobacter |
| D_0__Bacteria;D_1__Firmicutes;D_2__Clostridia;D_3__Thermoanaerobacterales;D_4__Thermodesulfobiaceae;D_5__Coprothermobacter |
| D_0__Bacteria;D_1__Firmicutes;D_2__Clostridia;Other;Other;Other |
| D_0__Bacteria;D_1__Firmicutes;D_2__Erysipelotrichia;D_3__Erysipelotrichales;D_4__Erysipelotrichaceae;D_5__Asteroleplasma |
| D_0__Bacteria;D_1__Firmicutes;D_2__Erysipelotrichia;D_3__Erysipelotrichales;D_4__Erysipelotrichaceae;D_5__Catenibacterium |
| D_0__Bacteria;D_1__Firmicutes;D_2__Erysipelotrichia;D_3__Erysipelotrichales;D_4__Erysipelotrichaceae;D_5__Erysipelothrix |
| D_0__Bacteria;D_1__Firmicutes;D_2__Erysipelotrichia;D_3__Erysipelotrichales;D_4__Erysipelotrichaceae;D_5__Incertae Sedis |
| D_0__Bacteria;D_1__Firmicutes;D_2__Erysipelotrichia;D_3__Erysipelotrichales;D_4__Erysipelotrichaceae;D_5__Solobacterium |
| D_0__Bacteria;D_1__Firmicutes;D_2__Erysipelotrichia;D_3__Erysipelotrichales;D_4__Erysipelotrichaceae;D_5__Turicibacter |
| D_0__Bacteria;D_1__Firmicutes;D_2__Erysipelotrichia;D_3__Erysipelotrichales;D_4__Erysipelotrichaceae;D_5__uncultured |
| D_0__Bacteria;D_1__Firmicutes;D_2__Negativicutes;D_3__Selenomonadales;D_4__Acidaminococcaceae;D_5__uncultured |
| D_0__Bacteria;D_1__Firmicutes;D_2__Negativicutes;D_3__Selenomonadales;D_4__Veillonellaceae;D_5__Anaerospora |
| D_0__Bacteria;D_1__Firmicutes;D_2__Negativicutes;D_3__Selenomonadales;D_4__Veillonellaceae;D_5__Dialister |
| D_0__Bacteria;D_1__Firmicutes;D_2__Negativicutes;D_3__Selenomonadales;D_4__Veillonellaceae;D_5__Megasphaera |
| D_0__Bacteria;D_1__Firmicutes;D_2__Negativicutes;D_3__Selenomonadales;D_4__Veillonellaceae;D_5__Negativicoccus |
| D_0__Bacteria;D_1__Firmicutes;D_2__Negativicutes;D_3__Selenomonadales;D_4__Veillonellaceae;D_5__Pelosinus |
| D_0__Bacteria;D_1__Firmicutes;D_2__Negativicutes;D_3__Selenomonadales;D_4__Veillonellaceae;D_5__Selenomonas |
| D_0__Bacteria;D_1__Firmicutes;D_2__Negativicutes;D_3__Selenomonadales;D_4__Veillonellaceae;D_5__Sporomusa |
| D_0__Bacteria;D_1__Firmicutes;D_2__Negativicutes;D_3__Selenomonadales;D_4__Veillonellaceae;D_5__Veillonella |
| D_0__Bacteria;D_1__Firmicutes;D_2__Negativicutes;D_3__Selenomonadales;D_4__Veillonellaceae;D_5__uncultured |
| D_0__Bacteria;D_1__Firmicutes;D_2__Negativicutes;D_3__Selenomonadales;D_4__Veillonellaceae;Other |
| D_0__Bacteria;D_1__Firmicutes;D_2__Negativicutes;D_3__Selenomonadales;D_4__uncultured;D_5__uncultured bacterium |
| D_0__Bacteria;D_1__Firmicutes;D_2__Negativicutes;D_3__Selenomonadales;D_4__uncultured;Other |
| D_0__Bacteria;D_1__Firmicutes;D_2__OPB54;D_3__uncultured Clostridia bacterium;D_4__;D_5__ |
| D_0__Bacteria;D_1__Firmicutes;D_2__OPB54;D_3__uncultured Clostridium sp.;D_4__;D_5__ |
| D_0__Bacteria;D_1__Firmicutes;D_2__OPB54;D_3__uncultured Firmicutes bacterium;D_4__;D_5__ |
| D_0__Bacteria;D_1__Firmicutes;D_2__OPB54;D_3__uncultured bacterium;D_4__;D_5__ |
| D_0__Bacteria;D_1__Firmicutes;D_2__OPB54;D_3__uncultured compost bacterium;D_4__;D_5__ |
| D_0__Bacteria;D_1__Firmicutes;D_2__OPB54;D_3__uncultured prokaryote;D_4__;D_5__ |
| D_0__Bacteria;D_1__Firmicutes;D_2__OPB54;Other;Other;Other |
| D_0__Bacteria;D_1__Firmicutes;Other;Other;Other;Other |

| |
|---|
| D_0__Bacteria;D_1__Fusobacteria;D_2__Fusobacteriia;D_3__Fusobacteriales;D_4__CFT112H7;D_5__uncultured bacterium |
| D_0__Bacteria;D_1__Fusobacteria;D_2__Fusobacteriia;D_3__Fusobacteriales;D_4__Fusobacteriaceae;D_5__Fusobacterium |
| D_0__Bacteria;D_1__Fusobacteria;D_2__Fusobacteriia;D_3__Fusobacteriales;D_4__Leptotrichiaceae;D_5__Leptotrichia |
| D_0__Bacteria;D_1__Fusobacteria;D_2__Fusobacteriia;D_3__Fusobacteriales;D_4__Leptotrichiaceae;D_5__uncultured |
| D_0__Bacteria;D_1__Gemmatimonadetes;D_2__Gemmatimonadetes;D_3__AT425-EubC11 terrestrial group;D_4__uncultured bacterium;D_5__ |
| D_0__Bacteria;D_1__Gemmatimonadetes;D_2__Gemmatimonadetes;D_3__AT425-EubC11 terrestrial group;Other;Other |
| D_0__Bacteria;D_1__Gemmatimonadetes;D_2__Gemmatimonadetes;D_3__BD2-11 terrestrial group;D_4__uncultured Gemmatimonadetes bacterium;D_5__ |
| D_0__Bacteria;D_1__Gemmatimonadetes;D_2__Gemmatimonadetes;D_3__BD2 11 terrestrial group;D_4__uncultured bacterium;D_5__ |
| D_0__Bacteria;D_1__Gemmatimonadetes;D_2__Gemmatimonadetes;D_3__BD2-11 terrestrial group;D_4__uncultured sediment bacterium;D_5__ |
| D_0__Bacteria;D_1__Gemmatimonadetes;D_2__Gemmatimonadetes;D_3__BD2-11 terrestrial group;Other;Other |
| D_0__Bacteria;D_1__Gemmatimonadetes;D_2__Gemmatimonadetes;D_3__Gemmatimonadales;D_4__Gemmatimonadaceae;D_5__Gemmatimonas |
| D_0__Bacteria;D_1__Gemmatimonadetes;D_2__Gemmatimonadetes;D_3__Gemmatimonadales;D_4__Gemmatimonadaceae;D_5__uncultured |
| D_0__Bacteria;D_1__Gemmatimonadetes;D_2__Gemmatimonadetes;D_3__Gemmatimonadales;D_4__Gemmatimonadaceae;Other |
| D_0__Bacteria;D_1__Gemmatimonadetes;D_2__Gemmatimonadetes;D_3__S0134 terrestrial group;D_4__uncultured Gemmatimonadetes bacterium;D_5__ |
| D_0__Bacteria;D_1__Gemmatimonadetes;D_2__Gemmatimonadetes;D_3__S0134 terrestrial group;D_4__uncultured bacterium;D_5__ |
| D_0__Bacteria;D_1__Gemmatimonadetes;D_2__Gemmatimonadetes;D_3__S0134 terrestrial group;Other;Other |
| D_0__Bacteria;D_1__JL-ETNP-Z39;D_2__uncultured bacterium;D_3__;D_4__;D_5__ |
| D_0__Bacteria;D_1__Lentisphaerae;D_2__Lentisphaeria;D_3__Victivallales;D_4__Victivallaceae;D_5__Victivallis |
| D_0__Bacteria;D_1__Lentisphaerae;D_2__PBS-III-20;D_3__uncultured bacterium;D_4__;D_5__ |
| D_0__Bacteria;D_1__NPL-UPA2;D_2__uncultured bacterium;D_3__;D_4__;D_5__ |
| D_0__Bacteria;D_1__NPL-UPA2;Other;Other;Other;Other |
| D_0__Bacteria;D_1__Nitrospirae;D_2__Nitrospira;D_3__Nitrospirales;D_4__0319-6A21;D_5__uncultured bacterium |
| D_0__Bacteria;D_1__Nitrospirae;D_2__Nitrospira;D_3__Nitrospirales;D_4__0319-6A21;Other |
| D_0__Bacteria;D_1__Nitrospirae;D_2__Nitrospira;D_3__Nitrospirales;D_4__4-29;D_5__uncultured bacterium |
| D_0__Bacteria;D_1__Nitrospirae;D_2__Nitrospira;D_3__Nitrospirales;D_4__MIZ17;D_5__uncultured bacterium |
| D_0__Bacteria;D_1__Nitrospirae;D_2__Nitrospira;D_3__Nitrospirales;D_4__Nitrospiraceae;D_5__Leptospirillum |
| D_0__Bacteria;D_1__Nitrospirae;D_2__Nitrospira;D_3__Nitrospirales;D_4__Nitrospiraceae;D_5__Nitrospira |
| D_0__Bacteria;D_1__Nitrospirae;D_2__Nitrospira;D_3__Nitrospirales;D_4__Nitrospiraceae;D_5__uncultured |
| D_0__Bacteria;D_1__Planctomycetes;D_2__BD7-11;D_3__uncultured bacterium;D_4__;D_5__ |
| D_0__Bacteria;D_1__Planctomycetes;D_2__BD7-11;D_3__uncultured planctomycete;D_4__;D_5__ |
| D_0__Bacteria;D_1__Planctomycetes;D_2__OM190;D_3__uncultured bacterium;D_4__;D_5__ |
| D_0__Bacteria;D_1__Planctomycetes;D_2__OM190;D_3__uncultured microorganism;D_4__;D_5__ |
| D_0__Bacteria;D_1__Planctomycetes;D_2__OM190;D_3__uncultured planctomycete;D_4__;D_5__ |

| |
|---|
| D_0__Bacteria;D_1__Planctomycetes;D_2__OM190;Other;Other;Other |
| D_0__Bacteria;D_1__Planctomycetes;D_2__Phycisphaerae;D_3__CCM11a;D_4__uncultured Planctomycetia bacterium;D_5__ |
| D_0__Bacteria;D_1__Planctomycetes;D_2__Phycisphaerae;D_3__CCM11a;D_4__uncultured bacterium;D_5__ |
| D_0__Bacteria;D_1__Planctomycetes;D_2__Phycisphaerae;D_3__CCM11a;Other;Other |
| D_0__Bacteria;D_1__Planctomycetes;D_2__Phycisphaerae;D_3__CP1a-3 termite group;D_4__uncultured planctomycete;D_5__ |
| D_0__Bacteria;D_1__Planctomycetes;D_2__Phycisphaerae;D_3__MSBL9;D_4__uncultured bacterium;D_5__ |
| D_0__Bacteria;D_1__Planctomycetes;D_2__Phycisphaerae;D_3__Phycisphaerales;D_4__Phycisphaeraceae;D_5__AKYG587 |
| D_0__Bacteria;D_1__Planctomycetes;D_2__Phycisphaerae;D_3__Phycisphaerales;D_4__Phycisphaeraceae;D_5__CL500-3 |
| D_0__Bacteria;D_1__Planctomycetes;D_2__Phycisphaerae;D_3__Phycisphaerales;D_4__Phycisphaeraceae;D_5__I-8 |
| D_0__Bacteria;D_1__Planctomycetes;D_2__Phycisphaerae;D_3__Phycisphaerales;D_4__Phycisphaeraceae;D_5__Phycisphaera |
| D_0__Bacteria;D_1__Planctomycetes;D_2__Phycisphaerae;D_3__Phycisphaerales;D_4__Phycisphaeraceae;D_5__SM1A02 |
| D_0__Bacteria;D_1__Planctomycetes;D_2__Phycisphaerae;D_3__Pla1 lineage;D_4__uncultured bacterium;D_5__ |
| D_0__Bacteria;D_1__Planctomycetes;D_2__Phycisphaerae;D_3__S-70;D_4__uncultured bacterium;D_5__ |
| D_0__Bacteria;D_1__Planctomycetes;D_2__Phycisphaerae;D_3__WD2101 soil group;D_4__uncultured bacterium;D_5__ |
| D_0__Bacteria;D_1__Planctomycetes;D_2__Phycisphaerae;D_3__WD2101 soil group;D_4__uncultured planctomycete;D_5__ |
| D_0__Bacteria;D_1__Planctomycetes;D_2__Phycisphaerae;D_3__WD2101 soil group;D_4__uncultured soil bacterium;D_5__ |
| D_0__Bacteria;D_1__Planctomycetes;D_2__Phycisphaerae;D_3__WD2101 soil group;Other;Other |
| D_0__Bacteria;D_1__Planctomycetes;D_2__Phycisphaerae;D_3__mle1-8;D_4__uncultured bacterium;D_5__ |
| D_0__Bacteria;D_1__Planctomycetes;D_2__Phycisphaerae;D_3__mle1-8;D_4__uncultured organism;D_5__ |
| D_0__Bacteria;D_1__Planctomycetes;D_2__Pla3 lineage;D_3__uncultured bacterium;D_4__;D_5__ |
| D_0__Bacteria;D_1__Planctomycetes;D_2__Pla3 lineage;D_3__uncultured planctomycete;D_4__;D_5__ |
| D_0__Bacteria;D_1__Planctomycetes;D_2__Pla3 lineage;Other;Other;Other |
| D_0__Bacteria;D_1__Planctomycetes;D_2__Pla4 lineage;D_3__uncultured bacterium;D_4__;D_5__ |
| D_0__Bacteria;D_1__Planctomycetes;D_2__Pla4 lineage;D_3__uncultured planctomycete;D_4__;D_5__ |
| D_0__Bacteria;D_1__Planctomycetes;D_2__Pla4 lineage;Other;Other;Other |
| D_0__Bacteria;D_1__Planctomycetes;D_2__Planctomycetacia;D_3__Planctomycetales;D_4__Planctomycetaceae;D_5__Blastopirellula |
| D_0__Bacteria;D_1__Planctomycetes;D_2__Planctomycetacia;D_3__Planctomycetales;D_4__Planctomycetaceae;D_5__Candidatus Nostocoida |
| D_0__Bacteria;D_1__Planctomycetes;D_2__Planctomycetacia;D_3__Planctomycetales;D_4__Planctomycetaceae;D_5__Gemmata |
| D_0__Bacteria;D_1__Planctomycetes;D_2__Planctomycetacia;D_3__Planctomycetales;D_4__Planctomycetaceae;D_5__Isosphaera |
| D_0__Bacteria;D_1__Planctomycetes;D_2__Planctomycetacia;D_3__Planctomycetales;D_4__Planctomycetaceae;D_5__Pir4 lineage |
| D_0__Bacteria;D_1__Planctomycetes;D_2__Planctomycetacia;D_3__Planctomycetales;D_4__Planctomycetaceae;D_5__Pirellula |
| D_0__Bacteria;D_1__Planctomycetes;D_2__Planctomycetacia;D_3__Planctomycetales;D_4__Planctomycetaceae;D_5__Planctomyces |
| D_0__Bacteria;D_1__Planctomycetes;D_2__Planctomycetacia;D_3__Planctomycetales;D_4__Planct |

| |
|---|
| omycetaceae;D_5__Rhodopirellula |
| D_0__Bacteria;D_1__Planctomycetes;D_2__Planctomycetacia;D_3__Planctomycetales;D_4__Planctomycetaceae;D_5__Schlesneria |
| D_0__Bacteria;D_1__Planctomycetes;D_2__Planctomycetacia;D_3__Planctomycetales;D_4__Planctomycetaceae;D_5__Singulisphaera |
| D_0__Bacteria;D_1__Planctomycetes;D_2__Planctomycetacia;D_3__Planctomycetales;D_4__Planctomycetaceae;D_5__Zavarzinella |
| D_0__Bacteria;D_1__Planctomycetes;D_2__Planctomycetacia;D_3__Planctomycetales;D_4__Planctomycetaceae;D_5__uncultured |
| D_0__Bacteria;D_1__Planctomycetes;D_2__Planctomycetacia;D_3__Planctomycetales;D_4__Planctomycetaceae;D_5__uncultured bacterium |
| D_0__Bacteria;D_1__Planctomycetes;D_2__Planctomycetacia;D_3__Planctomycetales;D_4__Planctomycetaceae;Other |
| D_0__Bacteria;D_1__Planctomycetes;D_2__vadinHA49;D_3__uncultured bacterium;D_4__;D_5__ |
| D_0__Bacteria;D_1__Planctomycetes;D_2__vadinHA49;Other;Other;Other |
| D_0__Bacteria;D_1__Proteobacteria;D_2__Alphaproteobacteria;D_3__Caulobacterales;D_4__Caulobacteraceae;D_5__Asticcacaulis |
| D_0__Bacteria;D_1__Proteobacteria;D_2__Alphaproteobacteria;D_3__Caulobacterales;D_4__Caulobacteraceae;D_5__Brevundimonas |
| D_0__Bacteria;D_1__Proteobacteria;D_2__Alphaproteobacteria;D_3__Caulobacterales;D_4__Caulobacteraceae;D_5__Caulobacter |
| D_0__Bacteria;D_1__Proteobacteria;D_2__Alphaproteobacteria;D_3__Caulobacterales;D_4__Caulobacteraceae;D_5__Phenylobacterium |
| D_0__Bacteria;D_1__Proteobacteria;D_2__Alphaproteobacteria;D_3__Caulobacterales;D_4__Caulobacteraceae;D_5__uncultured |
| D_0__Bacteria;D_1__Proteobacteria;D_2__Alphaproteobacteria;D_3__Caulobacterales;D_4__Caulobacteraceae;Other |
| D_0__Bacteria;D_1__Proteobacteria;D_2__Alphaproteobacteria;D_3__Caulobacterales;D_4__Hyphomonadaceae;D_5__Hirschia |
| D_0__Bacteria;D_1__Proteobacteria;D_2__Alphaproteobacteria;D_3__Caulobacterales;D_4__Hyphomonadaceae;D_5__Woodsholea |
| D_0__Bacteria;D_1__Proteobacteria;D_2__Alphaproteobacteria;D_3__Caulobacterales;D_4__Hyphomonadaceae;D_5__uncultured |
| D_0__Bacteria;D_1__Proteobacteria;D_2__Alphaproteobacteria;D_3__DB1-14;D_4__uncultured bacterium;D_5__ |
| D_0__Bacteria;D_1__Proteobacteria;D_2__Alphaproteobacteria;D_3__DB1-14;Other;Other |
| D_0__Bacteria;D_1__Proteobacteria;D_2__Alphaproteobacteria;D_3__E6aD10;D_4__uncultured organism;D_5__ |
| D_0__Bacteria;D_1__Proteobacteria;D_2__Alphaproteobacteria;D_3__E6aD10;Other;Other |
| D_0__Bacteria;D_1__Proteobacteria;D_2__Alphaproteobacteria;D_3__Rhizobiales;D_4__1174-901-12;D_5__uncultured Rhizobiales bacterium |
| D_0__Bacteria;D_1__Proteobacteria;D_2__Alphaproteobacteria;D_3__Rhizobiales;D_4__1174-901-12;D_5__uncultured bacterium |
| D_0__Bacteria;D_1__Proteobacteria;D_2__Alphaproteobacteria;D_3__Rhizobiales;D_4__1174-901-12;Other |
| D_0__Bacteria;D_1__Proteobacteria;D_2__Alphaproteobacteria;D_3__Rhizobiales;D_4__A0839;D_5__uncultured bacterium |
| D_0__Bacteria;D_1__Proteobacteria;D_2__Alphaproteobacteria;D_3__Rhizobiales;D_4__A0839;Other |
| D_0__Bacteria;D_1__Proteobacteria;D_2__Alphaproteobacteria;D_3__Rhizobiales;D_4__Aurantimonadaceae;D_5__Aurantimonas |
| D_0__Bacteria;D_1__Proteobacteria;D_2__Alphaproteobacteria;D_3__Rhizobiales;D_4__Aurantimonadaceae;D_5__Aureimonas |
| D_0__Bacteria;D_1__Proteobacteria;D_2__Alphaproteobacteria;D_3__Rhizobiales;D_4__Aurantimonadaceae;D_5__uncultured |
| D_0__Bacteria;D_1__Proteobacteria;D_2__Alphaproteobacteria;D_3__Rhizobiales;D_4__Aurantimonadaceae;Other |
| D_0__Bacteria;D_1__Proteobacteria;D_2__Alphaproteobacteria;D_3__Rhizobiales;D_4__Bartonellaceae;D_5__Bartonella |

| |
|---|
| D_0__Bacteria;D_1__Proteobacteria;D_2__Alphaproteobacteria;D_3__Rhizobiales;D_4__Beijerinckiaceae;D_5__Chelatococcus |
| D_0__Bacteria;D_1__Proteobacteria;D_2__Alphaproteobacteria;D_3__Rhizobiales;D_4__Beijerinckiaceae;D_5__Methylorosula |
| D_0__Bacteria;D_1__Proteobacteria;D_2__Alphaproteobacteria;D_3__Rhizobiales;D_4__Beijerinckiaceae;D_5__Methylovirgula |
| D_0__Bacteria;D_1__Proteobacteria;D_2__Alphaproteobacteria;D_3__Rhizobiales;D_4__Beijerinckiaceae;D_5__uncultured |
| D_0__Bacteria;D_1__Proteobacteria;D_2__Alphaproteobacteria;D_3__Rhizobiales;D_4__Beijerinckiaceae;Other |
| D_0__Bacteria;D_1__Proteobacteria;D_2__Alphaproteobacteria;D_3__Rhizobiales;D_4__Bradyrhizobiaceae;D_5__Afipia |
| D_0__Bacteria;D_1__Proteobacteria;D_2__Alphaproteobacteria;D_3__Rhizobiales;D_4__Bradyrhizobiaceae;D_5__Bosea |
| D_0__Bacteria;D_1__Proteobacteria;D_2__Alphaproteobacteria;D_3__Rhizobiales;D_4__Bradyrhizobiaceae;D_5__Bradyrhizobium |
| D_0__Bacteria;D_1__Proteobacteria;D_2__Alphaproteobacteria;D_3__Rhizobiales;D_4__Bradyrhizobiaceae;D_5__Nitrobacter |
| D_0__Bacteria;D_1__Proteobacteria;D_2__Alphaproteobacteria;D_3__Rhizobiales;D_4__Bradyrhizobiaceae;D_5__uncultured |
| D_0__Bacteria;D_1__Proteobacteria;D_2__Alphaproteobacteria;D_3__Rhizobiales;D_4__Bradyrhizobiaceae;Other |
| D_0__Bacteria;D_1__Proteobacteria;D_2__Alphaproteobacteria;D_3__Rhizobiales;D_4__Brucellaceae;D_5__Daeguia |
| D_0__Bacteria;D_1__Proteobacteria;D_2__Alphaproteobacteria;D_3__Rhizobiales;D_4__Brucellaceae;D_5__Ochrobactrum |
| D_0__Bacteria;D_1__Proteobacteria;D_2__Alphaproteobacteria;D_3__Rhizobiales;D_4__Brucellaceae;Other |
| D_0__Bacteria;D_1__Proteobacteria;D_2__Alphaproteobacteria;D_3__Rhizobiales;D_4__D05-2;Other |
| D_0__Bacteria;D_1__Proteobacteria;D_2__Alphaproteobacteria;D_3__Rhizobiales;D_4__DUNssu044;D_5__uncultured bacterium |
| D_0__Bacteria;D_1__Proteobacteria;D_2__Alphaproteobacteria;D_3__Rhizobiales;D_4__DUNssu044;Other |
| D_0__Bacteria;D_1__Proteobacteria;D_2__Alphaproteobacteria;D_3__Rhizobiales;D_4__DUNssu371;D_5__uncultured bacterium |
| D_0__Bacteria;D_1__Proteobacteria;D_2__Alphaproteobacteria;D_3__Rhizobiales;D_4__F0723;D_5__uncultured Brucella sp. |
| D_0__Bacteria;D_1__Proteobacteria;D_2__Alphaproteobacteria;D_3__Rhizobiales;D_4__F0723;D_5__uncultured bacterium |
| D_0__Bacteria;D_1__Proteobacteria;D_2__Alphaproteobacteria;D_3__Rhizobiales;D_4__F0723;Other |
| D_0__Bacteria;D_1__Proteobacteria;D_2__Alphaproteobacteria;D_3__Rhizobiales;D_4__FFCH5858;D_5__uncultured bacterium |
| D_0__Bacteria;D_1__Proteobacteria;D_2__Alphaproteobacteria;D_3__Rhizobiales;D_4__FukuN57;D_5__uncultured bacterium |
| D_0__Bacteria;D_1__Proteobacteria;D_2__Alphaproteobacteria;D_3__Rhizobiales;D_4__Hyphomicrobiaceae;D_5__Devosia |
| D_0__Bacteria;D_1__Proteobacteria;D_2__Alphaproteobacteria;D_3__Rhizobiales;D_4__Hyphomicrobiaceae;D_5__Hyphomicrobium |
| D_0__Bacteria;D_1__Proteobacteria;D_2__Alphaproteobacteria;D_3__Rhizobiales;D_4__Hyphomicrobiaceae;D_5__Pedomicrobium |
| D_0__Bacteria;D_1__Proteobacteria;D_2__Alphaproteobacteria;D_3__Rhizobiales;D_4__Hyphomicrobiaceae;D_5__Prosthecomicrobium |
| D_0__Bacteria;D_1__Proteobacteria;D_2__Alphaproteobacteria;D_3__Rhizobiales;D_4__Hyphomicrobiaceae;D_5__Rhodomicrobium |
| D_0__Bacteria;D_1__Proteobacteria;D_2__Alphaproteobacteria;D_3__Rhizobiales;D_4__Hyphomicrobiaceae;D_5__Rhodoplanes |
| D_0__Bacteria;D_1__Proteobacteria;D_2__Alphaproteobacteria;D_3__Rhizobiales;D_4__Hyphomicrobiaceae;D_5__uncultured |
| D_0__Bacteria;D_1__Proteobacteria;D_2__Alphaproteobacteria;D_3__Rhizobiales;D_4__Hyphomicrobiaceae;Other |

| |
|---|
| D_0__Bacteria;D_1__Proteobacteria;D_2__Alphaproteobacteria;D_3__Rhizobiales;D_4__JG34-KF-361;D_5__uncultured bacterium |
| D_0__Bacteria;D_1__Proteobacteria;D_2__Alphaproteobacteria;D_3__Rhizobiales;D_4__JG34-KF-361;D_5__uncultured forest soil bacterium |
| D_0__Bacteria;D_1__Proteobacteria;D_2__Alphaproteobacteria;D_3__Rhizobiales;D_4__JG34-KF-361;Other |
| D_0__Bacteria;D_1__Proteobacteria;D_2__Alphaproteobacteria;D_3__Rhizobiales;D_4__JG35-K1-AG5;D_5__uncultured bacterium |
| D_0__Bacteria;D_1__Proteobacteria;D_2__Alphaproteobacteria;D_3__Rhizobiales;D_4__KF-JG30-B3;D_5__uncultured bacterium |
| D_0__Bacteria;D_1__Proteobacteria;D_2__Alphaproteobacteria;D_3__Rhizobiales;D_4__MNG7;D_5__uncultured bacterium |
| D_0__Bacteria;D_1__Proteobacteria;D_2__Alphaproteobacteria;D_3__Rhizobiales;D_4__MNG7;Other |
| D_0__Bacteria;D_1__Proteobacteria;D_2__Alphaproteobacteria;D_3__Rhizobiales;D_4__Methylobacteriaceae;D_5__Meganema |
| D_0__Bacteria;D_1__Proteobacteria;D_2__Alphaproteobacteria;D_3__Rhizobiales;D_4__Methylobacteriaceae;D_5__Methylobacterium |
| D_0__Bacteria;D_1__Proteobacteria;D_2__Alphaproteobacteria;D_3__Rhizobiales;D_4__Methylobacteriaceae;D_5__Microvirga |
| D_0__Bacteria;D_1__Proteobacteria;D_2__Alphaproteobacteria;D_3__Rhizobiales;D_4__Methylobacteriaceae;D_5__uncultured |
| D_0__Bacteria;D_1__Proteobacteria;D_2__Alphaproteobacteria;D_3__Rhizobiales;D_4__Methylobacteriaceae;Other |
| D_0__Bacteria;D_1__Proteobacteria;D_2__Alphaproteobacteria;D_3__Rhizobiales;D_4__Methylocystaceae;D_5__Albibacter |
| D_0__Bacteria;D_1__Proteobacteria;D_2__Alphaproteobacteria;D_3__Rhizobiales;D_4__Methylocystaceae;D_5__Methylopila |
| D_0__Bacteria;D_1__Proteobacteria;D_2__Alphaproteobacteria;D_3__Rhizobiales;D_4__Methylocystaceae;D_5__Pleomorphomonas |
| D_0__Bacteria;D_1__Proteobacteria;D_2__Alphaproteobacteria;D_3__Rhizobiales;D_4__Methylocystaceae;Other |
| D_0__Bacteria;D_1__Proteobacteria;D_2__Alphaproteobacteria;D_3__Rhizobiales;D_4__Phyllobacteriaceae;D_5__Aquamicrobium |
| D_0__Bacteria;D_1__Proteobacteria;D_2__Alphaproteobacteria;D_3__Rhizobiales;D_4__Phyllobacteriaceae;D_5__Mesorhizobium |
| D_0__Bacteria;D_1__Proteobacteria;D_2__Alphaproteobacteria;D_3__Rhizobiales;D_4__Phyllobacteriaceae;D_5__Nitratireductor |
| D_0__Bacteria;D_1__Proteobacteria;D_2__Alphaproteobacteria;D_3__Rhizobiales;D_4__Phyllobacteriaceae;D_5__Phyllobacterium |
| D_0__Bacteria;D_1__Proteobacteria;D_2__Alphaproteobacteria;D_3__Rhizobiales;D_4__Phyllobacteriaceae;D_5__Pseudaminobacter |
| D_0__Bacteria;D_1__Proteobacteria;D_2__Alphaproteobacteria;D_3__Rhizobiales;D_4__Phyllobacteriaceae;D_5__uncultured |
| D_0__Bacteria;D_1__Proteobacteria;D_2__Alphaproteobacteria;D_3__Rhizobiales;D_4__Phyllobacteriaceae;Other |
| D_0__Bacteria;D_1__Proteobacteria;D_2__Alphaproteobacteria;D_3__Rhizobiales;D_4__Rhizobiaceae;D_5__Ensifer |
| D_0__Bacteria;D_1__Proteobacteria;D_2__Alphaproteobacteria;D_3__Rhizobiales;D_4__Rhizobiaceae;D_5__Kaistia |
| D_0__Bacteria;D_1__Proteobacteria;D_2__Alphaproteobacteria;D_3__Rhizobiales;D_4__Rhizobiaceae;D_5__Rhizobium |
| D_0__Bacteria;D_1__Proteobacteria;D_2__Alphaproteobacteria;D_3__Rhizobiales;D_4__Rhizobiaceae;D_5__Shinella |
| D_0__Bacteria;D_1__Proteobacteria;D_2__Alphaproteobacteria;D_3__Rhizobiales;D_4__Rhizobiaceae;Other |
| D_0__Bacteria;D_1__Proteobacteria;D_2__Alphaproteobacteria;D_3__Rhizobiales;D_4__Rhizobiales Incertae Sedis;D_5__Agaricicola |
| D_0__Bacteria;D_1__Proteobacteria;D_2__Alphaproteobacteria;D_3__Rhizobiales;D_4__Rhizobiales Incertae Sedis;D_5__Bauldia |
| D_0__Bacteria;D_1__Proteobacteria;D_2__Alphaproteobacteria;D_3__Rhizobiales;D_4__Rhizobiales Incertae Sedis;D_5__Nordella |

| |
|---|
| D_0__Bacteria;D_1__Proteobacteria;D_2__Alphaproteobacteria;D_3__Rhizobiales;D_4__Rhizobiales Incertae Sedis;D_5__Rhizomicrobium |
| D_0__Bacteria;D_1__Proteobacteria;D_2__Alphaproteobacteria;D_3__Rhizobiales;D_4__Rhodobiaceae;D_5__Parvibaculum |
| D_0__Bacteria;D_1__Proteobacteria;D_2__Alphaproteobacteria;D_3__Rhizobiales;D_4__Rhodobiaceae;D_5__Rhodobium |
| D_0__Bacteria;D_1__Proteobacteria;D_2__Alphaproteobacteria;D_3__Rhizobiales;D_4__Rhodobiaceae;D_5__Rhodoligotrophos |
| D_0__Bacteria;D_1__Proteobacteria;D_2__Alphaproteobacteria;D_3__Rhizobiales;D_4__Xanthobacteraceae;D_5__Ancylobacter |
| D_0__Bacteria;D_1__Proteobacteria;D_2__Alphaproteobacteria;D_3__Rhizobiales;D_4__Xanthobacteraceae;D_5__Labrys |
| D_0__Bacteria;D_1__Proteobacteria;D_2__Alphaproteobacteria;D_3__Rhizobiales;D_4__Xanthobacteraceae;D_5__Pseudolabrys |
| D_0__Bacteria;D_1__Proteobacteria;D_2__Alphaproteobacteria;D_3__Rhizobiales;D_4__Xanthobacteraceae;D_5__Pseudoxanthobacter |
| D_0__Bacteria;D_1__Proteobacteria;D_2__Alphaproteobacteria;D_3__Rhizobiales;D_4__Xanthobacteraceae;D_5__Xanthobacter |
| D_0__Bacteria;D_1__Proteobacteria;D_2__Alphaproteobacteria;D_3__Rhizobiales;D_4__Xanthobacteraceae;D_5__uncultured |
| D_0__Bacteria;D_1__Proteobacteria;D_2__Alphaproteobacteria;D_3__Rhizobiales;D_4__Xanthobacteraceae;Other |
| D_0__Bacteria;D_1__Proteobacteria;D_2__Alphaproteobacteria;D_3__Rhizobiales;D_4__alphaI cluster;D_5__uncultured bacterium |
| D_0__Bacteria;D_1__Proteobacteria;D_2__Alphaproteobacteria;D_3__Rhizobiales;D_4__alphaI cluster;D_5__uncultured forest soil bacterium |
| D_0__Bacteria;D_1__Proteobacteria;D_2__Alphaproteobacteria;D_3__Rhizobiales;D_4__alphaI cluster;Other |
| D_0__Bacteria;D_1__Proteobacteria;D_2__Alphaproteobacteria;D_3__Rhizobiales;D_4__uncultured;D_5__uncultured bacterium |
| D_0__Bacteria;D_1__Proteobacteria;D_2__Alphaproteobacteria;D_3__Rhizobiales;D_4__uncultured;Other |
| D_0__Bacteria;D_1__Proteobacteria;D_2__Alphaproteobacteria;D_3__Rhizobiales;Other;Other |
| D_0__Bacteria;D_1__Proteobacteria;D_2__Alphaproteobacteria;D_3__Rhodobacterales;D_4__Rhodobacteraceae;D_5__Albimonas |
| D_0__Bacteria;D_1__Proteobacteria;D_2__Alphaproteobacteria;D_3__Rhodobacterales;D_4__Rhodobacteraceae;D_5__Amaricoccus |
| D_0__Bacteria;D_1__Proteobacteria;D_2__Alphaproteobacteria;D_3__Rhodobacterales;D_4__Rhodobacteraceae;D_5__Defluviimonas |
| D_0__Bacteria;D_1__Proteobacteria;D_2__Alphaproteobacteria;D_3__Rhodobacterales;D_4__Rhodobacteraceae;D_5__Gemmobacter |
| D_0__Bacteria;D_1__Proteobacteria;D_2__Alphaproteobacteria;D_3__Rhodobacterales;D_4__Rhodobacteraceae;D_5__Paracoccus |
| D_0__Bacteria;D_1__Proteobacteria;D_2__Alphaproteobacteria;D_3__Rhodobacterales;D_4__Rhodobacteraceae;D_5__Rhodobacter |
| D_0__Bacteria;D_1__Proteobacteria;D_2__Alphaproteobacteria;D_3__Rhodobacterales;D_4__Rhodobacteraceae;D_5__Rubellimicrobium |
| D_0__Bacteria;D_1__Proteobacteria;D_2__Alphaproteobacteria;D_3__Rhodobacterales;D_4__Rhodobacteraceae;D_5__Tabrizicola |
| D_0__Bacteria;D_1__Proteobacteria;D_2__Alphaproteobacteria;D_3__Rhodobacterales;D_4__Rhodobacteraceae;D_5__Thioclava |
| D_0__Bacteria;D_1__Proteobacteria;D_2__Alphaproteobacteria;D_3__Rhodobacterales;D_4__Rhodobacteraceae;D_5__uncultured |
| D_0__Bacteria;D_1__Proteobacteria;D_2__Alphaproteobacteria;D_3__Rhodobacterales;D_4__Rhodobacteraceae;D_5__uncultured bacterium |
| D_0__Bacteria;D_1__Proteobacteria;D_2__Alphaproteobacteria;D_3__Rhodobacterales;D_4__Rhodobacteraceae;Other |
| D_0__Bacteria;D_1__Proteobacteria;D_2__Alphaproteobacteria;D_3__Rhodospirillales;D_4__AKYH478;D_5__uncultured alpha proteobacterium |
| D_0__Bacteria;D_1__Proteobacteria;D_2__Alphaproteobacteria;D_3__Rhodospirillales;D_4__AKYH478;D_5__uncultured bacterium |
| D_0__Bacteria;D_1__Proteobacteria;D_2__Alphaproteobacteria;D_3__Rhodospirillales;D_4__AKY |

| |
|---|
| H478;Other |
| D_0__Bacteria;D_1__Proteobacteria;D_2__Alphaproteobacteria;D_3__Rhodospirillales;D_4__Acetobacteraceae;D_5__Acetobacter |
| D_0__Bacteria;D_1__Proteobacteria;D_2__Alphaproteobacteria;D_3__Rhodospirillales;D_4__Acetobacteraceae;D_5__Acidicaldus |
| D_0__Bacteria;D_1__Proteobacteria;D_2__Alphaproteobacteria;D_3__Rhodospirillales;D_4__Acetobacteraceae;D_5__Acidiphilium |
| D_0__Bacteria;D_1__Proteobacteria;D_2__Alphaproteobacteria;D_3__Rhodospirillales;D_4__Acetobacteraceae;D_5__Acidocella |
| D_0__Bacteria;D_1__Proteobacteria;D_2__Alphaproteobacteria;D_3__Rhodospirillales;D_4__Acetobacteraceae;D_5__Asaia |
| D_0__Bacteria;D_1__Proteobacteria;D_2__Alphaproteobacteria;D_3__Rhodospirillales;D_4__Acetobacteraceae;D_5__Belnapia |
| D_0__Bacteria;D_1__Proteobacteria;D_2__Alphaproteobacteria;D_3__Rhodospirillales;D_4__Acetobacteraceae;D_5__Commensalibacter |
| D_0__Bacteria;D_1__Proteobacteria;D_2__Alphaproteobacteria;D_3__Rhodospirillales;D_4__Acetobacteraceae;D_5__Craurococcus |
| D_0__Bacteria;D_1__Proteobacteria;D_2__Alphaproteobacteria;D_3__Rhodospirillales;D_4__Acetobacteraceae;D_5__Gluconacetobacter |
| D_0__Bacteria;D_1__Proteobacteria;D_2__Alphaproteobacteria;D_3__Rhodospirillales;D_4__Acetobacteraceae;D_5__Gluconobacter |
| D_0__Bacteria;D_1__Proteobacteria;D_2__Alphaproteobacteria;D_3__Rhodospirillales;D_4__Acetobacteraceae;D_5__Komagataeibacter |
| D_0__Bacteria;D_1__Proteobacteria;D_2__Alphaproteobacteria;D_3__Rhodospirillales;D_4__Acetobacteraceae;D_5__Muricoccus |
| D_0__Bacteria;D_1__Proteobacteria;D_2__Alphaproteobacteria;D_3__Rhodospirillales;D_4__Acetobacteraceae;D_5__Rhodovastum |
| D_0__Bacteria;D_1__Proteobacteria;D_2__Alphaproteobacteria;D_3__Rhodospirillales;D_4__Acetobacteraceae;D_5__Roseomonas |
| D_0__Bacteria;D_1__Proteobacteria;D_2__Alphaproteobacteria;D_3__Rhodospirillales;D_4__Acetobacteraceae;D_5__Rubritepida |
| D_0__Bacteria;D_1__Proteobacteria;D_2__Alphaproteobacteria;D_3__Rhodospirillales;D_4__Acetobacteraceae;D_5__Saccharibacter |
| D_0__Bacteria;D_1__Proteobacteria;D_2__Alphaproteobacteria;D_3__Rhodospirillales;D_4__Acetobacteraceae;D_5__uncultured |
| D_0__Bacteria;D_1__Proteobacteria;D_2__Alphaproteobacteria;D_3__Rhodospirillales;D_4__Acetobacteraceae;Other |
| D_0__Bacteria;D_1__Proteobacteria;D_2__Alphaproteobacteria;D_3__Rhodospirillales;D_4__B79;D_5__uncultured bacterium |
| D_0__Bacteria;D_1__Proteobacteria;D_2__Alphaproteobacteria;D_3__Rhodospirillales;D_4__CCU22;Other |
| D_0__Bacteria;D_1__Proteobacteria;D_2__Alphaproteobacteria;D_3__Rhodospirillales;D_4__DA111;D_5__uncultured alpha proteobacterium |
| D_0__Bacteria;D_1__Proteobacteria;D_2__Alphaproteobacteria;D_3__Rhodospirillales;D_4__DA111;D_5__uncultured bacterium |
| D_0__Bacteria;D_1__Proteobacteria;D_2__Alphaproteobacteria;D_3__Rhodospirillales;D_4__DA111;D_5__uncultured forest soil bacterium |
| D_0__Bacteria;D_1__Proteobacteria;D_2__Alphaproteobacteria;D_3__Rhodospirillales;D_4__DA111;Other |
| D_0__Bacteria;D_1__Proteobacteria;D_2__Alphaproteobacteria;D_3__Rhodospirillales;D_4__I-10;D_5__uncultured bacterium |
| D_0__Bacteria;D_1__Proteobacteria;D_2__Alphaproteobacteria;D_3__Rhodospirillales;D_4__JG37-AG-20;D_5__uncultured bacterium |
| D_0__Bacteria;D_1__Proteobacteria;D_2__Alphaproteobacteria;D_3__Rhodospirillales;D_4__JG37-AG-20;Other |
| D_0__Bacteria;D_1__Proteobacteria;D_2__Alphaproteobacteria;D_3__Rhodospirillales;D_4__KCM-B-15;D_5__uncultured Rhodospirillaceae bacterium |
| D_0__Bacteria;D_1__Proteobacteria;D_2__Alphaproteobacteria;D_3__Rhodospirillales;D_4__KCM-B-15;D_5__uncultured bacterium |
| D_0__Bacteria;D_1__Proteobacteria;D_2__Alphaproteobacteria;D_3__Rhodospirillales;D_4__KCM-B-15;Other |
| D_0__Bacteria;D_1__Proteobacteria;D_2__Alphaproteobacteria;D_3__Rhodospirillales;D_4__KCM |

| |
|---|
| -B-60;D_5__uncultured Rhodospirillales bacterium |
| D_0__Bacteria;D_1__Proteobacteria;D_2__Alphaproteobacteria;D_3__Rhodospirillales;D_4__KCM B 60;D_5__uncultured bacterium |
| D_0__Bacteria;D_1__Proteobacteria;D_2__Alphaproteobacteria;D_3__Rhodospirillales;D_4__KCM-B-60;Other |
| D_0__Bacteria;D_1__Proteobacteria;D_2__Alphaproteobacteria;D_3__Rhodospirillales;D_4__MNC 12;D_5__uncultured bacterium |
| D_0__Bacteria;D_1__Proteobacteria;D_2__Alphaproteobacteria;D_3__Rhodospirillales;D_4__MND 8;D_5__uncultured bacterium |
| D_0__Bacteria;D_1__Proteobacteria;D_2__Alphaproteobacteria;D_3__Rhodospirillales;D_4__MND 8;Other |
| D_0__Bacteria;D_1__Proteobacteria;D_2__Alphaproteobacteria;D_3__Rhodospirillales;D_4__MSB-1E8;D_5__uncultured Rhodospirillales bacterium |
| D_0__Bacteria;D_1__Proteobacteria;D_2__Alphaproteobacteria;D_3__Rhodospirillales;D_4__MSB-1E8;D_5__uncultured alpha proteobacterium |
| D_0__Bacteria;D_1__Proteobacteria;D_2__Alphaproteobacteria;D_3__Rhodospirillales;D_4__MSB-1E8;D_5__uncultured bacterium |
| D_0__Bacteria;D_1__Proteobacteria;D_2__Alphaproteobacteria;D_3__Rhodospirillales;D_4__MSB-1E8;Other |
| D_0__Bacteria;D_1__Proteobacteria;D_2__Alphaproteobacteria;D_3__Rhodospirillales;D_4__Rhodospirillaceae;D_5__Azospirillum |
| D_0__Bacteria;D_1__Proteobacteria;D_2__Alphaproteobacteria;D_3__Rhodospirillales;D_4__Rhodospirillaceae;D_5__Defluviicoccus |
| D_0__Bacteria;D_1__Proteobacteria;D_2__Alphaproteobacteria;D_3__Rhodospirillales;D_4__Rhodospirillaceae;D_5__Desertibacter |
| D_0__Bacteria;D_1__Proteobacteria;D_2__Alphaproteobacteria;D_3__Rhodospirillales;D_4__Rhodospirillaceae;D_5__Dongia |
| D_0__Bacteria;D_1__Proteobacteria;D_2__Alphaproteobacteria;D_3__Rhodospirillales;D_4__Rhodospirillaceae;D_5__Elstera |
| D_0__Bacteria;D_1__Proteobacteria;D_2__Alphaproteobacteria;D_3__Rhodospirillales;D_4__Rhodospirillaceae;D_5__Ferrovibrio |
| D_0__Bacteria;D_1__Proteobacteria;D_2__Alphaproteobacteria;D_3__Rhodospirillales;D_4__Rhodospirillaceae;D_5__Inquilinus |
| D_0__Bacteria;D_1__Proteobacteria;D_2__Alphaproteobacteria;D_3__Rhodospirillales;D_4__Rhodospirillaceae;D_5__Pelagibius |
| D_0__Bacteria;D_1__Proteobacteria;D_2__Alphaproteobacteria;D_3__Rhodospirillales;D_4__Rhodospirillaceae;D_5__Skermanella |
| D_0__Bacteria;D_1__Proteobacteria;D_2__Alphaproteobacteria;D_3__Rhodospirillales;D_4__Rhodospirillaceae;D_5__Thalassobaculum |
| D_0__Bacteria;D_1__Proteobacteria;D_2__Alphaproteobacteria;D_3__Rhodospirillales;D_4__Rhodospirillaceae;D_5__Thalassospira |
| D_0__Bacteria;D_1__Proteobacteria;D_2__Alphaproteobacteria;D_3__Rhodospirillales;D_4__Rhodospirillaceae;D_5__uncultured |
| D_0__Bacteria;D_1__Proteobacteria;D_2__Alphaproteobacteria;D_3__Rhodospirillales;D_4__Rhodospirillaceae;Other |
| D_0__Bacteria;D_1__Proteobacteria;D_2__Alphaproteobacteria;D_3__Rhodospirillales;D_4__Rhodospirillales Incertae Sedis;D_5__Candidatus Alysiosphaera |
| D_0__Bacteria;D_1__Proteobacteria;D_2__Alphaproteobacteria;D_3__Rhodospirillales;D_4__Rhodospirillales Incertae Sedis;D_5__Geminicoccus |
| D_0__Bacteria;D_1__Proteobacteria;D_2__Alphaproteobacteria;D_3__Rhodospirillales;D_4__Rhodospirillales Incertae Sedis;D_5__Reyranella |
| D_0__Bacteria;D_1__Proteobacteria;D_2__Alphaproteobacteria;D_3__Rhodospirillales;D_4__Rhodospirillales Incertae Sedis;Other |
| D_0__Bacteria;D_1__Proteobacteria;D_2__Alphaproteobacteria;D_3__Rhodospirillales;Other;Other |
| D_0__Bacteria;D_1__Proteobacteria;D_2__Alphaproteobacteria;D_3__Rickettsiales;D_4__AKIW10 12;D_5__uncultured bacterium |
| D_0__Bacteria;D_1__Proteobacteria;D_2__Alphaproteobacteria;D_3__Rickettsiales;D_4__AKIW10 12;Other |
| D_0__Bacteria;D_1__Proteobacteria;D_2__Alphaproteobacteria;D_3__Rickettsiales;D_4__Anaplasmataceae;D_5__Wolbachia |
| D_0__Bacteria;D_1__Proteobacteria;D_2__Alphaproteobacteria;D_3__Rickettsiales;D_4__Anapla |

| |
|---|
| smataceae;D_5__uncultured |
| D_0__Bacteria;D_1__Proteobacteria;D_2__Alphaproteobacteria;D_3__Rickettsiales;D_4__EF100-94H03;D_5__uncultured bacterium |
| D_0__Bacteria;D_1__Proteobacteria;D_2__Alphaproteobacteria;D_3__Rickettsiales;D_4__Holosporaceae;D_5__uncultured |
| D_0__Bacteria;D_1__Proteobacteria;D_2__Alphaproteobacteria;D_3__Rickettsiales;D_4__LWSR-14;D_5__uncultured bacterium |
| D_0__Bacteria;D_1__Proteobacteria;D_2__Alphaproteobacteria;D_3__Rickettsiales;D_4__LWSR-14;Other |
| D_0__Bacteria;D_1__Proteobacteria;D_2__Alphaproteobacteria;D_3__Rickettsiales;D_4__RB446;D_5__uncultured bacterium |
| D_0__Bacteria;D_1__Proteobacteria;D_2__Alphaproteobacteria;D_3__Rickettsiales;D_4__Rickettsiaceae;D_5__Rickettsia |
| D_0__Bacteria;D_1__Proteobacteria;D_2__Alphaproteobacteria;D_3__Rickettsiales;D_4__Rickettsiaceae;D_5__uncultured |
| D_0__Bacteria;D_1__Proteobacteria;D_2__Alphaproteobacteria;D_3__Rickettsiales;D_4__Rickettsiaceae;Other |
| D_0__Bacteria;D_1__Proteobacteria;D_2__Alphaproteobacteria;D_3__Rickettsiales;D_4__Rickettsiales Incertae Sedis;D_5__Candidatus Captivus |
| D_0__Bacteria;D_1__Proteobacteria;D_2__Alphaproteobacteria;D_3__Rickettsiales;D_4__Rickettsiales Incertae Sedis;D_5__Candidatus Hepatincola |
| D_0__Bacteria;D_1__Proteobacteria;D_2__Alphaproteobacteria;D_3__Rickettsiales;D_4__Rickettsiales Incertae Sedis;D_5__Candidatus Odyssella |
| D_0__Bacteria;D_1__Proteobacteria;D_2__Alphaproteobacteria;D_3__Rickettsiales;D_4__Rickettsiales Incertae Sedis;D_5__Constrictibacter |
| D_0__Bacteria;D_1__Proteobacteria;D_2__Alphaproteobacteria;D_3__Rickettsiales;D_4__SM2D12;D_5__uncultured alpha proteobacterium |
| D_0__Bacteria;D_1__Proteobacteria;D_2__Alphaproteobacteria;D_3__Rickettsiales;D_4__SM2D12;D_5__uncultured bacterium |
| D_0__Bacteria;D_1__Proteobacteria;D_2__Alphaproteobacteria;D_3__Rickettsiales;D_4__SM2D12;D_5__uncultured organism |
| D_0__Bacteria;D_1__Proteobacteria;D_2__Alphaproteobacteria;D_3__Rickettsiales;D_4__SM2D12;Other |
| D_0__Bacteria;D_1__Proteobacteria;D_2__Alphaproteobacteria;D_3__Rickettsiales;D_4__TK34;D_5__uncultured bacterium |
| D_0__Bacteria;D_1__Proteobacteria;D_2__Alphaproteobacteria;D_3__Rickettsiales;D_4__TK34;Other |
| D_0__Bacteria;D_1__Proteobacteria;D_2__Alphaproteobacteria;D_3__Rickettsiales;D_4__uncultured;D_5__uncultured bacterium |
| D_0__Bacteria;D_1__Proteobacteria;D_2__Alphaproteobacteria;D_3__Rickettsiales;Other;Other |
| D_0__Bacteria;D_1__Proteobacteria;D_2__Alphaproteobacteria;D_3__Sneathiellales;D_4__Sneathiellaceae;D_5__uncultured |
| D_0__Bacteria;D_1__Proteobacteria;D_2__Alphaproteobacteria;D_3__Sphingomonadales;D_4__7B-8;D_5__uncultured bacterium |
| D_0__Bacteria;D_1__Proteobacteria;D_2__Alphaproteobacteria;D_3__Sphingomonadales;D_4__7B-8;Other |
| D_0__Bacteria;D_1__Proteobacteria;D_2__Alphaproteobacteria;D_3__Sphingomonadales;D_4__DSSF69;Other |
| D_0__Bacteria;D_1__Proteobacteria;D_2__Alphaproteobacteria;D_3__Sphingomonadales;D_4__Ellin6055;D_5__uncultured bacterium |
| D_0__Bacteria;D_1__Proteobacteria;D_2__Alphaproteobacteria;D_3__Sphingomonadales;D_4__Ellin6055;Other |
| D_0__Bacteria;D_1__Proteobacteria;D_2__Alphaproteobacteria;D_3__Sphingomonadales;D_4__Erythrobacteraceae;D_5__Altererythrobacter |
| D_0__Bacteria;D_1__Proteobacteria;D_2__Alphaproteobacteria;D_3__Sphingomonadales;D_4__Erythrobacteraceae;D_5__Erythrobacter |
| D_0__Bacteria;D_1__Proteobacteria;D_2__Alphaproteobacteria;D_3__Sphingomonadales;D_4__Erythrobacteraceae;D_5__Porphyrobacter |
| D_0__Bacteria;D_1__Proteobacteria;D_2__Alphaproteobacteria;D_3__Sphingomonadales;D_4__Erythrobacteraceae;D_5__uncultured |
| D_0__Bacteria;D_1__Proteobacteria;D_2__Alphaproteobacteria;D_3__Sphingomonadales;D_4__Erythrobacteraceae;Other |

| |
|---|
| D_0__Bacteria;D_1__Proteobacteria;D_2__Alphaproteobacteria;D_3__Sphingomonadales;D_4__JG34-KF-161;D_5__uncultured bacterium |
| D_0__Bacteria;D_1__Proteobacteria;D_2__Alphaproteobacteria;D_3__Sphingomonadales;D_4__JG34-KF-161;D_5__uncultured soil bacterium |
| D_0__Bacteria;D_1__Proteobacteria;D_2__Alphaproteobacteria;D_3__Sphingomonadales;D_4__JG34-KF-161;Other |
| D_0__Bacteria;D_1__Proteobacteria;D_2__Alphaproteobacteria;D_3__Sphingomonadales;D_4__Sphingomonadaceae;D_5__Novosphingobium |
| D_0__Bacteria;D_1__Proteobacteria;D_2__Alphaproteobacteria;D_3__Sphingomonadales;D_4__Sphingomonadaceae;D_5__Sandaracinobacter |
| D_0__Bacteria;D_1__Proteobacteria;D_2__Alphaproteobacteria;D_3__Sphingomonadales;D_4__Sphingomonadaceae;D_5__Sandarakinorhabdus |
| D_0__Bacteria;D_1__Proteobacteria;D_2__Alphaproteobacteria;D_3__Sphingomonadales;D_4__Sphingomonadaceae;D_5__Sphingobium |
| D_0__Bacteria;D_1__Proteobacteria;D_2__Alphaproteobacteria;D_3__Sphingomonadales;D_4__Sphingomonadaceae;D_5__Sphingomicrobium |
| D_0__Bacteria;D_1__Proteobacteria;D_2__Alphaproteobacteria;D_3__Sphingomonadales;D_4__Sphingomonadaceae;D_5__Sphingomonas |
| D_0__Bacteria;D_1__Proteobacteria;D_2__Alphaproteobacteria;D_3__Sphingomonadales;D_4__Sphingomonadaceae;D_5__Sphingopyxis |
| D_0__Bacteria;D_1__Proteobacteria;D_2__Alphaproteobacteria;D_3__Sphingomonadales;D_4__Sphingomonadaceae;D_5__Sphingorhabdus |
| D_0__Bacteria;D_1__Proteobacteria;D_2__Alphaproteobacteria;D_3__Sphingomonadales;D_4__Sphingomonadaceae;D_5__Zymomonas |
| D_0__Bacteria;D_1__Proteobacteria;D_2__Alphaproteobacteria;D_3__Sphingomonadales;D_4__Sphingomonadaceae;D_5__uncultured |
| D_0__Bacteria;D_1__Proteobacteria;D_2__Alphaproteobacteria;D_3__Sphingomonadales;D_4__Sphingomonadaceae;Other |
| D_0__Bacteria;D_1__Proteobacteria;D_2__Alphaproteobacteria;D_3__Sphingomonadales;D_4__WW2-159;Other |
| D_0__Bacteria;D_1__Proteobacteria;D_2__Alphaproteobacteria;D_3__Sphingomonadales;Other;Other |
| D_0__Bacteria;D_1__Proteobacteria;D_2__Alphaproteobacteria;Other;Other;Other |
| D_0__Bacteria;D_1__Proteobacteria;D_2__Betaproteobacteria;D_3__B1-7BS;D_4__uncultured bacterium;D_5__ |
| D_0__Bacteria;D_1__Proteobacteria;D_2__Betaproteobacteria;D_3__Burkholderiales;D_4__Alcaligenaceae;D_5__Achromobacter |
| D_0__Bacteria;D_1__Proteobacteria;D_2__Betaproteobacteria;D_3__Burkholderiales;D_4__Alcaligenaceae;D_5__Advenella |
| D_0__Bacteria;D_1__Proteobacteria;D_2__Betaproteobacteria;D_3__Burkholderiales;D_4__Alcaligenaceae;D_5__Alcaligenes |
| D_0__Bacteria;D_1__Proteobacteria;D_2__Betaproteobacteria;D_3__Burkholderiales;D_4__Alcaligenaceae;D_5__Oligella |
| D_0__Bacteria;D_1__Proteobacteria;D_2__Betaproteobacteria;D_3__Burkholderiales;D_4__Alcaligenaceae;D_5__Parapusillimonas |
| D_0__Bacteria;D_1__Proteobacteria;D_2__Betaproteobacteria;D_3__Burkholderiales;D_4__Alcaligenaceae;D_5__Pusillimonas |
| D_0__Bacteria;D_1__Proteobacteria;D_2__Betaproteobacteria;D_3__Burkholderiales;D_4__Alcaligenaceae;D_5__Sutterella |
| D_0__Bacteria;D_1__Proteobacteria;D_2__Betaproteobacteria;D_3__Burkholderiales;D_4__Alcaligenaceae;D_5__uncultured |
| D_0__Bacteria;D_1__Proteobacteria;D_2__Betaproteobacteria;D_3__Burkholderiales;D_4__Alcaligenaceae;Other |
| D_0__Bacteria;D_1__Proteobacteria;D_2__Betaproteobacteria;D_3__Burkholderiales;D_4__Burkholderiaceae;D_5__Burkholderia |
| D_0__Bacteria;D_1__Proteobacteria;D_2__Betaproteobacteria;D_3__Burkholderiales;D_4__Burkholderiaceae;D_5__Candidatus Glomeribacter |
| D_0__Bacteria;D_1__Proteobacteria;D_2__Betaproteobacteria;D_3__Burkholderiales;D_4__Burkholderiaceae;D_5__Candidatus Tremblaya |
| D_0__Bacteria;D_1__Proteobacteria;D_2__Betaproteobacteria;D_3__Burkholderiales;D_4__Burkholderiaceae;D_5__Cupriavidus |
| D_0__Bacteria;D_1__Proteobacteria;D_2__Betaproteobacteria;D_3__Burkholderiales;D_4__Burkh |

| |
|---|
| olderiaceae;D_5__Lautropia |
| D_0__Bacteria;D_1__Proteobacteria;D_2__Betaproteobacteria;D_3__Burkholderiales;D_4__Burkholderiaceae;D_5__Limnobacter |
| D_0__Bacteria;D_1__Proteobacteria;D_2__Betaproteobacteria;D_3__Burkholderiales;D_4__Burkholderiaceae;D_5__Polynucleobacter |
| D_0__Bacteria;D_1__Proteobacteria;D_2__Betaproteobacteria;D_3__Burkholderiales;D_4__Burkholderiaceae;D_5__Ralstonia |
| D_0__Bacteria;D_1__Proteobacteria;D_2__Betaproteobacteria;D_3__Burkholderiales;D_4__Comamonadaceae;D_5__Acidovorax |
| D_0__Bacteria;D_1__Proteobacteria;D_2__Betaproteobacteria;D_3__Burkholderiales;D_4__Comamonadaceae;D_5__Alicycliphilus |
| D_0__Bacteria;D_1__Proteobacteria;D_2__Betaproteobacteria;D_3__Burkholderiales;D_4__Comamonadaceae;D_5__Aquabacterium |
| D_0__Bacteria;D_1__Proteobacteria;D_2__Betaproteobacteria;D_3__Burkholderiales;D_4__Comamonadaceae;D_5__Aquincola |
| D_0__Bacteria;D_1__Proteobacteria;D_2__Betaproteobacteria;D_3__Burkholderiales;D_4__Comamonadaceae;D_5__Azohydromonas |
| D_0__Bacteria;D_1__Proteobacteria;D_2__Betaproteobacteria;D_3__Burkholderiales;D_4__Comamonadaceae;D_5__Brachymonas |
| D_0__Bacteria;D_1__Proteobacteria;D_2__Betaproteobacteria;D_3__Burkholderiales;D_4__Comamonadaceae;D_5__Caenimonas |
| D_0__Bacteria;D_1__Proteobacteria;D_2__Betaproteobacteria;D_3__Burkholderiales;D_4__Comamonadaceae;D_5__Caldimonas |
| D_0__Bacteria;D_1__Proteobacteria;D_2__Betaproteobacteria;D_3__Burkholderiales;D_4__Comamonadaceae;D_5__Chlorochromatium |
| D_0__Bacteria;D_1__Proteobacteria;D_2__Betaproteobacteria;D_3__Burkholderiales;D_4__Comamonadaceae;D_5__Comamonas |
| D_0__Bacteria;D_1__Proteobacteria;D_2__Betaproteobacteria;D_3__Burkholderiales;D_4__Comamonadaceae;D_5__Curvibacter |
| D_0__Bacteria;D_1__Proteobacteria;D_2__Betaproteobacteria;D_3__Burkholderiales;D_4__Comamonadaceae;D_5__Delftia |
| D_0__Bacteria;D_1__Proteobacteria;D_2__Betaproteobacteria;D_3__Burkholderiales;D_4__Comamonadaceae;D_5__Hydrogenophaga |
| D_0__Bacteria;D_1__Proteobacteria;D_2__Betaproteobacteria;D_3__Burkholderiales;D_4__Comamonadaceae;D_5__Ideonella |
| D_0__Bacteria;D_1__Proteobacteria;D_2__Betaproteobacteria;D_3__Burkholderiales;D_4__Comamonadaceae;D_5__Leptothrix |
| D_0__Bacteria;D_1__Proteobacteria;D_2__Betaproteobacteria;D_3__Burkholderiales;D_4__Comamonadaceae;D_5__Limnohabitans |
| D_0__Bacteria;D_1__Proteobacteria;D_2__Betaproteobacteria;D_3__Burkholderiales;D_4__Comamonadaceae;D_5__Ottowia |
| D_0__Bacteria;D_1__Proteobacteria;D_2__Betaproteobacteria;D_3__Burkholderiales;D_4__Comamonadaceae;D_5__Paucibacter |
| D_0__Bacteria;D_1__Proteobacteria;D_2__Betaproteobacteria;D_3__Burkholderiales;D_4__Comamonadaceae;D_5__Pelomonas |
| D_0__Bacteria;D_1__Proteobacteria;D_2__Betaproteobacteria;D_3__Burkholderiales;D_4__Comamonadaceae;D_5__Piscinibacter |
| D_0__Bacteria;D_1__Proteobacteria;D_2__Betaproteobacteria;D_3__Burkholderiales;D_4__Comamonadaceae;D_5__Polaromonas |
| D_0__Bacteria;D_1__Proteobacteria;D_2__Betaproteobacteria;D_3__Burkholderiales;D_4__Comamonadaceae;D_5__Ramlibacter |
| D_0__Bacteria;D_1__Proteobacteria;D_2__Betaproteobacteria;D_3__Burkholderiales;D_4__Comamonadaceae;D_5__Rhizobacter |
| D_0__Bacteria;D_1__Proteobacteria;D_2__Betaproteobacteria;D_3__Burkholderiales;D_4__Comamonadaceae;D_5__Schlegelella |
| D_0__Bacteria;D_1__Proteobacteria;D_2__Betaproteobacteria;D_3__Burkholderiales;D_4__Comamonadaceae;D_5__Simplicispira |
| D_0__Bacteria;D_1__Proteobacteria;D_2__Betaproteobacteria;D_3__Burkholderiales;D_4__Comamonadaceae;D_5__Tepidimonas |
| D_0__Bacteria;D_1__Proteobacteria;D_2__Betaproteobacteria;D_3__Burkholderiales;D_4__Comamonadaceae;D_5__Variovorax |
| D_0__Bacteria;D_1__Proteobacteria;D_2__Betaproteobacteria;D_3__Burkholderiales;D_4__Comam |

| |
|---|
| onadaceae;D_5__Xenophilus |
| D_0__Bacteria;D_1__Proteobacteria;D_2__Betaproteobacteria;D_3__Burkholderiales;D_4__Comamonadaceae;D_5__uncultured |
| D_0__Bacteria;D_1__Proteobacteria;D_2__Betaproteobacteria;D_3__Burkholderiales;D_4__Comamonadaceae;Other |
| D_0__Bacteria;D_1__Proteobacteria;D_2__Betaproteobacteria;D_3__Burkholderiales;D_4__Oxalobacteraceae;D_5__Herbaspirillum |
| D_0__Bacteria;D_1__Proteobacteria;D_2__Betaproteobacteria;D_3__Burkholderiales;D_4__Oxalobacteraceae;D_5__Herminiimonas |
| D_0__Bacteria;D_1__Proteobacteria;D_2__Betaproteobacteria;D_3__Burkholderiales;D_4__Oxalobacteraceae;D_5__Janthinobacterium |
| D_0__Bacteria;D_1__Proteobacteria;D_2__Betaproteobacteria;D_3__Burkholderiales;D_4__Oxalobacteraceae;D_5__Massilia |
| D_0__Bacteria;D_1__Proteobacteria;D_2__Betaproteobacteria;D_3__Burkholderiales;D_4__Oxalobacteraceae;D_5__Noviherbaspirillum |
| D_0__Bacteria;D_1__Proteobacteria;D_2__Betaproteobacteria;D_3__Burkholderiales;D_4__Oxalobacteraceae;D_5__Undibacterium |
| D_0__Bacteria;D_1__Proteobacteria;D_2__Betaproteobacteria;D_3__Burkholderiales;D_4__Oxalobacteraceae;D_5__uncultured |
| D_0__Bacteria;D_1__Proteobacteria;D_2__Betaproteobacteria;D_3__Burkholderiales;D_4__Oxalobacteraceae;Other |
| D_0__Bacteria;D_1__Proteobacteria;D_2__Betaproteobacteria;D_3__Burkholderiales;Other;Other |
| D_0__Bacteria;D_1__Proteobacteria;D_2__Betaproteobacteria;D_3__Hot Creek 32;D_4__uncultured bacterium;D_5__ |
| D_0__Bacteria;D_1__Proteobacteria;D_2__Betaproteobacteria;D_3__Hydrogenophilales;D_4__Hydrogenophilaceae;D_5__Ferritrophicum |
| D_0__Bacteria;D_1__Proteobacteria;D_2__Betaproteobacteria;D_3__Hydrogenophilales;D_4__Hydrogenophilaceae;D_5__Hydrogenophilus |
| D_0__Bacteria;D_1__Proteobacteria;D_2__Betaproteobacteria;D_3__Hydrogenophilales;D_4__Hydrogenophilaceae;D_5__Tepidiphilus |
| D_0__Bacteria;D_1__Proteobacteria;D_2__Betaproteobacteria;D_3__Hydrogenophilales;D_4__Hydrogenophilaceae;D_5__Thiobacillus |
| D_0__Bacteria;D_1__Proteobacteria;D_2__Betaproteobacteria;D_3__Hydrogenophilales;D_4__Hydrogenophilaceae;D_5__uncultured |
| D_0__Bacteria;D_1__Proteobacteria;D_2__Betaproteobacteria;D_3__Methylophilales;D_4__Methylophilaceae;D_5__Methylobacillus |
| D_0__Bacteria;D_1__Proteobacteria;D_2__Betaproteobacteria;D_3__Methylophilales;D_4__Methylophilaceae;D_5__Methylophilus |
| D_0__Bacteria;D_1__Proteobacteria;D_2__Betaproteobacteria;D_3__Methylophilales;D_4__Methylophilaceae;D_5__Methylotenera |
| D_0__Bacteria;D_1__Proteobacteria;D_2__Betaproteobacteria;D_3__Methylophilales;D_4__Methylophilaceae;D_5__OM43 clade |
| D_0__Bacteria;D_1__Proteobacteria;D_2__Betaproteobacteria;D_3__Methylophilales;D_4__Methylophilaceae;D_5__PRD01a011B |
| D_0__Bacteria;D_1__Proteobacteria;D_2__Betaproteobacteria;D_3__Methylophilales;D_4__Methylophilaceae;D_5__uncultured |
| D_0__Bacteria;D_1__Proteobacteria;D_2__Betaproteobacteria;D_3__Methylophilales;D_4__Methylophilaceae;Other |
| D_0__Bacteria;D_1__Proteobacteria;D_2__Betaproteobacteria;D_3__Neisseriales;D_4__Neisseriaceae;D_5__Kingella |
| D_0__Bacteria;D_1__Proteobacteria;D_2__Betaproteobacteria;D_3__Neisseriales;D_4__Neisseriaceae;D_5__Neisseria |
| D_0__Bacteria;D_1__Proteobacteria;D_2__Betaproteobacteria;D_3__Neisseriales;D_4__Neisseriaceae;D_5__Snodgrassella |
| D_0__Bacteria;D_1__Proteobacteria;D_2__Betaproteobacteria;D_3__Neisseriales;D_4__Neisseriaceae;D_5__Vogesella |
| D_0__Bacteria;D_1__Proteobacteria;D_2__Betaproteobacteria;D_3__Neisseriales;D_4__Neisseriaceae;D_5__uncultured |
| D_0__Bacteria;D_1__Proteobacteria;D_2__Betaproteobacteria;D_3__Neisseriales;D_4__Neisseriaceae;Other |
| D_0__Bacteria;D_1__Proteobacteria;D_2__Betaproteobacteria;D_3__Nitrosomonadales;D_4__Gall |

| |
|---|
| ionellaceae;D_5__Candidatus Nitrotoga |
| D_0__Bacteria;D_1__Proteobacteria;D_2__Betaproteobacteria;D_3__Nitrosomonadales;D_4__Gallionellaceae;D_5__Gallionella |
| D_0__Bacteria;D_1__Proteobacteria;D_2__Betaproteobacteria;D_3__Nitrosomonadales;D_4__Gallionellaceae;D_5__Sideroxydans |
| D_0__Bacteria;D_1__Proteobacteria;D_2__Betaproteobacteria;D_3__Nitrosomonadales;D_4__Gallionellaceae;D_5__uncultured |
| D_0__Bacteria;D_1__Proteobacteria;D_2__Betaproteobacteria;D_3__Nitrosomonadales;D_4__Gallionellaceae;Other |
| D_0__Bacteria;D_1__Proteobacteria;D_2__Betaproteobacteria;D_3__Nitrosomonadales;D_4__Nitrosomonadaceae;D_5__Nitrosomonas |
| D_0__Bacteria;D_1__Proteobacteria;D_2__Betaproteobacteria;D_3__Nitrosomonadales;D_4__Nitrosomonadaceae;D_5__Nitrosospira |
| D_0__Bacteria;D_1__Proteobacteria;D_2__Betaproteobacteria;D_3__Nitrosomonadales;D_4__Nitrosomonadaceae;D_5__uncultured |
| D_0__Bacteria;D_1__Proteobacteria;D_2__Betaproteobacteria;D_3__Nitrosomonadales;D_4__Nitrosomonadaceae;Other |
| D_0__Bacteria;D_1__Proteobacteria;D_2__Betaproteobacteria;D_3__Procabacteriales;D_4__Procabacteriaceae;D_5__Procabacter |
| D_0__Bacteria;D_1__Proteobacteria;D_2__Betaproteobacteria;D_3__Rhodocyclales;D_4__Rhodocyclaceae;D_5__Azoarcus |
| D_0__Bacteria;D_1__Proteobacteria;D_2__Betaproteobacteria;D_3__Rhodocyclales;D_4__Rhodocyclaceae;D_5__Azospira |
| D_0__Bacteria;D_1__Proteobacteria;D_2__Betaproteobacteria;D_3__Rhodocyclales;D_4__Rhodocyclaceae;D_5__Candidatus Accumulibacter |
| D_0__Bacteria;D_1__Proteobacteria;D_2__Betaproteobacteria;D_3__Rhodocyclales;D_4__Rhodocyclaceae;D_5__Dechloromonas |
| D_0__Bacteria;D_1__Proteobacteria;D_2__Betaproteobacteria;D_3__Rhodocyclales;D_4__Rhodocyclaceae;D_5__Denitratisoma |
| D_0__Bacteria;D_1__Proteobacteria;D_2__Betaproteobacteria;D_3__Rhodocyclales;D_4__Rhodocyclaceae;D_5__Methyloversatilis |
| D_0__Bacteria;D_1__Proteobacteria;D_2__Betaproteobacteria;D_3__Rhodocyclales;D_4__Rhodocyclaceae;D_5__Propionivibrio |
| D_0__Bacteria;D_1__Proteobacteria;D_2__Betaproteobacteria;D_3__Rhodocyclales;D_4__Rhodocyclaceae;D_5__Thauera |
| D_0__Bacteria;D_1__Proteobacteria;D_2__Betaproteobacteria;D_3__Rhodocyclales;D_4__Rhodocyclaceae;D_5__Uliginosibacterium |
| D_0__Bacteria;D_1__Proteobacteria;D_2__Betaproteobacteria;D_3__Rhodocyclales;D_4__Rhodocyclaceae;D_5__Zoogloea |
| D_0__Bacteria;D_1__Proteobacteria;D_2__Betaproteobacteria;D_3__Rhodocyclales;D_4__Rhodocyclaceae;D_5__uncultured |
| D_0__Bacteria;D_1__Proteobacteria;D_2__Betaproteobacteria;D_3__Rhodocyclales;D_4__Rhodocyclaceae;Other |
| D_0__Bacteria;D_1__Proteobacteria;D_2__Betaproteobacteria;D_3__SC-I-84;D_4__uncultured bacterium;D_5__ |
| D_0__Bacteria;D_1__Proteobacteria;D_2__Betaproteobacteria;D_3__SC-I-84;D_4__uncultured beta proteobacterium;D_5__ |
| D_0__Bacteria;D_1__Proteobacteria;D_2__Betaproteobacteria;D_3__SC-I-84;D_4__uncultured prokaryote;D_5__ |
| D_0__Bacteria;D_1__Proteobacteria;D_2__Betaproteobacteria;D_3__SC-I-84;Other;Other |
| D_0__Bacteria;D_1__Proteobacteria;D_2__Betaproteobacteria;D_3__TRA3-20;D_4__uncultured bacterium;D_5__ |
| D_0__Bacteria;D_1__Proteobacteria;D_2__Betaproteobacteria;D_3__TRA3-20;D_4__uncultured beta proteobacterium;D_5__ |
| D_0__Bacteria;D_1__Proteobacteria;D_2__Betaproteobacteria;D_3__TRA3-20;Other;Other |
| D_0__Bacteria;D_1__Proteobacteria;D_2__Betaproteobacteria;D_3__UCT N117;D_4__uncultured bacterium;D_5__ |
| D_0__Bacteria;D_1__Proteobacteria;D_2__Betaproteobacteria;Other;Other;Other |
| D_0__Bacteria;D_1__Proteobacteria;D_2__Deltaproteobacteria;D_3__43F-1404R;D_4__uncultured bacterium;D_5__ |

| |
|---|
| D_0__Bacteria;D_1__Proteobacteria;D_2__Deltaproteobacteria;D_3__Bdellovibrionales;D_4__Bacteriovoracaceae;D_5__Bacteriovorax |
| D_0__Bacteria;D_1__Proteobacteria;D_2__Deltaproteobacteria;D_3__Bdellovibrionales;D_4__Bacteriovoracaceae;D_5__Peredibacter |
| D_0__Bacteria;D_1__Proteobacteria;D_2__Deltaproteobacteria;D_3__Bdellovibrionales;D_4__Bacteriovoracaceae;D_5__uncultured |
| D_0__Bacteria;D_1__Proteobacteria;D_2__Deltaproteobacteria;D_3__Bdellovibrionales;D_4__Bacteriovoracaceae;Other |
| D_0__Bacteria;D_1__Proteobacteria;D_2__Deltaproteobacteria;D_3__Bdellovibrionales;D_4__Bdellovibrionaceae;D_5__Bdellovibrio |
| D_0__Bacteria;D_1__Proteobacteria;D_2__Deltaproteobacteria;D_3__Bdellovibrionales;D_4__Bdellovibrionaceae;D_5__OM27 clade |
| D_0__Bacteria;D_1__Proteobacteria;D_2__Deltaproteobacteria;D_3__Desulfarculales;D_4__Desulfarculaceae;D_5__Desulfarculus |
| D_0__Bacteria;D_1__Proteobacteria;D_2__Deltaproteobacteria;D_3__Desulfarculales;D_4__Desulfarculaceae;D_5__uncultured |
| D_0__Bacteria;D_1__Proteobacteria;D_2__Deltaproteobacteria;D_3__Desulfobacterales;D_4__Desulfobulbaceae;D_5__Desulfobulbus |
| D_0__Bacteria;D_1__Proteobacteria;D_2__Deltaproteobacteria;D_3__Desulfobacterales;D_4__Desulfobulbaceae;D_5__Desulfocapsa |
| D_0__Bacteria;D_1__Proteobacteria;D_2__Deltaproteobacteria;D_3__Desulfobacterales;D_4__Nitrospinaceae;D_5__Candidatus Entotheonella |
| D_0__Bacteria;D_1__Proteobacteria;D_2__Deltaproteobacteria;D_3__Desulfobacterales;D_4__Nitrospinaceae;D_5__uncultured |
| D_0__Bacteria;D_1__Proteobacteria;D_2__Deltaproteobacteria;D_3__Desulfurellales;D_4__Desulfurellaceae;D_5__uncultured |
| D_0__Bacteria;D_1__Proteobacteria;D_2__Deltaproteobacteria;D_3__Desulfuromonadales;D_4__AKYG597;Other |
| D_0__Bacteria;D_1__Proteobacteria;D_2__Deltaproteobacteria;D_3__Desulfuromonadales;D_4__BVA18;D_5__uncultured bacterium |
| D_0__Bacteria;D_1__Proteobacteria;D_2__Deltaproteobacteria;D_3__Desulfuromonadales;D_4__BVA18;Other |
| D_0__Bacteria;D_1__Proteobacteria;D_2__Deltaproteobacteria;D_3__Desulfuromonadales;D_4__Desulfuromonadaceae;D_5__Desulfuromonas |
| D_0__Bacteria;D_1__Proteobacteria;D_2__Deltaproteobacteria;D_3__Desulfuromonadales;D_4__Desulfuromonadaceae;D_5__Pelobacter |
| D_0__Bacteria;D_1__Proteobacteria;D_2__Deltaproteobacteria;D_3__Desulfuromonadales;D_4__GR-WP33-58;D_5__uncultured bacterium |
| D_0__Bacteria;D_1__Proteobacteria;D_2__Deltaproteobacteria;D_3__Desulfuromonadales;D_4__Geobacteraceae;D_5__Geobacter |
| D_0__Bacteria;D_1__Proteobacteria;D_2__Deltaproteobacteria;D_3__Desulfuromonadales;D_4__M20-Pitesti;Other |
| D_0__Bacteria;D_1__Proteobacteria;D_2__Deltaproteobacteria;D_3__Desulfuromonadales;Other;Other |
| D_0__Bacteria;D_1__Proteobacteria;D_2__Deltaproteobacteria;D_3__GR-WP33-30;D_4__uncultured bacterium;D_5__ |
| D_0__Bacteria;D_1__Proteobacteria;D_2__Deltaproteobacteria;D_3__GR-WP33-30;D_4__uncultured delta proteobacterium;D_5__ |
| D_0__Bacteria;D_1__Proteobacteria;D_2__Deltaproteobacteria;D_3__GR-WP33-30;D_4__uncultured soil bacterium;D_5__ |
| D_0__Bacteria;D_1__Proteobacteria;D_2__Deltaproteobacteria;D_3__GR-WP33-30;Other;Other |
| D_0__Bacteria;D_1__Proteobacteria;D_2__Deltaproteobacteria;D_3__Myxococcales;D_4__0319-6G20;D_5__uncultured Syntrophobacteraceae bacterium |
| D_0__Bacteria;D_1__Proteobacteria;D_2__Deltaproteobacteria;D_3__Myxococcales;D_4__0319-6G20;D_5__uncultured bacterium |
| D_0__Bacteria;D_1__Proteobacteria;D_2__Deltaproteobacteria;D_3__Myxococcales;D_4__0319-6G20;D_5__uncultured delta proteobacterium |
| D_0__Bacteria;D_1__Proteobacteria;D_2__Deltaproteobacteria;D_3__Myxococcales;D_4__0319-6G20;D_5__uncultured organism |
| D_0__Bacteria;D_1__Proteobacteria;D_2__Deltaproteobacteria;D_3__Myxococcales;D_4__0319-6G20;Other |
| D_0__Bacteria;D_1__Proteobacteria;D_2__Deltaproteobacteria;D_3__Myxococcales;D_4__Cystoba |

| |
|---|
| cteraceae;D_5__Anaeromyxobacter |
| D_0__Bacteria;D_1__Proteobacteria;D_2__Deltaproteobacteria;D_3__Myxococcales;D_4__Cystobacteraceae;Other |
| D_0__Bacteria;D_1__Proteobacteria;D_2__Deltaproteobacteria;D_3__Myxococcales;D_4__Elev-16S-1158;D_5__uncultured bacterium |
| D_0__Bacteria;D_1__Proteobacteria;D_2__Deltaproteobacteria;D_3__Myxococcales;D_4__FFCH16767;D_5__uncultured bacterium |
| D_0__Bacteria;D_1__Proteobacteria;D_2__Deltaproteobacteria;D_3__Myxococcales;D_4__Haliangiaceae;D_5__Haliangium |
| D_0__Bacteria;D_1__Proteobacteria;D_2__Deltaproteobacteria;D_3__Myxococcales;D_4__Myxococcaceae;Other |
| D_0__Bacteria;D_1__Proteobacteria;D_2__Deltaproteobacteria;D_3__Myxococcales;D_4__Nannocystaceae;D_5__Enhygromyxa |
| D_0__Bacteria;D_1__Proteobacteria;D_2__Deltaproteobacteria;D_3__Myxococcales;D_4__Nannocystaceae;D_5__Nannocystis |
| D_0__Bacteria;D_1__Proteobacteria;D_2__Deltaproteobacteria;D_3__Myxococcales;D_4__Nannocystaceae;D_5__uncultured |
| D_0__Bacteria;D_1__Proteobacteria;D_2__Deltaproteobacteria;D_3__Myxococcales;D_4__Nannocystaceae;D_5__uncultured delta proteobacterium |
| D_0__Bacteria;D_1__Proteobacteria;D_2__Deltaproteobacteria;D_3__Myxococcales;D_4__Nannocystaceae;Other |
| D_0__Bacteria;D_1__Proteobacteria;D_2__Deltaproteobacteria;D_3__Myxococcales;D_4__Phaselicystidaceae;D_5__Phaselicystis |
| D_0__Bacteria;D_1__Proteobacteria;D_2__Deltaproteobacteria;D_3__Myxococcales;D_4__Polyangiaceae;D_5__Byssovorax |
| D_0__Bacteria;D_1__Proteobacteria;D_2__Deltaproteobacteria;D_3__Myxococcales;D_4__Polyangiaceae;D_5__Chondromyces |
| D_0__Bacteria;D_1__Proteobacteria;D_2__Deltaproteobacteria;D_3__Myxococcales;D_4__Polyangiaceae;D_5__Sorangium |
| D_0__Bacteria;D_1__Proteobacteria;D_2__Deltaproteobacteria;D_3__Myxococcales;D_4__Polyangiaceae;D_5__uncultured |
| D_0__Bacteria;D_1__Proteobacteria;D_2__Deltaproteobacteria;D_3__Myxococcales;D_4__Polyangiaceae;Other |
| D_0__Bacteria;D_1__Proteobacteria;D_2__Deltaproteobacteria;D_3__Myxococcales;D_4__Sandaracinaceae;D_5__Sandaracinus |
| D_0__Bacteria;D_1__Proteobacteria;D_2__Deltaproteobacteria;D_3__Myxococcales;D_4__Sandaracinaceae;D_5__uncultured Myxococcales bacterium |
| D_0__Bacteria;D_1__Proteobacteria;D_2__Deltaproteobacteria;D_3__Myxococcales;D_4__Sandaracinaceae;D_5__uncultured bacterium |
| D_0__Bacteria;D_1__Proteobacteria;D_2__Deltaproteobacteria;D_3__Myxococcales;D_4__Sandaracinaceae;D_5__uncultured delta proteobacterium |
| D_0__Bacteria;D_1__Proteobacteria;D_2__Deltaproteobacteria;D_3__Myxococcales;D_4__Sandaracinaceae;D_5__uncultured soil bacterium |
| D_0__Bacteria;D_1__Proteobacteria;D_2__Deltaproteobacteria;D_3__Myxococcales;D_4__Sandaracinaceae;Other |
| D_0__Bacteria;D_1__Proteobacteria;D_2__Deltaproteobacteria;D_3__Myxococcales;D_4__VHS-B3-70;D_5__uncultured bacterium |
| D_0__Bacteria;D_1__Proteobacteria;D_2__Deltaproteobacteria;D_3__Myxococcales;D_4__mle1-27;D_5__uncultured bacterium |
| D_0__Bacteria;D_1__Proteobacteria;D_2__Deltaproteobacteria;D_3__Myxococcales;D_4__mle1-27;D_5__uncultured delta proteobacterium |
| D_0__Bacteria;D_1__Proteobacteria;D_2__Deltaproteobacteria;D_3__Myxococcales;D_4__mle1-27;Other |
| D_0__Bacteria;D_1__Proteobacteria;D_2__Deltaproteobacteria;D_3__Myxococcales;D_4__uncultured;D_5__uncultured Cystobacteraceae bacterium |
| D_0__Bacteria;D_1__Proteobacteria;D_2__Deltaproteobacteria;D_3__Myxococcales;D_4__uncultured;D_5__uncultured Polyangiaceae bacterium |
| D_0__Bacteria;D_1__Proteobacteria;D_2__Deltaproteobacteria;D_3__Myxococcales;D_4__uncultured;D_5__uncultured bacterium |
| D_0__Bacteria;D_1__Proteobacteria;D_2__Deltaproteobacteria;D_3__Myxococcales;D_4__uncultured;D_5__uncultured compost bacterium |
| D_0__Bacteria;D_1__Proteobacteria;D_2__Deltaproteobacteria;D_3__Myxococcales;D_4__uncultu |

| |
|---|
| red;D_5__uncultured delta proteobacterium |
| D_0__Bacteria;D_1__Proteobacteria;D_2__Deltaproteobacteria;D_3__Myxococcales;D_4__uncultured;D_5__uncultured organism |
| D_0__Bacteria;D_1__Proteobacteria;D_2__Deltaproteobacteria;D_3__Myxococcales;D_4__uncultured;Other |
| D_0__Bacteria;D_1__Proteobacteria;D_2__Deltaproteobacteria;D_3__Myxococcales;Other;Other |
| D_0__Bacteria;D_1__Proteobacteria;D_2__Deltaproteobacteria;D_3__Sh765B-TzT-29;D_4__uncultured bacterium;D_5__ |
| D_0__Bacteria;D_1__Proteobacteria;D_2__Deltaproteobacteria;D_3__Sh765B-TzT-29;Other;Other |
| D_0__Bacteria;D_1__Proteobacteria;D_2__Deltaproteobacteria;D_3__Syntrophobacterales;D_4__Syntrophaceae;D_5__Smithella |
| D_0__Bacteria;D_1__Proteobacteria;D_2__Deltaproteobacteria;D_3__Syntrophobacterales;D_4__Syntrophaceae;D_5__Syntrophus |
| D_0__Bacteria;D_1__Proteobacteria;D_2__Deltaproteobacteria;D_3__Syntrophobacterales;D_4__Syntrophaceae;D_5__uncultured |
| D_0__Bacteria;D_1__Proteobacteria;D_2__Deltaproteobacteria;D_3__Syntrophobacterales;D_4__Syntrophobacteraceae;D_5__Syntrophobacter |
| D_0__Bacteria;D_1__Proteobacteria;D_2__Deltaproteobacteria;Other;Other;Other |
| D_0__Bacteria;D_1__Proteobacteria;D_2__Epsilonproteobacteria;D_3__Campylobacterales;D_4__Campylobacteraceae;D_5__Arcobacter |
| D_0__Bacteria;D_1__Proteobacteria;D_2__Epsilonproteobacteria;D_3__Campylobacterales;D_4__Campylobacteraceae;D_5__Campylobacter |
| D_0__Bacteria;D_1__Proteobacteria;D_2__Epsilonproteobacteria;D_3__Campylobacterales;D_4__Helicobacteraceae;D_5__Sulfuricurvum |
| D_0__Bacteria;D_1__Proteobacteria;D_2__Epsilonproteobacteria;D_3__Campylobacterales;D_4__Helicobacteraceae;D_5__Sulfurimonas |
| D_0__Bacteria;D_1__Proteobacteria;D_2__Epsilonproteobacteria;D_3__Campylobacterales;D_4__Helicobacteraceae;D_5__Wolinella |
| D_0__Bacteria;D_1__Proteobacteria;D_2__Gammaproteobacteria;D_3__34P16;D_4__uncultured bacterium;D_5__ |
| D_0__Bacteria;D_1__Proteobacteria;D_2__Gammaproteobacteria;D_3__34P16;Other;Other |
| D_0__Bacteria;D_1__Proteobacteria;D_2__Gammaproteobacteria;D_3__Aeromonadales;D_4__Aeromonadaceae;D_5__Aeromonas |
| D_0__Bacteria;D_1__Proteobacteria;D_2__Gammaproteobacteria;D_3__Aeromonadales;D_4__Aeromonadaceae;D_5__Oceanisphaera |
| D_0__Bacteria;D_1__Proteobacteria;D_2__Gammaproteobacteria;D_3__Aeromonadales;D_4__Aeromonadaceae;D_5__Tolumonas |
| D_0__Bacteria;D_1__Proteobacteria;D_2__Gammaproteobacteria;D_3__Aeromonadales;D_4__Aeromonadaceae;Other |
| D_0__Bacteria;D_1__Proteobacteria;D_2__Gammaproteobacteria;D_3__Alteromonadales;D_4__Alteromonadaceae;D_5__BD1-7 clade |
| D_0__Bacteria;D_1__Proteobacteria;D_2__Gammaproteobacteria;D_3__Alteromonadales;D_4__Alteromonadaceae;D_5__Haliea |
| D_0__Bacteria;D_1__Proteobacteria;D_2__Gammaproteobacteria;D_3__Alteromonadales;D_4__Alteromonadaceae;D_5__Marinobacter |
| D_0__Bacteria;D_1__Proteobacteria;D_2__Gammaproteobacteria;D_3__Alteromonadales;D_4__Alteromonadaceae;D_5__OM60(NOR5) clade |
| D_0__Bacteria;D_1__Proteobacteria;D_2__Gammaproteobacteria;D_3__Alteromonadales;D_4__Alteromonadaceae;D_5__Simiduia |
| D_0__Bacteria;D_1__Proteobacteria;D_2__Gammaproteobacteria;D_3__Alteromonadales;D_4__Alteromonadaceae;D_5__uncultured |
| D_0__Bacteria;D_1__Proteobacteria;D_2__Gammaproteobacteria;D_3__Alteromonadales;D_4__Alteromonadaceae;Other |
| D_0__Bacteria;D_1__Proteobacteria;D_2__Gammaproteobacteria;D_3__Alteromonadales;D_4__Idiomarinaceae;D_5__Aliidiomarina |
| D_0__Bacteria;D_1__Proteobacteria;D_2__Gammaproteobacteria;D_3__Alteromonadales;D_4__Idiomarinaceae;D_5__Idiomarina |
| D_0__Bacteria;D_1__Proteobacteria;D_2__Gammaproteobacteria;D_3__Alteromonadales;D_4__Shewanellaceae;D_5__Shewanella |

| |
|---|
| D_0__Bacteria;D_1__Proteobacteria;D_2__Gammaproteobacteria;D_3__B38;D_4__uncultured bacterium;D_5__ |
| D_0__Bacteria;D_1__Proteobacteria;D_2__Gammaproteobacteria;D_3__BD72BR169;D_4__uncultured bacterium;D_5__ |
| D_0__Bacteria;D_1__Proteobacteria;D_2__Gammaproteobacteria;D_3__Cardiobacteriales;D_4__Cardiobacteriaceae;D_5__Cardiobacterium |
| D_0__Bacteria;D_1__Proteobacteria;D_2__Gammaproteobacteria;D_3__Chromatiales;D_4__Chromatiaceae;D_5__Nitrosococcus |
| D_0__Bacteria;D_1__Proteobacteria;D_2__Gammaproteobacteria;D_3__Chromatiales;D_4__Chromatiaceae;D_5__Rheinheimera |
| D_0__Bacteria;D_1__Proteobacteria;D_2__Gammaproteobacteria;D_3__Chromatiales;D_4__Ectothiorhodospiraceae;D_5__Acidiferrobacter |
| D_0__Bacteria;D_1__Proteobacteria;D_2__Gammaproteobacteria;D_3__Chromatiales;D_4__Ectothiorhodospiraceae;Other |
| D_0__Bacteria;D_1__Proteobacteria;D_2__Gammaproteobacteria;D_3__Chromatiales;Other;Other |
| D_0__Bacteria;D_1__Proteobacteria;D_2__Gammaproteobacteria;D_3__EC3;D_4__uncultured bacterium;D_5__ |
| D_0__Bacteria;D_1__Proteobacteria;D_2__Gammaproteobacteria;D_3__Enterobacteriales;D_4__Enterobacteriaceae;D_5__Arsenophonus |
| D_0__Bacteria;D_1__Proteobacteria;D_2__Gammaproteobacteria;D_3__Enterobacteriales;D_4__Enterobacteriaceae;D_5__Buchnera |
| D_0__Bacteria;D_1__Proteobacteria;D_2__Gammaproteobacteria;D_3__Enterobacteriales;D_4__Enterobacteriaceae;D_5__Citrobacter |
| D_0__Bacteria;D_1__Proteobacteria;D_2__Gammaproteobacteria;D_3__Enterobacteriales;D_4__Enterobacteriaceae;D_5__Cronobacter |
| D_0__Bacteria;D_1__Proteobacteria;D_2__Gammaproteobacteria;D_3__Enterobacteriales;D_4__Enterobacteriaceae;D_5__Dickeya |
| D_0__Bacteria;D_1__Proteobacteria;D_2__Gammaproteobacteria;D_3__Enterobacteriales;D_4__Enterobacteriaceae;D_5__Enterobacter |
| D_0__Bacteria;D_1__Proteobacteria;D_2__Gammaproteobacteria;D_3__Enterobacteriales;D_4__Enterobacteriaceae;D_5__Erwinia |
| D_0__Bacteria;D_1__Proteobacteria;D_2__Gammaproteobacteria;D_3__Enterobacteriales;D_4__Enterobacteriaceae;D_5__Escherichia-Shigella |
| D_0__Bacteria;D_1__Proteobacteria;D_2__Gammaproteobacteria;D_3__Enterobacteriales;D_4__Enterobacteriaceae;D_5__Klebsiella |
| D_0__Bacteria;D_1__Proteobacteria;D_2__Gammaproteobacteria;D_3__Enterobacteriales;D_4__Enterobacteriaceae;D_5__Pantoea |
| D_0__Bacteria;D_1__Proteobacteria;D_2__Gammaproteobacteria;D_3__Enterobacteriales;D_4__Enterobacteriaceae;D_5__Pectobacterium |
| D_0__Bacteria;D_1__Proteobacteria;D_2__Gammaproteobacteria;D_3__Enterobacteriales;D_4__Enterobacteriaceae;D_5__Plesiomonas |
| D_0__Bacteria;D_1__Proteobacteria;D_2__Gammaproteobacteria;D_3__Enterobacteriales;D_4__Enterobacteriaceae;D_5__Proteus |
| D_0__Bacteria;D_1__Proteobacteria;D_2__Gammaproteobacteria;D_3__Enterobacteriales;D_4__Enterobacteriaceae;D_5__Raoultella |
| D_0__Bacteria;D_1__Proteobacteria;D_2__Gammaproteobacteria;D_3__Enterobacteriales;D_4__Enterobacteriaceae;D_5__Salmonella |
| D_0__Bacteria;D_1__Proteobacteria;D_2__Gammaproteobacteria;D_3__Enterobacteriales;D_4__Enterobacteriaceae;D_5__Serratia |
| D_0__Bacteria;D_1__Proteobacteria;D_2__Gammaproteobacteria;D_3__Enterobacteriales;D_4__Enterobacteriaceae;D_5__Tatumella |
| D_0__Bacteria;D_1__Proteobacteria;D_2__Gammaproteobacteria;D_3__Enterobacteriales;D_4__Enterobacteriaceae;D_5__Trabulsiella |
| D_0__Bacteria;D_1__Proteobacteria;D_2__Gammaproteobacteria;D_3__Enterobacteriales;D_4__Enterobacteriaceae;D_5__Yersinia |
| D_0__Bacteria;D_1__Proteobacteria;D_2__Gammaproteobacteria;D_3__Enterobacteriales;D_4__Enterobacteriaceae;D_5__uncultured |
| D_0__Bacteria;D_1__Proteobacteria;D_2__Gammaproteobacteria;D_3__Enterobacteriales;D_4__Enterobacteriaceae;Other |
| D_0__Bacteria;D_1__Proteobacteria;D_2__Gammaproteobacteria;D_3__KI89A clade;D_4__uncultured bacterium;D_5__ |
| D_0__Bacteria;D_1__Proteobacteria;D_2__Gammaproteobacteria;D_3__KI89A |

| |
|---|
| clade;D_4__uncultured soil bacterium;D_5__ |
| D_0__Bacteria;D_1__Proteobacteria;D_2__Gammaproteobacteria;D_3__KI89A clade;Other;Other |
| D_0__Bacteria;D_1__Proteobacteria;D_2__Gammaproteobacteria;D_3__Legionellales;D_4__Coxiellaceae;D_5__Aquicella |
| D_0__Bacteria;D_1__Proteobacteria;D_2__Gammaproteobacteria;D_3__Legionellales;D_4__Coxiellaceae;D_5__Coxiella |
| D_0__Bacteria;D_1__Proteobacteria;D_2__Gammaproteobacteria;D_3__Legionellales;D_4__Coxiellaceae;D_5__Diplorickettsia |
| D_0__Bacteria;D_1__Proteobacteria;D_2__Gammaproteobacteria;D_3__Legionellales;D_4__Coxiellaceae;D_5__Rickettsiella |
| D_0__Bacteria;D_1__Proteobacteria;D_2__Gammaproteobacteria;D_3__Legionellales;D_4__Coxiellaceae;D_5__Rickettsiella sp. 5-186-2 |
| D_0__Bacteria;D_1__Proteobacteria;D_2__Gammaproteobacteria;D_3__Legionellales;D_4__Coxiellaceae;D_5__uncultured |
| D_0__Bacteria;D_1__Proteobacteria;D_2__Gammaproteobacteria;D_3__Legionellales;D_4__Coxiellaceae;Other |
| D_0__Bacteria;D_1__Proteobacteria;D_2__Gammaproteobacteria;D_3__Legionellales;D_4__Legionellaceae;D_5__Legionella |
| D_0__Bacteria;D_1__Proteobacteria;D_2__Gammaproteobacteria;D_3__Legionellales;D_4__Legionellaceae;D_5__uncultured |
| D_0__Bacteria;D_1__Proteobacteria;D_2__Gammaproteobacteria;D_3__Methylococcales;D_4__Crenotrichaceae;D_5__Crenothrix |
| D_0__Bacteria;D_1__Proteobacteria;D_2__Gammaproteobacteria;D_3__Methylococcales;D_4__Methylococcaceae;D_5__Methylobacter |
| D_0__Bacteria;D_1__Proteobacteria;D_2__Gammaproteobacteria;D_3__Methylococcales;D_4__Methylococcaceae;D_5__Methylocaldum |
| D_0__Bacteria;D_1__Proteobacteria;D_2__Gammaproteobacteria;D_3__Methylococcales;D_4__Methylococcaceae;D_5__Methylomonas |
| D_0__Bacteria;D_1__Proteobacteria;D_2__Gammaproteobacteria;D_3__NKB5;D_4__uncultured bacterium;D_5__ |
| D_0__Bacteria;D_1__Proteobacteria;D_2__Gammaproteobacteria;D_3__NKB5;D_4__uncultured organism;D_5__ |
| D_0__Bacteria;D_1__Proteobacteria;D_2__Gammaproteobacteria;D_3__NKB5;D_4__uncultured soil bacterium;D_5__ |
| D_0__Bacteria;D_1__Proteobacteria;D_2__Gammaproteobacteria;D_3__NKB5;Other;Other |
| D_0__Bacteria;D_1__Proteobacteria;D_2__Gammaproteobacteria;D_3__Oceanospirillales;D_4__CrystalBog021C3;D_5__uncultured bacterium |
| D_0__Bacteria;D_1__Proteobacteria;D_2__Gammaproteobacteria;D_3__Oceanospirillales;D_4__CrystalBog021C3;Other |
| D_0__Bacteria;D_1__Proteobacteria;D_2__Gammaproteobacteria;D_3__Oceanospirillales;D_4__Halomonadaceae;D_5__Carnimonas |
| D_0__Bacteria;D_1__Proteobacteria;D_2__Gammaproteobacteria;D_3__Oceanospirillales;D_4__Halomonadaceae;D_5__Halomonas |
| D_0__Bacteria;D_1__Proteobacteria;D_2__Gammaproteobacteria;D_3__Oceanospirillales;D_4__Halomonadaceae;D_5__Zymobacter |
| D_0__Bacteria;D_1__Proteobacteria;D_2__Gammaproteobacteria;D_3__Oceanospirillales;D_4__Halomonadaceae;Other |
| D_0__Bacteria;D_1__Proteobacteria;D_2__Gammaproteobacteria;D_3__Oceanospirillales;D_4__Oceanospirillaceae;D_5__Marinomonas |
| D_0__Bacteria;D_1__Proteobacteria;D_2__Gammaproteobacteria;D_3__Oceanospirillales;D_4__Oceanospirillaceae;D_5__Pseudospirillum |
| D_0__Bacteria;D_1__Proteobacteria;D_2__Gammaproteobacteria;D_3__Oceanospirillales;D_4__SAR86 clade;D_5__uncultured marine bacterium |
| D_0__Bacteria;D_1__Proteobacteria;D_2__Gammaproteobacteria;D_3__Oceanospirillales;Other;Other |
| D_0__Bacteria;D_1__Proteobacteria;D_2__Gammaproteobacteria;D_3__Orbales;D_4__Orbaceae;D_5__Gilliamella |
| D_0__Bacteria;D_1__Proteobacteria;D_2__Gammaproteobacteria;D_3__Orbales;D_4__Orbaceae;D_5__Orbus |
| D_0__Bacteria;D_1__Proteobacteria;D_2__Gammaproteobacteria;D_3__Orbales;D_4__Orbaceae;Other |

| |
|---|
| D_0__Bacteria;D_1__Proteobacteria;D_2__Gammaproteobacteria;D_3__Order Incertae Sedis;D_4__Family Incertae Sedis;D_5__Marinicella |
| D_0__Bacteria;D_1__Proteobacteria;D_2__Gammaproteobacteria;D_3__PYR10d3;D_4__uncultured gamma proteobacterium;D_5__ |
| D_0__Bacteria;D_1__Proteobacteria;D_2__Gammaproteobacteria;D_3__Pasteurellales;D_4__Pasteurellaceae;D_5__Aggregatibacter |
| D_0__Bacteria;D_1__Proteobacteria;D_2__Gammaproteobacteria;D_3__Pasteurellales;D_4__Pasteurellaceae;D_5__Haemophilus |
| D_0__Bacteria;D_1__Proteobacteria;D_2__Gammaproteobacteria;D_3__Pasteurellales;D_4__Pasteurellaceae;D_5__Mannheimia |
| D_0__Bacteria;D_1__Proteobacteria;D_2__Gammaproteobacteria;D_3__Pasteurellales;D_4__Pasteurellaceae;D_5__Necropsobacter |
| D_0__Bacteria;D_1__Proteobacteria;D_2__Gammaproteobacteria;D_3__Pasteurellales;D_4__Pasteurellaceae;Other |
| D_0__Bacteria;D_1__Proteobacteria;D_2__Gammaproteobacteria;D_3__Pseudomonadales;D_4__Moraxellaceae;D_5__Acinetobacter |
| D_0__Bacteria;D_1__Proteobacteria;D_2__Gammaproteobacteria;D_3__Pseudomonadales;D_4__Moraxellaceae;D_5__Alkanindiges |
| D_0__Bacteria;D_1__Proteobacteria;D_2__Gammaproteobacteria;D_3__Pseudomonadales;D_4__Moraxellaceae;D_5__Enhydrobacter |
| D_0__Bacteria;D_1__Proteobacteria;D_2__Gammaproteobacteria;D_3__Pseudomonadales;D_4__Moraxellaceae;D_5__Moraxella |
| D_0__Bacteria;D_1__Proteobacteria;D_2__Gammaproteobacteria;D_3__Pseudomonadales;D_4__Moraxellaceae;D_5__Perlucidibaca |
| D_0__Bacteria;D_1__Proteobacteria;D_2__Gammaproteobacteria;D_3__Pseudomonadales;D_4__Moraxellaceae;D_5__Psychrobacter |
| D_0__Bacteria;D_1__Proteobacteria;D_2__Gammaproteobacteria;D_3__Pseudomonadales;D_4__Moraxellaceae;D_5__uncultured |
| D_0__Bacteria;D_1__Proteobacteria;D_2__Gammaproteobacteria;D_3__Pseudomonadales;D_4__Pseudomonadaceae;D_5__Azotobacter |
| D_0__Bacteria;D_1__Proteobacteria;D_2__Gammaproteobacteria;D_3__Pseudomonadales;D_4__Pseudomonadaceae;D_5__Cellvibrio |
| D_0__Bacteria;D_1__Proteobacteria;D_2__Gammaproteobacteria;D_3__Pseudomonadales;D_4__Pseudomonadaceae;D_5__Pseudomonas |
| D_0__Bacteria;D_1__Proteobacteria;D_2__Gammaproteobacteria;D_3__Pseudomonadales;D_4__Pseudomonadaceae;Other |
| D_0__Bacteria;D_1__Proteobacteria;D_2__Gammaproteobacteria;D_3__Pseudomonadales;Other;Other |
| D_0__Bacteria;D_1__Proteobacteria;D_2__Gammaproteobacteria;D_3__Salinisphaerales;D_4__Salinisphaeraceae;D_5__uncultured |
| D_0__Bacteria;D_1__Proteobacteria;D_2__Gammaproteobacteria;D_3__Thiotrichales;D_4__CHAB-XI-27;D_5__uncultured bacterium |
| D_0__Bacteria;D_1__Proteobacteria;D_2__Gammaproteobacteria;D_3__Thiotrichales;D_4__EV818SWSAP88;D_5__uncultured bacterium |
| D_0__Bacteria;D_1__Proteobacteria;D_2__Gammaproteobacteria;D_3__Thiotrichales;D_4__Piscirickettsiaceae;D_5__Methylophaga |
| D_0__Bacteria;D_1__Proteobacteria;D_2__Gammaproteobacteria;D_3__Thiotrichales;D_4__Thiotrichaceae;D_5__Beggiatoa |
| D_0__Bacteria;D_1__Proteobacteria;D_2__Gammaproteobacteria;D_3__Thiotrichales;D_4__Thiotrichaceae;D_5__Methylohalomonas |
| D_0__Bacteria;D_1__Proteobacteria;D_2__Gammaproteobacteria;D_3__Vibrionales;D_4__Vibrionaceae;D_5__Photobacterium |
| D_0__Bacteria;D_1__Proteobacteria;D_2__Gammaproteobacteria;D_3__Xanthomonadales;D_4__JTB255 marine benthic group;D_5__uncultured bacterium |
| D_0__Bacteria;D_1__Proteobacteria;D_2__Gammaproteobacteria;D_3__Xanthomonadales;D_4__JTB255 marine benthic group;Other |
| D_0__Bacteria;D_1__Proteobacteria;D_2__Gammaproteobacteria;D_3__Xanthomonadales;D_4__Nevskiaceae;D_5__Alkanibacter |
| D_0__Bacteria;D_1__Proteobacteria;D_2__Gammaproteobacteria;D_3__Xanthomonadales;D_4__Nevskiaceae;D_5__Hydrocarboniphaga |
| D_0__Bacteria;D_1__Proteobacteria;D_2__Gammaproteobacteria;D_3__Xanthomonadales;D_4__Nevskiaceae;D_5__Nevskia |

| |
|---|
| D_0__Bacteria;D_1__Proteobacteria;D_2__Gammaproteobacteria;D_3__Xanthomonadales;D_4__Solimonadaceae;D_5__Fontimonas |
| D_0__Bacteria;D_1__Proteobacteria;D_2__Gammaproteobacteria;D_3__Xanthomonadales;D_4__Solimonadaceae;D_5__Solimonas |
| D_0__Bacteria;D_1__Proteobacteria;D_2__Gammaproteobacteria;D_3__Xanthomonadales;D_4__Solimonadaceae;D_5__uncultured |
| D_0__Bacteria;D_1__Proteobacteria;D_2__Gammaproteobacteria;D_3__Xanthomonadales;D_4__Xanthomonadaceae;D_5__Arenimonas |
| D_0__Bacteria;D_1__Proteobacteria;D_2__Gammaproteobacteria;D_3__Xanthomonadales;D_4__Xanthomonadaceae;D_5__Dokdonella |
| D_0__Bacteria;D_1__Proteobacteria;D_2__Gammaproteobacteria;D_3__Xanthomonadales;D_4__Xanthomonadaceae;D_5__Dyella |
| D_0__Bacteria;D_1__Proteobacteria;D_2__Gammaproteobacteria;D_3__Xanthomonadales;D_4__Xanthomonadaceae;D_5__Luteibacter |
| D_0__Bacteria;D_1__Proteobacteria;D_2__Gammaproteobacteria;D_3__Xanthomonadales;D_4__Xanthomonadaceae;D_5__Luteimonas |
| D_0__Bacteria;D_1__Proteobacteria;D_2__Gammaproteobacteria;D_3__Xanthomonadales;D_4__Xanthomonadaceae;D_5__Lysobacter |
| D_0__Bacteria;D_1__Proteobacteria;D_2__Gammaproteobacteria;D_3__Xanthomonadales;D_4__Xanthomonadaceae;D_5__Panacagrimonas |
| D_0__Bacteria;D_1__Proteobacteria;D_2__Gammaproteobacteria;D_3__Xanthomonadales;D_4__Xanthomonadaceae;D_5__Pseudofulvimonas |
| D_0__Bacteria;D_1__Proteobacteria;D_2__Gammaproteobacteria;D_3__Xanthomonadales;D_4__Xanthomonadaceae;D_5__Pseudoxanthomonas |
| D_0__Bacteria;D_1__Proteobacteria;D_2__Gammaproteobacteria;D_3__Xanthomonadales;D_4__Xanthomonadaceae;D_5__Rhodanobacter |
| D_0__Bacteria;D_1__Proteobacteria;D_2__Gammaproteobacteria;D_3__Xanthomonadales;D_4__Xanthomonadaceae;D_5__Silanimonas |
| D_0__Bacteria;D_1__Proteobacteria;D_2__Gammaproteobacteria;D_3__Xanthomonadales;D_4__Xanthomonadaceae;D_5__Stenotrophomonas |
| D_0__Bacteria;D_1__Proteobacteria;D_2__Gammaproteobacteria;D_3__Xanthomonadales;D_4__Xanthomonadaceae;D_5__Tahibacter |
| D_0__Bacteria;D_1__Proteobacteria;D_2__Gammaproteobacteria;D_3__Xanthomonadales;D_4__Xanthomonadaceae;D_5__Thermomonas |
| D_0__Bacteria;D_1__Proteobacteria;D_2__Gammaproteobacteria;D_3__Xanthomonadales;D_4__Xanthomonadaceae;D_5__Xanthomonas |
| D_0__Bacteria;D_1__Proteobacteria;D_2__Gammaproteobacteria;D_3__Xanthomonadales;D_4__Xanthomonadaceae;D_5__uncultured |
| D_0__Bacteria;D_1__Proteobacteria;D_2__Gammaproteobacteria;D_3__Xanthomonadales;D_4__Xanthomonadaceae;Other |
| D_0__Bacteria;D_1__Proteobacteria;D_2__Gammaproteobacteria;D_3__Xanthomonadales;D_4__Xanthomonadales Incertae Sedis;D_5__Steroidobacter |
| D_0__Bacteria;D_1__Proteobacteria;D_2__Gammaproteobacteria;D_3__Xanthomonadales;D_4__Xanthomonadales Incertae Sedis;D_5__uncultured |
| D_0__Bacteria;D_1__Proteobacteria;D_2__Gammaproteobacteria;D_3__Xanthomonadales;D_4__Xanthomonadales Incertae Sedis;Other |
| D_0__Bacteria;D_1__Proteobacteria;D_2__Gammaproteobacteria;D_3__Xanthomonadales;D_4__uncultured;D_5__uncultured bacterium |
| D_0__Bacteria;D_1__Proteobacteria;D_2__Gammaproteobacteria;D_3__Xanthomonadales;D_4__uncultured;D_5__uncultured gamma proteobacterium |
| D_0__Bacteria;D_1__Proteobacteria;D_2__Gammaproteobacteria;D_3__Xanthomonadales;D_4__uncultured;D_5__uncultured proteobacterium |
| D_0__Bacteria;D_1__Proteobacteria;D_2__Gammaproteobacteria;D_3__Xanthomonadales;D_4__uncultured;D_5__uncultured soil bacterium |
| D_0__Bacteria;D_1__Proteobacteria;D_2__Gammaproteobacteria;D_3__Xanthomonadales;D_4__uncultured;Other |
| D_0__Bacteria;D_1__Proteobacteria;D_2__Gammaproteobacteria;D_3__Xanthomonadales;Other;Other |
| D_0__Bacteria;D_1__Proteobacteria;D_2__Gammaproteobacteria;D_3__aaa34a10;D_4__uncultured bacterium;D_5__ |
| D_0__Bacteria;D_1__Proteobacteria;D_2__Gammaproteobacteria;Other;Other;Other |
| D_0__Bacteria;D_1__Proteobacteria;D_2__SK259;D_3__uncultured bacterium;D_4__;D_5__ |

| |
|---|
| D_0__Bacteria;D_1__Proteobacteria;D_2__SPOTSOCT00m83;D_3__uncultured bacterium;D_4__;D_5__ |
| D_0__Bacteria;D_1__Proteobacteria;D_2__SPOTSOCT00m83;Other;Other;Other |
| D_0__Bacteria;D_1__Proteobacteria;D_2__TA18;D_3__uncultured bacterium;D_4__;D_5__ |
| D_0__Bacteria;D_1__Proteobacteria;D_2__TA18;D_3__uncultured delta proteobacterium;D_4__;D_5__ |
| D_0__Bacteria;D_1__Proteobacteria;D_2__TA18;Other;Other;Other |
| D_0__Bacteria;D_1__Proteobacteria;D_2__Zetaproteobacteria;D_3__Mariprofundales;D_4__Mariprofundaceae;D_5__Mariprofundus |
| D_0__Bacteria;D_1__Proteobacteria;Other;Other;Other;Other |
| D_0__Bacteria;D_1__RsaHF231;D_2__uncultured bacterium;D_3__;D_4__;D_5__ |
| D_0__Bacteria;D_1__SHA-109;D_2__uncultured bacterium;D_3__;D_4__;D_5__ |
| D_0__Bacteria;D_1__SHA-109;D_2__uncultured soil bacterium;D_3__;D_4__;D_5__ |
| D_0__Bacteria;D_1__SHA-109;Other;Other;Other;Other |
| D_0__Bacteria;D_1__SM2F11;D_2__uncultured bacterium;D_3__;D_4__;D_5__ |
| D_0__Bacteria;D_1__Spirochaetae;D_2__Spirochaetes;D_3__Spirochaetales;D_4__Leptospiraceae;D_5__Turneriella |
| D_0__Bacteria;D_1__Spirochaetae;D_2__Spirochaetes;D_3__Spirochaetales;D_4__Spirochaetaceae;D_5__Spirochaeta |
| D_0__Bacteria;D_1__Spirochaetae;D_2__Spirochaetes;D_3__Spirochaetales;D_4__Spirochaetaceae;D_5__Treponema |
| D_0__Bacteria;D_1__Synergistetes;D_2__Synergistia;D_3__Synergistales;D_4__Synergistaceae;D_5__uncultured |
| D_0__Bacteria;D_1__TM6;D_2__uncultured bacterium;D_3__;D_4__;D_5__ |
| D_0__Bacteria;D_1__TM6;D_2__uncultured candidate division TM6 bacterium;D_3__;D_4__;D_5__ |
| D_0__Bacteria;D_1__TM6;D_2__uncultured organism;D_3__;D_4__;D_5__ |
| D_0__Bacteria;D_1__TM6;Other;Other;Other;Other |
| D_0__Bacteria;D_1__Tenericutes;D_2__Mollicutes;D_3__Entomoplasmatales;D_4__Entomoplasmatales Incertae Sedis;D_5__Candidatus Hepatoplasma |
| D_0__Bacteria;D_1__Tenericutes;D_2__Mollicutes;D_3__Entomoplasmatales;D_4__Spiroplasmataceae;D_5__Spiroplasma |
| D_0__Bacteria;D_1__Tenericutes;D_2__Mollicutes;D_3__Haloplasmatales;D_4__Haloplasmataceae;D_5__Haloplasma |
| D_0__Bacteria;D_1__Tenericutes;D_2__Mollicutes;D_3__Mycoplasmatales;D_4__Mycoplasmataceae;D_5__Candidatus Lumbricincola |
| D_0__Bacteria;D_1__Tenericutes;D_2__Mollicutes;D_3__Mycoplasmatales;D_4__Mycoplasmataceae;D_5__Mycoplasma |
| D_0__Bacteria;D_1__Tenericutes;D_2__Mollicutes;D_3__NB1-n;D_4__uncultured bacterium;D_5__ |
| D_0__Bacteria;D_1__Tenericutes;D_2__Mollicutes;D_3__RF9;D_4__uncultured bacterium;D_5__ |
| D_0__Bacteria;D_1__Thermotogae;D_2__Thermotogae;D_3__Thermotogales;D_4__Thermotogaceae;D_5__GAL15 |
| D_0__Bacteria;D_1__Verrucomicrobia;D_2__OPB35 soil group;D_3__Unknown Order;D_4__Unknown Family;D_5__Pedosphaera |
| D_0__Bacteria;D_1__Verrucomicrobia;D_2__OPB35 soil group;D_3__uncultured Verrucomicrobia bacterium;D_4__;D_5__ |
| D_0__Bacteria;D_1__Verrucomicrobia;D_2__OPB35 soil group;D_3__uncultured Verrucomicrobia subdivision 3 bacterium;D_4__;D_5__ |
| D_0__Bacteria;D_1__Verrucomicrobia;D_2__OPB35 soil group;D_3__uncultured bacterium;D_4__;D_5__ |
| D_0__Bacteria;D_1__Verrucomicrobia;D_2__OPB35 soil group;D_3__uncultured soil bacterium;D_4__;D_5__ |
| D_0__Bacteria;D_1__Verrucomicrobia;D_2__OPB35 soil group;Other;Other;Other |

| |
|---|
| D_0__Bacteria;D_1__Verrucomicrobia;D_2__Opitutae;D_3__Opitutales;D_4__Opitutaceae;D_5__Alterococcus |
| D_0__Bacteria;D_1__Verrucomicrobia;D_2__Opitutae;D_3__Opitutales;D_4__Opitutaceae;D_5__Opitutus |
| D_0__Bacteria;D_1__Verrucomicrobia;D_2__Opitutae;D_3__Puniceicoccales;D_4__Puniceicoccaceae;D_5__Cerasicoccus |
| D_0__Bacteria;D_1__Verrucomicrobia;D_2__Opitutae;D_3__vadinHA64;D_4__uncultured bacterium;D_5__ |
| D_0__Bacteria;D_1__Verrucomicrobia;D_2__S-BQ2-57 soil group;D_3__uncultured Verrucomicrobia bacterium;D_4__;D_5__ |
| D_0__Bacteria;D_1__Verrucomicrobia;D_2__S-BQ2-57 soil group;D_3__uncultured bacterium;D_4__;D_5__ |
| D_0__Bacteria;D_1__Verrucomicrobia;D_2__Spartobacteria;D_3__Chthoniobacterales;D_4__01D2Z36;D_5__uncultured bacterium |
| D_0__Bacteria;D_1__Verrucomicrobia;D_2__Spartobacteria;D_3__Chthoniobacterales;D_4__01D2Z36;D_5__uncultured cyanobacterium |
| D_0__Bacteria;D_1__Verrucomicrobia;D_2__Spartobacteria;D_3__Chthoniobacterales;D_4__Chthoniobacteraceae;D_5__Chthoniobacter |
| D_0__Bacteria;D_1__Verrucomicrobia;D_2__Spartobacteria;D_3__Chthoniobacterales;D_4__DA101 soil group;D_5__uncultured Verrucomicrobia bacterium |
| D_0__Bacteria;D_1__Verrucomicrobia;D_2__Spartobacteria;D_3__Chthoniobacterales;D_4__DA101 soil group;D_5__uncultured bacterium |
| D_0__Bacteria;D_1__Verrucomicrobia;D_2__Spartobacteria;D_3__Chthoniobacterales;D_4__DA101 soil group;Other |
| D_0__Bacteria;D_1__Verrucomicrobia;D_2__Spartobacteria;D_3__Chthoniobacterales;D_4__FukuN18 freshwater group;D_5__uncultured bacterium |
| D_0__Bacteria;D_1__Verrucomicrobia;D_2__Spartobacteria;D_3__Chthoniobacterales;D_4__LD29;D_5__uncultured bacterium |
| D_0__Bacteria;D_1__Verrucomicrobia;D_2__Spartobacteria;D_3__Chthoniobacterales;D_4__LD29;Other |
| D_0__Bacteria;D_1__Verrucomicrobia;D_2__Spartobacteria;D_3__Chthoniobacterales;D_4__Xiphinematobacteraceae;D_5__Candidatus Xiphinematobacter |
| D_0__Bacteria;D_1__Verrucomicrobia;D_2__Spartobacteria;D_3__Chthoniobacterales;Other;Other |
| D_0__Bacteria;D_1__Verrucomicrobia;D_2__Verrucomicrobia Incertae Sedis;D_3__Unknown Order;D_4__Unknown Family;D_5__Candidatus Methylacidiphilum |
| D_0__Bacteria;D_1__Verrucomicrobia;D_2__Verrucomicrobia Incertae Sedis;D_3__Unknown Order;D_4__Unknown Family;D_5__Candidatus Omnitrophus |
| D_0__Bacteria;D_1__Verrucomicrobia;D_2__Verrucomicrobiae;D_3__Verrucomicrobiales;D_4__DEV007;D_5__uncultured organism |
| D_0__Bacteria;D_1__Verrucomicrobia;D_2__Verrucomicrobiae;D_3__Verrucomicrobiales;D_4__Verrucomicrobiaceae;D_5__Haloferula |
| D_0__Bacteria;D_1__Verrucomicrobia;D_2__Verrucomicrobiae;D_3__Verrucomicrobiales;D_4__Verrucomicrobiaceae;D_5__Luteolibacter |
| D_0__Bacteria;D_1__Verrucomicrobia;D_2__Verrucomicrobiae;D_3__Verrucomicrobiales;D_4__Verrucomicrobiaceae;D_5__Prosthecobacter |
| D_0__Bacteria;D_1__Verrucomicrobia;D_2__Verrucomicrobiae;D_3__Verrucomicrobiales;D_4__Verrucomicrobiaceae;D_5__Roseimicrobium |
| D_0__Bacteria;D_1__Verrucomicrobia;D_2__Verrucomicrobiae;D_3__Verrucomicrobiales;D_4__Verrucomicrobiaceae;D_5__Verrucomicrobium |
| D_0__Bacteria;D_1__Verrucomicrobia;D_2__Verrucomicrobiae;D_3__Verrucomicrobiales;D_4__Verrucomicrobiaceae;D_5__uncultured |
| D_0__Bacteria;D_1__Verrucomicrobia;D_2__Verrucomicrobiae;D_3__Verrucomicrobiales;D_4__Verrucomicrobiaceae;Other |
| D_0__Bacteria;D_1__WCHB1-60;D_2__uncultured Candidatus Saccharibacteria sp.;D_3__;D_4__;D_5__ |
| D_0__Bacteria;D_1__WCHB1-60;D_2__uncultured bacterium;D_3__;D_4__;D_5__ |
| D_0__Bacteria;D_1__WCHB1-60;D_2__uncultured soil bacterium;D_3__;D_4__;D_5__ |
| D_0__Bacteria;D_1__WCHB1-60;Other;Other;Other;Other |
| D_0__Bacteria;D_1__WD272;D_2__uncultured bacterium;D_3__;D_4__;D_5__ |

| |
|---|
| D_0__Bacteria;D_1__WD272;Other;Other;Other;Other |
| D_0__Bacteria;Other;Other;Other;Other;Other |
| D_0__Eukaryota;D_1__Excavata;D_2__Discoba;D_3__Discicristata;D_4__Euglenozoa;D_5__Kinetoplastea |
| D_0__Eukaryota;D_1__Excavata;D_2__Discoba;D_3__Jakobida;D_4__Andalucia;D_5__Uncultured Jakobida |
| D_0__Eukaryota;D_1__Opisthokonta;D_2__Holozoa;D_3__Metazoa;D_4__Animalia;D_5__Craniata |
| D_0__Eukaryota;D_1__Opisthokonta;D_2__Nucletmycea;D_3__Fungi;D_4__Dikarya;D_5__Ascomycota |
| D_0__Eukaryota;D_1__Opisthokonta;D_2__Nucletmycea;D_3__Fungi;D_4__Dikarya;D_5__Basidiomycota |
| D_0__Eukaryota;D_1__Opisthokonta;D_2__Nucletmycea;D_3__Fungi;D_4__Zygomycota;D_5__Mucoromycotina |
| D_0__Eukaryota;D_1__RT5iin25;D_2__uncultured Eimeriidae;D_3__;D_4__;D_5__ |
| D_0__Eukaryota;D_1__SAR;D_2__Alveolata;D_3__Ciliophora;D_4__Intramacronucleata;D_5__Conthreep |
| D_0__Eukaryota;D_1__SAR;D_2__Stramenopiles;D_3__MAST-12;D_4__MAST-12C;Other |
| Unassigned;Other;Other;Other;Other;Other |

Appendix B

Total Yeast

Taxonomy k_Fungi;p_Ascomycota;c_Archaeorhizomycetes;o_Archaeorhizomycetales;f_Archaeorhizomycetaceae;g_Archaeorhizomyces;s_Archaeorhizomyces sp k_Fungi;p_Ascomycota;c_Arthoniomycetes;o_Arthoniales;f_Roccellaceae;g_Roccella;s_Roccella boryi k_Fungi;p_Ascomycota;c_Dothideomycetes;o_Botryosphaeriales;f_Botryosphaeriaceae;g_Botryosphaeria;s_Botryosphaeria sp k_Fungi;p_Ascomycota;c_Dothideomycetes;o_Botryosphaeriales;f_Botryosphaeriaceae;g_Diplodia;s_Diplodia mutila k_Fungi;p_Ascomycota;c_Dothideomycetes;o_Botryosphaeriales;f_Botryosphaeriaceae;g_Diplodia;s_Diplodia seriata k_Fungi;p_Ascomycota;c_Dothideomycetes;o_Botryosphaeriales;f_Botryosphaeriaceae;g_Dothiorella;s_Dothiorella iberica k_Fungi;p_Ascomycota;c_Dothideomycetes;o_Botryosphaeriales;f_Botryosphaeriaceae;g_Dothiorella;s_Dothiorella sarmentorum k_Fungi;p_Ascomycota;c_Dothideomycetes;o_Botryosphaeriales;f_Botryosphaeriaceae;g_Dothiorella;s_Dothiorella vidmadera k_Fungi;p_Ascomycota;c_Dothideomycetes;o_Botryosphaeriales;f_Botryosphaeriaceae;g_Lasiodiplodia;s_Lasiodiplodia subglobosa k_Fungi;p_Ascomycota;c_Dothideomycetes;o_Botryosphaeriales;f_Botryosphaeriaceae;g_Macrophomina;s_Macrophomina phaseolina k_Fungi;p_Ascomycota;c_Dothideomycetes;o_Botryosphaeriales;f_Botryosphaeriaceae;g_Microdiplodia;s_Microdiplodia sp GSL2_4_1 k_Fungi;p_Ascomycota;c_Dothideomycetes;o_Botryosphaeriales;f_Botryosphaeriaceae;g_Neofusicoccum;s_Neofusicoccum parvum k_Fungi;p_Ascomycota;c_Dothideomycetes;o_Botryosphaeriales;f_Botryosphaeriaceae;g_Saccharata;s_Saccharata sp 1 ICMP 18939 k_Fungi;p_Ascomycota;c_Dothideomycetes;o_Botryosphaeriales;f_Botryosphaeriaceae;g_Sphaeropsis;s_Sphaeropsis sapinea k_Fungi;p_Ascomycota;c_Dothideomycetes;o_Botryosphaeriales;f_Incertae sedis;g_Camarosporium;s_Camarosporium aloes k_Fungi;p_Ascomycota;c_Dothideomycetes;o_Botryosphaeriales;f_Incertae sedis;g_Camarosporium;s_Camarosporium sp k_Fungi;p_Ascomycota;c_Dothideomycetes;o_Botryosphaeriales;f_unidentified;g_unidentified;s_Botryosphaeriales sp k_Fungi;p_Ascomycota;c_Dothideomycetes;o_Capnodiales;f_Antennulariellaceae;g_Heteroconium;s_Heteroconium sp 115_114E k_Fungi;p_Ascomycota;c_Dothideomycetes;o_Capnodiales;f_Capnodiaceae;g_Capnodium;s_Capnodium sp k_Fungi;p_Ascomycota;c_Dothideomycetes;o_Capnodiales;f_Capnodiaceae;g_Capnodium;s_Capnodium sp FF_2011 k_Fungi;p_Ascomycota;c_Dothideomycetes;o_Capnodiales;f_Capnodiaceae;g_Scorias;s_Scorias spongiosa k_Fungi;p_Ascomycota;c_Dothideomycetes;o_Capnodiales;f_Davidiellaceae;g_Cladosporium;s_Cladosporium cladosporioides k_Fungi;p_Ascomycota;c_Dothideomycetes;o_Capnodiales;f_Davidiellaceae;g_Cladosporium;s_Cladosporium dominicanum

| k__Fungi;p__ | Ascomycota;c__ | Dothideomycetes;o__ | Capnodiales;f__ | Davidiellaceae;g__ | Cladosporium;s__ | Cladosporium exasperatum |
|---|---|---|---|---|---|---|
| k__Fungi;p__ | Ascomycota;c__ | Dothideomycetes;o__ | Capnodiales;f__ | Davidiellaceae;g__ | Cladosporium;s__ | Cladosporium fusiforme |
| k__Fungi;p__ | Ascomycota;c__ | Dothideomycetes;o__ | Capnodiales;f__ | Davidiellaceae;g__ | Cladosporium;s__ | Cladosporium grevilleae |
| k__Fungi;p__ | Ascomycota;c__ | Dothideomycetes;o__ | Capnodiales;f__ | Davidiellaceae;g__ | Cladosporium;s__ | Cladosporium halotolerans |
| k__Fungi;p__ | Ascomycota;c__ | Dothideomycetes;o__ | Capnodiales;f__ | Davidiellaceae;g__ | Cladosporium;s__ | Cladosporium pseudiridis |
| k__Fungi;p__ | Ascomycota;c__ | Dothideomycetes;o__ | Capnodiales;f__ | Davidiellaceae;g__ | Cladosporium;s__ | Cladosporium ramotenellum |
| k__Fungi;p__ | Ascomycota;c__ | Dothideomycetes;o__ | Capnodiales;f__ | Davidiellaceae;g__ | Cladosporium;s__ | Cladosporium sp 08CK033 |
| k__Fungi;p__ | Ascomycota;c__ | Dothideomycetes;o__ | Capnodiales;f__ | Davidiellaceae;g__ | Cladosporium;s__ | Cladosporium sp MPI03 |
| k__Fungi;p__ | Ascomycota;c__ | Dothideomycetes;o__ | Capnodiales;f__ | Davidiellaceae;g__ | Cladosporium;s__ | Cladosporium sphaerospermum |
| k__Fungi;p__ | Ascomycota;c__ | Dothideomycetes;o__ | Capnodiales;f__ | Davidiellaceae;g__ | Davidiella;s__ | Davidiella tassiana |
| k__Fungi;p__ | Ascomycota;c__ | Dothideomycetes;o__ | Capnodiales;f__ | Davidiellaceae;g__ | unidentified;s__ | Davidiellaceae sp 2 FH 2011 |
| k__Fungi;p__ | Ascomycota;c__ | Dothideomycetes;o__ | Capnodiales;f__ | Incertae sedis;g__ | Arthrocatena;s__ | Arthrocatena tenebrio |
| k__Fungi;p__ | Ascomycota;c__ | Dothideomycetes;o__ | Capnodiales;f__ | Incertae sedis;g__ | Capnobotryella;s__ | Capnobotryella sp |
| k__Fungi;p__ | Ascomycota;c__ | Dothideomycetes;o__ | Capnodiales;f__ | Incertae sedis;g__ | Capnobotryella;s__ | Capnobotryella sp MA 4642 |
| k__Fungi;p__ | Ascomycota;c__ | Dothideomycetes;o__ | Capnodiales;f__ | Incertae sedis;g__ | Hispidoconidioma;s__ | Hispidoconidioma sp |
| k__Fungi;p__ | Ascomycota;c__ | Dothideomycetes;o__ | Capnodiales;f__ | Incertae sedis;g__ | Meristemomyces;s__ | Meristemomyces frigidus |
| k__Fungi;p__ | Ascomycota;c__ | Dothideomycetes;o__ | Capnodiales;f__ | Incertae sedis;g__ | Phaeotheca;s__ | Phaeotheca triangularis |
| k__Fungi;p__ | Ascomycota;c__ | Dothideomycetes;o__ | Capnodiales;f__ | Incertae sedis;g__ | Pseudotaeniolina;s__ | Pseudotaeniolina globosa |
| k__Fungi;p__ | Ascomycota;c__ | Dothideomycetes;o__ | Capnodiales;f__ | Incertae sedis;g__ | Rachicladosporium;s__ | Rachicladosporium inconspicuum |
| k__Fungi;p__ | Ascomycota;c__ | Dothideomycetes;o__ | Capnodiales;f__ | Incertae sedis;g__ | Rachicladosporium;s__ | Rachicladosporium luculiae |
| k__Fungi;p__ | Ascomycota;c__ | Dothideomycetes;o__ | Capnodiales;f__ | Incertae sedis;g__ | Rachicladosporium;s__ | Rachicladosporium sp HX6 |
| k__Fungi;p__ | Ascomycota;c__ | Dothideomycetes;o__ | Capnodiales;f__ | Incertae sedis;g__ | Toxicocladosporium;s__ | Toxicocladosporium banksiae |
| k__Fungi;p__ | Ascomycota;c__ | Dothideomycetes;o__ | Capnodiales;f__ | Incertae sedis;g__ | Toxicocladosporium;s__ | Toxicocladosporium leucadendri |
| k__Fungi;p__ | Ascomycota;c__ | Dothideomycetes;o__ | Capnodiales;f__ | Incertae sedis;g__ | Toxicocladosporium;s__ | Toxicocladosporium rubrigenum |
| k__Fungi;p__ | Ascomycota;c__ | Dothideomycetes;o__ | Capnodiales;f__ | Incertae sedis;g__ | Toxicocladosporium;s__ | Toxicocladosporium strelitziae |
| k__Fungi;p__ | Ascomycota;c__ | Dothideomycetes;o__ | Capnodiales;f__ | Incertae sedis;g__ | Xenomeris;s__ | Xenomeris juniperi |
| k__Fungi;p__ | Ascomycota;c__ | Dothideomycetes;o__ | Capnodiales;f__ | Mycosphaerellaceae;g__ | Cercospora;s__ | Cercospora eremochloae |
| k__Fungi;p__ | Ascomycota;c__ | Dothideomycetes;o__ | Capnodiales;f__ | Mycosphaerellaceae;g__ | Cercospora;s__ | Cercospora olivascens |
| k__Fungi;p__ | Ascomycota;c__ | Dothideomycetes;o__ | Capnodiales;f__ | Mycosphaerellaceae;g__ | Cercosporella;s__ | Cercosporella virgaureae |
| k__Fungi;p__ | Ascomycota;c__ | Dothideomycetes;o__ | Capnodiales;f__ | Mycosphaerellaceae;g__ | Mycosphaerella;s__ | Mycosphaerella medusae |
| k__Fungi;p__ | Ascomycota;c__ | Dothideomycetes;o__ | Capnodiales;f__ | Mycosphaerellaceae;g__ | Mycosphaerella;s__ | Mycosphaerella sp |
| k__Fungi;p__ | Ascomycota;c__ | Dothideomycetes;o__ | Capnodiales;f__ | Mycosphaerellaceae;g__ | Mycosphaerella;s__ | Mycosphaerella sp CPC 12200 |
| k__Fungi;p__ | Ascomycota;c__ | Dothideomycetes;o__ | Capnodiales;f__ | Mycosphaerellaceae;g__ | Mycosphaerella;s__ | Mycosphaerella ulmi |
| k__Fungi;p__ | Ascomycota;c__ | Dothideomycetes;o__ | Capnodiales;f__ | Mycosphaerellaceae;g__ | Mycovellosiella;s__ | Mycovellosiella passalorioides |
| k__Fungi;p__ | Ascomycota;c__ | Dothideomycetes;o__ | Capnodiales;f__ | Mycosphaerellaceae;g__ | Passalora;s__ | Passalora dissiliens |
| k__Fungi;p__ | Ascomycota;c__ | Dothideomycetes;o__ | Capnodiales;f__ | Mycosphaerellaceae;g__ | Periconiella;s__ | Periconiella sp IZ 1379 |
| k__Fungi;p__ | Ascomycota;c__ | Dothideomycetes;o__ | Capnodiales;f__ | Mycosphaerellaceae;g__ | Phaeothecoidea;s__ | Phaeothecoidea intermedia |
| k__Fungi;p__ | Ascomycota;c__ | Dothideomycetes;o__ | Capnodiales;f__ | Mycosphaerellaceae;g__ | Ramularia;s__ | Ramularia cynarae |
| k__Fungi;p__ | Ascomycota;c__ | Dothideomycetes;o__ | Capnodiales;f__ | Mycosphaerellaceae;g__ | Ramularia;s__ | Ramularia sp |

| | | | | | | |
|---|---|---|---|---|---|---|
| k_Fungi;p | Ascomycota;c | Dothideomycetes;o | Capnodiales;f | Mycosphaerellaceae;g | Ramularia;s | Ramularia stellenboschensis |
| k_Fungi;p | Ascomycota;c | Dothideomycetes;o | Capnodiales;f | Mycosphaerellaceae;g | Ruptoseptoria;s | Ruptoseptoria unedonis |
| k_Fungi;p | Ascomycota;c | Dothideomycetes;o | Capnodiales;f | Mycosphaerellaceae;g | Septoria;s | Septoria lycopicola |
| k_Fungi;p | Ascomycota;c | Dothideomycetes;o | Capnodiales;f | Mycosphaerellaceae;g | Septoria;s | Septoria sp |
| k_Fungi;p | Ascomycota;c | Dothideomycetes;o | Capnodiales;f | Mycosphaerellaceae;g | Septoria;s | Septoria sp TCM_6 |
| k_Fungi;p | Ascomycota;c | Dothideomycetes;o | Capnodiales;f | Mycosphaerellaceae;g | Uwebraunia;s | Uwebraunia dekkeri |
| k_Fungi;p | Ascomycota;c | Dothideomycetes;o | Capnodiales;f | Mycosphaerellaceae;g | Xenosonderhenia;s | Xenosonderhenia syzygii |
| k_Fungi;p | Ascomycota;c | Dothideomycetes;o | Capnodiales;f | Mycosphaerellaceae;g | unidentified;s | Mycosphaerellaceae sp |
| k_Fungi;p | Ascomycota;c | Dothideomycetes;o | Capnodiales;f | Mycosphaerellaceae;g | unidentified;s | uncultured Mycosphaerellaceae |
| k_Fungi;p | Ascomycota;c | Dothideomycetes;o | Capnodiales;f | Teratosphaeriaceae;g | Catenulostroma;s | Catenulostroma hermanusense |
| k_Fungi;p | Ascomycota;c | Dothideomycetes;o | Capnodiales;f | Teratosphaeriaceae;g | Devriesia;s | Devriesia fraseriae |
| k_Fungi;p | Ascomycota;c | Dothideomycetes;o | Capnodiales;f | Teratosphaeriaceae;g | Devriesia;s | Devriesia modesta |
| k_Fungi;p | Ascomycota;c | Dothideomycetes;o | Capnodiales;f | Teratosphaeriaceae;g | Devriesia;s | Devriesia sp |
| k_Fungi;p | Ascomycota;c | Dothideomycetes;o | Capnodiales;f | Teratosphaeriaceae;g | Hortaea;s | Hortaea thailandica |
| k_Fungi;p | Ascomycota;c | Dothideomycetes;o | Capnodiales;f | Teratosphaeriaceae;g | Myrtapenidiella;s | Myrtapenidiella corymbia |
| k_Fungi;p | Ascomycota;c | Dothideomycetes;o | Capnodiales;f | Teratosphaeriaceae;g | Penidiella;s | Penidiella rigidophora |
| k_Fungi;p | Ascomycota;c | Dothideomycetes;o | Capnodiales;f | Teratosphaeriaceae;g | Penidiella;s | Penidiella tenuiramis |
| k_Fungi;p | Ascomycota;c | Dothideomycetes;o | Capnodiales;f | Teratosphaeriaceae;g | Teratosphaeria;s | Teratosphaeria jonkershoekensis |
| k_Fungi;p | Ascomycota;c | Dothideomycetes;o | Capnodiales;f | Teratosphaeriaceae;g | Teratosphaeria;s | Teratosphaeria mexicana |
| k_Fungi;p | Ascomycota;c | Dothideomycetes;o | Capnodiales;f | Teratosphaeriaceae;g | Teratosphaeria;s | Teratosphaeria parva |
| k_Fungi;p | Ascomycota;c | Dothideomycetes;o | Capnodiales;f | Teratosphaeriaceae;g | Teratosphaeria;s | Teratosphaeria sp SGE7 |
| k_Fungi;p | Ascomycota;c | Dothideomycetes;o | Capnodiales;f | Teratosphaeriaceae;g | Teratosphaeria;s | Teratosphaeria toledana |
| k_Fungi;p | Ascomycota;c | Dothideomycetes;o | Capnodiales;f | Teratosphaeriaceae;g | unidentified;s | Teratosphaeriaceae sp |
| k_Fungi;p | Ascomycota;c | Dothideomycetes;o | Capnodiales;f | Teratosphaeriaceae;g | unidentified;s | uncultured Teratosphaeriaceae |
| k_Fungi;p | Ascomycota;c | Dothideomycetes;o | Capnodiales;f | unidentified;g | unidentified;s | Capnodiales sp |
| k_Fungi;p | Ascomycota;c | Dothideomycetes;o | Capnodiales;f | unidentified;g | unidentified;s | Neodevriesiaceae sp CCFEE 5569 |
| k_Fungi;p | Ascomycota;c | Dothideomycetes;o | Capnodiales;f | unidentified;g | unidentified;s | uncultured Capnodiales |
| k_Fungi;p | Ascomycota;c | Dothideomycetes;o | Capnodiales;f | unidentified;g | unidentified;s | uncultured Devriesia |
| k_Fungi;p | Ascomycota;c | Dothideomycetes;o | Dothideales;f | Dothideaceae;g | Endoconidioma;s | Endoconidioma populi |
| k_Fungi;p | Ascomycota;c | Dothideomycetes;o | Dothideales;f | Dothioraceae;g | Aureobasidium;s | Aureobasidium pullulans |
| k_Fungi;p | Ascomycota;c | Dothideomycetes;o | Dothideales;f | Dothioraceae;g | Aureobasidium;s | Aureobasidium sp |
| k_Fungi;p | Ascomycota;c | Dothideomycetes;o | Dothideales;f | Dothioraceae;g | Hormonema;s | Hormonema sp |
| k_Fungi;p | Ascomycota;c | Dothideomycetes;o | Dothideales;f | Dothioraceae;g | Hormonema;s | Hormonema sp F_054,258 |
| k_Fungi;p | Ascomycota;c | Dothideomycetes;o | Dothideales;f | Dothioraceae;g | Kabatiella;s | Kabatiella lini |
| k_Fungi;p | Ascomycota;c | Dothideomycetes;o | Dothideales;f | Dothioraceae;g | Pringsheimia;s | Pringsheimia euphorbiae |
| k_Fungi;p | Ascomycota;c | Dothideomycetes;o | Dothideales;f | Dothioraceae;g | Pringsheimia;s | Pringsheimia sp |
| k_Fungi;p | Ascomycota;c | Dothideomycetes;o | Dothideales;f | Dothioraceae;g | Selenophoma;s | Selenophoma mahoniae |
| k_Fungi;p | Ascomycota;c | Dothideomycetes;o | Dothideales;f | Dothioraceae;g | Sydowia;s | Sydowia sp |
| k_Fungi;p | Ascomycota;c | Dothideomycetes;o | Dothideales;f | Dothioraceae;g | unidentified;s | Dothioraceae sp |

| | | | | | | |
|---|---|---|---|---|---|---|
| k__Fungi;p__ | Ascomycota;c__ | Dothideomycetes;o__ | Hysteriales;f__ | Gloniaceae;g__ | Cenococcum;s__ | Cenococcum geophilum |
| k__Fungi;p__ | Ascomycota;c__ | Dothideomycetes;o__ | Hysteriales;f__ | Gloniaceae;g__ | Cenococcum;s__ | Cenococcum sp |
| k__Fungi;p__ | Ascomycota;c__ | Dothideomycetes;o__ | Hysteriales;f__ | Gloniaceae;g__ | unidentified;s__ | Gloniaceae sp |
| k__Fungi;p__ | Ascomycota;c__ | Dothideomycetes;o__ | Incertae sedis;f__ | Eremomycetaceae;g__ | Arthrographis;s__ | Arthrographis sp |
| k__Fungi;p__ | Ascomycota;c__ | Dothideomycetes;o__ | Incertae sedis;f__ | Incertae sedis;g__ | Leptospora;s__ | Leptospora rubella |
| k__Fungi;p__ | Ascomycota;c__ | Dothideomycetes;o__ | Incertae sedis;f__ | Incertae sedis;g__ | Monodictys;s__ | Monodictys sp 3 JAS 2013 |
| k__Fungi;p__ | Ascomycota;c__ | Dothideomycetes;o__ | Incertae sedis;f__ | Incertae sedis;g__ | Phaeosclera;s__ | Phaeosclera sp |
| k__Fungi;p__ | Ascomycota;c__ | Dothideomycetes;o__ | Incertae sedis;f__ | Incertae sedis;g__ | Rhizopycnis;s__ | Rhizopycnis vagum |
| k__Fungi;p__ | Ascomycota;c__ | Dothideomycetes;o__ | Incertae sedis;f__ | Incertae sedis;g__ | Zymoseptoria;s__ | Zymoseptoria verkleyi |
| k__Fungi;p__ | Ascomycota;c__ | Dothideomycetes;o__ | Incertae sedis;f__ | Roesleriaceae;g__ | Roesleria;s__ | Roesleria subterranea |
| k__Fungi;p__ | Ascomycota;c__ | Dothideomycetes;o__ | Myriangiales;f__ | Elsinoaceae;g__ | Elsinoe;s__ | Elsinoe proteae |
| k__Fungi;p__ | Ascomycota;c__ | Dothideomycetes;o__ | Myriangiales;f__ | Incertae sedis;g__ | Endosporium;s__ | Endosporium aviarium |
| k__Fungi;p__ | Ascomycota;c__ | Dothideomycetes;o__ | Myriangiales;f__ | Incertae sedis;g__ | Endosporium;s__ | Endosporium populi_tremuloidis |
| k__Fungi;p__ | Ascomycota;c__ | Dothideomycetes;o__ | Myriangiales;f__ | Incertae sedis;g__ | Endosporium;s__ | Endosporium sp |
| k__Fungi;p__ | Ascomycota;c__ | Dothideomycetes;o__ | Myriangiales;f__ | unidentified;g__ | unidentified;s__ | Myriangiales sp |
| k__Fungi;p__ | Ascomycota;c__ | Dothideomycetes;o__ | Pleosporales;f__ | Cucurbitariaceae;g__ | Curreya;s__ | Curreya austroafricana |
| k__Fungi;p__ | Ascomycota;c__ | Dothideomycetes;o__ | Pleosporales;f__ | Cucurbitariaceae;g__ | Curreya;s__ | Curreya sp |
| k__Fungi;p__ | Ascomycota;c__ | Dothideomycetes;o__ | Pleosporales;f__ | Cucurbitariaceae;g__ | Pyrenochaetopsis;s__ | Pyrenochaetopsis leptospora |
| k__Fungi;p__ | Ascomycota;c__ | Dothideomycetes;o__ | Pleosporales;f__ | Cucurbitariaceae;g__ | unidentified;s__ | Cucurbitariaceae sp |
| k__Fungi;p__ | Ascomycota;c__ | Dothideomycetes;o__ | Pleosporales;f__ | Didymosphaeriaceae;g__ | Didymosphaeria;s__ | Didymosphaeria sp |
| k__Fungi;p__ | Ascomycota;c__ | Dothideomycetes;o__ | Pleosporales;f__ | Didymosphaeriaceae;g__ | Roussoella;s__ | Roussoella japanensis |
| k__Fungi;p__ | Ascomycota;c__ | Dothideomycetes;o__ | Pleosporales;f__ | Didymosphaeriaceae;g__ | Roussoella;s__ | Roussoella thailandica |
| k__Fungi;p__ | Ascomycota;c__ | Dothideomycetes;o__ | Pleosporales;f__ | Dothidotthiaceae;g__ | Spencermartinsia;s__ | Spencermartinsia viticola |
| k__Fungi;p__ | Ascomycota;c__ | Dothideomycetes;o__ | Pleosporales;f__ | Incertae sedis;g__ | Ascochyta;s__ | Ascochyta fabae |
| k__Fungi;p__ | Ascomycota;c__ | Dothideomycetes;o__ | Pleosporales;f__ | Incertae sedis;g__ | Ascochyta;s__ | Ascochyta manawaorae |
| k__Fungi;p__ | Ascomycota;c__ | Dothideomycetes;o__ | Pleosporales;f__ | Incertae sedis;g__ | Berkleasmium;s__ | Berkleasmium sp |
| k__Fungi;p__ | Ascomycota;c__ | Dothideomycetes;o__ | Pleosporales;f__ | Incertae sedis;g__ | Boeremia;s__ | Boeremia exigua var. populi |
| k__Fungi;p__ | Ascomycota;c__ | Dothideomycetes;o__ | Pleosporales;f__ | Incertae sedis;g__ | Dictyosporium;s__ | Dictyosporium stellatum |
| k__Fungi;p__ | Ascomycota;c__ | Dothideomycetes;o__ | Pleosporales;f__ | Incertae sedis;g__ | Didymella;s__ | Didymella applanata |
| k__Fungi;p__ | Ascomycota;c__ | Dothideomycetes;o__ | Pleosporales;f__ | Incertae sedis;g__ | Didymella;s__ | Didymella sp |
| k__Fungi;p__ | Ascomycota;c__ | Dothideomycetes;o__ | Pleosporales;f__ | Incertae sedis;g__ | Didymella;s__ | Didymella urticicola |
| k__Fungi;p__ | Ascomycota;c__ | Dothideomycetes;o__ | Pleosporales;f__ | Incertae sedis;g__ | Didymella;s__ | Didymella vitalbina |
| k__Fungi;p__ | Ascomycota;c__ | Dothideomycetes;o__ | Pleosporales;f__ | Incertae sedis;g__ | Herpotrichia;s__ | Herpotrichia parasitica |
| k__Fungi;p__ | Ascomycota;c__ | Dothideomycetes;o__ | Pleosporales;f__ | Incertae sedis;g__ | Letendraea;s__ | Letendraea sp |
| k__Fungi;p__ | Ascomycota;c__ | Dothideomycetes;o__ | Pleosporales;f__ | Incertae sedis;g__ | Macroventuria;s__ | Macroventuria anomochaeta |
| k__Fungi;p__ | Ascomycota;c__ | Dothideomycetes;o__ | Pleosporales;f__ | Incertae sedis;g__ | Mycocentrospora;s__ | Mycocentrospora acerina |
| k__Fungi;p__ | Ascomycota;c__ | Dothideomycetes;o__ | Pleosporales;f__ | Incertae sedis;g__ | Neophaeosphaeria;s__ | Neophaeosphaeria sp |
| k__Fungi;p__ | Ascomycota;c__ | Dothideomycetes;o__ | Pleosporales;f__ | Incertae sedis;g__ | Ochrocladosporium;s__ | Ochrocladosporium sp |
| k__Fungi;p__ | Ascomycota;c__ | Dothideomycetes;o__ | Pleosporales;f__ | Incertae sedis;g__ | Paraphoma;s__ | Paraphoma chrysanthemicola |

| k__Fungi;p__ | Ascomycota;c__ | Dothideomycetes;o__ | Pleosporales;f__ | Incertae sedis;g__ | Paraphoma;s__ | Paraphoma sp |
|---|---|---|---|---|---|---|
| k__Fungi;p__ | Ascomycota;c__ | Dothideomycetes;o__ | Pleosporales;f__ | Incertae sedis;g__ | Periconia;s__ | Periconia sp |
| k__Fungi;p__ | Ascomycota;c__ | Dothideomycetes;o__ | Pleosporales;f__ | Incertae sedis;g__ | Periconia;s__ | Periconia sp CY191 |
| k__Fungi;p__ | Ascomycota;c__ | Dothideomycetes;o__ | Pleosporales;f__ | Incertae sedis;g__ | Peyronellaea;s__ | Peyronellaea sancta |
| k__Fungi;p__ | Ascomycota;c__ | Dothideomycetes;o__ | Pleosporales;f__ | Incertae sedis;g__ | Phoma;s__ | Phoma bulgarica |
| k__Fungi;p__ | Ascomycota;c__ | Dothideomycetes;o__ | Pleosporales;f__ | Incertae sedis;g__ | Phoma;s__ | Phoma crystallifera |
| k__Fungi;p__ | Ascomycota;c__ | Dothideomycetes;o__ | Pleosporales;f__ | Incertae sedis;g__ | Phoma;s__ | Phoma huancayensis |
| k__Fungi;p__ | Ascomycota;c__ | Dothideomycetes;o__ | Pleosporales;f__ | Incertae sedis;g__ | Phoma;s__ | Phoma infossa |
| k__Fungi;p__ | Ascomycota;c__ | Dothideomycetes;o__ | Pleosporales;f__ | Incertae sedis;g__ | Phoma;s__ | Phoma koolunga |
| k__Fungi;p__ | Ascomycota;c__ | Dothideomycetes;o__ | Pleosporales;f__ | Incertae sedis;g__ | Phoma;s__ | Phoma microchlamydospora |
| k__Fungi;p__ | Ascomycota;c__ | Dothideomycetes;o__ | Pleosporales;f__ | Incertae sedis;g__ | Phoma;s__ | Phoma multirostrata |
| k__Fungi;p__ | Ascomycota;c__ | Dothideomycetes;o__ | Pleosporales;f__ | Incertae sedis;g__ | Phoma;s__ | Phoma paspali |
| k__Fungi;p__ | Ascomycota;c__ | Dothideomycetes;o__ | Pleosporales;f__ | Incertae sedis;g__ | Phoma;s__ | Phoma plurivora |
| k__Fungi;p__ | Ascomycota;c__ | Dothideomycetes;o__ | Pleosporales;f__ | Incertae sedis;g__ | Phoma;s__ | Phoma saxea |
| k__Fungi;p__ | Ascomycota;c__ | Dothideomycetes;o__ | Pleosporales;f__ | Incertae sedis;g__ | Phoma;s__ | Phoma sp |
| k__Fungi;p__ | Ascomycota;c__ | Dothideomycetes;o__ | Pleosporales;f__ | Incertae sedis;g__ | Phoma;s__ | Phoma sp A15 |
| k__Fungi;p__ | Ascomycota;c__ | Dothideomycetes;o__ | Pleosporales;f__ | Incertae sedis;g__ | Phoma;s__ | Phoma sp RU080 |
| k__Fungi;p__ | Ascomycota;c__ | Dothideomycetes;o__ | Pleosporales;f__ | Incertae sedis;g__ | Phoma;s__ | Phoma sp SLH2_16 |
| k__Fungi;p__ | Ascomycota;c__ | Dothideomycetes;o__ | Pleosporales;f__ | Incertae sedis;g__ | Pyrenochaeta;s__ | Pyrenochaeta lycopersici |
| k__Fungi;p__ | Ascomycota;c__ | Dothideomycetes;o__ | Pleosporales;f__ | Incertae sedis;g__ | Pyrenochaeta;s__ | Pyrenochaeta sp |
| k__Fungi;p__ | Ascomycota;c__ | Dothideomycetes;o__ | Pleosporales;f__ | Incertae sedis;g__ | Pyrenochaeta;s__ | Pyrenochaeta sp ZLY_2010b |
| k__Fungi;p__ | Ascomycota;c__ | Dothideomycetes;o__ | Pleosporales;f__ | Incertae sedis;g__ | Stagonosporopsis;s__ | Stagonosporopsis ajacis |
| k__Fungi;p__ | Ascomycota;c__ | Dothideomycetes;o__ | Pleosporales;f__ | Incertae sedis;g__ | Stagonosporopsis;s__ | Stagonosporopsis dorenboschii |
| k__Fungi;p__ | Ascomycota;c__ | Dothideomycetes;o__ | Pleosporales;f__ | Incertae sedis;g__ | unidentified;s__ | Pleosporales sp |
| k__Fungi;p__ | Ascomycota;c__ | Dothideomycetes;o__ | Pleosporales;f__ | Leptosphaeriaceae;g__ | Coniothyrium;s__ | Coniothyrium carteri |
| k__Fungi;p__ | Ascomycota;c__ | Dothideomycetes;o__ | Pleosporales;f__ | Leptosphaeriaceae;g__ | Coniothyrium;s__ | Coniothyrium sidae |
| k__Fungi;p__ | Ascomycota;c__ | Dothideomycetes;o__ | Pleosporales;f__ | Leptosphaeriaceae;g__ | Coniothyrium;s__ | Coniothyrium sp JK27 |
| k__Fungi;p__ | Ascomycota;c__ | Dothideomycetes;o__ | Pleosporales;f__ | Leptosphaeriaceae;g__ | Coniothyrium;s__ | Coniothyrium sp NRRL 66000 |
| k__Fungi;p__ | Ascomycota;c__ | Dothideomycetes;o__ | Pleosporales;f__ | Leptosphaeriaceae;g__ | Leptosphaeria;s__ | Leptosphaeria contecta |
| k__Fungi;p__ | Ascomycota;c__ | Dothideomycetes;o__ | Pleosporales;f__ | Leptosphaeriaceae;g__ | Leptosphaeria;s__ | Leptosphaeria sp |
| k__Fungi;p__ | Ascomycota;c__ | Dothideomycetes;o__ | Pleosporales;f__ | Leptosphaeriaceae;g__ | Leptosphaeria;s__ | Leptosphaeria sp MH_2001 |
| k__Fungi;p__ | Ascomycota;c__ | Dothideomycetes;o__ | Pleosporales;f__ | Leptosphaeriaceae;g__ | Leptosphaeria;s__ | Leptosphaeria weimeri |
| k__Fungi;p__ | Ascomycota;c__ | Dothideomycetes;o__ | Pleosporales;f__ | Leptosphaeriaceae;g__ | Neosetophoma;s__ | Neosetophoma sp |
| k__Fungi;p__ | Ascomycota;c__ | Dothideomycetes;o__ | Pleosporales;f__ | Leptosphaeriaceae;g__ | Plenodomus;s__ | Plenodomus confertus |
| k__Fungi;p__ | Ascomycota;c__ | Dothideomycetes;o__ | Pleosporales;f__ | Leptosphaeriaceae;g__ | Subplenodomus;s__ | Subplenodomus violicola |
| k__Fungi;p__ | Ascomycota;c__ | Dothideomycetes;o__ | Pleosporales;f__ | Leptosphaeriaceae;g__ | unidentified;s__ | Leptosphaeriaceae sp |
| k__Fungi;p__ | Ascomycota;c__ | Dothideomycetes;o__ | Pleosporales;f__ | Lophiostomataceae;g__ | Lophiostoma;s__ | Lophiostoma cf cynaroidis A33 |
| k__Fungi;p__ | Ascomycota;c__ | Dothideomycetes;o__ | Pleosporales;f__ | Lophiostomataceae;g__ | Lophiostoma;s__ | Lophiostoma compressum |
| k__Fungi;p__ | Ascomycota;c__ | Dothideomycetes;o__ | Pleosporales;f__ | Lophiostomataceae;g__ | Lophiostoma;s__ | Lophiostoma cynaroidis |

| k_Fungi;p | Ascomycota;c | Dothideomycetes;o | Pleosporales;f | Lophiostomataceae;g | Lophiostoma;s | Lophiostoma sp |
|---|---|---|---|---|---|---|
| k_Fungi;p | Ascomycota;c | Dothideomycetes;o | Pleosporales;f | Lophiostomataceae;g | Lophiostoma;s | Lophiostoma sp CBS 109932 |
| k_Fungi;p | Ascomycota;c | Dothideomycetes;o | Pleosporales;f | Lophiostomataceae;g | Lophiostoma;s | Lophiostoma sp DMW2181 |
| k_Fungi;p | Ascomycota;c | Dothideomycetes;o | Pleosporales;f | Massarinaceae;g | Helminthosporium;s | Helminthosporium solani |
| k_Fungi;p | Ascomycota;c | Dothideomycetes;o | Pleosporales;f | Massarinaceae;g | Massarina;s | Massarina albocarnis |
| k_Fungi;p | Ascomycota;c | Dothideomycetes;o | Pleosporales;f | Montagnulaceae;g | Paraconiothyrium;s | Paraconiothyrium africanum |
| k_Fungi;p | Ascomycota;c | Dothideomycetes;o | Pleosporales;f | Montagnulaceae;g | Paraconiothyrium;s | Paraconiothyrium hawaiiense |
| k_Fungi;p | Ascomycota;c | Dothideomycetes;o | Pleosporales;f | Montagnulaceae;g | Paraconiothyrium;s | Paraconiothyrium sp NO237 |
| k_Fungi;p | Ascomycota;c | Dothideomycetes;o | Pleosporales;f | Montagnulaceae;g | Paraconiothyrium;s | Paraconiothyrium variabile |
| k_Fungi;p | Ascomycota;c | Dothideomycetes;o | Pleosporales;f | Montagnulaceae;g | Paraphaeosphaeria;s | Paraphaeosphaeria pilleata |
| k_Fungi;p | Ascomycota;c | Dothideomycetes;o | Pleosporales;f | Phaeosphaeriaceae;g | Ampelomyces;s | Ampelomyces sp LK_2010 |
| k_Fungi;p | Ascomycota;c | Dothideomycetes;o | Pleosporales;f | Phaeosphaeriaceae;g | Ophiosphaerella;s | Ophiosphaerella herpotricha |
| k_Fungi;p | Ascomycota;c | Dothideomycetes;o | Pleosporales;f | Phaeosphaeriaceae;g | Ophiosphaerella;s | Ophiosphaerella sp |
| k_Fungi;p | Ascomycota;c | Dothideomycetes;o | Pleosporales;f | Phaeosphaeriaceae;g | Phaeosphaeria;s | Phaeosphaeria sp |
| k_Fungi;p | Ascomycota;c | Dothideomycetes;o | Pleosporales;f | Phaeosphaeriaceae;g | Phaeosphaeria;s | Phaeosphaeria sp 20081120 |
| k_Fungi;p | Ascomycota;c | Dothideomycetes;o | Pleosporales;f | Phaeosphaeriaceae;g | Phaeosphaeria;s | Phaeosphaeria sp HKC12 |
| k_Fungi;p | Ascomycota;c | Dothideomycetes;o | Pleosporales;f | Phaeosphaeriaceae;g | Phaeosphaeria;s | Phaeosphaeria sp TMS_2011 |
| k_Fungi;p | Ascomycota;c | Dothideomycetes;o | Pleosporales;f | Phaeosphaeriaceae;g | Phaeosphaeria;s | Phaeosphaeria triglochinicola |
| k_Fungi;p | Ascomycota;c | Dothideomycetes;o | Pleosporales;f | Phaeosphaeriaceae;g | Phaeosphaeria;s | Phaeosphaeria typharum |
| k_Fungi;p | Ascomycota;c | Dothideomycetes;o | Pleosporales;f | Phaeosphaeriaceae;g | Sclerostagonospora;s | Sclerostagonospora sp |
| k_Fungi;p | Ascomycota;c | Dothideomycetes;o | Pleosporales;f | Phaeosphaeriaceae;g | Setophaeosphaeria;s | Setophaeosphaeria sp |
| k_Fungi;p | Ascomycota;c | Dothideomycetes;o | Pleosporales;f | Phaeosphaeriaceae;g | Stagonospora;s | Stagonospora sp VegaE2_84 |
| k_Fungi;p | Ascomycota;c | Dothideomycetes;o | Pleosporales;f | Phaeosphaeriaceae;g | unidentified;s | Phaeosphaeriaceae sp |
| k_Fungi;p | Ascomycota;c | Dothideomycetes;o | Pleosporales;f | Pleomassariaceae;g | Trematosphaeria;s | Trematosphaeria pertusa |
| k_Fungi;p | Ascomycota;c | Dothideomycetes;o | Pleosporales;f | Pleomassariaceae;g | unidentified;s | Pleomassariaceae sp |
| k_Fungi;p | Ascomycota;c | Dothideomycetes;o | Pleosporales;f | Pleosporaceae;g | Alternaria;s | Alternaria alternata |
| k_Fungi;p | Ascomycota;c | Dothideomycetes;o | Pleosporales;f | Pleosporaceae;g | Alternaria;s | Alternaria helianthiinficiens |
| k_Fungi;p | Ascomycota;c | Dothideomycetes;o | Pleosporales;f | Pleosporaceae;g | Alternaria;s | Alternaria leptinellae |
| k_Fungi;p | Ascomycota;c | Dothideomycetes;o | Pleosporales;f | Pleosporaceae;g | Alternaria;s | Alternaria simsimi |
| k_Fungi;p | Ascomycota;c | Dothideomycetes;o | Pleosporales;f | Pleosporaceae;g | Alternaria;s | Alternaria soliaridae |
| k_Fungi;p | Ascomycota;c | Dothideomycetes;o | Pleosporales;f | Pleosporaceae;g | Alternaria;s | Alternaria sp |
| k_Fungi;p | Ascomycota;c | Dothideomycetes;o | Pleosporales;f | Pleosporaceae;g | Alternaria;s | Alternaria sp E08 |
| k_Fungi;p | Ascomycota;c | Dothideomycetes;o | Pleosporales;f | Pleosporaceae;g | Alternaria;s | Alternaria tenuissima |
| k_Fungi;p | Ascomycota;c | Dothideomycetes;o | Pleosporales;f | Pleosporaceae;g | Bipolaris;s | Bipolaris iridis |
| k_Fungi;p | Ascomycota;c | Dothideomycetes;o | Pleosporales;f | Pleosporaceae;g | Bipolaris;s | Bipolaris maydis |
| k_Fungi;p | Ascomycota;c | Dothideomycetes;o | Pleosporales;f | Pleosporaceae;g | Chalastospora;s | Chalastospora ellipsoidea |
| k_Fungi;p | Ascomycota;c | Dothideomycetes;o | Pleosporales;f | Pleosporaceae;g | Chalastospora;s | Chalastospora obclavata |
| k_Fungi;p | Ascomycota;c | Dothideomycetes;o | Pleosporales;f | Pleosporaceae;g | Cochliobolus;s | Cochliobolus homomorphus |
| k_Fungi;p | Ascomycota;c | Dothideomycetes;o | Pleosporales;f | Pleosporaceae;g | Curvularia;s | Curvularia hawaiiensis |

| k__Fungi;p__ | Ascomycota;c__ | Dothideomycetes;o__ | Pleosporales;f__ | Pleosporaceae;g__ | Curvularia;s__ | Curvularia inaequalis |
|---|---|---|---|---|---|---|
| k__Fungi;p__ | Ascomycota;c__ | Dothideomycetes;o__ | Pleosporales;f__ | Pleosporaceae;g__ | Curvularia;s__ | Curvularia lunata |
| k__Fungi;p__ | Ascomycota;c__ | Dothideomycetes;o__ | Pleosporales;f__ | Pleosporaceae;g__ | Dendryphion;s__ | Dendryphion sp |
| k__Fungi;p__ | Ascomycota;c__ | Dothideomycetes;o__ | Pleosporales;f__ | Pleosporaceae;g__ | Drechslera;s__ | Drechslera nobleae |
| k__Fungi;p__ | Ascomycota;c__ | Dothideomycetes;o__ | Pleosporales;f__ | Pleosporaceae;g__ | Drechslera;s__ | Drechslera phlei |
| k__Fungi;p__ | Ascomycota;c__ | Dothideomycetes;o__ | Pleosporales;f__ | Pleosporaceae;g__ | Drechslera;s__ | Drechslera sp BAFC 3419 |
| k__Fungi;p__ | Ascomycota;c__ | Dothideomycetes;o__ | Pleosporales;f__ | Pleosporaceae;g__ | Embellisia;s__ | Embellisia planifunda |
| k__Fungi;p__ | Ascomycota;c__ | Dothideomycetes;o__ | Pleosporales;f__ | Pleosporaceae;g__ | Epicoccum;s__ | Epicoccum nigrum |
| k__Fungi;p__ | Ascomycota;c__ | Dothideomycetes;o__ | Pleosporales;f__ | Pleosporaceae;g__ | Epicoccum;s__ | Epicoccum sp NFW7 |
| k__Fungi;p__ | Ascomycota;c__ | Dothideomycetes;o__ | Pleosporales;f__ | Pleosporaceae;g__ | Lewia;s__ | Lewia infectoria |
| k__Fungi;p__ | Ascomycota;c__ | Dothideomycetes;o__ | Pleosporales;f__ | Pleosporaceae;g__ | Neocamarosporium;s__ | Neocamarosporium goegapense |
| k__Fungi;p__ | Ascomycota;c__ | Dothideomycetes;o__ | Pleosporales;f__ | Pleosporaceae;g__ | Pleospora;s__ | Pleospora halimiones |
| k__Fungi;p__ | Ascomycota;c__ | Dothideomycetes;o__ | Pleosporales;f__ | Pleosporaceae;g__ | Pleospora;s__ | Pleospora herbarum |
| k__Fungi;p__ | Ascomycota;c__ | Dothideomycetes;o__ | Pleosporales;f__ | Pleosporaceae;g__ | Pleospora;s__ | Pleospora scirpicola |
| k__Fungi;p__ | Ascomycota;c__ | Dothideomycetes;o__ | Pleosporales;f__ | Pleosporaceae;g__ | Pyrenophora;s__ | Pyrenophora avenae |
| k__Fungi;p__ | Ascomycota;c__ | Dothideomycetes;o__ | Pleosporales;f__ | Pleosporaceae;g__ | Pyrenophora;s__ | Pyrenophora lolii |
| k__Fungi;p__ | Ascomycota;c__ | Dothideomycetes;o__ | Pleosporales;f__ | Pleosporaceae;g__ | Stemphylium;s__ | Stemphylium loti |
| k__Fungi;p__ | Ascomycota;c__ | Dothideomycetes;o__ | Pleosporales;f__ | Pleosporaceae;g__ | Ulocladium;s__ | Ulocladium chartarum |
| k__Fungi;p__ | Ascomycota;c__ | Dothideomycetes;o__ | Pleosporales;f__ | Pleosporaceae;g__ | Ulocladium;s__ | Ulocladium sp H1F2 |
| k__Fungi;p__ | Ascomycota;c__ | Dothideomycetes;o__ | Pleosporales;f__ | Pleosporaceae;g__ | unidentified;s__ | Pleosporaceae sp |
| k__Fungi;p__ | Ascomycota;c__ | Dothideomycetes;o__ | Pleosporales;f__ | Pleosporaceae;g__ | unidentified;s__ | Pleosporaceae sp RS_5 |
| k__Fungi;p__ | Ascomycota;c__ | Dothideomycetes;o__ | Pleosporales;f__ | Sporormiaceae;g__ | Preussia;s__ | Preussia flanaganii |
| k__Fungi;p__ | Ascomycota;c__ | Dothideomycetes;o__ | Pleosporales;f__ | Sporormiaceae;g__ | Preussia;s__ | Preussia polymorpha |
| k__Fungi;p__ | Ascomycota;c__ | Dothideomycetes;o__ | Pleosporales;f__ | Sporormiaceae;g__ | Preussia;s__ | Preussia sp |
| k__Fungi;p__ | Ascomycota;c__ | Dothideomycetes;o__ | Pleosporales;f__ | Sporormiaceae;g__ | Sporormia;s__ | Sporormia sp |
| k__Fungi;p__ | Ascomycota;c__ | Dothideomycetes;o__ | Pleosporales;f__ | Sporormiaceae;g__ | Westerdykella;s__ | Westerdykella dispersa |
| k__Fungi;p__ | Ascomycota;c__ | Dothideomycetes;o__ | Pleosporales;f__ | Sporormiaceae;g__ | Westerdykella;s__ | Westerdykella multispora |
| k__Fungi;p__ | Ascomycota;c__ | Dothideomycetes;o__ | Pleosporales;f__ | Sporormiaceae;g__ | unidentified;s__ | Sporormiaceae sp |
| k__Fungi;p__ | Ascomycota;c__ | Dothideomycetes;o__ | Pleosporales;f__ | Testudinaceae;g__ | Lepidosphaeria;s__ | Lepidosphaeria nicotiae |
| k__Fungi;p__ | Ascomycota;c__ | Dothideomycetes;o__ | Pleosporales;f__ | unidentified;g__ | unidentified;s__ | Pleosporales sp |
| k__Fungi;p__ | Ascomycota;c__ | Dothideomycetes;o__ | Pleosporales;f__ | unidentified;g__ | unidentified;s__ | Pleosporales sp E8604b |
| k__Fungi;p__ | Ascomycota;c__ | Dothideomycetes;o__ | Pleosporales;f__ | unidentified;g__ | unidentified;s__ | Pleosporales sp REF142 |
| k__Fungi;p__ | Ascomycota;c__ | Dothideomycetes;o__ | Pleosporales;f__ | unidentified;g__ | unidentified;s__ | Pleosporales sp XS55m2 |
| k__Fungi;p__ | Ascomycota;c__ | Dothideomycetes;o__ | Pleosporales;f__ | unidentified;g__ | unidentified;s__ | fungal endophyte WMS23 |
| k__Fungi;p__ | Ascomycota;c__ | Dothideomycetes;o__ | Pleosporales;f__ | unidentified;g__ | unidentified;s__ | uncultured Pleosporales |
| k__Fungi;p__ | Ascomycota;c__ | Dothideomycetes;o__ | Tubeufiales;f__ | Tubeufiaceae;g__ | Helicoma;s__ | Helicoma sp NRRL 66050 |
| k__Fungi;p__ | Ascomycota;c__ | Dothideomycetes;o__ | Tubeufiales;f__ | Tubeufiaceae;g__ | Thaxteriellopsis;s__ | Thaxteriellopsis lignicola |
| k__Fungi;p__ | Ascomycota;c__ | Dothideomycetes;o__ | Tubeufiales;f__ | Tubeufiaceae;g__ | Tubeufia;s__ | Tubeufia cerea |
| k__Fungi;p__ | Ascomycota;c__ | Dothideomycetes;o__ | Venturiales;f__ | Venturiaceae;g__ | Cylindrosympodium;s__ | Cylindrosympodium lauri |

| | | | | | | |
|---|---|---|---|---|---|---|
| k__Fungi;p__ | Ascomycota;c__ | Dothideomycetes;o__ | Venturiales;f__ | Venturiaceae;g__ | Venturia;s__ | Venturia hystrioides |
| k__Fungi;p__ | Ascomycota;c__ | Dothideomycetes;o__ | Venturiales;f__ | Venturiaceae;g__ | Venturia;s__ | Venturia inaequalis |
| k__Fungi;p__ | Ascomycota;c__ | Dothideomycetes;o__ | Venturiales;f__ | Venturiaceae;g__ | Veronaeopsis;s__ | Veronaeopsis simplex |
| k__Fungi;p__ | Ascomycota;c__ | Dothideomycetes;o__ | Venturiales;f__ | Venturiaceae;g__ | unidentified;s__ | Venturiaceae sp |
| k__Fungi;p__ | Ascomycota;c__ | Dothideomycetes;o__ | unidentified;f__ | unidentified;g__ | unidentified;s__ | Dothideomycetes sp |
| k__Fungi;p__ | Ascomycota;c__ | Dothideomycetes;o__ | unidentified;f__ | unidentified;g__ | unidentified;s__ | Dothideomycetes sp 11147 |
| k__Fungi;p__ | Ascomycota;c__ | Dothideomycetes;o__ | unidentified;f__ | unidentified;g__ | unidentified;s__ | Dothideomycetes sp CCFEE 5409 |
| k__Fungi;p__ | Ascomycota;c__ | Dothideomycetes;o__ | unidentified;f__ | unidentified;g__ | unidentified;s__ | Dothideomycetes sp DC3081 |
| k__Fungi;p__ | Ascomycota;c__ | Eurotiomycetes;o__ | Arachnomycetales;f__ | Arachnomycetaceae;g__ | Arachnomyces;s__ | Arachnomyces gracilis |
| k__Fungi;p__ | Ascomycota;c__ | Eurotiomycetes;o__ | Chaetothyriales;f__ | Chaetothyriaceae;g__ | Cyphellophora;s__ | Cyphellophora reptans |
| k__Fungi;p__ | Ascomycota;c__ | Eurotiomycetes;o__ | Chaetothyriales;f__ | Chaetothyriaceae;g__ | Cyphellophora;s__ | Cyphellophora sp |
| k__Fungi;p__ | Ascomycota;c__ | Eurotiomycetes;o__ | Chaetothyriales;f__ | Chaetothyriaceae;g__ | Cyphellophora;s__ | Cyphellophora vermispora |
| k__Fungi;p__ | Ascomycota;c__ | Eurotiomycetes;o__ | Chaetothyriales;f__ | Chaetothyriaceae;g__ | unidentified;s__ | uncultured Knufia |
| k__Fungi;p__ | Ascomycota;c__ | Eurotiomycetes;o__ | Chaetothyriales;f__ | Herpotrichiellaceae;g__ | Capronia;s__ | Capronia coronata |
| k__Fungi;p__ | Ascomycota;c__ | Eurotiomycetes;o__ | Chaetothyriales;f__ | Herpotrichiellaceae;g__ | Capronia;s__ | Capronia epimyces |
| k__Fungi;p__ | Ascomycota;c__ | Eurotiomycetes;o__ | Chaetothyriales;f__ | Herpotrichiellaceae;g__ | Capronia;s__ | Capronia pilosella |
| k__Fungi;p__ | Ascomycota;c__ | Eurotiomycetes;o__ | Chaetothyriales;f__ | Herpotrichiellaceae;g__ | Capronia;s__ | Capronia semi-immersa |
| k__Fungi;p__ | Ascomycota;c__ | Eurotiomycetes;o__ | Chaetothyriales;f__ | Herpotrichiellaceae;g__ | Capronia;s__ | Capronia sp |
| k__Fungi;p__ | Ascomycota;c__ | Eurotiomycetes;o__ | Chaetothyriales;f__ | Herpotrichiellaceae;g__ | Cladophialophora;s__ | Cladophialophora arxii |
| k__Fungi;p__ | Ascomycota;c__ | Eurotiomycetes;o__ | Chaetothyriales;f__ | Herpotrichiellaceae;g__ | Cladophialophora;s__ | Cladophialophora chaetospira |
| k__Fungi;p__ | Ascomycota;c__ | Eurotiomycetes;o__ | Chaetothyriales;f__ | Herpotrichiellaceae;g__ | Cladophialophora;s__ | Cladophialophora modesta |
| k__Fungi;p__ | Ascomycota;c__ | Eurotiomycetes;o__ | Chaetothyriales;f__ | Herpotrichiellaceae;g__ | Cladophialophora;s__ | Cladophialophora proteae |
| k__Fungi;p__ | Ascomycota;c__ | Eurotiomycetes;o__ | Chaetothyriales;f__ | Herpotrichiellaceae;g__ | Cladophialophora;s__ | Cladophialophora sp |
| k__Fungi;p__ | Ascomycota;c__ | Eurotiomycetes;o__ | Chaetothyriales;f__ | Herpotrichiellaceae;g__ | Cladophialophora;s__ | Cladophialophora sp Sh18 |
| k__Fungi;p__ | Ascomycota;c__ | Eurotiomycetes;o__ | Chaetothyriales;f__ | Herpotrichiellaceae;g__ | Cladophialophora;s__ | Cladophialophora sp TRN488 |
| k__Fungi;p__ | Ascomycota;c__ | Eurotiomycetes;o__ | Chaetothyriales;f__ | Herpotrichiellaceae;g__ | Cladophialophora;s__ | Cladophialophora yegresii |
| k__Fungi;p__ | Ascomycota;c__ | Eurotiomycetes;o__ | Chaetothyriales;f__ | Herpotrichiellaceae;g__ | Exophiala;s__ | Exophiala aquamarina |
| k__Fungi;p__ | Ascomycota;c__ | Eurotiomycetes;o__ | Chaetothyriales;f__ | Herpotrichiellaceae;g__ | Exophiala;s__ | Exophiala crusticola |
| k__Fungi;p__ | Ascomycota;c__ | Eurotiomycetes;o__ | Chaetothyriales;f__ | Herpotrichiellaceae;g__ | Exophiala;s__ | Exophiala equina |
| k__Fungi;p__ | Ascomycota;c__ | Eurotiomycetes;o__ | Chaetothyriales;f__ | Herpotrichiellaceae;g__ | Exophiala;s__ | Exophiala eucalyptorum |
| k__Fungi;p__ | Ascomycota;c__ | Eurotiomycetes;o__ | Chaetothyriales;f__ | Herpotrichiellaceae;g__ | Exophiala;s__ | Exophiala lacus |
| k__Fungi;p__ | Ascomycota;c__ | Eurotiomycetes;o__ | Chaetothyriales;f__ | Herpotrichiellaceae;g__ | Exophiala;s__ | Exophiala oligosperma |
| k__Fungi;p__ | Ascomycota;c__ | Eurotiomycetes;o__ | Chaetothyriales;f__ | Herpotrichiellaceae;g__ | Exophiala;s__ | Exophiala opportunistica |
| k__Fungi;p__ | Ascomycota;c__ | Eurotiomycetes;o__ | Chaetothyriales;f__ | Herpotrichiellaceae;g__ | Exophiala;s__ | Exophiala phaeomuriformis |
| k__Fungi;p__ | Ascomycota;c__ | Eurotiomycetes;o__ | Chaetothyriales;f__ | Herpotrichiellaceae;g__ | Exophiala;s__ | Exophiala pisciphila |
| k__Fungi;p__ | Ascomycota;c__ | Eurotiomycetes;o__ | Chaetothyriales;f__ | Herpotrichiellaceae;g__ | Exophiala;s__ | Exophiala salmonis |
| k__Fungi;p__ | Ascomycota;c__ | Eurotiomycetes;o__ | Chaetothyriales;f__ | Herpotrichiellaceae;g__ | Exophiala;s__ | Exophiala sideris |
| k__Fungi;p__ | Ascomycota;c__ | Eurotiomycetes;o__ | Chaetothyriales;f__ | Herpotrichiellaceae;g__ | Exophiala;s__ | Exophiala sp |
| k__Fungi;p__ | Ascomycota;c__ | Eurotiomycetes;o__ | Chaetothyriales;f__ | Herpotrichiellaceae;g__ | Exophiala;s__ | Exophiala sp CPC 12171 |

| k Fungi;p | Ascomycota;c | Eurotiomycetes;o | Chaetothyriales;f | Herpotrichiellaceae;g | Exophiala;s | Exophiala sp EXP0371F |
|---|---|---|---|---|---|---|
| k Fungi;p | Ascomycota;c | Eurotiomycetes;o | Chaetothyriales;f | Herpotrichiellaceae;g | Exophiala;s | Exophiala sp Ppf18 |
| k Fungi;p | Ascomycota;c | Eurotiomycetes;o | Chaetothyriales;f | Herpotrichiellaceae;g | Exophiala;s | Exophiala xenobiotica |
| k Fungi;p | Ascomycota;c | Eurotiomycetes;o | Chaetothyriales;f | Herpotrichiellaceae;g | Phaeococcomyces;s | Phaeococcomyces aff nigricans P40D010 |
| k Fungi;p | Ascomycota;c | Eurotiomycetes;o | Chaetothyriales;f | Herpotrichiellaceae;g | Phaeococcomyces;s | Phaeococcomyces catenatus |
| k Fungi;p | Ascomycota;c | Eurotiomycetes;o | Chaetothyriales;f | Herpotrichiellaceae;g | Phaeococcomyces;s | Phaeococcomyces mexicanus |
| k Fungi;p | Ascomycota;c | Eurotiomycetes;o | Chaetothyriales;f | Herpotrichiellaceae;g | Phaeococcomyces;s | Phaeococcomyces sp |
| k Fungi;p | Ascomycota;c | Eurotiomycetes;o | Chaetothyriales;f | Herpotrichiellaceae;g | Phaeomoniella;s | Phaeomoniella dura |
| k Fungi;p | Ascomycota;c | Eurotiomycetes;o | Chaetothyriales;f | Herpotrichiellaceae;g | Phaeomoniella;s | Phaeomoniella prunicola |
| k Fungi;p | Ascomycota;c | Eurotiomycetes;o | Chaetothyriales;f | Herpotrichiellaceae;g | Phaeomoniella;s | Phaeomoniella sp |
| k Fungi;p | Ascomycota;c | Eurotiomycetes;o | Chaetothyriales;f | Herpotrichiellaceae;g | Phaeomoniella;s | Phaeomoniella sp 3 ICMP 18946 |
| k Fungi;p | Ascomycota;c | Eurotiomycetes;o | Chaetothyriales;f | Herpotrichiellaceae;g | Phialophora;s | Phialophora geniculata |
| k Fungi;p | Ascomycota;c | Eurotiomycetes;o | Chaetothyriales;f | Herpotrichiellaceae;g | Phialophora;s | Phialophora hyalina |
| k Fungi;p | Ascomycota;c | Eurotiomycetes;o | Chaetothyriales;f | Herpotrichiellaceae;g | Phialophora;s | Phialophora livistonae |
| k Fungi;p | Ascomycota;c | Eurotiomycetes;o | Chaetothyriales;f | Herpotrichiellaceae;g | Rhinocladiella;s | Rhinocladiella sp EXP0525F |
| k Fungi;p | Ascomycota;c | Eurotiomycetes;o | Chaetothyriales;f | Herpotrichiellaceae;g | Rhinocladiella;s | Rhinocladiella sp MA 4765 |
| k Fungi;p | Ascomycota;c | Eurotiomycetes;o | Chaetothyriales;f | Herpotrichiellaceae;g | Rhinocladiella;s | Rhinocladiella sp S1 |
| k Fungi;p | Ascomycota;c | Eurotiomycetes;o | Chaetothyriales;f | Herpotrichiellaceae;g | Rhinocladiella;s | Rhinocladiella sp S3 |
| k Fungi;p | Ascomycota;c | Eurotiomycetes;o | Chaetothyriales;f | Herpotrichiellaceae;g | Rhinocladiella;s | Rhinocladiella sp SH10 |
| k Fungi;p | Ascomycota;c | Eurotiomycetes;o | Chaetothyriales;f | Herpotrichiellaceae;g | Rhinocladiella;s | Rhinocladiella sp h2 |
| k Fungi;p | Ascomycota;c | Eurotiomycetes;o | Chaetothyriales;f | Herpotrichiellaceae;g | unidentified;s | Herpotrichiellaceae sp |
| k Fungi;p | Ascomycota;c | Eurotiomycetes;o | Chaetothyriales;f | Incertae sedis;g | Bradymyces;s | Bradymyces alpinus |
| k Fungi;p | Ascomycota;c | Eurotiomycetes;o | Chaetothyriales;f | Incertae sedis;g | Bradymyces;s | Bradymyces oncorhynchi |
| k Fungi;p | Ascomycota;c | Eurotiomycetes;o | Chaetothyriales;f | Incertae sedis;g | Coniosporium;s | Coniosporium apollinis |
| k Fungi;p | Ascomycota;c | Eurotiomycetes;o | Chaetothyriales;f | Incertae sedis;g | Coniosporium;s | Coniosporium sp |
| k Fungi;p | Ascomycota;c | Eurotiomycetes;o | Chaetothyriales;f | Incertae sedis;g | Coniosporium;s | Coniosporium sp SL1131 |
| k Fungi;p | Ascomycota;c | Eurotiomycetes;o | Chaetothyriales;f | Incertae sedis;g | Coniosporium;s | Coniosporium sp h6 |
| k Fungi;p | Ascomycota;c | Eurotiomycetes;o | Chaetothyriales;f | Incertae sedis;g | Hyalocladosporiella;s | Hyalocladosporiella tectonae |
| k Fungi;p | Ascomycota;c | Eurotiomycetes;o | Chaetothyriales;f | unidentified;g | unidentified;s | Chaetothyriales sp |
| k Fungi;p | Ascomycota;c | Eurotiomycetes;o | Chaetothyriales;f | unidentified;g | unidentified;s | Chaetothyriales sp M Camp4 |
| k Fungi;p | Ascomycota;c | Eurotiomycetes;o | Chaetothyriales;f | unidentified;g | unidentified;s | Chaetothyriales sp NY516 |
| k Fungi;p | Ascomycota;c | Eurotiomycetes;o | Chaetothyriales;f | unidentified;g | unidentified;s | uncultured Chaetothyriales |
| k Fungi;p | Ascomycota;c | Eurotiomycetes;o | Eurotiales;f | Incertae sedis;g | Thermomyces;s | Thermomyces lanuginosus |
| k Fungi;p | Ascomycota;c | Eurotiomycetes;o | Eurotiales;f | Trichocomaceae;g | Aspergillus;s | Aspergillus amstelodami |
| k Fungi;p | Ascomycota;c | Eurotiomycetes;o | Eurotiales;f | Trichocomaceae;g | Aspergillus;s | Aspergillus austroafricanus |
| k Fungi;p | Ascomycota;c | Eurotiomycetes;o | Eurotiales;f | Trichocomaceae;g | Aspergillus;s | Aspergillus biplanus |
| k Fungi;p | Ascomycota;c | Eurotiomycetes;o | Eurotiales;f | Trichocomaceae;g | Aspergillus;s | Aspergillus caesiellus |
| k Fungi;p | Ascomycota;c | Eurotiomycetes;o | Eurotiales;f | Trichocomaceae;g | Aspergillus;s | Aspergillus calidoustus |
| k Fungi;p | Ascomycota;c | Eurotiomycetes;o | Eurotiales;f | Trichocomaceae;g | Aspergillus;s | Aspergillus carbonarius |

| k_Fungi;p | Ascomycota;c | Eurotiomycetes;o | Eurotiales;f | Trichocomaceae;g | Aspergillus;s | Aspergillus cibarius |
|---|---|---|---|---|---|---|
| k_Fungi;p | Ascomycota;c | Eurotiomycetes;o | Eurotiales;f | Trichocomaceae;g | Aspergillus;s | Aspergillus deflectus |
| k_Fungi;p | Ascomycota;c | Eurotiomycetes;o | Eurotiales;f | Trichocomaceae;g | Aspergillus;s | Aspergillus flavus |
| k_Fungi;p | Ascomycota;c | Eurotiomycetes;o | Eurotiales;f | Trichocomaceae;g | Aspergillus;s | Aspergillus flocculosus |
| k_Fungi;p | Ascomycota;c | Eurotiomycetes;o | Eurotiales;f | Trichocomaceae;g | Aspergillus;s | Aspergillus heyangensis |
| k_Fungi;p | Ascomycota;c | Eurotiomycetes;o | Eurotiales;f | Trichocomaceae;g | Aspergillus;s | Aspergillus iizukae |
| k_Fungi;p | Ascomycota;c | Eurotiomycetes;o | Eurotiales;f | Trichocomaceae;g | Aspergillus;s | Aspergillus insuetus |
| k_Fungi;p | Ascomycota;c | Eurotiomycetes;o | Eurotiales;f | Trichocomaceae;g | Aspergillus;s | Aspergillus lanosus |
| k_Fungi;p | Ascomycota;c | Eurotiomycetes;o | Eurotiales;f | Trichocomaceae;g | Aspergillus;s | Aspergillus ochraceus |
| k_Fungi;p | Ascomycota;c | Eurotiomycetes;o | Eurotiales;f | Trichocomaceae;g | Aspergillus;s | Aspergillus pseudodeflectus |
| k_Fungi;p | Ascomycota;c | Eurotiomycetes;o | Eurotiales;f | Trichocomaceae;g | Aspergillus;s | Aspergillus quadrilineatus |
| k_Fungi;p | Ascomycota;c | Eurotiomycetes;o | Eurotiales;f | Trichocomaceae;g | Aspergillus;s | Aspergillus ruber |
| k_Fungi;p | Ascomycota;c | Eurotiomycetes;o | Eurotiales;f | Trichocomaceae;g | Aspergillus;s | Aspergillus sclerotiorum |
| k_Fungi;p | Ascomycota;c | Eurotiomycetes;o | Eurotiales;f | Trichocomaceae;g | Aspergillus;s | Aspergillus sp |
| k_Fungi;p | Ascomycota;c | Eurotiomycetes;o | Eurotiales;f | Trichocomaceae;g | Aspergillus;s | Aspergillus sp CBS 50465 |
| k_Fungi;p | Ascomycota;c | Eurotiomycetes;o | Eurotiales;f | Trichocomaceae;g | Aspergillus;s | Aspergillus subsessilis |
| k_Fungi;p | Ascomycota;c | Eurotiomycetes;o | Eurotiales;f | Trichocomaceae;g | Aspergillus;s | Aspergillus tanneri |
| k_Fungi;p | Ascomycota;c | Eurotiomycetes;o | Eurotiales;f | Trichocomaceae;g | Aspergillus;s | Aspergillus unilateralis |
| k_Fungi;p | Ascomycota;c | Eurotiomycetes;o | Eurotiales;f | Trichocomaceae;g | Aspergillus;s | Aspergillus ustus |
| k_Fungi;p | Ascomycota;c | Eurotiomycetes;o | Eurotiales;f | Trichocomaceae;g | Aspergillus;s | Aspergillus wentii |
| k_Fungi;p | Ascomycota;c | Eurotiomycetes;o | Eurotiales;f | Trichocomaceae;g | Aspergillus;s | Aspergillus xerophilus |
| k_Fungi;p | Ascomycota;c | Eurotiomycetes;o | Eurotiales;f | Trichocomaceae;g | Byssochlamys;s | Byssochlamys spectabilis |
| k_Fungi;p | Ascomycota;c | Eurotiomycetes;o | Eurotiales;f | Trichocomaceae;g | Emericella;s | Emericella navahoensis |
| k_Fungi;p | Ascomycota;c | Eurotiomycetes;o | Eurotiales;f | Trichocomaceae;g | Emericella;s | Emericella olivicola |
| k_Fungi;p | Ascomycota;c | Eurotiomycetes;o | Eurotiales;f | Trichocomaceae;g | Neosartorya;s | Neosartorya hiratsukae |
| k_Fungi;p | Ascomycota;c | Eurotiomycetes;o | Eurotiales;f | Trichocomaceae;g | Neosartorya;s | Neosartorya sp |
| k_Fungi;p | Ascomycota;c | Eurotiomycetes;o | Eurotiales;f | Trichocomaceae;g | Paecilomyces;s | Paecilomyces marquandii |
| k_Fungi;p | Ascomycota;c | Eurotiomycetes;o | Eurotiales;f | Trichocomaceae;g | Paecilomyces;s | Paecilomyces penicillatus |
| k_Fungi;p | Ascomycota;c | Eurotiomycetes;o | Eurotiales;f | Trichocomaceae;g | Paecilomyces;s | Paecilomyces sp |
| k_Fungi;p | Ascomycota;c | Eurotiomycetes;o | Eurotiales;f | Trichocomaceae;g | Penicillium;s | Penicillium angulare |
| k_Fungi;p | Ascomycota;c | Eurotiomycetes;o | Eurotiales;f | Trichocomaceae;g | Penicillium;s | Penicillium bialowiezense |
| k_Fungi;p | Ascomycota;c | Eurotiomycetes;o | Eurotiales;f | Trichocomaceae;g | Penicillium;s | Penicillium bilaiae |
| k_Fungi;p | Ascomycota;c | Eurotiomycetes;o | Eurotiales;f | Trichocomaceae;g | Penicillium;s | Penicillium brevicompactum |
| k_Fungi;p | Ascomycota;c | Eurotiomycetes;o | Eurotiales;f | Trichocomaceae;g | Penicillium;s | Penicillium buchwaldii |
| k_Fungi;p | Ascomycota;c | Eurotiomycetes;o | Eurotiales;f | Trichocomaceae;g | Penicillium;s | Penicillium cainii |
| k_Fungi;p | Ascomycota;c | Eurotiomycetes;o | Eurotiales;f | Trichocomaceae;g | Penicillium;s | Penicillium canariense |
| k_Fungi;p | Ascomycota;c | Eurotiomycetes;o | Eurotiales;f | Trichocomaceae;g | Penicillium;s | Penicillium canescens |
| k_Fungi;p | Ascomycota;c | Eurotiomycetes;o | Eurotiales;f | Trichocomaceae;g | Penicillium;s | Penicillium cf parviverrucosum CMV_2013 |
| k_Fungi;p | Ascomycota;c | Eurotiomycetes;o | Eurotiales;f | Trichocomaceae;g | Penicillium;s | Penicillium chrysogenum |

| k__Fungi;p__ | Ascomycota;c__ | Eurotiomycetes;o__ | Eurotiales;f__ | Trichocomaceae;g__ | Penicillium;s__ | Penicillium citrinum |
| k__Fungi;p__ | Ascomycota;c__ | Eurotiomycetes;o__ | Eurotiales;f__ | Trichocomaceae;g__ | Penicillium;s__ | Penicillium commune |
| k__Fungi;p__ | Ascomycota;c__ | Eurotiomycetes;o__ | Eurotiales;f__ | Trichocomaceae;g__ | Penicillium;s__ | Penicillium corylophilum |
| k__Fungi;p__ | Ascomycota;c__ | Eurotiomycetes;o__ | Eurotiales;f__ | Trichocomaceae;g__ | Penicillium;s__ | Penicillium decumbens |
| k__Fungi;p__ | Ascomycota;c__ | Eurotiomycetes;o__ | Eurotiales;f__ | Trichocomaceae;g__ | Penicillium;s__ | Penicillium digitatum |
| k__Fungi;p__ | Ascomycota;c__ | Eurotiomycetes;o__ | Eurotiales;f__ | Trichocomaceae;g__ | Penicillium;s__ | Penicillium donkii |
| k__Fungi;p__ | Ascomycota;c__ | Eurotiomycetes;o__ | Eurotiales;f__ | Trichocomaceae;g__ | Penicillium;s__ | Penicillium expansum |
| k__Fungi;p__ | Ascomycota;c__ | Eurotiomycetes;o__ | Eurotiales;f__ | Trichocomaceae;g__ | Penicillium;s__ | Penicillium georgiense |
| k__Fungi;p__ | Ascomycota;c__ | Eurotiomycetes;o__ | Eurotiales;f__ | Trichocomaceae;g__ | Penicillium;s__ | Penicillium griseofulvum |
| k__Fungi;p__ | Ascomycota;c__ | Eurotiomycetes;o__ | Eurotiales;f__ | Trichocomaceae;g__ | Penicillium;s__ | Penicillium humicoloides |
| k__Fungi;p__ | Ascomycota;c__ | Eurotiomycetes;o__ | Eurotiales;f__ | Trichocomaceae;g__ | Penicillium;s__ | Penicillium janczewski |
| k__Fungi;p__ | Ascomycota;c__ | Eurotiomycetes;o__ | Eurotiales;f__ | Trichocomaceae;g__ | Penicillium;s__ | Penicillium javanicum |
| k__Fungi;p__ | Ascomycota;c__ | Eurotiomycetes;o__ | Eurotiales;f__ | Trichocomaceae;g__ | Penicillium;s__ | Penicillium klebahnii |
| k__Fungi;p__ | Ascomycota;c__ | Eurotiomycetes;o__ | Eurotiales;f__ | Trichocomaceae;g__ | Penicillium;s__ | Penicillium lapidosum |
| k__Fungi;p__ | Ascomycota;c__ | Eurotiomycetes;o__ | Eurotiales;f__ | Trichocomaceae;g__ | Penicillium;s__ | Penicillium madriti |
| k__Fungi;p__ | Ascomycota;c__ | Eurotiomycetes;o__ | Eurotiales;f__ | Trichocomaceae;g__ | Penicillium;s__ | Penicillium malacaense |
| k__Fungi;p__ | Ascomycota;c__ | Eurotiomycetes;o__ | Eurotiales;f__ | Trichocomaceae;g__ | Penicillium;s__ | Penicillium malachiteum |
| k__Fungi;p__ | Ascomycota;c__ | Eurotiomycetes;o__ | Eurotiales;f__ | Trichocomaceae;g__ | Penicillium;s__ | Penicillium malmesburiense |
| k__Fungi;p__ | Ascomycota;c__ | Eurotiomycetes;o__ | Eurotiales;f__ | Trichocomaceae;g__ | Penicillium;s__ | Penicillium megasporum |
| k__Fungi;p__ | Ascomycota;c__ | Eurotiomycetes;o__ | Eurotiales;f__ | Trichocomaceae;g__ | Penicillium;s__ | Penicillium menonorum |
| k__Fungi;p__ | Ascomycota;c__ | Eurotiomycetes;o__ | Eurotiales;f__ | Trichocomaceae;g__ | Penicillium;s__ | Penicillium meridianum |
| k__Fungi;p__ | Ascomycota;c__ | Eurotiomycetes;o__ | Eurotiales;f__ | Trichocomaceae;g__ | Penicillium;s__ | Penicillium mononematosum |
| k__Fungi;p__ | Ascomycota;c__ | Eurotiomycetes;o__ | Eurotiales;f__ | Trichocomaceae;g__ | Penicillium;s__ | Penicillium multicolor |
| k__Fungi;p__ | Ascomycota;c__ | Eurotiomycetes;o__ | Eurotiales;f__ | Trichocomaceae;g__ | Penicillium;s__ | Penicillium novae-zeelandiae |
| k__Fungi;p__ | Ascomycota;c__ | Eurotiomycetes;o__ | Eurotiales;f__ | Trichocomaceae;g__ | Penicillium;s__ | Penicillium ochrochloron |
| k__Fungi;p__ | Ascomycota;c__ | Eurotiomycetes;o__ | Eurotiales;f__ | Trichocomaceae;g__ | Penicillium;s__ | Penicillium olsonii |
| k__Fungi;p__ | Ascomycota;c__ | Eurotiomycetes;o__ | Eurotiales;f__ | Trichocomaceae;g__ | Penicillium;s__ | Penicillium onobense |
| k__Fungi;p__ | Ascomycota;c__ | Eurotiomycetes;o__ | Eurotiales;f__ | Trichocomaceae;g__ | Penicillium;s__ | Penicillium paneum |
| k__Fungi;p__ | Ascomycota;c__ | Eurotiomycetes;o__ | Eurotiales;f__ | Trichocomaceae;g__ | Penicillium;s__ | Penicillium parvulum |
| k__Fungi;p__ | Ascomycota;c__ | Eurotiomycetes;o__ | Eurotiales;f__ | Trichocomaceae;g__ | Penicillium;s__ | Penicillium parvum |
| k__Fungi;p__ | Ascomycota;c__ | Eurotiomycetes;o__ | Eurotiales;f__ | Trichocomaceae;g__ | Penicillium;s__ | Penicillium psychrosexualis |
| k__Fungi;p__ | Ascomycota;c__ | Eurotiomycetes;o__ | Eurotiales;f__ | Trichocomaceae;g__ | Penicillium;s__ | Penicillium restrictum |
| k__Fungi;p__ | Ascomycota;c__ | Eurotiomycetes;o__ | Eurotiales;f__ | Trichocomaceae;g__ | Penicillium;s__ | Penicillium rubidurum |
| k__Fungi;p__ | Ascomycota;c__ | Eurotiomycetes;o__ | Eurotiales;f__ | Trichocomaceae;g__ | Penicillium;s__ | Penicillium samsonii |
| k__Fungi;p__ | Ascomycota;c__ | Eurotiomycetes;o__ | Eurotiales;f__ | Trichocomaceae;g__ | Penicillium;s__ | Penicillium sclerotigenum |
| k__Fungi;p__ | Ascomycota;c__ | Eurotiomycetes;o__ | Eurotiales;f__ | Trichocomaceae;g__ | Penicillium;s__ | Penicillium sizovae |
| k__Fungi;p__ | Ascomycota;c__ | Eurotiomycetes;o__ | Eurotiales;f__ | Trichocomaceae;g__ | Penicillium;s__ | Penicillium skrjabinii |
| k__Fungi;p__ | Ascomycota;c__ | Eurotiomycetes;o__ | Eurotiales;f__ | Trichocomaceae;g__ | Penicillium;s__ | Penicillium sp |
| k__Fungi;p__ | Ascomycota;c__ | Eurotiomycetes;o__ | Eurotiales;f__ | Trichocomaceae;g__ | Penicillium;s__ | Penicillium sp ASR_254 |

| k__Fungi;p__ | Ascomycota;c__ | Eurotiomycetes;o__ | Eurotiales;f__ | Trichocomaceae;g__ | Penicillium;s__ | Penicillium sp ASR_284 |
|---|---|---|---|---|---|---|
| k__Fungi;p__ | Ascomycota;c__ | Eurotiomycetes;o__ | Eurotiales;f__ | Trichocomaceae;g__ | Penicillium;s__ | Penicillium sp FG48 |
| k__Fungi;p__ | Ascomycota;c__ | Eurotiomycetes;o__ | Eurotiales;f__ | Trichocomaceae;g__ | Penicillium;s__ | Penicillium sp FL_2010ac |
| k__Fungi;p__ | Ascomycota;c__ | Eurotiomycetes;o__ | Eurotiales;f__ | Trichocomaceae;g__ | Penicillium;s__ | Penicillium sp M7 |
| k__Fungi;p__ | Ascomycota;c__ | Eurotiomycetes;o__ | Eurotiales;f__ | Trichocomaceae;g__ | Penicillium;s__ | Penicillium sp NRRL 28159 |
| k__Fungi;p__ | Ascomycota;c__ | Eurotiomycetes;o__ | Eurotiales;f__ | Trichocomaceae;g__ | Penicillium;s__ | Penicillium sp NRRL 35637 |
| k__Fungi;p__ | Ascomycota;c__ | Eurotiomycetes;o__ | Eurotiales;f__ | Trichocomaceae;g__ | Penicillium;s__ | Penicillium sp YM3II |
| k__Fungi;p__ | Ascomycota;c__ | Eurotiomycetes;o__ | Eurotiales;f__ | Trichocomaceae;g__ | Penicillium;s__ | Penicillium spathulatum |
| k__Fungi;p__ | Ascomycota;c__ | Eurotiomycetes;o__ | Eurotiales;f__ | Trichocomaceae;g__ | Penicillium;s__ | Penicillium tularense |
| k__Fungi;p__ | Ascomycota;c__ | Eurotiomycetes;o__ | Eurotiales;f__ | Trichocomaceae;g__ | Penicillium;s__ | Penicillium vanoranjei |
| k__Fungi;p__ | Ascomycota;c__ | Eurotiomycetes;o__ | Eurotiales;f__ | Trichocomaceae;g__ | Penicillium;s__ | Penicillium vinaceum |
| k__Fungi;p__ | Ascomycota;c__ | Eurotiomycetes;o__ | Eurotiales;f__ | Trichocomaceae;g__ | Penicillium;s__ | Penicillium viridicatum |
| k__Fungi;p__ | Ascomycota;c__ | Eurotiomycetes;o__ | Eurotiales;f__ | Trichocomaceae;g__ | Penicillium;s__ | Penicillium wotroi |
| k__Fungi;p__ | Ascomycota;c__ | Eurotiomycetes;o__ | Eurotiales;f__ | Trichocomaceae;g__ | Phialosimplex;s__ | Phialosimplex chlamydosporus |
| k__Fungi;p__ | Ascomycota;c__ | Eurotiomycetes;o__ | Eurotiales;f__ | Trichocomaceae;g__ | Rasamsonia;s__ | Rasamsonia piperina |
| k__Fungi;p__ | Ascomycota;c__ | Eurotiomycetes;o__ | Eurotiales;f__ | Trichocomaceae;g__ | Sagenomella;s__ | Sagenomella diversispora |
| k__Fungi;p__ | Ascomycota;c__ | Eurotiomycetes;o__ | Eurotiales;f__ | Trichocomaceae;g__ | Sagenomella;s__ | Sagenomella sp ASR_61 |
| k__Fungi;p__ | Ascomycota;c__ | Eurotiomycetes;o__ | Eurotiales;f__ | Trichocomaceae;g__ | Sagenomella;s__ | Sagenomella sp HMH_2007a |
| k__Fungi;p__ | Ascomycota;c__ | Eurotiomycetes;o__ | Eurotiales;f__ | Trichocomaceae;g__ | Talaromyces;s__ | Talaromyces calidicanius |
| k__Fungi;p__ | Ascomycota;c__ | Eurotiomycetes;o__ | Eurotiales;f__ | Trichocomaceae;g__ | Talaromyces;s__ | Talaromyces flavovirens |
| k__Fungi;p__ | Ascomycota;c__ | Eurotiomycetes;o__ | Eurotiales;f__ | Trichocomaceae;g__ | Talaromyces;s__ | Talaromyces luteus |
| k__Fungi;p__ | Ascomycota;c__ | Eurotiomycetes;o__ | Eurotiales;f__ | Trichocomaceae;g__ | Talaromyces;s__ | Talaromyces purpureus |
| k__Fungi;p__ | Ascomycota;c__ | Eurotiomycetes;o__ | Eurotiales;f__ | Trichocomaceae;g__ | Talaromyces;s__ | Talaromyces purpurogenus |
| k__Fungi;p__ | Ascomycota;c__ | Eurotiomycetes;o__ | Eurotiales;f__ | Trichocomaceae;g__ | Talaromyces;s__ | Talaromyces rotundus |
| k__Fungi;p__ | Ascomycota;c__ | Eurotiomycetes;o__ | Eurotiales;f__ | Trichocomaceae;g__ | Talaromyces;s__ | Talaromyces sp |
| k__Fungi;p__ | Ascomycota;c__ | Eurotiomycetes;o__ | Eurotiales;f__ | Trichocomaceae;g__ | Talaromyces;s__ | Talaromyces stollii |
| k__Fungi;p__ | Ascomycota;c__ | Eurotiomycetes;o__ | Eurotiales;f__ | Trichocomaceae;g__ | Talaromyces;s__ | Talaromyces viridulus |
| k__Fungi;p__ | Ascomycota;c__ | Eurotiomycetes;o__ | Eurotiales;f__ | Trichocomaceae;g__ | unidentified;s__ | Trichocomaceae sp |
| k__Fungi;p__ | Ascomycota;c__ | Eurotiomycetes;o__ | Eurotiales;f__ | unidentified;g__ | unidentified;s__ | Eurotiales sp |
| k__Fungi;p__ | Ascomycota;c__ | Eurotiomycetes;o__ | Eurotiales;f__ | unidentified;g__ | unidentified;s__ | uncultured Aspergillus |
| k__Fungi;p__ | Ascomycota;c__ | Eurotiomycetes;o__ | Eurotiales;f__ | unidentified;g__ | unidentified;s__ | uncultured Eurotiales |
| k__Fungi;p__ | Ascomycota;c__ | Eurotiomycetes;o__ | Incertae sedis;f__ | Incertae sedis;g__ | Sarcinomyces;s__ | Sarcinomyces crustaceus |
| k__Fungi;p__ | Ascomycota;c__ | Eurotiomycetes;o__ | Incertae sedis;f__ | Incertae sedis;g__ | Sarcinomyces;s__ | Sarcinomyces petricola |
| k__Fungi;p__ | Ascomycota;c__ | Eurotiomycetes;o__ | Incertae sedis;f__ | Incertae sedis;g__ | Sarcinomyces;s__ | Sarcinomyces sp MA 4620 |
| k__Fungi;p__ | Ascomycota;c__ | Eurotiomycetes;o__ | Incertae sedis;f__ | Incertae sedis;g__ | Sarcinomyces;s__ | Sarcinomyces sp MA 4676 |
| k__Fungi;p__ | Ascomycota;c__ | Eurotiomycetes;o__ | Incertae sedis;f__ | Incertae sedis;g__ | Sarcinomyces;s__ | Sarcinomyces sp SL_2011 |
| k__Fungi;p__ | Ascomycota;c__ | Eurotiomycetes;o__ | Incertae sedis;f__ | Monascaceae;g__ | Monascus;s__ | Monascus purpureus |
| k__Fungi;p__ | Ascomycota;c__ | Eurotiomycetes;o__ | Onygenales;f__ | Ajellomycetaceae;g__ | Ajellomyces;s__ | Ajellomyces crescens |
| k__Fungi;p__ | Ascomycota;c__ | Eurotiomycetes;o__ | Onygenales;f__ | Ajellomycetaceae;g__ | Polytolypa;s__ | Polytolypa hystricis |

| | | | | | |
|---|---|---|---|---|---|
| k__Fungi;p__ | Ascomycota;c__ | Eurotiomycetes;o__ | Onygenales;f__ | Ajellomycetaceae;g__ | Spiromastix;s__ Spiromastix sp F19 |
| k__Fungi;p__ | Ascomycota;c__ | Eurotiomycetes;o__ | Onygenales;f__ | Ajellomycetaceae;g__ | Spiromastix;s__ Spiromastix warcupii |
| k__Fungi;p__ | Ascomycota;c__ | Eurotiomycetes;o__ | Onygenales;f__ | Arthrodermataceae;g__ | Ctenomyces;s__ Ctenomyces sp |
| k__Fungi;p__ | Ascomycota;c__ | Eurotiomycetes;o__ | Onygenales;f__ | Arthrodermataceae;g__ | Trichophyton;s__ Trichophyton ajelloi |
| k__Fungi;p__ | Ascomycota;c__ | Eurotiomycetes;o__ | Onygenales;f__ | Gymnoascaceae;g__ | Amauproscopsis;s__ Amauproscopsis perforata |
| k__Fungi;p__ | Ascomycota;c__ | Eurotiomycetes;o__ | Onygenales;f__ | Gymnoascaceae;g__ | Gymnoascus;s__ Gymnoascus reesii |
| k__Fungi;p__ | Ascomycota;c__ | Eurotiomycetes;o__ | Onygenales;f__ | Gymnoascaceae;g__ | Gymnoascus;s__ Gymnoascus sp |
| k__Fungi;p__ | Ascomycota;c__ | Eurotiomycetes;o__ | Onygenales;f__ | Gymnoascaceae;g__ | Kraurogymnocarpa;s__ Kraurogymnocarpa trochleospora |
| k__Fungi;p__ | Ascomycota;c__ | Eurotiomycetes;o__ | Onygenales;f__ | Onygenaceae;g__ | Auxarthron;s__ Auxarthron alboluteum |
| k__Fungi;p__ | Ascomycota;c__ | Eurotiomycetes;o__ | Onygenales;f__ | Onygenaceae;g__ | Auxarthron;s__ Auxarthron concentricum |
| k__Fungi;p__ | Ascomycota;c__ | Eurotiomycetes;o__ | Onygenales;f__ | Onygenaceae;g__ | Auxarthron;s__ Auxarthron ostraviense |
| k__Fungi;p__ | Ascomycota;c__ | Eurotiomycetes;o__ | Onygenales;f__ | Onygenaceae;g__ | Auxarthron;s__ Auxarthron sp |
| k__Fungi;p__ | Ascomycota;c__ | Eurotiomycetes;o__ | Onygenales;f__ | Onygenaceae;g__ | Auxarthron;s__ Auxarthron sp UAMH 1592 |
| k__Fungi;p__ | Ascomycota;c__ | Eurotiomycetes;o__ | Onygenales;f__ | Onygenaceae;g__ | Auxarthron;s__ Auxarthron umbrinum |
| k__Fungi;p__ | Ascomycota;c__ | Eurotiomycetes;o__ | Onygenales;f__ | Onygenaceae;g__ | Auxarthron;s__ Auxarthron zuffianum |
| k__Fungi;p__ | Ascomycota;c__ | Eurotiomycetes;o__ | Onygenales;f__ | Onygenaceae;g__ | Chrysosporium;s__ Chrysosporium lobatum |
| k__Fungi;p__ | Ascomycota;c__ | Eurotiomycetes;o__ | Onygenales;f__ | Onygenaceae;g__ | Chrysosporium;s__ Chrysosporium pilosum |
| k__Fungi;p__ | Ascomycota;c__ | Eurotiomycetes;o__ | Onygenales;f__ | Onygenaceae;g__ | Chrysosporium;s__ Chrysosporium sp |
| k__Fungi;p__ | Ascomycota;c__ | Eurotiomycetes;o__ | Onygenales;f__ | Onygenaceae;g__ | unidentified;s__ Onygenaceae sp |
| k__Fungi;p__ | Ascomycota;c__ | Eurotiomycetes;o__ | Onygenales;f__ | unidentified;g__ | unidentified;s__ Onygenales sp |
| k__Fungi;p__ | Ascomycota;c__ | Eurotiomycetes;o__ | Onygenales;f__ | unidentified;g__ | unidentified;s__ uncultured Emmonsia |
| k__Fungi;p__ | Ascomycota;c__ | Eurotiomycetes;o__ | Pyrenulales;f__ | Pyrenulaceae;g__ | Pyrenula;s__ Pyrenula macrospora |
| k__Fungi;p__ | Ascomycota;c__ | Eurotiomycetes;o__ | Verrucariales;f__ | Verrucariaceae;g__ | Endocarpon;s__ Endocarpon pusillum |
| k__Fungi;p__ | Ascomycota;c__ | Eurotiomycetes;o__ | Verrucariales;f__ | Verrucariaceae;g__ | Staurothele;s__ Staurothele areolata |
| k__Fungi;p__ | Ascomycota;c__ | Eurotiomycetes;o__ | Verrucariales;f__ | Verrucariaceae;g__ | Verrucaria;s__ Verrucaria sp A Orange 16664 |
| k__Fungi;p__ | Ascomycota;c__ | Eurotiomycetes;o__ | Verrucariales;f__ | Verrucariaceae;g__ | unidentified;s__ Verrucariaceae sp |
| k__Fungi;p__ | Ascomycota;c__ | Eurotiomycetes;o__ | Verrucariales;f__ | unidentified;g__ | unidentified;s__ Verrucariales sp |
| k__Fungi;p__ | Ascomycota;c__ | Eurotiomycetes;o__ | unidentified;f__ | unidentified;g__ | unidentified;s__ Eurotiomycetes sp |
| k__Fungi;p__ | Ascomycota;c__ | Eurotiomycetes;o__ | unidentified;f__ | unidentified;g__ | unidentified;s__ Eurotiomycetes sp TC28 |
| k__Fungi;p__ | Ascomycota;c__ | Incertae sedis;o__ | Incertae sedis;f__ | Incertae sedis;g__ | Calcarisporiella;s__ Calcarisporiella sp |
| k__Fungi;p__ | Ascomycota;c__ | Incertae sedis;o__ | Incertae sedis;f__ | Incertae sedis;g__ | Calcarisporiella;s__ Calcarisporiella sp NUH37 |
| k__Fungi;p__ | Ascomycota;c__ | Incertae sedis;o__ | Incertae sedis;f__ | Incertae sedis;g__ | Camposporium;s__ Camposporium antennatum |
| k__Fungi;p__ | Ascomycota;c__ | Incertae sedis;o__ | Incertae sedis;f__ | Incertae sedis;g__ | Chaetospermum;s__ Chaetospermum chaetosporum |
| k__Fungi;p__ | Ascomycota;c__ | Incertae sedis;o__ | Incertae sedis;f__ | Incertae sedis;g__ | Chaetosphaeronema;s__ Chaetosphaeronema sp MP13 ZW_2013 |
| k__Fungi;p__ | Ascomycota;c__ | Incertae sedis;o__ | Incertae sedis;f__ | Incertae sedis;g__ | Chalara;s__ Chalara sp |
| k__Fungi;p__ | Ascomycota;c__ | Incertae sedis;o__ | Incertae sedis;f__ | Incertae sedis;g__ | Collembolispora;s__ Collembolispora barbata |
| k__Fungi;p__ | Ascomycota;c__ | Incertae sedis;o__ | Incertae sedis;f__ | Incertae sedis;g__ | Cordana;s__ Cordana sp HRM_2012 |
| k__Fungi;p__ | Ascomycota;c__ | Incertae sedis;o__ | Incertae sedis;f__ | Incertae sedis;g__ | Gorgomyces;s__ Gorgomyces honrubiae |
| k__Fungi;p__ | Ascomycota;c__ | Incertae sedis;o__ | Incertae sedis;f__ | Incertae sedis;g__ | Gyoerffyella;s__ Gyoerffyella sp B54J5 | k__Fungi;p__Ascomycota;c__Incertae sedis;o__Incertae sedis;f__Incertae sedis;g__Hansfordia;s__Hansfordia sp XC_2012 k__Fungi;p__Ascomycota;c__Incertae sedis;o__Incertae sedis;f__Incertae sedis;g__Knufia;s__Knufia endospora k__Fungi;p__Ascomycota;c__Incertae sedis;o__Incertae sedis;f__Incertae sedis;g__Knufia;s__Knufia sp k__Fungi;p__Ascomycota;c__Incertae sedis;o__Incertae sedis;f__Incertae sedis;g__Leptodiscella;s__Leptodiscella sp F277786 k__Fungi;p__Ascomycota;c__Incertae sedis;o__Incertae sedis;f__Incertae sedis;g__Leptodiscella;s__Leptodiscella sp FMR 10885 k__Fungi;p__Ascomycota;c__Incertae sedis;o__Incertae sedis;f__Incertae sedis;g__Ochroconis;s__Ochroconis sp k__Fungi;p__Ascomycota;c__Incertae sedis;o__Incertae sedis;f__Incertae sedis;g__Ochroconis;s__Ochroconis sp GH_2013 k__Fungi;p__Ascomycota;c__Incertae sedis;o__Incertae sedis;f__Incertae sedis;g__Ochroconis;s__Ochroconis tshawytschae k__Fungi;p__Ascomycota;c__Incertae sedis;o__Incertae sedis;f__Incertae sedis;g__Phaeocytostroma;s__Phaeocytostroma ambiguum k__Fungi;p__Ascomycota;c__Incertae sedis;o__Incertae sedis;f__Incertae sedis;g__Polyscytalum;s__Polyscytalum pustulans k__Fungi;p__Ascomycota;c__Incertae sedis;o__Incertae sedis;f__Incertae sedis;g__Retroconis;s__Retroconis sp SR k__Fungi;p__Ascomycota;c__Incertae sedis;o__Incertae sedis;f__Incertae sedis;g__Rhinocladium;s__Rhinocladium lesnei k__Fungi;p__Ascomycota;c__Incertae sedis;o__Incertae sedis;f__Incertae sedis;g__Scolecobasidium;s__Scolecobasidium constrictum k__Fungi;p__Ascomycota;c__Incertae sedis;o__Incertae sedis;f__Incertae sedis;g__Slimacomyces;s__Slimacomyces isiola k__Fungi;p__Ascomycota;c__Incertae sedis;o__Incertae sedis;f__Incertae sedis;g__Spegazzinia;s__Spegazzinia sp k__Fungi;p__Ascomycota;c__Incertae sedis;o__Incertae sedis;f__Incertae sedis;g__Sporendonema;s__Sporendonema purpurascens k__Fungi;p__Ascomycota;c__Incertae sedis;o__Incertae sedis;f__Incertae sedis;g__Torula;s__Torula sp k__Fungi;p__Ascomycota;c__Incertae sedis;o__Incertae sedis;f__Incertae sedis;g__Vermispora;s__Vermispora fusarina k__Fungi;p__Ascomycota;c__Incertae sedis;o__Incertae sedis;f__Incertae sedis;g__Vermispora;s__Vermispora spermatophaga k__Fungi;p__Ascomycota;c__Incertae sedis;o__Incertae sedis;f__Incertae sedis;g__Veronaea;s__Veronaea japonica k__Fungi;p__Ascomycota;c__Incertae sedis;o__Incertae sedis;f__Incertae sedis;g__Vestigium;s__Vestigium trifidum k__Fungi;p__Ascomycota;c__Incertae sedis;o__Incertae sedis;f__Incertae sedis;g__Wojnowicia;s__Wojnowicia viburni k__Fungi;p__Ascomycota;c__Incertae sedis;o__Incertae sedis;f__Incertae sedis;g__unidentified;s__Ascomycota sp k__Fungi;p__Ascomycota;c__Incertae sedis;o__Incertae sedis;f__Pseudeurotiaceae;g__Leuconeurospora;s__Leuconeurospora sp k__Fungi;p__Ascomycota;c__Incertae sedis;o__Incertae sedis;f__Pseudeurotiaceae;g__Pseudeurotium;s__Pseudeurotium hygrophilum k__Fungi;p__Ascomycota;c__Incertae sedis;o__Incertae sedis;f__Pseudeurotiaceae;g__unidentified;s__Pseudeurotiaceae sp k__Fungi;p__Ascomycota;c__Lecanoromycetes;o__Acarosporales;f__Acarosporaceae;g__Acarospora;s__Acarospora fulvoviridula k__Fungi;p__Ascomycota;c__Lecanoromycetes;o__Acarosporales;f__Acarosporaceae;g__Acarospora;s__Acarospora nitrophila k__Fungi;p__Ascomycota;c__Lecanoromycetes;o__Acarosporales;f__Acarosporaceae;g__Acarospora;s__Acarospora rosulata k__Fungi;p__Ascomycota;c__Lecanoromycetes;o__Acarosporales;f__Acarosporaceae;g__Acarospora;s__Acarospora smaragdula k__Fungi;p__Ascomycota;c__Lecanoromycetes;o__Agyriales;f__Trapeliaceae;g__Sarea;s__Sarea resinae k__Fungi;p__Ascomycota;c__Lecanoromycetes;o__Candelariales;f__Candelariaceae;g__Candelaria;s__Candelaria pacifica k__Fungi;p__Ascomycota;c__Lecanoromycetes;o__Candelariales;f__Candelariaceae;g__Placomaronea;s__Placomaronea fuegiana k__Fungi;p__Ascomycota;c__Lecanoromycetes;o__Incertae sedis;f__Coniocybaceae;g__Chaenotheca;s__Chaenotheca cinerea k__Fungi;p__Ascomycota;c__Lecanoromycetes;o__Incertae sedis;f__Coniocybaceae;g__Chaenotheca;s__Chaenotheca gracillima k__Fungi;p__Ascomycota;c__Lecanoromycetes;o__Incertae sedis;f__Coniocybaceae;g__Chaenotheca;s__Chaenotheca trichialis k__Fungi;p__Ascomycota;c__Lecanoromycetes;o__Lecanorales;f__Incertae sedis;g__Lecania;s__Lecania cyrtella k__Fungi;p__Ascomycota;c__Lecanoromycetes;o__Lecanorales;f__Parmeliaceae;g__Anzia;s__Anzia pseudocolpota k__Fungi;p__Ascomycota;c__Lecanoromycetes;o__Lecanorales;f__Parmeliaceae;g__Evernia;s__Evernia prunastri

| | | | | | | |
|---|---|---|---|---|---|---|
| k__Fungi;p__ | Ascomycota;c__ | Lecanoromycetes;o__ | Lecanorales;f__ | Parmeliaceae;g__ | Flavoparmelia;s__ | Flavoparmelia caperata |
| k__Fungi;p__ | Ascomycota;c__ | Lecanoromycetes;o__ | Lecanorales;f__ | Parmeliaceae;g__ | Flavopunctelia;s__ | Flavopunctelia borrerioides |
| k__Fungi;p__ | Ascomycota;c__ | Lecanoromycetes;o__ | Lecanorales;f__ | Parmeliaceae;g__ | Flavopunctelia;s__ | Flavopunctelia flaventior |
| k__Fungi;p__ | Ascomycota;c__ | Lecanoromycetes;o__ | Lecanorales;f__ | Parmeliaceae;g__ | Hypogymnia;s__ | Hypogymnia physodes |
| k__Fungi;p__ | Ascomycota;c__ | Lecanoromycetes;o__ | Lecanorales;f__ | Parmeliaceae;g__ | Hypotrachyna;s__ | Hypotrachyna revoluta |
| k__Fungi;p__ | Ascomycota;c__ | Lecanoromycetes;o__ | Lecanorales;f__ | Parmeliaceae;g__ | Melanohalea;s__ | Melanohalea aff subolivacea SL_2012 |
| k__Fungi;p__ | Ascomycota;c__ | Lecanoromycetes;o__ | Lecanorales;f__ | Parmeliaceae;g__ | Parmotrema;s__ | Parmotrema crinitum |
| k__Fungi;p__ | Ascomycota;c__ | Lecanoromycetes;o__ | Lecanorales;f__ | Parmeliaceae;g__ | Punctelia;s__ | Punctelia jeckeri |
| k__Fungi;p__ | Ascomycota;c__ | Lecanoromycetes;o__ | Lecanorales;f__ | Parmeliaceae;g__ | Usnea;s__ | Usnea ceratina |
| k__Fungi;p__ | Ascomycota;c__ | Lecanoromycetes;o__ | Lecanorales;f__ | Parmeliaceae;g__ | Usnea;s__ | Usnea cornuta |
| k__Fungi;p__ | Ascomycota;c__ | Lecanoromycetes;o__ | Lecanorales;f__ | Parmeliaceae;g__ | Usnea;s__ | Usnea esperantiana |
| k__Fungi;p__ | Ascomycota;c__ | Lecanoromycetes;o__ | Lecanorales;f__ | Parmeliaceae;g__ | Usnea;s__ | Usnea flavocardia |
| k__Fungi;p__ | Ascomycota;c__ | Lecanoromycetes;o__ | Lecanorales;f__ | Parmeliaceae;g__ | Usnea;s__ | Usnea glabrata |
| k__Fungi;p__ | Ascomycota;c__ | Lecanoromycetes;o__ | Lecanorales;f__ | Parmeliaceae;g__ | Usnea;s__ | Usnea glabrescens |
| k__Fungi;p__ | Ascomycota;c__ | Lecanoromycetes;o__ | Lecanorales;f__ | Parmeliaceae;g__ | Usnea;s__ | Usnea intermedia |
| k__Fungi;p__ | Ascomycota;c__ | Lecanoromycetes;o__ | Lecanorales;f__ | Parmeliaceae;g__ | Usnea;s__ | Usnea subfloridana |
| k__Fungi;p__ | Ascomycota;c__ | Lecanoromycetes;o__ | Lecanorales;f__ | Parmeliaceae;g__ | Usnea;s__ | Usnea wasmuthii |
| k__Fungi;p__ | Ascomycota;c__ | Lecanoromycetes;o__ | Lecanorales;f__ | Parmeliaceae;g__ | unidentified;s__ | Parmeliaceae sp |
| k__Fungi;p__ | Ascomycota;c__ | Lecanoromycetes;o__ | Lecanorales;f__ | Ramalinaceae;g__ | Ramalina;s__ | Ramalina calicaris |
| k__Fungi;p__ | Ascomycota;c__ | Lecanoromycetes;o__ | Lecanorales;f__ | Ramalinaceae;g__ | Ramalina;s__ | Ramalina farinacea |
| k__Fungi;p__ | Ascomycota;c__ | Lecanoromycetes;o__ | Lecanorales;f__ | Ramalinaceae;g__ | Ramalina;s__ | Ramalina leptocarpha |
| k__Fungi;p__ | Ascomycota;c__ | Lecanoromycetes;o__ | Lecanorales;f__ | unidentified;g__ | unidentified;s__ | Lecanorales sp |
| k__Fungi;p__ | Ascomycota;c__ | Lecanoromycetes;o__ | Pertusariales;f__ | Megasporaceae;g__ | Aspicilia;s__ | Aspicilia sp Nordin 6003 |
| k__Fungi;p__ | Ascomycota;c__ | Lecanoromycetes;o__ | Rhizocarpales;f__ | Catillariaceae;g__ | Catillaria;s__ | Catillaria nigroclavata |
| k__Fungi;p__ | Ascomycota;c__ | Lecanoromycetes;o__ | Teloschistales;f__ | Caliciaceae;g__ | Amandinea;s__ | Amandinea punctata |
| k__Fungi;p__ | Ascomycota;c__ | Lecanoromycetes;o__ | Teloschistales;f__ | Physciaceae;g__ | Buellia;s__ | Buellia griseovirens |
| k__Fungi;p__ | Ascomycota;c__ | Lecanoromycetes;o__ | Teloschistales;f__ | Physciaceae;g__ | Buellia;s__ | Buellia schaereri |
| k__Fungi;p__ | Ascomycota;c__ | Lecanoromycetes;o__ | Teloschistales;f__ | Physciaceae;g__ | Hyperphyscia;s__ | Hyperphyscia adglutinata |
| k__Fungi;p__ | Ascomycota;c__ | Lecanoromycetes;o__ | Teloschistales;f__ | Physciaceae;g__ | Physcia;s__ | Physcia leptalea |
| k__Fungi;p__ | Ascomycota;c__ | Lecanoromycetes;o__ | Teloschistales;f__ | Physciaceae;g__ | Physcia;s__ | Physcia sp |
| k__Fungi;p__ | Ascomycota;c__ | Lecanoromycetes;o__ | Teloschistales;f__ | Physciaceae;g__ | Physconia;s__ | Physconia muscigena |
| k__Fungi;p__ | Ascomycota;c__ | Lecanoromycetes;o__ | Teloschistales;f__ | Physciaceae;g__ | Physconia;s__ | Physconia perisidiosa |
| k__Fungi;p__ | Ascomycota;c__ | Lecanoromycetes;o__ | Teloschistales;f__ | Teloschistaceae;g__ | Caloplaca;s__ | Caloplaca obscurella |
| k__Fungi;p__ | Ascomycota;c__ | Lecanoromycetes;o__ | Teloschistales;f__ | Teloschistaceae;g__ | Xanthomendoza;s__ | Xanthomendoza oregana |
| k__Fungi;p__ | Ascomycota;c__ | Lecanoromycetes;o__ | unidentified;f__ | unidentified;g__ | unidentified;s__ | Lecanoromycetes sp |
| k__Fungi;p__ | Ascomycota;c__ | Leotiomycetes;o__ | Erysiphales;f__ | Erysiphaceae;g__ | Erysiphe;s__ | Erysiphe necator |
| k__Fungi;p__ | Ascomycota;c__ | Leotiomycetes;o__ | Erysiphales;f__ | Erysiphaceae;g__ | Golovinomyces;s__ | Golovinomyces asterum |
| k__Fungi;p__ | Ascomycota;c__ | Leotiomycetes;o__ | Erysiphales;f__ | Erysiphaceae;g__ | Golovinomyces;s__ | Golovinomyces sonchicola |
| k__Fungi;p__ | Ascomycota;c__ | Leotiomycetes;o__ | Erysiphales;f__ | Erysiphaceae;g__ | Podosphaera;s__ | Podosphaera astericola | k__Fungi;p__Ascomycota;c__Leotiomycetes;o__Erysiphales;f__Erysiphaceae;g__Podosphaera;s__Podosphaera sp
k__Fungi;p__Ascomycota;c__Leotiomycetes;o__Helotiales;f__Dermateaceae;g__Gloeosporium;s__Gloeosporium phormii
k__Fungi;p__Ascomycota;c__Leotiomycetes;o__Helotiales;f__Dermateaceae;g__Marssonina;s__Marssonina brunnea f sp multigermtubi
k__Fungi;p__Ascomycota;c__Leotiomycetes;o__Helotiales;f__Dermateaceae;g__Mollisia;s__Mollisia ventosa
k__Fungi;p__Ascomycota;c__Leotiomycetes;o__Helotiales;f__Dermateaceae;g__unidentified;s__Dermateaceae sp
k__Fungi;p__Ascomycota;c__Leotiomycetes;o__Helotiales;f__Helotiaceae;g__Articulospora;s__Articulospora sp
k__Fungi;p__Ascomycota;c__Leotiomycetes;o__Helotiales;f__Helotiaceae;g__Crocicreas;s__Crocicreas sp
k__Fungi;p__Ascomycota;c__Leotiomycetes;o__Helotiales;f__Helotiaceae;g__Hymenoscyphus;s__Hymenoscyphus sp 1558
k__Fungi;p__Ascomycota;c__Leotiomycetes;o__Helotiales;f__Helotiaceae;g__Hymenoscyphus;s__Hymenoscyphus sp SR_F14
k__Fungi;p__Ascomycota;c__Leotiomycetes;o__Helotiales;f__Helotiaceae;g__Neobulgaria;s__Neobulgaria sp
k__Fungi;p__Ascomycota;c__Leotiomycetes;o__Helotiales;f__Helotiaceae;g__Tricladium;s__Tricladium sp
k__Fungi;p__Ascomycota;c__Leotiomycetes;o__Helotiales;f__Helotiaceae;g__unidentified;s__Helotiaceae sp
k__Fungi;p__Ascomycota;c__Leotiomycetes;o__Helotiales;f__Helotiaceae;g__unidentified;s__uncultured Ascocoryne
k__Fungi;p__Ascomycota;c__Leotiomycetes;o__Helotiales;f__Helotiaceae;g__unidentified;s__uncultured Helotiaceae
k__Fungi;p__Ascomycota;c__Leotiomycetes;o__Helotiales;f__Hyaloscyphaceae;g__Albotricha;s__Albotricha sp FC_2190
k__Fungi;p__Ascomycota;c__Leotiomycetes;o__Helotiales;f__Hyaloscyphaceae;g__Cistella;s__Cistella sp KUS_F52527
k__Fungi;p__Ascomycota;c__Leotiomycetes;o__Helotiales;f__Hyaloscyphaceae;g__Hyaloscypha;s__Hyaloscypha sp
k__Fungi;p__Ascomycota;c__Leotiomycetes;o__Helotiales;f__Hyaloscyphaceae;g__Mycoarthris;s__Mycoarthris corallina
k__Fungi;p__Ascomycota;c__Leotiomycetes;o__Helotiales;f__Hyaloscyphaceae;g__Trichopeziza;s__Trichopeziza mollissima
k__Fungi;p__Ascomycota;c__Leotiomycetes;o__Helotiales;f__Hyaloscyphaceae;g__Trichopezizella;s__Trichopezizella otanii
k__Fungi;p__Ascomycota;c__Leotiomycetes;o__Helotiales;f__Hyaloscyphaceae;g__unidentified;s__Hyaloscyphaceae sp
k__Fungi;p__Ascomycota;c__Leotiomycetes;o__Helotiales;f__Incertae sedis;g__Bisporella;s__Bisporella citrina
k__Fungi;p__Ascomycota;c__Leotiomycetes;o__Helotiales;f__Incertae sedis;g__Cadophora;s__Cadophora luteo-olivacea
k__Fungi;p__Ascomycota;c__Leotiomycetes;o__Helotiales;f__Incertae sedis;g__Cadophora;s__Cadophora sp
k__Fungi;p__Ascomycota;c__Leotiomycetes;o__Helotiales;f__Incertae sedis;g__Dactylaria;s__Dactylaria dimorphospora
k__Fungi;p__Ascomycota;c__Leotiomycetes;o__Helotiales;f__Incertae sedis;g__Glarea;s__Glarea lozoyensis
k__Fungi;p__Ascomycota;c__Leotiomycetes;o__Helotiales;f__Incertae sedis;g__Helicodendron;s__Helicodendron sp
k__Fungi;p__Ascomycota;c__Leotiomycetes;o__Helotiales;f__Incertae sedis;g__Infundichalara;s__Infundichalara sp
k__Fungi;p__Ascomycota;c__Leotiomycetes;o__Helotiales;f__Incertae sedis;g__Scytalidium;s__Scytalidium circinatum
k__Fungi;p__Ascomycota;c__Leotiomycetes;o__Helotiales;f__Incertae sedis;g__Scytalidium;s__Scytalidium sp
k__Fungi;p__Ascomycota;c__Leotiomycetes;o__Helotiales;f__Incertae sedis;g__Scytalidium;s__Scytalidium sp TMS_2011
k__Fungi;p__Ascomycota;c__Leotiomycetes;o__Helotiales;f__Incertae sedis;g__Spirosphaera;s__Spirosphaera cupreorufescens
k__Fungi;p__Ascomycota;c__Leotiomycetes;o__Helotiales;f__Incertae sedis;g__Tetracladium;s__Tetracladium ellipsoideum
k__Fungi;p__Ascomycota;c__Leotiomycetes;o__Helotiales;f__Incertae sedis;g__Tetracladium;s__Tetracladium marchalianum
k__Fungi;p__Ascomycota;c__Leotiomycetes;o__Helotiales;f__Incertae sedis;g__Tetracladium;s__Tetracladium maxilliforme
k__Fungi;p__Ascomycota;c__Leotiomycetes;o__Helotiales;f__Incertae sedis;g__Tetracladium;s__Tetracladium sp
k__Fungi;p__Ascomycota;c__Leotiomycetes;o__Helotiales;f__Incertae sedis;g__Tetracladium;s__Tetracladium sp J3
k__Fungi;p__Ascomycota;c__Leotiomycetes;o__Helotiales;f__Incertae sedis;g__Trimmatostroma;s__Trimmatostroma cordae
k__Fungi;p__Ascomycota;c__Leotiomycetes;o__Helotiales;f__Incertae sedis;g__Trimmatostroma;s__Trimmatostroma salinum

| k_Fungi;p | Ascomycota;c | Leotiomycetes;o | Helotiales;f | Incertae sedis;g | Trimmatostroma;s | Trimmatostroma sp MT658 |
| k_Fungi;p | Ascomycota;c | Leotiomycetes;o | Helotiales;f | Incertae sedis;g | unidentified;s | Helotiales sp |
| k_Fungi;p | Ascomycota;c | Leotiomycetes;o | Helotiales;f | Phacidiaceae;g | Phacidium;s | Phacidium lacerum |
| k_Fungi;p | Ascomycota;c | Leotiomycetes;o | Helotiales;f | Rutstroemiaceae;g | Rutstroemia;s | Rutstroemia sp |
| k_Fungi;p | Ascomycota;c | Leotiomycetes;o | Helotiales;f | Rutstroemiaceae;g | unidentified;s | Rutstroemiaceae sp |
| k_Fungi;p | Ascomycota;c | Leotiomycetes;o | Helotiales;f | Sclerotiniaceae;g | Botrytis;s | Botrytis caroliniana |
| k_Fungi;p | Ascomycota;c | Leotiomycetes;o | Helotiales;f | Sclerotiniaceae;g | Monilinia;s | Monilinia sp F0612 |
| k_Fungi;p | Ascomycota;c | Leotiomycetes;o | Helotiales;f | Sclerotiniaceae;g | Sclerotinia;s | Sclerotinia sclerotiorum |
| k_Fungi;p | Ascomycota;c | Leotiomycetes;o | Helotiales;f | Vibrisseaceae;g | Phialocephala;s | Phialocephala fortinii |
| k_Fungi;p | Ascomycota;c | Leotiomycetes;o | Helotiales;f | Vibrisseaceae;g | Phialocephala;s | Phialocephala sp |
| k_Fungi;p | Ascomycota;c | Leotiomycetes;o | Helotiales;f | Vibrisseaceae;g | Vibrissea;s | Vibrissea filisporia |
| k_Fungi;p | Ascomycota;c | Leotiomycetes;o | Helotiales;f | unidentified;g | unidentified;s | Helotiales sp |
| k_Fungi;p | Ascomycota;c | Leotiomycetes;o | Helotiales;f | unidentified;g | unidentified;s | Helotiales sp EXP0568F |
| k_Fungi;p | Ascomycota;c | Leotiomycetes;o | Helotiales;f | unidentified;g | unidentified;s | uncultured Helotiales |
| k_Fungi;p | Ascomycota;c | Leotiomycetes;o | Incertae sedis;f | Incertae sedis;g | Collophora;s | Collophora sp |
| k_Fungi;p | Ascomycota;c | Leotiomycetes;o | Incertae sedis;f | Incertae sedis;g | Cyclaneusma;s | Cyclaneusma minus |
| k_Fungi;p | Ascomycota;c | Leotiomycetes;o | Incertae sedis;f | Incertae sedis;g | Geomyces;s | Geomyces auratus |
| k_Fungi;p | Ascomycota;c | Leotiomycetes;o | Incertae sedis;f | Incertae sedis;g | Geomyces;s | Geomyces sp UFMGCB 5981 |
| k_Fungi;p | Ascomycota;c | Leotiomycetes;o | Incertae sedis;f | Incertae sedis;g | Leohumicola;s | Leohumicola minima |
| k_Fungi;p | Ascomycota;c | Leotiomycetes;o | Incertae sedis;f | Myxotrichaceae;g | Gymnostellatospora;s | Gymnostellatospora frigida |
| k_Fungi;p | Ascomycota;c | Leotiomycetes;o | Incertae sedis;f | Myxotrichaceae;g | Malbranchea;s | Malbranchea flocciformis |
| k_Fungi;p | Ascomycota;c | Leotiomycetes;o | Incertae sedis;f | Myxotrichaceae;g | Myxotrichum;s | Myxotrichum sp OUCMBI101149 |
| k_Fungi;p | Ascomycota;c | Leotiomycetes;o | Incertae sedis;f | Myxotrichaceae;g | Oidiodendron;s | Oidiodendron chlamydosporicum |
| k_Fungi;p | Ascomycota;c | Leotiomycetes;o | Incertae sedis;f | Myxotrichaceae;g | Oidiodendron;s | Oidiodendron sp |
| k_Fungi;p | Ascomycota;c | Leotiomycetes;o | Incertae sedis;f | Myxotrichaceae;g | Oidiodendron;s | Oidiodendron sp 15PA14 |
| k_Fungi;p | Ascomycota;c | Leotiomycetes;o | Incertae sedis;f | Myxotrichaceae;g | Pseudogymnoascus;s | Pseudogymnoascus verrucosus |
| k_Fungi;p | Ascomycota;c | Leotiomycetes;o | Incertae sedis;f | Myxotrichaceae;g | unidentified;s | Myxotrichaceae sp BESC246d |
| k_Fungi;p | Ascomycota;c | Leotiomycetes;o | Incertae sedis;f | unidentified;g | unidentified;s | Leotiomycetes sp |
| k_Fungi;p | Ascomycota;c | Leotiomycetes;o | Leotiales;f | Leotiaceae;g | Pezoloma;s | Pezoloma ciliifera |
| k_Fungi;p | Ascomycota;c | Leotiomycetes;o | Rhytismatales;f | Rhytismataceae;g | Lophodermium;s | Lophodermium agathidis |
| k_Fungi;p | Ascomycota;c | Leotiomycetes;o | Thelebolales;f | Thelebolaceae;g | unidentified;s | uncultured Thelebolaceae |
| k_Fungi;p | Ascomycota;c | Leotiomycetes;o | unidentified;f | unidentified;g | unidentified;s | Leotiomycetes sp |
| k_Fungi;p | Ascomycota;c | Orbiliomycetes;o | Orbiliales;f | Orbiliaceae;g | Arthrobotrys;s | Arthrobotrys brochopaga |
| k_Fungi;p | Ascomycota;c | Orbiliomycetes;o | Orbiliales;f | Orbiliaceae;g | Arthrobotrys;s | Arthrobotrys conoides |
| k_Fungi;p | Ascomycota;c | Orbiliomycetes;o | Orbiliales;f | Orbiliaceae;g | Arthrobotrys;s | Arthrobotrys oligospora |
| k_Fungi;p | Ascomycota;c | Orbiliomycetes;o | Orbiliales;f | Orbiliaceae;g | Arthrobotrys;s | Arthrobotrys oudemansii |
| k_Fungi;p | Ascomycota;c | Orbiliomycetes;o | Orbiliales;f | Orbiliaceae;g | Arthrobotrys;s | Arthrobotrys psychrophila |
| k_Fungi;p | Ascomycota;c | Orbiliomycetes;o | Orbiliales;f | Orbiliaceae;g | Arthrobotrys;s | Arthrobotrys sp ATCC MYA 4125 |
| k_Fungi;p | Ascomycota;c | Orbiliomycetes;o | Orbiliales;f | Orbiliaceae;g | Arthrobotrys;s | Arthrobotrys sp C45 |

| k__Fungi;p__ | Ascomycota;c__ | Orbiliomycetes;o__ | Orbiliales;f__ | Orbiliaceae;g__ | Dactylella;s__ | Dactylella ramosa |
|---|---|---|---|---|---|---|
| k__Fungi;p__ | Ascomycota;c__ | Orbiliomycetes;o__ | Orbiliales;f__ | Orbiliaceae;g__ | Dactylella;s__ | Dactylella sp |
| k__Fungi;p__ | Ascomycota;c__ | Orbiliomycetes;o__ | Orbiliales;f__ | Orbiliaceae;g__ | Duddingtonia;s__ | Duddingtonia flagrans |
| k__Fungi;p__ | Ascomycota;c__ | Orbiliomycetes;o__ | Orbiliales;f__ | Orbiliaceae;g__ | unidentified;s__ | Orbiliaceae sp |
| k__Fungi;p__ | Ascomycota;c__ | Orbiliomycetes;o__ | Orbiliales;f__ | Orbiliaceae;g__ | unidentified;s__ | uncultured Arthrobotrys |
| k__Fungi;p__ | Ascomycota;c__ | Orbiliomycetes;o__ | Orbiliales;f__ | unidentified;g__ | unidentified;s__ | Orbiliales sp |
| k__Fungi;p__ | Ascomycota;c__ | Orbiliomycetes;o__ | unidentified;f__ | unidentified;g__ | unidentified;s__ | Orbiliomycetes sp |
| k__Fungi;p__ | Ascomycota;c__ | Pezizomycetes;o__ | Pezizales;f__ | Ascobolaceae;g__ | Ascobolus;s__ | Ascobolus sp |
| k__Fungi;p__ | Ascomycota;c__ | Pezizomycetes;o__ | Pezizales;f__ | Ascobolaceae;g__ | unidentified;s__ | Ascobolaceae sp |
| k__Fungi;p__ | Ascomycota;c__ | Pezizomycetes;o__ | Pezizales;f__ | Morchellaceae;g__ | Morchella;s__ | Morchella septimelata |
| k__Fungi;p__ | Ascomycota;c__ | Pezizomycetes;o__ | Pezizales;f__ | Pezizaceae;g__ | Eremiomyces;s__ | Eremiomyces echinulatus |
| k__Fungi;p__ | Ascomycota;c__ | Pezizomycetes;o__ | Pezizales;f__ | Pezizaceae;g__ | Peziza;s__ | Peziza domiciliana |
| k__Fungi;p__ | Ascomycota;c__ | Pezizomycetes;o__ | Pezizales;f__ | Pezizaceae;g__ | Peziza;s__ | Peziza granularis |
| k__Fungi;p__ | Ascomycota;c__ | Pezizomycetes;o__ | Pezizales;f__ | Pezizaceae;g__ | Peziza;s__ | Peziza nivalis |
| k__Fungi;p__ | Ascomycota;c__ | Pezizomycetes;o__ | Pezizales;f__ | Pezizaceae;g__ | Peziza;s__ | Peziza sp GYYL_G005 |
| k__Fungi;p__ | Ascomycota;c__ | Pezizomycetes;o__ | Pezizales;f__ | Pezizaceae;g__ | Peziza;s__ | Peziza sp KH_97_129 |
| k__Fungi;p__ | Ascomycota;c__ | Pezizomycetes;o__ | Pezizales;f__ | Pezizaceae;g__ | Peziza;s__ | Peziza subcitrina |
| k__Fungi;p__ | Ascomycota;c__ | Pezizomycetes;o__ | Pezizales;f__ | Pezizaceae;g__ | unidentified;s__ | Pezizaceae sp |
| k__Fungi;p__ | Ascomycota;c__ | Pezizomycetes;o__ | Pezizales;f__ | Pezizaceae;g__ | unidentified;s__ | uncultured Pezizaceae |
| k__Fungi;p__ | Ascomycota;c__ | Pezizomycetes;o__ | Pezizales;f__ | Pyronemataceae;g__ | Aleuria;s__ | Aleuria aurantia |
| k__Fungi;p__ | Ascomycota;c__ | Pezizomycetes;o__ | Pezizales;f__ | Pyronemataceae;g__ | Ascorhizoctonia;s__ | Ascorhizoctonia sp |
| k__Fungi;p__ | Ascomycota;c__ | Pezizomycetes;o__ | Pezizales;f__ | Pyronemataceae;g__ | Genea;s__ | Genea hispidula |
| k__Fungi;p__ | Ascomycota;c__ | Pezizomycetes;o__ | Pezizales;f__ | Pyronemataceae;g__ | Geopyxis;s__ | Geopyxis sp |
| k__Fungi;p__ | Ascomycota;c__ | Pezizomycetes;o__ | Pezizales;f__ | Pyronemataceae;g__ | Pseudaleuria;s__ | Pseudaleuria sp |
| k__Fungi;p__ | Ascomycota;c__ | Pezizomycetes;o__ | Pezizales;f__ | Pyronemataceae;g__ | Scutellinia;s__ | Scutellinia sp |
| k__Fungi;p__ | Ascomycota;c__ | Pezizomycetes;o__ | Pezizales;f__ | Pyronemataceae;g__ | Scutellinia;s__ | Scutellinia torrentis |
| k__Fungi;p__ | Ascomycota;c__ | Pezizomycetes;o__ | Pezizales;f__ | Pyronemataceae;g__ | Tricharina;s__ | Tricharina sp |
| k__Fungi;p__ | Ascomycota;c__ | Pezizomycetes;o__ | Pezizales;f__ | Pyronemataceae;g__ | unidentified;s__ | Pyronemataceae sp |
| k__Fungi;p__ | Ascomycota;c__ | Pezizomycetes;o__ | Pezizales;f__ | Sarcosomataceae;g__ | unidentified;s__ | Sarcosomataceae sp3_G1_SLL2_3 |
| k__Fungi;p__ | Ascomycota;c__ | Pezizomycetes;o__ | Pezizales;f__ | Tuberaceae;g__ | Tuber;s__ | Tuber whetstonense |
| k__Fungi;p__ | Ascomycota;c__ | Pezizomycetes;o__ | Pezizales;f__ | unidentified;g__ | unidentified;s__ | Pezizales sp |
| k__Fungi;p__ | Ascomycota;c__ | Pezizomycetes;o__ | Pezizales;f__ | unidentified;g__ | unidentified;s__ | Pezizales sp r225 |
| k__Fungi;p__ | Ascomycota;c__ | Pezizomycetes;o__ | unidentified;f__ | unidentified;g__ | unidentified;s__ | Pezizomycetes sp |
| k__Fungi;p__ | Ascomycota;c__ | Pezizomycetes;o__ | unidentified;f__ | unidentified;g__ | unidentified;s__ | Pezizomycetes sp genotype 38 |
| k__Fungi;p__ | Ascomycota;c__ | Saccharomycetes;o__ | Saccharomycetales;f__ | Debaryomycetaceae;g__ | Meyerozyma;s__ | Meyerozyma caribbica |
| k__Fungi;p__ | Ascomycota;c__ | Saccharomycetes;o__ | Saccharomycetales;f__ | Debaryomycetaceae;g__ | Meyerozyma;s__ | Meyerozyma guilliermondii |
| k__Fungi;p__ | Ascomycota;c__ | Saccharomycetes;o__ | Saccharomycetales;f__ | Debaryomycetaceae;g__ | Priceomyces;s__ | Priceomyces carsonii |
| k__Fungi;p__ | Ascomycota;c__ | Saccharomycetes;o__ | Saccharomycetales;f__ | Dipodascaceae;g__ | Basidioascus;s__ | Basidioascus magus |
| k__Fungi;p__ | Ascomycota;c__ | Saccharomycetes;o__ | Saccharomycetales;f__ | Dipodascaceae;g__ | unidentified;s__ | Dipodascaceae sp |

| k_Fungi;p | Ascomycota;c | Saccharomycetes;o | Saccharomycetales;f | Incertae sedis;g | Candida;s | Candida aaseri |
|---|---|---|---|---|---|---|
| k_Fungi;p | Ascomycota;c | Saccharomycetes;o | Saccharomycetales;f | Incertae sedis;g | Candida;s | Candida apicola |
| k_Fungi;p | Ascomycota;c | Saccharomycetes;o | Saccharomycetales;f | Incertae sedis;g | Candida;s | Candida boidinii |
| k_Fungi;p | Ascomycota;c | Saccharomycetes;o | Saccharomycetales;f | Incertae sedis;g | Candida;s | Candida carvajalis |
| k_Fungi;p | Ascomycota;c | Saccharomycetes;o | Saccharomycetales;f | Incertae sedis;g | Candida;s | Candida haemulonis |
| k_Fungi;p | Ascomycota;c | Saccharomycetes;o | Saccharomycetales;f | Incertae sedis;g | Candida;s | Candida membranifaciens |
| k_Fungi;p | Ascomycota;c | Saccharomycetes;o | Saccharomycetales;f | Incertae sedis;g | Candida;s | Candida norvegica |
| k_Fungi;p | Ascomycota;c | Saccharomycetes;o | Saccharomycetales;f | Incertae sedis;g | Candida;s | Candida orthopsilosis |
| k_Fungi;p | Ascomycota;c | Saccharomycetes;o | Saccharomycetales;f | Incertae sedis;g | Candida;s | Candida parapsilosis |
| k_Fungi;p | Ascomycota;c | Saccharomycetes;o | Saccharomycetales;f | Incertae sedis;g | Candida;s | Candida railenensis |
| k_Fungi;p | Ascomycota;c | Saccharomycetes;o | Saccharomycetales;f | Incertae sedis;g | Candida;s | Candida sp |
| k_Fungi;p | Ascomycota;c | Saccharomycetes;o | Saccharomycetales;f | Incertae sedis;g | Candida;s | Candida tropicalis |
| k_Fungi;p | Ascomycota;c | Saccharomycetes;o | Saccharomycetales;f | Incertae sedis;g | Candida;s | Candida xylopsoci |
| k_Fungi;p | Ascomycota;c | Saccharomycetes;o | Saccharomycetales;f | Incertae sedis;g | Candida;s | Candida zeylanoides |
| k_Fungi;p | Ascomycota;c | Saccharomycetes;o | Saccharomycetales;f | Incertae sedis;g | Cyberlindnera;s | Cyberlindnera jadinii |
| k_Fungi;p | Ascomycota;c | Saccharomycetes;o | Saccharomycetales;f | Incertae sedis;g | Debaryomyces;s | Debaryomyces hansenii |
| k_Fungi;p | Ascomycota;c | Saccharomycetes;o | Saccharomycetales;f | Incertae sedis;g | Debaryomyces;s | Debaryomyces nepalensis |
| k_Fungi;p | Ascomycota;c | Saccharomycetes;o | Saccharomycetales;f | Incertae sedis;g | Lodderomyces;s | Lodderomyces elongisporus |
| k_Fungi;p | Ascomycota;c | Saccharomycetes;o | Saccharomycetales;f | Incertae sedis;g | Wickerhamomyces;s | Wickerhamomyces anomalus |
| k_Fungi;p | Ascomycota;c | Saccharomycetes;o | Saccharomycetales;f | Incertae sedis;g | unidentified;s | Saccharomycetales sp |
| k_Fungi;p | Ascomycota;c | Saccharomycetes;o | Saccharomycetales;f | Lipomycetaceae;g | Lipomyces;s | Lipomyces lipofer |
| k_Fungi;p | Ascomycota;c | Saccharomycetes;o | Saccharomycetales;f | Lipomycetaceae;g | Lipomyces;s | Lipomyces tetrasporus |
| k_Fungi;p | Ascomycota;c | Saccharomycetes;o | Saccharomycetales;f | Metschnikowiaceae;g | Metschnikowia;s | Metschnikowia chrysoperlae |
| k_Fungi;p | Ascomycota;c | Saccharomycetes;o | Saccharomycetales;f | Metschnikowiaceae;g | Metschnikowia;s | Metschnikowia pulcherrima |
| k_Fungi;p | Ascomycota;c | Saccharomycetes;o | Saccharomycetales;f | Pichiaceae;g | Dekkera;s | Dekkera bruxellensis |
| k_Fungi;p | Ascomycota;c | Saccharomycetes;o | Saccharomycetales;f | Pichiaceae;g | Issatchenkia;s | Issatchenkia orientalis |
| k_Fungi;p | Ascomycota;c | Saccharomycetes;o | Saccharomycetales;f | Pichiaceae;g | Issatchenkia;s | Issatchenkia terricola |
| k_Fungi;p | Ascomycota;c | Saccharomycetes;o | Saccharomycetales;f | Pichiaceae;g | Kregervanrija;s | Kregervanrija fluxuum |
| k_Fungi;p | Ascomycota;c | Saccharomycetes;o | Saccharomycetales;f | Pichiaceae;g | Pichia;s | Pichia fermentans |
| k_Fungi;p | Ascomycota;c | Saccharomycetes;o | Saccharomycetales;f | Pichiaceae;g | Pichia;s | Pichia membranifaciens |
| k_Fungi;p | Ascomycota;c | Saccharomycetes;o | Saccharomycetales;f | Pichiaceae;g | Pichia;s | Pichia sp |
| k_Fungi;p | Ascomycota;c | Saccharomycetes;o | Saccharomycetales;f | Pichiaceae;g | Pichia;s | Pichia sp CBS 209 |
| k_Fungi;p | Ascomycota;c | Saccharomycetes;o | Saccharomycetales;f | Saccharomycetaceae;g | Kazachstania;s | Kazachstania aerobia |
| k_Fungi;p | Ascomycota;c | Saccharomycetes;o | Saccharomycetales;f | Saccharomycetaceae;g | Lachancea;s | Lachancea meyersii |
| k_Fungi;p | Ascomycota;c | Saccharomycetes;o | Saccharomycetales;f | Saccharomycetaceae;g | Lachancea;s | Lachancea thermotolerans |
| k_Fungi;p | Ascomycota;c | Saccharomycetes;o | Saccharomycetales;f | Saccharomycetaceae;g | Saccharomyces;s | Saccharomyces bayanus |
| k_Fungi;p | Ascomycota;c | Saccharomycetes;o | Saccharomycetales;f | Saccharomycetaceae;g | Saccharomyces;s | Saccharomyces cerevisiae |
| k_Fungi;p | Ascomycota;c | Saccharomycetes;o | Saccharomycetales;f | Saccharomycetaceae;g | Saccharomyces;s | Saccharomyces kudriavzevii |
| k_Fungi;p | Ascomycota;c | Saccharomycetes;o | Saccharomycetales;f | Saccharomycetaceae;g | Torulaspora;s | Torulaspora delbrueckii | k_Fungi;p_Ascomycota;c_Saccharomycetes;o_Saccharomycetales;f_Saccharomycetaceae;g_Zygosaccharomyces;s_Zygosaccharomyces bailii k_Fungi;p_Ascomycota;c_Saccharomycetes;o_Saccharomycetales;f_Saccharomycetaceae;g_Zygosaccharomyces;s_Zygosaccharomyces parabailii k_Fungi;p_Ascomycota;c_Saccharomycetes;o_Saccharomycetales;f_Saccharomycodaceae;g_Hanseniaspora;s_Hanseniaspora osmophila k_Fungi;p_Ascomycota;c_Saccharomycetes;o_Saccharomycetales;f_Saccharomycodaceae;g_Hanseniaspora;s_Hanseniaspora uvarum k_Fungi;p_Ascomycota;c_Saccharomycetes;o_Saccharomycetales;f_Saccharomycodaceae;g_Hanseniaspora;s_Hanseniaspora valbyensis k_Fungi;p_Ascomycota;c_Saccharomycetes;o_Saccharomycetales;f_Saccharomycodaceae;g_Saccharomycodes;s_Saccharomycodes ludwigii k_Fungi;p_Ascomycota;c_Saccharomycetes;o_Saccharomycetales;f_Saccharomycopsidaceae;g_Saccharomycopsis;s_Saccharomycopsis schoenii k_Fungi;p_Ascomycota;c_Saccharomycetes;o_Saccharomycetales;f_Trichomonascaceae;g_Blastobotrys;s_Blastobotrys proliferans k_Fungi;p_Ascomycota;c_Saccharomycetes;o_Saccharomycetales;f_Trichomonascaceae;g_Blastobotrys;s_Blastobotrys raffinosifermentans k_Fungi;p_Ascomycota;c_Saccharomycetes;o_Saccharomycetales;f_Trichomonascaceae;g_Blastobotrys;s_Blastobotrys serpentis k_Fungi;p_Ascomycota;c_Saccharomycetes;o_Saccharomycetales;f_Trichomonascaceae;g_Zygoascus;s_Zygoascus hellenicus k_Fungi;p_Ascomycota;c_Saccharomycetes;o_Saccharomycetales;f_Trichomonascaceae;g_Zygoascus;s_Zygoascus meyerae k_Fungi;p_Ascomycota;c_Saccharomycetes;o_Saccharomycetales;f_unidentified;g_unidentified;s_Saccharomycetales sp k_Fungi;p_Ascomycota;c_Saccharomycetes;o_unidentified;f_unidentified;g_unidentified;s_saccharomycete sp NZSBHB_Te_Awa1 k_Fungi;p_Ascomycota;c_Sordariomycetes;o_Chaetosphaeriales;f_Chaetosphaeriaceae;g_Chaetosphaeria;s_Chaetosphaeria sp k_Fungi;p_Ascomycota;c_Sordariomycetes;o_Chaetosphaeriales;f_Chaetosphaeriaceae;g_Menispora;s_Menispora ciliata k_Fungi;p_Ascomycota;c_Sordariomycetes;o_Coniochaetales;f_Coniochaetaceae;g_Coniochaeta;s_Coniochaeta cateniformis k_Fungi;p_Ascomycota;c_Sordariomycetes;o_Coniochaetales;f_Coniochaetaceae;g_Coniochaeta;s_Coniochaeta sp k_Fungi;p_Ascomycota;c_Sordariomycetes;o_Coniochaetales;f_Coniochaetaceae;g_Lecythophora;s_Lecythophora fasciculata k_Fungi;p_Ascomycota;c_Sordariomycetes;o_Coniochaetales;f_Coniochaetaceae;g_Lecythophora;s_Lecythophora sp k_Fungi;p_Ascomycota;c_Sordariomycetes;o_Coniochaetales;f_Coniochaetaceae;g_unidentified;s_Coniochaetaceae sp k_Fungi;p_Ascomycota;c_Sordariomycetes;o_Coniochaetales;f_Incertae sedis;g_Wallrothiella;s_Wallrothiella subiculosa k_Fungi;p_Ascomycota;c_Sordariomycetes;o_Coniochaetales;f_unidentified;g_unidentified;s_Coniochaetales sp k_Fungi;p_Ascomycota;c_Sordariomycetes;o_Diaporthales;f_Diaporthaceae;g_Diaporthe;s_Diaporthe ambigua k_Fungi;p_Ascomycota;c_Sordariomycetes;o_Diaporthales;f_Diaporthaceae;g_Diaporthe;s_Diaporthe sp k_Fungi;p_Ascomycota;c_Sordariomycetes;o_Diaporthales;f_Diaporthaceae;g_Phomopsis;s_Phomopsis cotoneastri k_Fungi;p_Ascomycota;c_Sordariomycetes;o_Diaporthales;f_Incertae sedis;g_Valsaria;s_Valsaria ceratoniae k_Fungi;p_Ascomycota;c_Sordariomycetes;o_Diaporthales;f_Schizoparmaceae;g_Coniella;s_Coniella fragariae k_Fungi;p_Ascomycota;c_Sordariomycetes;o_Diaporthales;f_Valsaceae;g_Valsa;s_Valsa fabianae k_Fungi;p_Ascomycota;c_Sordariomycetes;o_Diaporthales;f_Valsaceae;g_unidentified;s_Valsaceae sp k_Fungi;p_Ascomycota;c_Sordariomycetes;o_Diaporthales;f_unidentified;g_unidentified;s_uncultured Diaporthales k_Fungi;p_Ascomycota;c_Sordariomycetes;o_Glomerellales;f_Annulatascaceae;g_Conlarium;s_Conlarium sp k_Fungi;p_Ascomycota;c_Sordariomycetes;o_Glomerellales;f_Annulatascaceae;g_Conlarium;s_Conlarium sp KO_2013 k_Fungi;p_Ascomycota;c_Sordariomycetes;o_Glomerellales;f_Apiosporaceae;g_unidentified;s_Apiosporaceae sp k_Fungi;p_Ascomycota;c_Sordariomycetes;o_Glomerellales;f_Glomerellaceae;g_unidentified;s_Glomerellaceae sp k_Fungi;p_Ascomycota;c_Sordariomycetes;o_Hypocreales;f_Bionectriaceae;g_Clonostachys;s_Clonostachys rosea f. catenulata k_Fungi;p_Ascomycota;c_Sordariomycetes;o_Hypocreales;f_Bionectriaceae;g_Hydropisphaera;s_Hydropisphaera erubescens k_Fungi;p_Ascomycota;c_Sordariomycetes;o_Hypocreales;f_Bionectriaceae;g_Mycoarachis;s_Mycoarachis inversa k_Fungi;p_Ascomycota;c_Sordariomycetes;o_Hypocreales;f_Bionectriaceae;g_Stephanonectria;s_Stephanonectria sp k__Fungi;p__Ascomycota;c__Sordariomycetes;o__Hypocreales;f__Bionectriaceae;g__unidentified;s__Bionectriaceae sp k__Fungi;p__Ascomycota;c__Sordariomycetes;o__Hypocreales;f__Clavicipitaceae;g__Harposporium;s__Harposporium bysmatosporum k__Fungi;p__Ascomycota;c__Sordariomycetes;o__Hypocreales;f__Clavicipitaceae;g__Metacordyceps;s__Metacordyceps chlamydosporia k__Fungi;p__Ascomycota;c__Sordariomycetes;o__Hypocreales;f__Clavicipitaceae;g__Metarhizium;s__Metarhizium anisopliae k__Fungi;p__Ascomycota;c__Sordariomycetes;o__Hypocreales;f__Clavicipitaceae;g__Metarhizium;s__Metarhizium flavoviride k__Fungi;p__Ascomycota;c__Sordariomycetes;o__Hypocreales;f__Clavicipitaceae;g__Metarhizium;s__Metarhizium lepidiotae k__Fungi;p__Ascomycota;c__Sordariomycetes;o__Hypocreales;f__Clavicipitaceae;g__Pochonia;s__Pochonia bulbillosa k__Fungi;p__Ascomycota;c__Sordariomycetes;o__Hypocreales;f__Clavicipitaceae;g__unidentified;s__Clavicipitaceae sp k__Fungi;p__Ascomycota;c__Sordariomycetes;o__Hypocreales;f__Cordycipitaceae;g__Beauveria;s__Beauveria pseudobassiana k__Fungi;p__Ascomycota;c__Sordariomycetes;o__Hypocreales;f__Cordycipitaceae;g__Beauveria;s__Beauveria sp k__Fungi;p__Ascomycota;c__Sordariomycetes;o__Hypocreales;f__Cordycipitaceae;g__Cordyceps;s__Cordyceps bassiana k__Fungi;p__Ascomycota;c__Sordariomycetes;o__Hypocreales;f__Cordycipitaceae;g__Lecanicillium;s__Lecanicillium kalimantanense k__Fungi;p__Ascomycota;c__Sordariomycetes;o__Hypocreales;f__Cordycipitaceae;g__Lecanicillium;s__Lecanicillium longisporum k__Fungi;p__Ascomycota;c__Sordariomycetes;o__Hypocreales;f__Cordycipitaceae;g__Lecanicillium;s__Lecanicillium primulinum k__Fungi;p__Ascomycota;c__Sordariomycetes;o__Hypocreales;f__Cordycipitaceae;g__unidentified;s__Cordycipitaceae sp k__Fungi;p__Ascomycota;c__Sordariomycetes;o__Hypocreales;f__Hypocreaceae;g__Acrostalagmus;s__Acrostalagmus luteoalbus k__Fungi;p__Ascomycota;c__Sordariomycetes;o__Hypocreales;f__Hypocreaceae;g__Hypocrea;s__Hypocrea atroviridis k__Fungi;p__Ascomycota;c__Sordariomycetes;o__Hypocreales;f__Hypocreaceae;g__Hypocrea;s__Hypocrea jecorina k__Fungi;p__Ascomycota;c__Sordariomycetes;o__Hypocreales;f__Hypocreaceae;g__Hypocrea;s__Hypocrea novae-zelandiae k__Fungi;p__Ascomycota;c__Sordariomycetes;o__Hypocreales;f__Hypocreaceae;g__Hypomyces;s__Hypomyces virescens k__Fungi;p__Ascomycota;c__Sordariomycetes;o__Hypocreales;f__Hypocreaceae;g__Trichoderma;s__Trichoderma aeroaquaticum k__Fungi;p__Ascomycota;c__Sordariomycetes;o__Hypocreales;f__Hypocreaceae;g__Trichoderma;s__Trichoderma amazonicum k__Fungi;p__Ascomycota;c__Sordariomycetes;o__Hypocreales;f__Hypocreaceae;g__Trichoderma;s__Trichoderma austrokoningii k__Fungi;p__Ascomycota;c__Sordariomycetes;o__Hypocreales;f__Hypocreaceae;g__Trichoderma;s__Trichoderma harzianum k__Fungi;p__Ascomycota;c__Sordariomycetes;o__Hypocreales;f__Hypocreaceae;g__Trichoderma;s__Trichoderma koningiopsis k__Fungi;p__Ascomycota;c__Sordariomycetes;o__Hypocreales;f__Hypocreaceae;g__Trichoderma;s__Trichoderma pubescens k__Fungi;p__Ascomycota;c__Sordariomycetes;o__Hypocreales;f__Hypocreaceae;g__Trichoderma;s__Trichoderma sp k__Fungi;p__Ascomycota;c__Sordariomycetes;o__Hypocreales;f__Hypocreaceae;g__Trichoderma;s__Trichoderma sp 1212_03 k__Fungi;p__Ascomycota;c__Sordariomycetes;o__Hypocreales;f__Hypocreaceae;g__Trichoderma;s__Trichoderma spirale k__Fungi;p__Ascomycota;c__Sordariomycetes;o__Hypocreales;f__Hypocreaceae;g__Trichoderma;s__Trichoderma velutinum k__Fungi;p__Ascomycota;c__Sordariomycetes;o__Hypocreales;f__Hypocreaceae;g__unidentified;s__Hypocreaceae sp k__Fungi;p__Ascomycota;c__Sordariomycetes;o__Hypocreales;f__Incertae sedis;g__Acremonium;s__Acremonium alcalophilum k__Fungi;p__Ascomycota;c__Sordariomycetes;o__Hypocreales;f__Incertae sedis;g__Acremonium;s__Acremonium alternatum k__Fungi;p__Ascomycota;c__Sordariomycetes;o__Hypocreales;f__Incertae sedis;g__Acremonium;s__Acremonium blochii k__Fungi;p__Ascomycota;c__Sordariomycetes;o__Hypocreales;f__Incertae sedis;g__Acremonium;s__Acremonium charticola k__Fungi;p__Ascomycota;c__Sordariomycetes;o__Hypocreales;f__Incertae sedis;g__Acremonium;s__Acremonium chrysogenum k__Fungi;p__Ascomycota;c__Sordariomycetes;o__Hypocreales;f__Incertae sedis;g__Acremonium;s__Acremonium furcatum k__Fungi;p__Ascomycota;c__Sordariomycetes;o__Hypocreales;f__Incertae sedis;g__Acremonium;s__Acremonium fusidioides k__Fungi;p__Ascomycota;c__Sordariomycetes;o__Hypocreales;f__Incertae sedis;g__Acremonium;s__Acremonium parvum

| | | | | | | | |
|---|---|---|---|---|---|---|---|
| k__Fungi;p__ | Ascomycota;c__ | Sordariomycetes;o__ | Hypocreales;f__ | Incertae sedis;g__ | Acremonium;s__ | Acremonium persicinum | |
| k__Fungi;p__ | Ascomycota;c__ | Sordariomycetes;o__ | Hypocreales;f__ | Incertae sedis;g__ | Acremonium;s__ | Acremonium rutilum | |
| k__Fungi;p__ | Ascomycota;c__ | Sordariomycetes;o__ | Hypocreales;f__ | Incertae sedis;g__ | Acremonium;s__ | Acremonium sp | |
| k__Fungi;p__ | Ascomycota;c__ | Sordariomycetes;o__ | Hypocreales;f__ | Incertae sedis;g__ | Acremonium;s__ | Acremonium sp 904C | |
| k__Fungi;p__ | Ascomycota;c__ | Sordariomycetes;o__ | Hypocreales;f__ | Incertae sedis;g__ | Acremonium;s__ | Acremonium sp BCC 14080 | |
| k__Fungi;p__ | Ascomycota;c__ | Sordariomycetes;o__ | Hypocreales;f__ | Incertae sedis;g__ | Acremonium;s__ | Acremonium sp CCF3791 | |
| k__Fungi;p__ | Ascomycota;c__ | Sordariomycetes;o__ | Hypocreales;f__ | Incertae sedis;g__ | Acremonium;s__ | Acremonium sp OUCMBI101028 | |
| k__Fungi;p__ | Ascomycota;c__ | Sordariomycetes;o__ | Hypocreales;f__ | Incertae sedis;g__ | Acremonium;s__ | Acremonium spinosum | |
| k__Fungi;p__ | Ascomycota;c__ | Sordariomycetes;o__ | Hypocreales;f__ | Incertae sedis;g__ | Geosmithia;s__ | Geosmithia sp HF12048 | |
| k__Fungi;p__ | Ascomycota;c__ | Sordariomycetes;o__ | Hypocreales;f__ | Incertae sedis;g__ | Ilyonectria;s__ | Ilyonectria estremocensis | |
| k__Fungi;p__ | Ascomycota;c__ | Sordariomycetes;o__ | Hypocreales;f__ | Incertae sedis;g__ | Ilyonectria;s__ | Ilyonectria liriodendri | |
| k__Fungi;p__ | Ascomycota;c__ | Sordariomycetes;o__ | Hypocreales;f__ | Incertae sedis;g__ | Ilyonectria;s__ | Ilyonectria macrodidyma | |
| k__Fungi;p__ | Ascomycota;c__ | Sordariomycetes;o__ | Hypocreales;f__ | Incertae sedis;g__ | Ilyonectria;s__ | Ilyonectria mors-panacis | |
| k__Fungi;p__ | Ascomycota;c__ | Sordariomycetes;o__ | Hypocreales;f__ | Incertae sedis;g__ | Ilyonectria;s__ | Ilyonectria robusta | |
| k__Fungi;p__ | Ascomycota;c__ | Sordariomycetes;o__ | Hypocreales;f__ | Incertae sedis;g__ | Myrothecium;s__ | Myrothecium sp | |
| k__Fungi;p__ | Ascomycota;c__ | Sordariomycetes;o__ | Hypocreales;f__ | Incertae sedis;g__ | Myrothecium;s__ | Myrothecium tongaense | |
| k__Fungi;p__ | Ascomycota;c__ | Sordariomycetes;o__ | Hypocreales;f__ | Incertae sedis;g__ | Sarocladium;s__ | Sarocladium kiliense | |
| k__Fungi;p__ | Ascomycota;c__ | Sordariomycetes;o__ | Hypocreales;f__ | Incertae sedis;g__ | Sarocladium;s__ | Sarocladium sp | |
| k__Fungi;p__ | Ascomycota;c__ | Sordariomycetes;o__ | Hypocreales;f__ | Incertae sedis;g__ | Sarocladium;s__ | Sarocladium strictum | |
| k__Fungi;p__ | Ascomycota;c__ | Sordariomycetes;o__ | Hypocreales;f__ | Incertae sedis;g__ | Stachybotrys;s__ | Stachybotrys microspora | |
| k__Fungi;p__ | Ascomycota;c__ | Sordariomycetes;o__ | Hypocreales;f__ | Incertae sedis;g__ | Stachybotrys;s__ | Stachybotrys oleronensis | |
| k__Fungi;p__ | Ascomycota;c__ | Sordariomycetes;o__ | Hypocreales;f__ | Incertae sedis;g__ | Stachybotrys;s__ | Stachybotrys sp | |
| k__Fungi;p__ | Ascomycota;c__ | Sordariomycetes;o__ | Hypocreales;f__ | Incertae sedis;g__ | Stilbella;s__ | Stilbella sp | |
| k__Fungi;p__ | Ascomycota;c__ | Sordariomycetes;o__ | Hypocreales;f__ | Incertae sedis;g__ | unidentified;s__ | Hypocreales sp | |
| k__Fungi;p__ | Ascomycota;c__ | Sordariomycetes;o__ | Hypocreales;f__ | Nectriaceae;g__ | Cylindrocarpon;s__ | Cylindrocarpon sp | |
| k__Fungi;p__ | Ascomycota;c__ | Sordariomycetes;o__ | Hypocreales;f__ | Nectriaceae;g__ | Fusarium;s__ | Fusarium delphinoides | |
| k__Fungi;p__ | Ascomycota;c__ | Sordariomycetes;o__ | Hypocreales;f__ | Nectriaceae;g__ | Fusarium;s__ | Fusarium kelerajum | |
| k__Fungi;p__ | Ascomycota;c__ | Sordariomycetes;o__ | Hypocreales;f__ | Nectriaceae;g__ | Fusarium;s__ | Fusarium keratoplasticum | |
| k__Fungi;p__ | Ascomycota;c__ | Sordariomycetes;o__ | Hypocreales;f__ | Nectriaceae;g__ | Fusarium;s__ | Fusarium oxysporum | |
| k__Fungi;p__ | Ascomycota;c__ | Sordariomycetes;o__ | Hypocreales;f__ | Nectriaceae;g__ | Fusarium;s__ | Fusarium pseudensiforme | |
| k__Fungi;p__ | Ascomycota;c__ | Sordariomycetes;o__ | Hypocreales;f__ | Nectriaceae;g__ | Fusarium;s__ | Fusarium sp | |
| k__Fungi;p__ | Ascomycota;c__ | Sordariomycetes;o__ | Hypocreales;f__ | Nectriaceae;g__ | Fusarium;s__ | Fusarium sp IP_87 | |
| k__Fungi;p__ | Ascomycota;c__ | Sordariomycetes;o__ | Hypocreales;f__ | Nectriaceae;g__ | Fusarium;s__ | Fusarium sp NG_H06b | |
| k__Fungi;p__ | Ascomycota;c__ | Sordariomycetes;o__ | Hypocreales;f__ | Nectriaceae;g__ | Fusarium;s__ | Fusarium sporotrichioides | |
| k__Fungi;p__ | Ascomycota;c__ | Sordariomycetes;o__ | Hypocreales;f__ | Nectriaceae;g__ | Fusarium;s__ | uncultured Fusarium sp | |
| k__Fungi;p__ | Ascomycota;c__ | Sordariomycetes;o__ | Hypocreales;f__ | Nectriaceae;g__ | Fusidium;s__ | Fusidium griseum | |
| k__Fungi;p__ | Ascomycota;c__ | Sordariomycetes;o__ | Hypocreales;f__ | Nectriaceae;g__ | Haematonectria;s__ | Haematonectria haematococca | |
| k__Fungi;p__ | Ascomycota;c__ | Sordariomycetes;o__ | Hypocreales;f__ | Nectriaceae;g__ | Mariannaea;s__ | Mariannaea superimposita | |
| k__Fungi;p__ | Ascomycota;c__ | Sordariomycetes;o__ | Hypocreales;f__ | Nectriaceae;g__ | Nectria;s__ | Nectria ramulariae | |

| k__Fungi;p__ | Ascomycota;c__ | Sordariomycetes;o__ | Hypocreales;f__ | Nectriaceae;g__ | Nectria;s__ | Nectria sp ZQZ_2012 |
| k__Fungi;p__ | Ascomycota;c__ | Sordariomycetes;o__ | Hypocreales;f__ | Nectriaceae;g__ | Neonectria;s__ | Neonectria sp 1f |
| k__Fungi;p__ | Ascomycota;c__ | Sordariomycetes;o__ | Hypocreales;f__ | Nectriaceae;g__ | Stylonectria;s__ | Stylonectria sp |
| k__Fungi;p__ | Ascomycota;c__ | Sordariomycetes;o__ | Hypocreales;f__ | Nectriaceae;g__ | Volutella;s__ | Volutella ciliata |
| k__Fungi;p__ | Ascomycota;c__ | Sordariomycetes;o__ | Hypocreales;f__ | Nectriaceae;g__ | unidentified;s__ | Nectriaceae sp |
| k__Fungi;p__ | Ascomycota;c__ | Sordariomycetes;o__ | Hypocreales;f__ | Niessliaceae;g__ | Monocillium;s__ | Monocillium indicum |
| k__Fungi;p__ | Ascomycota;c__ | Sordariomycetes;o__ | Hypocreales;f__ | Ophiocordycipitaceae;g__ | Haptocillium;s__ | Haptocillium zeosporum |
| k__Fungi;p__ | Ascomycota;c__ | Sordariomycetes;o__ | Hypocreales;f__ | unidentified;g__ | unidentified;s__ | Hypocreales sp |
| k__Fungi;p__ | Ascomycota;c__ | Sordariomycetes;o__ | Hypocreales;f__ | unidentified;g__ | unidentified;s__ | Hypocreales sp GPO_CO_01_H6 |
| k__Fungi;p__ | Ascomycota;c__ | Sordariomycetes;o__ | Hypocreales;f__ | unidentified;g__ | unidentified;s__ | Hypocreales sp O_1_LILB_26_5k |
| k__Fungi;p__ | Ascomycota;c__ | Sordariomycetes;o__ | Incertae sedis;f__ | Incertae sedis;g__ | Cryptovalsa;s__ | Cryptovalsa ampelina |
| k__Fungi;p__ | Ascomycota;c__ | Sordariomycetes;o__ | Incertae sedis;f__ | Incertae sedis;g__ | Custingophora;s__ | Custingophora olivacea |
| k__Fungi;p__ | Ascomycota;c__ | Sordariomycetes;o__ | Incertae sedis;f__ | Incertae sedis;g__ | Eucasphaeria;s__ | Eucasphaeria capensis |
| k__Fungi;p__ | Ascomycota;c__ | Sordariomycetes;o__ | Incertae sedis;f__ | Incertae sedis;g__ | Myrmecridium;s__ | Myrmecridium schulzeri |
| k__Fungi;p__ | Ascomycota;c__ | Sordariomycetes;o__ | Incertae sedis;f__ | Incertae sedis;g__ | Myrmecridium;s__ | Myrmecridium sp |
| k__Fungi;p__ | Ascomycota;c__ | Sordariomycetes;o__ | Incertae sedis;f__ | Plectosphaerellaceae;g__ | Gibellulopsis;s__ | Gibellulopsis sp YH_2012 |
| k__Fungi;p__ | Ascomycota;c__ | Sordariomycetes;o__ | Incertae sedis;f__ | Plectosphaerellaceae;g__ | Lectera;s__ | Lectera longa |
| k__Fungi;p__ | Ascomycota;c__ | Sordariomycetes;o__ | Incertae sedis;f__ | Plectosphaerellaceae;g__ | Verticillium;s__ | Verticillium dahliae |
| k__Fungi;p__ | Ascomycota;c__ | Sordariomycetes;o__ | Lulworthiales;f__ | Lulworthiaceae;g__ | Lulwoana;s__ | Lulwoana sp CCF3788 |
| k__Fungi;p__ | Ascomycota;c__ | Sordariomycetes;o__ | Lulworthiales;f__ | Lulworthiaceae;g__ | Zalerion;s__ | Zalerion arboricola |
| k__Fungi;p__ | Ascomycota;c__ | Sordariomycetes;o__ | Magnaporthales;f__ | Magnaporthaceae;g__ | unidentified;s__ | Magnaporthaceae sp |
| k__Fungi;p__ | Ascomycota;c__ | Sordariomycetes;o__ | Melanosporales;f__ | Ceratostomataceae;f | Sphaerodes;s__ | Sphaerodes sp SMCD2220 |
| k__Fungi;p__ | Ascomycota;c__ | Sordariomycetes;o__ | Microascales;f__ | Halosphaeriaceae;g__ | Cirrenalia;s__ | Cirrenalia macrocephala |
| k__Fungi;p__ | Ascomycota;c__ | Sordariomycetes;o__ | Microascales;f__ | Incertae sedis;g__ | Cephalotrichiella;s__ | Cephalotrichiella penicillata |
| k__Fungi;p__ | Ascomycota;c__ | Sordariomycetes;o__ | Microascales;f__ | Microascaceae;g__ | Graphium;s__ | Graphium basitruncatum |
| k__Fungi;p__ | Ascomycota;c__ | Sordariomycetes;o__ | Microascales;f__ | Microascaceae;g__ | Pseudallescheria;s__ | Pseudallescheria boydii |
| k__Fungi;p__ | Ascomycota;c__ | Sordariomycetes;o__ | Microascales;f__ | Microascaceae;g__ | Scedosporium;s__ | Scedosporium prolificans |
| k__Fungi;p__ | Ascomycota;c__ | Sordariomycetes;o__ | Microascales;f__ | Microascaceae;g__ | unidentified;s__ | Microascaceae sp |
| k__Fungi;p__ | Ascomycota;c__ | Sordariomycetes;o__ | Microascales;f__ | unidentified;g__ | unidentified;s__ | Microascales sp |
| k__Fungi;p__ | Ascomycota;c__ | Sordariomycetes;o__ | Sordariales;f__ | Cephalothecaceae;g__ | Cephalotheca;s__ | Cephalotheca sulfurea |
| k__Fungi;p__ | Ascomycota;c__ | Sordariomycetes;o__ | Sordariales;f__ | Cephalothecaceae;g__ | Phialemonium;s__ | Phialemonium atrogriseum |
| k__Fungi;p__ | Ascomycota;c__ | Sordariomycetes;o__ | Sordariales;f__ | Cephalothecaceae;g__ | unidentified;s__ | Cephalothecaceae sp |
| k__Fungi;p__ | Ascomycota;c__ | Sordariomycetes;o__ | Sordariales;f__ | Chaetomiaceae;g__ | Chaetomium;s__ | Chaetomium caprinum |
| k__Fungi;p__ | Ascomycota;c__ | Sordariomycetes;o__ | Sordariales;f__ | Chaetomiaceae;g__ | Chaetomium;s__ | Chaetomium erectum |
| k__Fungi;p__ | Ascomycota;c__ | Sordariomycetes;o__ | Sordariales;f__ | Chaetomiaceae;g__ | Chaetomium;s__ | Chaetomium iranianum |
| k__Fungi;p__ | Ascomycota;c__ | Sordariomycetes;o__ | Sordariales;f__ | Chaetomiaceae;g__ | Chaetomium;s__ | Chaetomium medusarum |
| k__Fungi;p__ | Ascomycota;c__ | Sordariomycetes;o__ | Sordariales;f__ | Chaetomiaceae;g__ | Chaetomium;s__ | Chaetomium nigricolor |
| k__Fungi;p__ | Ascomycota;c__ | Sordariomycetes;o__ | Sordariales;f__ | Chaetomiaceae;g__ | Chaetomium;s__ | Chaetomium sp |
| k__Fungi;p__ | Ascomycota;c__ | Sordariomycetes;o__ | Sordariales;f__ | Chaetomiaceae;g__ | Chaetomium;s__ | Chaetomium sp CBS 123940 |

| | | | | | | |
|---|---|---|---|---|---|---|
| k__Fungi;p__ | Ascomycota;c__ | Sordariomycetes;o__ | Sordariales;f__ | Chaetomiaceae;g__ | Chaetomium;s__ | Chaetomium sp YJM 2013 |
| k__Fungi;p__ | Ascomycota;c__ | Sordariomycetes;o__ | Sordariales;f__ | Chaetomiaceae;g__ | Humicola;s__ | Humicola grisea var. grisea |
| k__Fungi;p__ | Ascomycota;c__ | Sordariomycetes;o__ | Sordariales;f__ | Chaetomiaceae;g__ | Humicola;s__ | Humicola nigrescens |
| k__Fungi;p__ | Ascomycota;c__ | Sordariomycetes;o__ | Sordariales;f__ | Chaetomiaceae;g__ | Thielavia;s__ | Thielavia basicola |
| k__Fungi;p__ | Ascomycota;c__ | Sordariomycetes;o__ | Sordariales;f__ | Chaetomiaceae;g__ | Thielavia;s__ | Thielavia microspora |
| k__Fungi;p__ | Ascomycota;c__ | Sordariomycetes;o__ | Sordariales;f__ | Chaetomiaceae;g__ | unidentified;s__ | Chaetomiaceae sp |
| k__Fungi;p__ | Ascomycota;c__ | Sordariomycetes;o__ | Sordariales;f__ | Chaetomiaceae;g__ | unidentified;s__ | uncultured Zopfiella |
| k__Fungi;p__ | Ascomycota;c__ | Sordariomycetes;o__ | Sordariales;f__ | Incertae sedis;g__ | Ramophialophora;s__ | Ramophialophora sp FMR 9523 |
| k__Fungi;p__ | Ascomycota;c__ | Sordariomycetes;o__ | Sordariales;f__ | Lasiosphaeriaceae;g__ | Apodus;s__ | Apodus sp |
| k__Fungi;p__ | Ascomycota;c__ | Sordariomycetes;o__ | Sordariales;f__ | Lasiosphaeriaceae;g__ | Arnium;s__ | Arnium sp |
| k__Fungi;p__ | Ascomycota;c__ | Sordariomycetes;o__ | Sordariales;f__ | Lasiosphaeriaceae;g__ | Cercophora;s__ | Cercophora sp |
| k__Fungi;p__ | Ascomycota;c__ | Sordariomycetes;o__ | Sordariales;f__ | Lasiosphaeriaceae;g__ | Cladorrhinum;s__ | Cladorrhinum sp |
| k__Fungi;p__ | Ascomycota;c__ | Sordariomycetes;o__ | Sordariales;f__ | Lasiosphaeriaceae;g__ | Cladorrhinum;s__ | Cladorrhinum sp MJ 2014 |
| k__Fungi;p__ | Ascomycota;c__ | Sordariomycetes;o__ | Sordariales;f__ | Lasiosphaeriaceae;g__ | Podospora;s__ | Podospora communis |
| k__Fungi;p__ | Ascomycota;c__ | Sordariomycetes;o__ | Sordariales;f__ | Lasiosphaeriaceae;g__ | Podospora;s__ | Podospora decipiens |
| k__Fungi;p__ | Ascomycota;c__ | Sordariomycetes;o__ | Sordariales;f__ | Lasiosphaeriaceae;g__ | Podospora;s__ | Podospora pyriformis |
| k__Fungi;p__ | Ascomycota;c__ | Sordariomycetes;o__ | Sordariales;f__ | Lasiosphaeriaceae;g__ | Podospora;s__ | Podospora sp |
| k__Fungi;p__ | Ascomycota;c__ | Sordariomycetes;o__ | Sordariales;f__ | Lasiosphaeriaceae;g__ | Schizothecium;s__ | Schizothecium curvisporum |
| k__Fungi;p__ | Ascomycota;c__ | Sordariomycetes;o__ | Sordariales;f__ | Lasiosphaeriaceae;g__ | Schizothecium;s__ | Schizothecium glutinans |
| k__Fungi;p__ | Ascomycota;c__ | Sordariomycetes;o__ | Sordariales;f__ | Lasiosphaeriaceae;g__ | Schizothecium;s__ | Schizothecium miniglutinans |
| k__Fungi;p__ | Ascomycota;c__ | Sordariomycetes;o__ | Sordariales;f__ | Lasiosphaeriaceae;g__ | Schizothecium;s__ | Schizothecium sp |
| k__Fungi;p__ | Ascomycota;c__ | Sordariomycetes;o__ | Sordariales;f__ | Lasiosphaeriaceae;g__ | unidentified;s__ | Lasiosphaeriaceae sp |
| k__Fungi;p__ | Ascomycota;c__ | Sordariomycetes;o__ | Sordariales;f__ | Lasiosphaeriaceae;g__ | unidentified;s__ | uncultured Cercophora |
| k__Fungi;p__ | Ascomycota;c__ | Sordariomycetes;o__ | Sordariales;f__ | Lasiosphaeriaceae;g__ | unidentified;s__ | uncultured Podospora |
| k__Fungi;p__ | Ascomycota;c__ | Sordariomycetes;o__ | Sordariales;f__ | Sordariaceae;g__ | Sordaria;s__ | Sordaria fimicola |
| k__Fungi;p__ | Ascomycota;c__ | Sordariomycetes;o__ | Sordariales;f__ | unidentified;g__ | unidentified;s__ | Sordariales sp |
| k__Fungi;p__ | Ascomycota;c__ | Sordariomycetes;o__ | Trichosphaeriales;f__ | Incertae sedis;g__ | unidentified;s__ | Trichosphaeriales sp |
| k__Fungi;p__ | Ascomycota;c__ | Sordariomycetes;o__ | Xylariales;f__ | Amphisphaeriaceae;g__ | Adisciso;s__ | Adisciso kaki |
| k__Fungi;p__ | Ascomycota;c__ | Sordariomycetes;o__ | Xylariales;f__ | Amphisphaeriaceae;g__ | Bartalinia;s__ | Bartalinia robillardoides |
| k__Fungi;p__ | Ascomycota;c__ | Sordariomycetes;o__ | Xylariales;f__ | Amphisphaeriaceae;g__ | Immersidiscosia;s__ | Immersidiscosia eucalypti |
| k__Fungi;p__ | Ascomycota;c__ | Sordariomycetes;o__ | Xylariales;f__ | Amphisphaeriaceae;g__ | Monochaetia;s__ | Monochaetia monochaeta |
| k__Fungi;p__ | Ascomycota;c__ | Sordariomycetes;o__ | Xylariales;f__ | Amphisphaeriaceae;g__ | Pestalotiopsis;s__ | Pestalotiopsis rosea |
| k__Fungi;p__ | Ascomycota;c__ | Sordariomycetes;o__ | Xylariales;f__ | Amphisphaeriaceae;g__ | Pestalotiopsis;s__ | Pestalotiopsis sp E 000535668 |
| k__Fungi;p__ | Ascomycota;c__ | Sordariomycetes;o__ | Xylariales;f__ | Amphisphaeriaceae;g__ | Pestalotiopsis;s__ | Pestalotiopsis sp LH251 |
| k__Fungi;p__ | Ascomycota;c__ | Sordariomycetes;o__ | Xylariales;f__ | Amphisphaeriaceae;g__ | Truncatella;s__ | Truncatella angustata |
| k__Fungi;p__ | Ascomycota;c__ | Sordariomycetes;o__ | Xylariales;f__ | Amphisphaeriaceae;g__ | unidentified;s__ | Amphisphaeriaceae sp |
| k__Fungi;p__ | Ascomycota;c__ | Sordariomycetes;o__ | Xylariales;f__ | Hyponectriaceae;g__ | unidentified;s__ | Hyponectriaceae sp |
| k__Fungi;p__ | Ascomycota;c__ | Sordariomycetes;o__ | Xylariales;f__ | Incertae sedis;g__ | Coniocessia;s__ | Coniocessia nodulisporioides |
| k__Fungi;p__ | Ascomycota;c__ | Sordariomycetes;o__ | Xylariales;f__ | Incertae sedis;g__ | Leiosphaerella;s__ | Leiosphaerella lycopodina |

| k__Fungi;p__ | Ascomycota;c__ | Sordariomycetes;o__ | Xylariales;f__ | Incertae sedis;g__ | Microdochium;s__ | Microdochium bolleyi |
|---|---|---|---|---|---|---|
| k__Fungi;p__ | Ascomycota;c__ | Sordariomycetes;o__ | Xylariales;f__ | Incertae sedis;g__ | Microdochium;s__ | Microdochium sp |
| k__Fungi;p__ | Ascomycota;c__ | Sordariomycetes;o__ | Xylariales;f__ | Incertae sedis;g__ | Monographella;s__ | Monographella nivalis |
| k__Fungi;p__ | Ascomycota;c__ | Sordariomycetes;o__ | Xylariales;f__ | Incertae sedis;g__ | Monosporascus;s__ | Monosporascus sp 28 YS 2010 |
| k__Fungi;p__ | Ascomycota;c__ | Sordariomycetes;o__ | Xylariales;f__ | Xylariaceae;g__ | Calceomyces;s__ | Calceomyces lacunosus |
| k__Fungi;p__ | Ascomycota;c__ | Sordariomycetes;o__ | Xylariales;f__ | Xylariaceae;g__ | Coniolariella;s__ | Coniolariella ershadii |
| k__Fungi;p__ | Ascomycota;c__ | Sordariomycetes;o__ | Xylariales;f__ | Xylariaceae;g__ | Coniolariella;s__ | Coniolariella hispanica |
| k__Fungi;p__ | Ascomycota;c__ | Sordariomycetes;o__ | Xylariales;f__ | Xylariaceae;g__ | Hypoxylon;s__ | Hypoxylon commutatum |
| k__Fungi;p__ | Ascomycota;c__ | Sordariomycetes;o__ | Xylariales;f__ | Xylariaceae;g__ | Poronia;s__ | Poronia punctata |
| k__Fungi;p__ | Ascomycota;c__ | Sordariomycetes;o__ | Xylariales;f__ | Xylariaceae;g__ | Stromatoneurospora;s__ | Stromatoneurospora phoenix |
| k__Fungi;p__ | Ascomycota;c__ | Sordariomycetes;o__ | Xylariales;f__ | Xylariaceae;g__ | Xylaria;s__ | Xylaria striata |
| k__Fungi;p__ | Ascomycota;c__ | Sordariomycetes;o__ | Xylariales;f__ | unidentified;g__ | unidentified;s__ | Xylariales sp |
| k__Fungi;p__ | Ascomycota;c__ | Sordariomycetes;o__ | unidentified;f__ | unidentified;g__ | unidentified;s__ | Sordariomycetes sp |
| k__Fungi;p__ | Ascomycota;c__ | Sordariomycetes;o__ | unidentified;f__ | unidentified;g__ | unidentified;s__ | Sordariomycetes sp 11332 |
| k__Fungi;p__ | Ascomycota;c__ | Taphrinomycetes;o__ | Taphrinales;f__ | Taphrinaceae;g__ | Lalaria;s__ | Lalaria carpini |
| k__Fungi;p__ | Ascomycota;c__ | Taphrinomycetes;o__ | Taphrinales;f__ | Taphrinaceae;g__ | Lalaria;s__ | Lalaria inositophila |
| k__Fungi;p__ | Ascomycota;c__ | Taphrinomycetes;o__ | Taphrinales;f__ | Taphrinaceae;g__ | Taphrina;s__ | Taphrina caerulescens |
| k__Fungi;p__ | Ascomycota;c__ | Taphrinomycetes;o__ | Taphrinales;f__ | Taphrinaceae;g__ | Taphrina;s__ | Taphrina communis |
| k__Fungi;p__ | Ascomycota;c__ | Taphrinomycetes;o__ | Taphrinales;f__ | Taphrinaceae;g__ | Taphrina;s__ | Taphrina pruni |
| k__Fungi;p__ | Ascomycota;c__ | Taphrinomycetes;o__ | Taphrinales;f__ | Taphrinaceae;g__ | unidentified;s__ | Taphrinaceae sp |
| k__Fungi;p__ | Ascomycota;c__ | unidentified;o__ | unidentified;f__ | unidentified;g__ | unidentified;s__ | Ascomycota sp |
| k__Fungi;p__ | Ascomycota;c__ | unidentified;o__ | unidentified;f__ | unidentified;g__ | unidentified;s__ | Ascomycota sp AR 2010 |
| k__Fungi;p__ | Ascomycota;c__ | unidentified;o__ | unidentified;f__ | unidentified;g__ | unidentified;s__ | Ascomycota sp FL 2010c |
| k__Fungi;p__ | Ascomycota;c__ | unidentified;o__ | unidentified;f__ | unidentified;g__ | unidentified;s__ | Ascomycota sp IBWF77 89A |
| k__Fungi;p__ | Ascomycota;c__ | unidentified;o__ | unidentified;f__ | unidentified;g__ | unidentified;s__ | ascomycete sp IZ 1147 |
| k__Fungi;p__ | Ascomycota;c__ | unidentified;o__ | unidentified;f__ | unidentified;g__ | unidentified;s__ | ascomycete sp IZ 962 |
| k__Fungi;p__ | Ascomycota;c__ | unidentified;o__ | unidentified;f__ | unidentified;g__ | unidentified;s__ | ascomycete sp MA 4907 |
| k__Fungi;p__ | Ascomycota;c__ | unidentified;o__ | unidentified;f__ | unidentified;g__ | unidentified;s__ | ascomycete sp MA 4950 |
| k__Fungi;p__ | Ascomycota;c__ | unidentified;o__ | unidentified;f__ | unidentified;g__ | unidentified;s__ | fungal contaminant of Leptosphaeria sp |
| k__Fungi;p__ | Ascomycota;c__ | unidentified;o__ | unidentified;f__ | unidentified;g__ | unidentified;s__ | leaf litter ascomycete strain its341 |
| k__Fungi;p__ | Ascomycota;c__ | unidentified;o__ | unidentified;f__ | unidentified;g__ | unidentified;s__ | melanized limestone ascomycete CR 2004 |
| k__Fungi;p__ | Ascomycota;c__ | unidentified;o__ | unidentified;f__ | unidentified;g__ | unidentified;s__ | uncultured Ascomycota |
| k__Fungi;p__ | Ascomycota;c__ | unidentified;o__ | unidentified;f__ | unidentified;g__ | unidentified;s__ | uncultured Pezizomycotina |
| k__Fungi;p__ | Ascomycota;c__ | unidentified;o__ | unidentified;f__ | unidentified;g__ | unidentified;s__ | uncultured Phialemonium |
| k__Fungi;p__ | Ascomycota;c__ | unidentified;o__ | unidentified;f__ | unidentified;g__ | unidentified;s__ | uncultured Zalerion |
| k__Fungi;p__ | Basidiomycota;c__ | Agaricomycetes;o__ | Agaricales;f__ | Agaricaceae;g__ | Agaricus;s__ | Agaricus bisporus |
| k__Fungi;p__ | Basidiomycota;c__ | Agaricomycetes;o__ | Agaricales;f__ | Agaricaceae;g__ | Agaricus;s__ | Agaricus bitorquis |
| k__Fungi;p__ | Basidiomycota;c__ | Agaricomycetes;o__ | Agaricales;f__ | Agaricaceae;g__ | Agaricus;s__ | Agaricus comtulus |
| k__Fungi;p__ | Basidiomycota;c__ | Agaricomycetes;o__ | Agaricales;f__ | Agaricaceae;g__ | Agaricus;s__ | Agaricus devoniensis |

| k__Fungi;p__ | Basidiomycota;c__ | Agaricomycetes;o__ | Agaricales;f__ | Agaricaceae;g__ | Agaricus;s__ | Agaricus phaeolepidotus |
| k__Fungi;p__ | Basidiomycota;c__ | Agaricomycetes;o__ | Agaricales;f__ | Agaricaceae;g__ | Agaricus;s__ | Agaricus pseudopratensis |
| k__Fungi;p__ | Basidiomycota;c__ | Agaricomycetes;o__ | Agaricales;f__ | Agaricaceae;g__ | Bovista;s__ | Bovista plumbea |
| k__Fungi;p__ | Basidiomycota;c__ | Agaricomycetes;o__ | Agaricales;f__ | Agaricaceae;g__ | Calvatia;s__ | Calvatia cyathiformis |
| k__Fungi;p__ | Basidiomycota;c__ | Agaricomycetes;o__ | Agaricales;f__ | Agaricaceae;g__ | Calvatia;s__ | Calvatia fragilis |
| k__Fungi;p__ | Basidiomycota;c__ | Agaricomycetes;o__ | Agaricales;f__ | Agaricaceae;g__ | Chamaemyces;s__ | Chamaemyces sp |
| k__Fungi;p__ | Basidiomycota;c__ | Agaricomycetes;o__ | Agaricales;f__ | Agaricaceae;g__ | Chlorophyllum;s__ | Chlorophyllum molybdites |
| k__Fungi;p__ | Basidiomycota;c__ | Agaricomycetes;o__ | Agaricales;f__ | Agaricaceae;g__ | Coprinus;s__ | Coprinus comatus |
| k__Fungi;p__ | Basidiomycota;c__ | Agaricomycetes;o__ | Agaricales;f__ | Agaricaceae;g__ | Coprinus;s__ | Coprinus phaeopunctatus |
| k__Fungi;p__ | Basidiomycota;c__ | Agaricomycetes;o__ | Agaricales;f__ | Agaricaceae;g__ | Coprinus;s__ | Coprinus sp |
| k__Fungi;p__ | Basidiomycota;c__ | Agaricomycetes;o__ | Agaricales;f__ | Agaricaceae;g__ | Cyathus;s__ | Cyathus olla |
| k__Fungi;p__ | Basidiomycota;c__ | Agaricomycetes;o__ | Agaricales;f__ | Agaricaceae;g__ | Cystolepiota;s__ | Cystolepiota pulverulenta |
| k__Fungi;p__ | Basidiomycota;c__ | Agaricomycetes;o__ | Agaricales;f__ | Agaricaceae;g__ | Lepiota;s__ | Lepiota cf fraterna PS 2011 |
| k__Fungi;p__ | Basidiomycota;c__ | Agaricomycetes;o__ | Agaricales;f__ | Agaricaceae;g__ | Lepiota;s__ | Lepiota farinolens |
| k__Fungi;p__ | Basidiomycota;c__ | Agaricomycetes;o__ | Agaricales;f__ | Agaricaceae;g__ | Lepiota;s__ | Lepiota haemorrhagica |
| k__Fungi;p__ | Basidiomycota;c__ | Agaricomycetes;o__ | Agaricales;f__ | Agaricaceae;g__ | Lepiota;s__ | Lepiota rufipes |
| k__Fungi;p__ | Basidiomycota;c__ | Agaricomycetes;o__ | Agaricales;f__ | Agaricaceae;g__ | Lepiota;s__ | Lepiota subincarnata |
| k__Fungi;p__ | Basidiomycota;c__ | Agaricomycetes;o__ | Agaricales;f__ | Agaricaceae;g__ | Leucoagaricus;s__ | Leucoagaricus americanus |
| k__Fungi;p__ | Basidiomycota;c__ | Agaricomycetes;o__ | Agaricales;f__ | Agaricaceae;g__ | Leucoagaricus;s__ | Leucoagaricus barssii |
| k__Fungi;p__ | Basidiomycota;c__ | Agaricomycetes;o__ | Agaricales;f__ | Agaricaceae;g__ | Leucoagaricus;s__ | Leucoagaricus leucothites |
| k__Fungi;p__ | Basidiomycota;c__ | Agaricomycetes;o__ | Agaricales;f__ | Agaricaceae;g__ | Leucoagaricus;s__ | Leucoagaricus rubrobrunneus |
| k__Fungi;p__ | Basidiomycota;c__ | Agaricomycetes;o__ | Agaricales;f__ | Agaricaceae;g__ | Leucoagaricus;s__ | Leucoagaricus tener |
| k__Fungi;p__ | Basidiomycota;c__ | Agaricomycetes;o__ | Agaricales;f__ | Agaricaceae;g__ | Leucocoprinus;s__ | Leucocoprinus cepistipes |
| k__Fungi;p__ | Basidiomycota;c__ | Agaricomycetes;o__ | Agaricales;f__ | Agaricaceae;g__ | Leucocoprinus;s__ | Leucocoprinus cretaceus |
| k__Fungi;p__ | Basidiomycota;c__ | Agaricomycetes;o__ | Agaricales;f__ | Agaricaceae;g__ | Lycoperdon;s__ | Lycoperdon ericaeum |
| k__Fungi;p__ | Basidiomycota;c__ | Agaricomycetes;o__ | Agaricales;f__ | Agaricaceae;g__ | Lycoperdon;s__ | Lycoperdon pratense |
| k__Fungi;p__ | Basidiomycota;c__ | Agaricomycetes;o__ | Agaricales;f__ | Agaricaceae;g__ | Lycoperdon;s__ | Lycoperdon pyriforme |
| k__Fungi;p__ | Basidiomycota;c__ | Agaricomycetes;o__ | Agaricales;f__ | Agaricaceae;g__ | Melanophyllum;s__ | Melanophyllum haematospermum |
| k__Fungi;p__ | Basidiomycota;c__ | Agaricomycetes;o__ | Agaricales;f__ | Agaricaceae;g__ | Morganella;s__ | Morganella sp YR 2013 |
| k__Fungi;p__ | Basidiomycota;c__ | Agaricomycetes;o__ | Agaricales;f__ | Agaricaceae;g__ | Tulostoma;s__ | Tulostoma brumale |
| k__Fungi;p__ | Basidiomycota;c__ | Agaricomycetes;o__ | Agaricales;f__ | Agaricaceae;g__ | Tulostoma;s__ | Tulostoma sp KH 2011b |
| k__Fungi;p__ | Basidiomycota;c__ | Agaricomycetes;o__ | Agaricales;f__ | Agaricaceae;g__ | unidentified;s__ | Agaricaceae sp |
| k__Fungi;p__ | Basidiomycota;c__ | Agaricomycetes;o__ | Agaricales;f__ | Agaricaceae;g__ | unidentified;s__ | uncultured Tulostoma |
| k__Fungi;p__ | Basidiomycota;c__ | Agaricomycetes;o__ | Agaricales;f__ | Bolbitiaceae;g__ | Conocybe;s__ | Conocybe brachypodii |
| k__Fungi;p__ | Basidiomycota;c__ | Agaricomycetes;o__ | Agaricales;f__ | Bolbitiaceae;g__ | Conocybe;s__ | Conocybe dunensis |
| k__Fungi;p__ | Basidiomycota;c__ | Agaricomycetes;o__ | Agaricales;f__ | Bolbitiaceae;g__ | Conocybe;s__ | Conocybe inopinata |
| k__Fungi;p__ | Basidiomycota;c__ | Agaricomycetes;o__ | Agaricales;f__ | Bolbitiaceae;g__ | Conocybe;s__ | Conocybe pseudocrispa |
| k__Fungi;p__ | Basidiomycota;c__ | Agaricomycetes;o__ | Agaricales;f__ | Clavariaceae;g__ | Clavaria;s__ | Clavaria sp |
| k__Fungi;p__ | Basidiomycota;c__ | Agaricomycetes;o__ | Agaricales;f__ | Clavariaceae;g__ | unidentified;s__ | Clavariaceae sp |

| k_Fungi;p | Basidiomycota;c | Agaricomycetes;o | Agaricales;f | Cortinariaceae;g | Cortinarius;s | Cortinarius pansa |
|---|---|---|---|---|---|---|
| k_Fungi;p | Basidiomycota;c | Agaricomycetes;o | Agaricales;f | Cortinariaceae;g | Cortinarius;s | Cortinarius sp |
| k_Fungi;p | Basidiomycota;c | Agaricomycetes;o | Agaricales;f | Entolomataceae;g | Clitopilus;s | Clitopilus scyphoides |
| k_Fungi;p | Basidiomycota;c | Agaricomycetes;o | Agaricales;f | Entolomataceae;g | Clitopilus;s | Clitopilus sp |
| k_Fungi;p | Basidiomycota;c | Agaricomycetes;o | Agaricales;f | Entolomataceae;g | Entoloma;s | Entoloma aff iodiolens JC_201108041 |
| k_Fungi;p | Basidiomycota;c | Agaricomycetes;o | Agaricales;f | Entolomataceae;g | Entoloma;s | Entoloma byssisedum |
| k_Fungi;p | Basidiomycota;c | Agaricomycetes;o | Agaricales;f | Entolomataceae;g | Entoloma;s | Entoloma byssisedum var byssisedum |
| k_Fungi;p | Basidiomycota;c | Agaricomycetes;o | Agaricales;f | Entolomataceae;g | Entoloma;s | Entoloma graphitipes f. cystidiatum |
| k_Fungi;p | Basidiomycota;c | Agaricomycetes;o | Agaricales;f | Entolomataceae;g | Entoloma;s | Entoloma perumbilicatum |
| k_Fungi;p | Basidiomycota;c | Agaricomycetes;o | Agaricales;f | Entolomataceae;g | Entoloma;s | Entoloma platyphylloides |
| k_Fungi;p | Basidiomycota;c | Agaricomycetes;o | Agaricales;f | Entolomataceae;g | Entoloma;s | Entoloma sp |
| k_Fungi;p | Basidiomycota;c | Agaricomycetes;o | Agaricales;f | Entolomataceae;g | Entoloma;s | Entoloma sp SAPA:1161 |
| k_Fungi;p | Basidiomycota;c | Agaricomycetes;o | Agaricales;f | Entolomataceae;g | Entoloma;s | Entoloma sphagneti |
| k_Fungi;p | Basidiomycota;c | Agaricomycetes;o | Agaricales;f | Entolomataceae;g | unidentified;s | Entolomataceae sp |
| k_Fungi;p | Basidiomycota;c | Agaricomycetes;o | Agaricales;f | Hygrophoraceae;g | Hygrocybe;s | Hygrocybe sp |
| k_Fungi;p | Basidiomycota;c | Agaricomycetes;o | Agaricales;f | Inocybaceae;g | Crepidotus;s | Crepidotus crocophyllus |
| k_Fungi;p | Basidiomycota;c | Agaricomycetes;o | Agaricales;f | Inocybaceae;g | Tubaria;s | Tubaria conspersa |
| k_Fungi;p | Basidiomycota;c | Agaricomycetes;o | Agaricales;f | Inocybaceae;g | Tubaria;s | Tubaria hiemalis var major |
| k_Fungi;p | Basidiomycota;c | Agaricomycetes;o | Agaricales;f | Lyophyllaceae;g | Lyophyllum;s | Lyophyllum caerulescens |
| k_Fungi;p | Basidiomycota;c | Agaricomycetes;o | Agaricales;f | Marasmiaceae;g | Gymnopus;s | Gymnopus brassicolens |
| k_Fungi;p | Basidiomycota;c | Agaricomycetes;o | Agaricales;f | Marasmiaceae;g | Gymnopus;s | Gymnopus luxurians |
| k_Fungi;p | Basidiomycota;c | Agaricomycetes;o | Agaricales;f | Marasmiaceae;g | Gymnopus;s | Gymnopus sp olrim406 |
| k_Fungi;p | Basidiomycota;c | Agaricomycetes;o | Agaricales;f | Marasmiaceae;g | Hydropus;s | Hydropus sp |
| k_Fungi;p | Basidiomycota;c | Agaricomycetes;o | Agaricales;f | Marasmiaceae;g | Marasmius;s | Marasmius hypophaeus |
| k_Fungi;p | Basidiomycota;c | Agaricomycetes;o | Agaricales;f | Mycenaceae;g | Mycena;s | Mycena sp |
| k_Fungi;p | Basidiomycota;c | Agaricomycetes;o | Agaricales;f | Mycenaceae;g | Mycena;s | Mycena sp HT01 |
| k_Fungi;p | Basidiomycota;c | Agaricomycetes;o | Agaricales;f | Physalacriaceae;g | Armillaria;s | Armillaria mellea |
| k_Fungi;p | Basidiomycota;c | Agaricomycetes;o | Agaricales;f | Physalacriaceae;g | Armillaria;s | Armillaria ostoyae |
| k_Fungi;p | Basidiomycota;c | Agaricomycetes;o | Agaricales;f | Physalacriaceae;g | Physalacria;s | Physalacria bambusae |
| k_Fungi;p | Basidiomycota;c | Agaricomycetes;o | Agaricales;f | Pluteaceae;g | Pluteus;s | Pluteus cinereofuscus |
| k_Fungi;p | Basidiomycota;c | Agaricomycetes;o | Agaricales;f | Psathyrellaceae;g | Coprinellus;s | Coprinellus curtus |
| k_Fungi;p | Basidiomycota;c | Agaricomycetes;o | Agaricales;f | Psathyrellaceae;g | Coprinellus;s | Coprinellus eurysporus |
| k_Fungi;p | Basidiomycota;c | Agaricomycetes;o | Agaricales;f | Psathyrellaceae;g | Coprinellus;s | Coprinellus fuscocystidiatus |
| k_Fungi;p | Basidiomycota;c | Agaricomycetes;o | Agaricales;f | Psathyrellaceae;g | Coprinellus;s | Coprinellus radians |
| k_Fungi;p | Basidiomycota;c | Agaricomycetes;o | Agaricales;f | Psathyrellaceae;g | Coprinellus;s | Coprinellus sabulicola |
| k_Fungi;p | Basidiomycota;c | Agaricomycetes;o | Agaricales;f | Psathyrellaceae;g | Coprinellus;s | Coprinellus sp |
| k_Fungi;p | Basidiomycota;c | Agaricomycetes;o | Agaricales;f | Psathyrellaceae;g | Coprinopsis;s | Coprinopsis calospora |
| k_Fungi;p | Basidiomycota;c | Agaricomycetes;o | Agaricales;f | Psathyrellaceae;g | Coprinopsis;s | Coprinopsis macrocephala |
| k_Fungi;p | Basidiomycota;c | Agaricomycetes;o | Agaricales;f | Psathyrellaceae;g | Coprinopsis;s | Coprinopsis patouillardii |

| k_Fungi;p | Basidiomycota;c | Agaricomycetes;o | Agaricales;f | Psathyrellaceae;g | Coprinopsis;s | Coprinopsis semitalis |
|---|---|---|---|---|---|---|
| k_Fungi;p | Basidiomycota;c | Agaricomycetes;o | Agaricales;f | Psathyrellaceae;g | Lacrymaria;s | Lacrymaria lacrymabunda |
| k_Fungi;p | Basidiomycota;c | Agaricomycetes;o | Agaricales;f | Psathyrellaceae;g | Parasola;s | Parasola kuehneri |
| k_Fungi;p | Basidiomycota;c | Agaricomycetes;o | Agaricales;f | Psathyrellaceae;g | Parasola;s | Parasola sp |
| k_Fungi;p | Basidiomycota;c | Agaricomycetes;o | Agaricales;f | Psathyrellaceae;g | Psathyrella;s | Psathyrella bipellis |
| k_Fungi;p | Basidiomycota;c | Agaricomycetes;o | Agaricales;f | Psathyrellaceae;g | Psathyrella;s | Psathyrella candolleana |
| k_Fungi;p | Basidiomycota;c | Agaricomycetes;o | Agaricales;f | Psathyrellaceae;g | Psathyrella;s | Psathyrella chondroderma |
| k_Fungi;p | Basidiomycota;c | Agaricomycetes;o | Agaricales;f | Psathyrellaceae;g | Psathyrella;s | Psathyrella longicauda |
| k_Fungi;p | Basidiomycota;c | Agaricomycetes;o | Agaricales;f | Psathyrellaceae;g | Psathyrella;s | Psathyrella obtusata |
| k_Fungi;p | Basidiomycota;c | Agaricomycetes;o | Agaricales;f | Psathyrellaceae;g | Psathyrella;s | Psathyrella piluliformis |
| k_Fungi;p | Basidiomycota;c | Agaricomycetes;o | Agaricales;f | Psathyrellaceae;g | Psathyrella;s | Psathyrella sp |
| k_Fungi;p | Basidiomycota;c | Agaricomycetes;o | Agaricales;f | Psathyrellaceae;g | Psathyrella;s | Psathyrella sp LO126_99 |
| k_Fungi;p | Basidiomycota;c | Agaricomycetes;o | Agaricales;f | Psathyrellaceae;g | unidentified;s | Psathyrellaceae sp |
| k_Fungi;p | Basidiomycota;c | Agaricomycetes;o | Agaricales;f | Psathyrellaceae;g | unidentified;s | uncultured Psathyrella |
| k_Fungi;p | Basidiomycota;c | Agaricomycetes;o | Agaricales;f | Schizophyllaceae;g | Schizophyllum;s | Schizophyllum commune |
| k_Fungi;p | Basidiomycota;c | Agaricomycetes;o | Agaricales;f | Strophariaceae;g | Agrocybe;s | Agrocybe pediades |
| k_Fungi;p | Basidiomycota;c | Agaricomycetes;o | Agaricales;f | Strophariaceae;g | Agrocybe;s | Agrocybe praecox |
| k_Fungi;p | Basidiomycota;c | Agaricomycetes;o | Agaricales;f | Strophariaceae;g | Galerina;s | Galerina atkinsoniana |
| k_Fungi;p | Basidiomycota;c | Agaricomycetes;o | Agaricales;f | Strophariaceae;g | Gymnopilus;s | Gymnopilus decipiens |
| k_Fungi;p | Basidiomycota;c | Agaricomycetes;o | Agaricales;f | Strophariaceae;g | Hebeloma;s | Hebeloma helodes |
| k_Fungi;p | Basidiomycota;c | Agaricomycetes;o | Agaricales;f | Strophariaceae;g | Hypholoma;s | Hypholoma fasciculare |
| k_Fungi;p | Basidiomycota;c | Agaricomycetes;o | Agaricales;f | Strophariaceae;g | Leratiomyces;s | Leratiomyces ceres |
| k_Fungi;p | Basidiomycota;c | Agaricomycetes;o | Agaricales;f | Strophariaceae;g | Pholiota;s | Pholiota gummosa |
| k_Fungi;p | Basidiomycota;c | Agaricomycetes;o | Agaricales;f | Strophariaceae;g | Pholiota;s | Pholiota lenta |
| k_Fungi;p | Basidiomycota;c | Agaricomycetes;o | Agaricales;f | Strophariaceae;g | Stropharia;s | Stropharia coronilla |
| k_Fungi;p | Basidiomycota;c | Agaricomycetes;o | Agaricales;f | Tricholomataceae;g | Clitocybe;s | Clitocybe metachroa |
| k_Fungi;p | Basidiomycota;c | Agaricomycetes;o | Agaricales;f | Tricholomataceae;g | Leucopaxillus;s | Leucopaxillus gentianeus |
| k_Fungi;p | Basidiomycota;c | Agaricomycetes;o | Agaricales;f | Tricholomataceae;g | Pseudoomphalina;s | Pseudoomphalina pachyphylla |
| k_Fungi;p | Basidiomycota;c | Agaricomycetes;o | Agaricales;f | Tricholomataceae;g | Tricholoma;s | Tricholoma populinum |
| k_Fungi;p | Basidiomycota;c | Agaricomycetes;o | Agaricales;f | Tricholomataceae;g | unidentified;s | Tricholomataceae sp |
| k_Fungi;p | Basidiomycota;c | Agaricomycetes;o | Agaricales;f | Typhulaceae;g | Typhula;s | Typhula sp |
| k_Fungi;p | Basidiomycota;c | Agaricomycetes;o | Agaricales;f | unidentified;g | unidentified;s | Agaricales sp |
| k_Fungi;p | Basidiomycota;c | Agaricomycetes;o | Atheliales;f | Atheliaceae;g | Amphinema;s | Amphinema sp |
| k_Fungi;p | Basidiomycota;c | Agaricomycetes;o | Atheliales;f | Atheliaceae;g | Tylospora;s | Tylospora sp |
| k_Fungi;p | Basidiomycota;c | Agaricomycetes;o | Atheliales;f | Atheliaceae;g | unidentified;s | Atheliaceae sp |
| k_Fungi;p | Basidiomycota;c | Agaricomycetes;o | Auriculariales;f | Incertae sedis;g | Auricularia;s | Auricularia auricula_judae |
| k_Fungi;p | Basidiomycota;c | Agaricomycetes;o | Auriculariales;f | Incertae sedis;g | Elmerina;s | Elmerina caryae |
| k_Fungi;p | Basidiomycota;c | Agaricomycetes;o | Auriculariales;f | Incertae sedis;g | Exidia;s | Exidia sp |
| k_Fungi;p | Basidiomycota;c | Agaricomycetes;o | Auriculariales;f | Incertae sedis;g | Exidiopsis;s | Exidiopsis plumbescens |

| k Fungi;p | Basidiomycota;c | Agaricomycetes;o | Auriculariales;f | Incertae sedis;g | Heterochaete;s | Heterochaete sp |
| k Fungi;p | Basidiomycota;c | Agaricomycetes;o | Auriculariales;f | Incertae sedis;g | Oliveonia;s | Oliveonia pauxilla |
| k Fungi;p | Basidiomycota;c | Agaricomycetes;o | Auriculariales;f | unidentified;g | unidentified;s | Auriculariales sp |
| k Fungi;p | Basidiomycota;c | Agaricomycetes;o | Boletales;f | Boletaceae;g | Boletus;s | Boletus eastwoodiae |
| k Fungi;p | Basidiomycota;c | Agaricomycetes;o | Boletales;f | Paxillaceae;g | Paxillus;s | Paxillus ammoniavirescens |
| k Fungi;p | Basidiomycota;c | Agaricomycetes;o | Boletales;f | Rhizopogonaceae;g | Rhizopogon;s | Rhizopogon arctostaphyli |
| k Fungi;p | Basidiomycota;c | Agaricomycetes;o | Boletales;f | Rhizopogonaceae;g | Rhizopogon;s | Rhizopogon ellenae |
| k Fungi;p | Basidiomycota;c | Agaricomycetes;o | Boletales;f | Rhizopogonaceae;g | Rhizopogon;s | Rhizopogon hawkerae |
| k Fungi;p | Basidiomycota;c | Agaricomycetes;o | Boletales;f | Rhizopogonaceae;g | Rhizopogon;s | Rhizopogon luteorubescens |
| k Fungi;p | Basidiomycota;c | Agaricomycetes;o | Boletales;f | Rhizopogonaceae;g | Rhizopogon;s | Rhizopogon occidentalis |
| k Fungi;p | Basidiomycota;c | Agaricomycetes;o | Boletales;f | Sclerodermataceae;g | Pisolithus;s | Pisolithus arhizus |
| k Fungi;p | Basidiomycota;c | Agaricomycetes;o | Boletales;f | Sclerodermataceae;g | Pisolithus;s | Pisolithus sp |
| k Fungi;p | Basidiomycota;c | Agaricomycetes;o | Boletales;f | Sclerodermataceae;g | Scleroderma;s | Scleroderma cepa |
| k Fungi;p | Basidiomycota;c | Agaricomycetes;o | Boletales;f | Suillaceae;g | Suillus;s | Suillus bovinus |
| k Fungi;p | Basidiomycota;c | Agaricomycetes;o | Boletales;f | Suillaceae;g | Suillus;s | Suillus caerulescens |
| k Fungi;p | Basidiomycota;c | Agaricomycetes;o | Boletales;f | Suillaceae;g | Suillus;s | Suillus collinitus |
| k Fungi;p | Basidiomycota;c | Agaricomycetes;o | Boletales;f | Suillaceae;g | Suillus;s | Suillus granulatus |
| k Fungi;p | Basidiomycota;c | Agaricomycetes;o | Boletales;f | Suillaceae;g | Suillus;s | Suillus mediterraneensis |
| k Fungi;p | Basidiomycota;c | Agaricomycetes;o | Boletales;f | Suillaceae;g | Suillus;s | Suillus pungens |
| k Fungi;p | Basidiomycota;c | Agaricomycetes;o | Boletales;f | Tapinellaceae;g | Tapinella;s | Tapinella panuoides |
| k Fungi;p | Basidiomycota;c | Agaricomycetes;o | Boletales;f | unidentified;g | unidentified;s | Boletales sp |
| k Fungi;p | Basidiomycota;c | Agaricomycetes;o | Cantharellales;f | Ceratobasidiaceae;g | Ceratobasidium;s | Ceratobasidium sp Eno3_3 |
| k Fungi;p | Basidiomycota;c | Agaricomycetes;o | Cantharellales;f | Ceratobasidiaceae;g | Rhizoctonia;s | Rhizoctonia sp |
| k Fungi;p | Basidiomycota;c | Agaricomycetes;o | Cantharellales;f | Ceratobasidiaceae;g | Thanatephorus;s | Thanatephorus cucumeris |
| k Fungi;p | Basidiomycota;c | Agaricomycetes;o | Cantharellales;f | Ceratobasidiaceae;g | unidentified;s | Ceratobasidiaceae sp |
| k Fungi;p | Basidiomycota;c | Agaricomycetes;o | Cantharellales;f | Ceratobasidiaceae;g | unidentified;s | uncultured Ceratobasidiaceae |
| k Fungi;p | Basidiomycota;c | Agaricomycetes;o | Cantharellales;f | Ceratobasidiaceae;g | unidentified;s | uncultured Thanatephorus |
| k Fungi;p | Basidiomycota;c | Agaricomycetes;o | Cantharellales;f | Ceratobasidiaceae;g | unidentified;s | uncultured Waitea |
| k Fungi;p | Basidiomycota;c | Agaricomycetes;o | Cantharellales;f | Hydnaceae;g | Sistotrema;s | Sistotrema oblongisporum |
| k Fungi;p | Basidiomycota;c | Agaricomycetes;o | Cantharellales;f | Hydnaceae;g | Sistotrema;s | Sistotrema sp |
| k Fungi;p | Basidiomycota;c | Agaricomycetes;o | Cantharellales;f | Incertae sedis;g | Minimedusa;s | Minimedusa sp |
| k Fungi;p | Basidiomycota;c | Agaricomycetes;o | Cantharellales;f | unidentified;g | unidentified;s | Cantharellales sp |
| k Fungi;p | Basidiomycota;c | Agaricomycetes;o | Corticiales;f | Corticiaceae;g | Laetisaria;s | Laetisaria arvalis |
| k Fungi;p | Basidiomycota;c | Agaricomycetes;o | Corticiales;f | Corticiaceae;g | Laetisaria;s | Laetisaria sp RhMY076Lzz7 |
| k Fungi;p | Basidiomycota;c | Agaricomycetes;o | Corticiales;f | Corticiaceae;g | Marchandiobasidium;s | Marchandiobasidium sp |
| k Fungi;p | Basidiomycota;c | Agaricomycetes;o | Corticiales;f | Corticiaceae;g | Punctularia;s | Punctularia sp XL_A10 |
| k Fungi;p | Basidiomycota;c | Agaricomycetes;o | Corticiales;f | Corticiaceae;g | Waitea;s | Waitea circinata |
| k Fungi;p | Basidiomycota;c | Agaricomycetes;o | Corticiales;f | Corticiaceae;g | unidentified;s | Corticiaceae sp |
| k Fungi;p | Basidiomycota;c | Agaricomycetes;o | Corticiales;f | Corticiaceae;g | unidentified;s | uncultured Corticiaceae |

| | | | | | | |
|---|---|---|---|---|---|---|
| k Fungi;p | Basidiomycota;c | Agaricomycetes;o | Corticiales;f | unidentified;g | unidentified;s | Corticiales sp |
| k Fungi;p | Basidiomycota;c | Agaricomycetes;o | Geastrales;f | Geastraceae;g | Geastrum;s | Geastrum floriforme |
| k Fungi;p | Basidiomycota;c | Agaricomycetes;o | Geastrales;f | Geastraceae;g | Geastrum;s | Geastrum minimum |
| k Fungi;p | Basidiomycota;c | Agaricomycetes;o | Geastrales;f | Geastraceae;g | Geastrum;s | Geastrum pectinatum |
| k Fungi;p | Basidiomycota;c | Agaricomycetes;o | Geastrales;f | Geastraceae;g | Geastrum;s | Geastrum sp TNS KH_AUS10_72 |
| k Fungi;p | Basidiomycota;c | Agaricomycetes;o | Geastrales;f | Geastraceae;g | Geastrum;s | Geastrum sp TNS KH_JPN10_747 |
| k Fungi;p | Basidiomycota;c | Agaricomycetes;o | Geastrales;f | Geastraceae;g | Geastrum;s | Geastrum sp TNS Sakamoto82 |
| k Fungi;p | Basidiomycota;c | Agaricomycetes;o | Geastrales;f | Geastraceae;g | Sphaerobolus;s | Sphaerobolus sp |
| k Fungi;p | Basidiomycota;c | Agaricomycetes;o | Geastrales;f | Geastraceae;g | unidentified;s | Geastraceae sp |
| k Fungi;p | Basidiomycota;c | Agaricomycetes;o | Geastrales;f | unidentified;g | unidentified;s | Geastrales sp |
| k Fungi;p | Basidiomycota;c | Agaricomycetes;o | Gloeophyllales;f | Gloeophyllaceae;g | Gloeophyllum;s | Gloeophyllum mexicanum |
| k Fungi;p | Basidiomycota;c | Agaricomycetes;o | Gomphales;f | Gomphaceae;g | Ramaria;s | Ramaria curta |
| k Fungi;p | Basidiomycota;c | Agaricomycetes;o | Hymenochaetales;f | Hymenochaetaceae;g | Fomitiporella;s | Fomitiporella sp Oe7 |
| k Fungi;p | Basidiomycota;c | Agaricomycetes;o | Hymenochaetales;f | Hymenochaetaceae;g | Inonotus;s | Inonotus andersonii |
| k Fungi;p | Basidiomycota;c | Agaricomycetes;o | Hymenochaetales;f | Hymenochaetaceae;g | Phellinus;s | Phellinus gilvus |
| k Fungi;p | Basidiomycota;c | Agaricomycetes;o | Hymenochaetales;f | Schizoporaceae;g | Hyphodontia;s | Hyphodontia astrocystidiata |
| k Fungi;p | Basidiomycota;c | Agaricomycetes;o | Hymenochaetales;f | Schizoporaceae;g | Hyphodontia;s | Hyphodontia quercina |
| k Fungi;p | Basidiomycota;c | Agaricomycetes;o | Hymenochaetales;f | Schizoporaceae;g | Hyphodontia;s | Hyphodontia radula |
| k Fungi;p | Basidiomycota;c | Agaricomycetes;o | Hymenochaetales;f | Schizoporaceae;g | Hyphodontia;s | Hyphodontia setulosa |
| k Fungi;p | Basidiomycota;c | Agaricomycetes;o | Hymenochaetales;f | Schizoporaceae;g | Xylodon;s | Xylodon rimosissimus |
| k Fungi;p | Basidiomycota;c | Agaricomycetes;o | Hymenochaetales;f | unidentified;g | unidentified;s | Hymenochaetales sp |
| k Fungi;p | Basidiomycota;c | Agaricomycetes;o | Phallales;f | Phallaceae;g | Phallus;s | Phallus impudicus |
| k Fungi;p | Basidiomycota;c | Agaricomycetes;o | Polyporales;f | Fomitopsidaceae;g | Antrodia;s | Antrodia carbonica |
| k Fungi;p | Basidiomycota;c | Agaricomycetes;o | Polyporales;f | Fomitopsidaceae;g | Dacryobolus;s | Dacryobolus karstenii |
| k Fungi;p | Basidiomycota;c | Agaricomycetes;o | Polyporales;f | Fomitopsidaceae;g | Fibroporia;s | Fibroporia vaillantii |
| k Fungi;p | Basidiomycota;c | Agaricomycetes;o | Polyporales;f | Fomitopsidaceae;g | Laetiporus;s | Laetiporus gilbertsonii |
| k Fungi;p | Basidiomycota;c | Agaricomycetes;o | Polyporales;f | Fomitopsidaceae;g | Postia;s | Postia sp Calen 65 |
| k Fungi;p | Basidiomycota;c | Agaricomycetes;o | Polyporales;f | Ganodermataceae;g | Ganoderma;s | Ganoderma adspersum |
| k Fungi;p | Basidiomycota;c | Agaricomycetes;o | Polyporales;f | Ganodermataceae;g | Ganoderma;s | Ganoderma annulare |
| k Fungi;p | Basidiomycota;c | Agaricomycetes;o | Polyporales;f | Ganodermataceae;g | Ganoderma;s | Ganoderma lucidum |
| k Fungi;p | Basidiomycota;c | Agaricomycetes;o | Polyporales;f | Ganodermataceae;g | Ganoderma;s | Ganoderma resinaceum |
| k Fungi;p | Basidiomycota;c | Agaricomycetes;o | Polyporales;f | Meripilaceae;g | Physisporinus;s | Physisporinus sp |
| k Fungi;p | Basidiomycota;c | Agaricomycetes;o | Polyporales;f | Meripilaceae;g | Rigidoporus;s | Rigidoporus sp |
| k Fungi;p | Basidiomycota;c | Agaricomycetes;o | Polyporales;f | Meruliaceae;g | Abortiporus;s | Abortiporus biennis |
| k Fungi;p | Basidiomycota;c | Agaricomycetes;o | Polyporales;f | Meruliaceae;g | Bjerkandera;s | Bjerkandera sp |
| k Fungi;p | Basidiomycota;c | Agaricomycetes;o | Polyporales;f | Meruliaceae;g | Mycoacia;s | Mycoacia nothofagi var. nothofagi |
| k Fungi;p | Basidiomycota;c | Agaricomycetes;o | Polyporales;f | Meruliaceae;g | Mycoacia;s | Mycoacia sp |
| k Fungi;p | Basidiomycota;c | Agaricomycetes;o | Polyporales;f | Meruliaceae;g | Phlebia;s | Phlebia sp |
| k Fungi;p | Basidiomycota;c | Agaricomycetes;o | Polyporales;f | Meruliaceae;g | Phlebia;s | Phlebia sp DABAC9 |

| k | Fungi;p | Basidiomycota;c | Agaricomycetes;o | Polyporales;f | Meruliaceae;g | Phlebia;s | Phlebia subserialis |
| k | Fungi;p | Basidiomycota;c | Agaricomycetes;o | Polyporales;f | Meruliaceae;g | Scopuloides;s | Scopuloides sp |
| k | Fungi;p | Basidiomycota;c | Agaricomycetes;o | Polyporales;f | Meruliaceae;g | Steccherinum;s | Steccherinum sp MLB 2010 |
| k | Fungi;p | Basidiomycota;c | Agaricomycetes;o | Polyporales;f | Meruliaceae;g | Uncobasidium;s | Uncobasidium sp |
| k | Fungi;p | Basidiomycota;c | Agaricomycetes;o | Polyporales;f | Phanerochaetaceae;g | Byssomerulius;s | Byssomerulius sp |
| k | Fungi;p | Basidiomycota;c | Agaricomycetes;o | Polyporales;f | Phanerochaetaceae;g | Ceriporia;s | Ceriporia lacerata |
| k | Fungi;p | Basidiomycota;c | Agaricomycetes;o | Polyporales;f | Phanerochaetaceae;g | Hyphodermella;s | Hyphodermella corrugata |
| k | Fungi;p | Basidiomycota;c | Agaricomycetes;o | Polyporales;f | Phanerochaetaceae;g | Phanerochaete;s | Phanerochaete omnivora |
| k | Fungi;p | Basidiomycota;c | Agaricomycetes;o | Polyporales;f | Phanerochaetaceae;g | Phanerochaete;s | Phanerochaete sordida |
| k | Fungi;p | Basidiomycota;c | Agaricomycetes;o | Polyporales;f | Phanerochaetaceae;g | Phanerochaete;s | Phanerochaete sp |
| k | Fungi;p | Basidiomycota;c | Agaricomycetes;o | Polyporales;f | Polyporaceae;g | Cinereomyces;s | Cinereomyces sp |
| k | Fungi;p | Basidiomycota;c | Agaricomycetes;o | Polyporales;f | Polyporaceae;g | Dichomitus;s | Dichomitus campestris |
| k | Fungi;p | Basidiomycota;c | Agaricomycetes;o | Polyporales;f | Polyporaceae;g | Fomes;s | Fomes fomentarius |
| k | Fungi;p | Basidiomycota;c | Agaricomycetes;o | Polyporales;f | Polyporaceae;g | Lentinus;s | Lentinus squarrosulus |
| k | Fungi;p | Basidiomycota;c | Agaricomycetes;o | Polyporales;f | Polyporaceae;g | Lopharia;s | Lopharia cinerascens |
| k | Fungi;p | Basidiomycota;c | Agaricomycetes;o | Polyporales;f | Polyporaceae;g | Rhodonia;s | Rhodonia placenta |
| k | Fungi;p | Basidiomycota;c | Agaricomycetes;o | Polyporales;f | Polyporaceae;g | Skeletocutis;s | Skeletocutis sp NMM 2009 |
| k | Fungi;p | Basidiomycota;c | Agaricomycetes;o | Polyporales;f | Polyporaceae;g | Trametes;s | Trametes versicolor |
| k | Fungi;p | Basidiomycota;c | Agaricomycetes;o | Polyporales;f | unidentified;g | unidentified;s | Polyporales sp |
| k | Fungi;p | Basidiomycota;c | Agaricomycetes;o | Russulales;f | Bondarzewiaceae;g | Heterobasidion;s | Heterobasidion annosum |
| k | Fungi;p | Basidiomycota;c | Agaricomycetes;o | Russulales;f | Bondarzewiaceae;g | Heterobasidion;s | Heterobasidion parviporum |
| k | Fungi;p | Basidiomycota;c | Agaricomycetes;o | Russulales;f | Peniophoraceae;g | Peniophora;s | Peniophora piceae |
| k | Fungi;p | Basidiomycota;c | Agaricomycetes;o | Russulales;f | Peniophoraceae;g | Peniophora;s | Peniophora pini |
| k | Fungi;p | Basidiomycota;c | Agaricomycetes;o | Russulales;f | Peniophoraceae;g | Peniophora;s | Peniophora sp MUCC804 |
| k | Fungi;p | Basidiomycota;c | Agaricomycetes;o | Russulales;f | Peniophoraceae;g | unidentified;s | Peniophoraceae sp |
| k | Fungi;p | Basidiomycota;c | Agaricomycetes;o | Russulales;f | Russulaceae;g | unidentified;s | Russulaceae sp |
| k | Fungi;p | Basidiomycota;c | Agaricomycetes;o | Russulales;f | Stephanosporaceae;g | Lindtneria;s | Lindtneria sp |
| k | Fungi;p | Basidiomycota;c | Agaricomycetes;o | Russulales;f | Stephanosporaceae;g | unidentified;s | Stephanosporaceae sp |
| k | Fungi;p | Basidiomycota;c | Agaricomycetes;o | Russulales;f | Stereaceae;g | Stereum;s | Stereum hirsutum |
| k | Fungi;p | Basidiomycota;c | Agaricomycetes;o | Russulales;f | Stereaceae;g | unidentified;s | Stereaceae sp |
| k | Fungi;p | Basidiomycota;c | Agaricomycetes;o | Russulales;f | unidentified;g | unidentified;s | Russulales sp |
| k | Fungi;p | Basidiomycota;c | Agaricomycetes;o | Sebacinales;f | Sebacinaceae;g | unidentified;s | Sebacinaceae sp |
| k | Fungi;p | Basidiomycota;c | Agaricomycetes;o | Sebacinales;f | Sebacinaceae;g | unidentified;s | uncultured Sebacina |
| k | Fungi;p | Basidiomycota;c | Agaricomycetes;o | Sebacinales;f | Sebacinaceae;g | unidentified;s | uncultured Sebacina mycobiont of Vicia sativa |
| k | Fungi;p | Basidiomycota;c | Agaricomycetes;o | Sebacinales;f | Sebacinales Group B;g | unidentified;s | Sebacinales Group B sp |
| k | Fungi;p | Basidiomycota;c | Agaricomycetes;o | Sebacinales;f | unidentified;g | unidentified;s | Sebacinales sp |
| k | Fungi;p | Basidiomycota;c | Agaricomycetes;o | Sebacinales;f | unidentified;g | unidentified;s | uncultured Sebacinales |
| k | Fungi;p | Basidiomycota;c | Agaricomycetes;o | Thelephorales;f | Thelephoraceae;g | Amaurodon;s | Amaurodon sp |
| k | Fungi;p | Basidiomycota;c | Agaricomycetes;o | Thelephorales;f | Thelephoraceae;g | Odontia;s | Odontia sp | k_Fungi;p_Basidiomycota;c_Agaricomycetes;o_Thelephorales;f_Thelephoraceae;g_Thelephora;s_Thelephora sp
k_Fungi;p_Basidiomycota;c_Agaricomycetes;o_Thelephorales;f_Thelephoraceae;g_Tomentella;s_Tomentella sp
k_Fungi;p_Basidiomycota;c_Agaricomycetes;o_Thelephorales;f_Thelephoraceae;g_Tomentella;s_Tomentella sublilacina
k_Fungi;p_Basidiomycota;c_Agaricomycetes;o_Thelephorales;f_Thelephoraceae;g_Tomentellopsis;s_Tomentellopsis sp
k_Fungi;p_Basidiomycota;c_Agaricomycetes;o_Thelephorales;f_Thelephoraceae;g_unidentified;s_Thelephoraceae sp
k_Fungi;p_Basidiomycota;c_Agaricomycetes;o_Trechisporales;f_Hydnodontaceae;g_Brevicellicium;s_Brevicellicium olivascens
k_Fungi;p_Basidiomycota;c_Agaricomycetes;o_Trechisporales;f_Hydnodontaceae;g_Sistotremastrum;s_Sistotremastrum guttuliferum
k_Fungi;p_Basidiomycota;c_Agaricomycetes;o_Trechisporales;f_Hydnodontaceae;g_Trechispora;s_Trechispora sp
k_Fungi;p_Basidiomycota;c_Agaricomycetes;o_Trechisporales;f_unidentified;g_unidentified;s_Trechisporales sp
k_Fungi;p_Basidiomycota;c_Agaricomycetes;o_unidentified;f_unidentified;g_unidentified;s_Agaricomycetes sp
k_Fungi;p_Basidiomycota;c_Agaricomycetes;o_unidentified;f_unidentified;g_unidentified;s_uncultured Agaricomycetes
k_Fungi;p_Basidiomycota;c_Agaricostilbomycetes;o_Agaricostilbales;f_Agaricostilbaceae;g_Bensingtonia;s_Bensingtonia sp PYCC 5562
k_Fungi;p_Basidiomycota;c_Agaricostilbomycetes;o_Agaricostilbales;f_Agaricostilbaceae;g_Bensingtonia;s_Bensingtonia sp PYCC 5566
k_Fungi;p_Basidiomycota;c_Agaricostilbomycetes;o_Agaricostilbales;f_Chionosphaeraceae;g_Kurtzmanomyces;s_Kurtzmanomyces sp
k_Fungi;p_Basidiomycota;c_Agaricostilbomycetes;o_Agaricostilbales;f_Chionosphaeraceae;g_Kurtzmanomyces;s_Kurtzmanomyces tardus
k_Fungi;p_Basidiomycota;c_Agaricostilbomycetes;o_Agaricostilbales;f_Chionosphaeraceae;g_Stilbum;s_Stilbum vulgare
k_Fungi;p_Basidiomycota;c_Agaricostilbomycetes;o_Agaricostilbales;f_Kondoaceae;g_Kondoa;s_Kondoa aeria
k_Fungi;p_Basidiomycota;c_Agaricostilbomycetes;o_Agaricostilbales;f_Kondoaceae;g_Kondoa;s_Kondoa malvinella
k_Fungi;p_Basidiomycota;c_Agaricostilbomycetes;o_unidentified;f_unidentified;g_unidentified;s_Agaricostilbomycetes sp
k_Fungi;p_Basidiomycota;c_Cystobasidiomycetes;o_Cystobasidiales;f_Cystobasidiaceae;g_Cystobasidium;s_Cystobasidium slooffiae
k_Fungi;p_Basidiomycota;c_Cystobasidiomycetes;o_Cystobasidiales;f_Cystobasidiaceae;g_Occultifur;s_Occultifur sp DMKU_SE59
k_Fungi;p_Basidiomycota;c_Cystobasidiomycetes;o_Erythrobasidiales;f_Incertae sedis;g_Erythrobasidium;s_Erythrobasidium hasegawianum
k_Fungi;p_Basidiomycota;c_Cystobasidiomycetes;o_Erythrobasidiales;f_unidentified;g_unidentified;s_uncultured Erythrobasidiales
k_Fungi;p_Basidiomycota;c_Cystobasidiomycetes;o_Incertae sedis;f_Incertae sedis;g_Sakaguchia;s_Sakaguchia sp G3
k_Fungi;p_Basidiomycota;c_Exobasidiomycetes;o_Microstromatales;f_Quambalariaceae;g_Quambalaria;s_Quambalaria cyanescens
k_Fungi;p_Basidiomycota;c_Incertae sedis;o_Malasseziales;f_Malasseziaceae;g_Malassezia;s_Malassezia globosa
k_Fungi;p_Basidiomycota;c_Incertae sedis;o_Malasseziales;f_Malasseziaceae;g_Malassezia;s_Malassezia restricta
k_Fungi;p_Basidiomycota;c_Incertae sedis;o_Malasseziales;f_Malasseziaceae;g_Malassezia;s_Malassezia sp
k_Fungi;p_Basidiomycota;c_Microbotryomycetes;o_Incertae sedis;f_Incertae sedis;g_Curvibasidium;s_Curvibasidium cygneicollum
k_Fungi;p_Basidiomycota;c_Microbotryomycetes;o_Leucosporidiales;f_Leucosporidiaceae;g_Leucosporidiella;s_Leucosporidiella creatinivora
k_Fungi;p_Basidiomycota;c_Microbotryomycetes;o_Leucosporidiales;f_Leucosporidiaceae;g_Leucosporidiella;s_Leucosporidiella yakutica
k_Fungi;p_Basidiomycota;c_Microbotryomycetes;o_Leucosporidiales;f_Leucosporidiaceae;g_Leucosporidium;s_Leucosporidium sp 8138 GP_2013
k_Fungi;p_Basidiomycota;c_Microbotryomycetes;o_Leucosporidiales;f_Leucosporidiaceae;g_Mastigobasidium;s_Mastigobasidium intermedium
k_Fungi;p_Basidiomycota;c_Microbotryomycetes;o_Leucosporidiales;f_Leucosporidiaceae;g_Mastigobasidium;s_Mastigobasidium sp
k_Fungi;p_Basidiomycota;c_Microbotryomycetes;o_Leucosporidiales;f_unidentified;g_unidentified;s_Leucosporidiales sp
k_Fungi;p_Basidiomycota;c_Microbotryomycetes;o_Microbotryales;f_Microbotryaceae;g_Microbotryum;s_Microbotryum adenopetalae
k_Fungi;p_Basidiomycota;c_Microbotryomycetes;o_Sporidiobolales;f_Incertae sedis;g_Rhodosporidium;s_Rhodosporidium babjevae
k_Fungi;p_Basidiomycota;c_Microbotryomycetes;o_Sporidiobolales;f_Incertae sedis;g_Rhodosporidium;s_Rhodosporidium diobovatum
k_Fungi;p_Basidiomycota;c_Microbotryomycetes;o_Sporidiobolales;f_Incertae sedis;g_Rhodosporidium;s_Rhodosporidium kratochvilovae

| | | | | | | | |
|---|---|---|---|---|---|---|---|
| k__Fungi;p__ | Basidiomycota;c__ | Microbotryomycetes;o__ | Sporidiobolales;f__ | Incertae sedis;g__ | Rhodotorula;s__ | Rhodotorula aff diffluens IMUFRJ 51950 |
| k__Fungi;p__ | Basidiomycota;c__ | Microbotryomycetes;o__ | Sporidiobolales;f__ | Incertae sedis;g__ | Rhodotorula;s__ | Rhodotorula araucariae |
| k__Fungi;p__ | Basidiomycota;c__ | Microbotryomycetes;o__ | Sporidiobolales;f__ | Incertae sedis;g__ | Rhodotorula;s__ | Rhodotorula aurantiaca |
| k__Fungi;p__ | Basidiomycota;c__ | Microbotryomycetes;o__ | Sporidiobolales;f__ | Incertae sedis;g__ | Rhodotorula;s__ | Rhodotorula bloemfonteinensis |
| k__Fungi;p__ | Basidiomycota;c__ | Microbotryomycetes;o__ | Sporidiobolales;f__ | Incertae sedis;g__ | Rhodotorula;s__ | Rhodotorula buffonii |
| k__Fungi;p__ | Basidiomycota;c__ | Microbotryomycetes;o__ | Sporidiobolales;f__ | Incertae sedis;g__ | Rhodotorula;s__ | Rhodotorula cresolica |
| k__Fungi;p__ | Basidiomycota;c__ | Microbotryomycetes;o__ | Sporidiobolales;f__ | Incertae sedis;g__ | Rhodotorula;s__ | Rhodotorula graminis |
| k__Fungi;p__ | Basidiomycota;c__ | Microbotryomycetes;o__ | Sporidiobolales;f__ | Incertae sedis;g__ | Rhodotorula;s__ | Rhodotorula ingeniosa |
| k__Fungi;p__ | Basidiomycota;c__ | Microbotryomycetes;o__ | Sporidiobolales;f__ | Incertae sedis;g__ | Rhodotorula;s__ | Rhodotorula lamellibrachiae |
| k__Fungi;p__ | Basidiomycota;c__ | Microbotryomycetes;o__ | Sporidiobolales;f__ | Incertae sedis;g__ | Rhodotorula;s__ | Rhodotorula laryngis |
| k__Fungi;p__ | Basidiomycota;c__ | Microbotryomycetes;o__ | Sporidiobolales;f__ | Incertae sedis;g__ | Rhodotorula;s__ | Rhodotorula mucilaginosa |
| k__Fungi;p__ | Basidiomycota;c__ | Microbotryomycetes;o__ | Sporidiobolales;f__ | Incertae sedis;g__ | Rhodotorula;s__ | Rhodotorula nothofagi |
| k__Fungi;p__ | Basidiomycota;c__ | Microbotryomycetes;o__ | Sporidiobolales;f__ | Incertae sedis;g__ | Rhodotorula;s__ | Rhodotorula oligophaga |
| k__Fungi;p__ | Basidiomycota;c__ | Microbotryomycetes;o__ | Sporidiobolales;f__ | Incertae sedis;g__ | Rhodotorula;s__ | Rhodotorula pustula |
| k__Fungi;p__ | Basidiomycota;c__ | Microbotryomycetes;o__ | Sporidiobolales;f__ | Incertae sedis;g__ | Rhodotorula;s__ | Rhodotorula sp |
| k__Fungi;p__ | Basidiomycota;c__ | Microbotryomycetes;o__ | Sporidiobolales;f__ | Incertae sedis;g__ | Rhodotorula;s__ | Rhodotorula sp JCM 11351 |
| k__Fungi;p__ | Basidiomycota;c__ | Microbotryomycetes;o__ | Sporidiobolales;f__ | Incertae sedis;g__ | Rhodotorula;s__ | Rhodotorula sp MJL_2011 |
| k__Fungi;p__ | Basidiomycota;c__ | Microbotryomycetes;o__ | Sporidiobolales;f__ | Incertae sedis;g__ | Sporobolomyces;s__ | Sporobolomyces coprosmae |
| k__Fungi;p__ | Basidiomycota;c__ | Microbotryomycetes;o__ | Sporidiobolales;f__ | Incertae sedis;g__ | Sporobolomyces;s__ | Sporobolomyces elongatus |
| k__Fungi;p__ | Basidiomycota;c__ | Microbotryomycetes;o__ | Sporidiobolales;f__ | Incertae sedis;g__ | Sporobolomyces;s__ | Sporobolomyces gracilis |
| k__Fungi;p__ | Basidiomycota;c__ | Microbotryomycetes;o__ | Sporidiobolales;f__ | Incertae sedis;g__ | Sporobolomyces;s__ | Sporobolomyces griseoflavus |
| k__Fungi;p__ | Basidiomycota;c__ | Microbotryomycetes;o__ | Sporidiobolales;f__ | Incertae sedis;g__ | Sporobolomyces;s__ | Sporobolomyces lactosus |
| k__Fungi;p__ | Basidiomycota;c__ | Microbotryomycetes;o__ | Sporidiobolales;f__ | Incertae sedis;g__ | Sporobolomyces;s__ | Sporobolomyces ogasawarensis |
| k__Fungi;p__ | Basidiomycota;c__ | Microbotryomycetes;o__ | Sporidiobolales;f__ | Incertae sedis;g__ | Sporobolomyces;s__ | Sporobolomyces oryzicola |
| k__Fungi;p__ | Basidiomycota;c__ | Microbotryomycetes;o__ | Sporidiobolales;f__ | Incertae sedis;g__ | Sporobolomyces;s__ | Sporobolomyces ruberrimus |
| k__Fungi;p__ | Basidiomycota;c__ | Microbotryomycetes;o__ | Sporidiobolales;f__ | Incertae sedis;g__ | Sporobolomyces;s__ | Sporobolomyces salicinus |
| k__Fungi;p__ | Basidiomycota;c__ | Microbotryomycetes;o__ | Sporidiobolales;f__ | Incertae sedis;g__ | Sporobolomyces;s__ | Sporobolomyces sp |
| k__Fungi;p__ | Basidiomycota;c__ | Microbotryomycetes;o__ | Sporidiobolales;f__ | Incertae sedis;g__ | Sporobolomyces;s__ | Sporobolomyces sp TD49 |
| k__Fungi;p__ | Basidiomycota;c__ | Microbotryomycetes;o__ | Sporidiobolales;f__ | Incertae sedis;g__ | Sporobolomyces;s__ | Sporobolomyces symmetricus |
| k__Fungi;p__ | Basidiomycota;c__ | Microbotryomycetes;o__ | Sporidiobolales;f__ | Incertae sedis;g__ | unidentified;s__ | Sporidiobolales sp |
| k__Fungi;p__ | Basidiomycota;c__ | Microbotryomycetes;o__ | Sporidiobolales;f__ | unidentified;g__ | unidentified;s__ | Sporidiobolales sp |
| k__Fungi;p__ | Basidiomycota;c__ | Microbotryomycetes;o__ | unidentified;f__ | unidentified;g__ | unidentified;s__ | Microbotryomycetes sp |
| k__Fungi;p__ | Basidiomycota;c__ | Pucciniomycetes;o__ | Pucciniales;f__ | Melampsoraceae;g__ | Melampsora;s__ | Melampsora iranica |
| k__Fungi;p__ | Basidiomycota;c__ | Pucciniomycetes;o__ | Pucciniales;f__ | Melampsoraceae;g__ | Melampsora;s__ | Melampsora medusae_populina |
| k__Fungi;p__ | Basidiomycota;c__ | Pucciniomycetes;o__ | Pucciniales;f__ | Melampsoraceae;g__ | Melampsora;s__ | Melampsora sp Mel G |
| k__Fungi;p__ | Basidiomycota;c__ | Pucciniomycetes;o__ | Pucciniales;f__ | Melampsoraceae;g__ | Melampsora;s__ | Melampsora sp Mel O |
| k__Fungi;p__ | Basidiomycota;c__ | Pucciniomycetes;o__ | Septobasidiales;f__ | Septobasidiaceae;g__ | Septobasidium;s__ | Septobasidium wilsonianum |
| k__Fungi;p__ | Basidiomycota;c__ | Pucciniomycetes;o__ | unidentified;f__ | unidentified;g__ | unidentified;s__ | Pucciniomycetes sp PIMO_247 |
| k__Fungi;p__ | Basidiomycota;c__ | Tremellomycetes;o__ | Cystofilobasidiales;f__ | Cystofilobasidiaceae;g__ | Cystofilobasidium;s__ | Cystofilobasidium infirmominiatum | k__Fungi;p__Basidiomycota;c__Tremellomycetes;o__Cystofilobasidiales;f__Cystofilobasidiaceae;g__Cystofilobasidium;s__Cystofilobasidium macerans k__Fungi;p__Basidiomycota;c__Tremellomycetes;o__Cystofilobasidiales;f__Cystofilobasidiaceae;g__Guehomyces;s__Guehomyces pullulans k__Fungi;p__Basidiomycota;c__Tremellomycetes;o__Cystofilobasidiales;f__Cystofilobasidiaceae;g__Itersonilia;s__Itersonilia perplexans k__Fungi;p__Basidiomycota;c__Tremellomycetes;o__Cystofilobasidiales;f__Cystofilobasidiaceae;g__Udeniomyces;s__Udeniomyces pannonicus k__Fungi;p__Basidiomycota;c__Tremellomycetes;o__Cystofilobasidiales;f__Cystofilobasidiaceae;g__Udeniomyces;s__Udeniomyces pyricola k__Fungi;p__Basidiomycota;c__Tremellomycetes;o__Cystofilobasidiales;f__unidentified;g__unidentified;s__Cystofilobasidiales sp k__Fungi;p__Basidiomycota;c__Tremellomycetes;o__Filobasidiales;f__Filobasidiaceae;g__Filobasidium;s__Filobasidium capsuligenum k__Fungi;p__Basidiomycota;c__Tremellomycetes;o__Filobasidiales;f__Filobasidiaceae;g__Filobasidium;s__Filobasidium floriforme k__Fungi;p__Basidiomycota;c__Tremellomycetes;o__Tremellales;f__Incertae sedis;g__Auriculibuller;s__Auriculibuller fuscus k__Fungi;p__Basidiomycota;c__Tremellomycetes;o__Tremellales;f__Incertae sedis;g__Biatoropsis;s__Biatoropsis usnearum k__Fungi;p__Basidiomycota;c__Tremellomycetes;o__Tremellales;f__Incertae sedis;g__Bullera;s__Bullera unica k__Fungi;p__Basidiomycota;c__Tremellomycetes;o__Tremellales;f__Incertae sedis;g__Cryptococcus;s__Cryptococcus adeliensis k__Fungi;p__Basidiomycota;c__Tremellomycetes;o__Tremellales;f__Incertae sedis;g__Cryptococcus;s__Cryptococcus aerius k__Fungi;p__Basidiomycota;c__Tremellomycetes;o__Tremellales;f__Incertae sedis;g__Cryptococcus;s__Cryptococcus aff amylolyticus AS 22501 k__Fungi;p__Basidiomycota;c__Tremellomycetes;o__Tremellales;f__Incertae sedis;g__Cryptococcus;s__Cryptococcus aff taibaiensis IMUFRJ 51982 k__Fungi;p__Basidiomycota;c__Tremellomycetes;o__Tremellales;f__Incertae sedis;g__Cryptococcus;s__Cryptococcus albidus var. ovalis k__Fungi;p__Basidiomycota;c__Tremellomycetes;o__Tremellales;f__Incertae sedis;g__Cryptococcus;s__Cryptococcus antarcticus k__Fungi;p__Basidiomycota;c__Tremellomycetes;o__Tremellales;f__Incertae sedis;g__Cryptococcus;s__Cryptococcus arrabidensis k__Fungi;p__Basidiomycota;c__Tremellomycetes;o__Tremellales;f__Incertae sedis;g__Cryptococcus;s__Cryptococcus bhutanensis k__Fungi;p__Basidiomycota;c__Tremellomycetes;o__Tremellales;f__Incertae sedis;g__Cryptococcus;s__Cryptococcus cerealis k__Fungi;p__Basidiomycota;c__Tremellomycetes;o__Tremellales;f__Incertae sedis;g__Cryptococcus;s__Cryptococcus chernovii k__Fungi;p__Basidiomycota;c__Tremellomycetes;o__Tremellales;f__Incertae sedis;g__Cryptococcus;s__Cryptococcus diffluens k__Fungi;p__Basidiomycota;c__Tremellomycetes;o__Tremellales;f__Incertae sedis;g__Cryptococcus;s__Cryptococcus dimennae k__Fungi;p__Basidiomycota;c__Tremellomycetes;o__Tremellales;f__Incertae sedis;g__Cryptococcus;s__Cryptococcus filicatus k__Fungi;p__Basidiomycota;c__Tremellomycetes;o__Tremellales;f__Incertae sedis;g__Cryptococcus;s__Cryptococcus friedmannii k__Fungi;p__Basidiomycota;c__Tremellomycetes;o__Tremellales;f__Incertae sedis;g__Cryptococcus;s__Cryptococcus fuscescens k__Fungi;p__Basidiomycota;c__Tremellomycetes;o__Tremellales;f__Incertae sedis;g__Cryptococcus;s__Cryptococcus heimaeyensis k__Fungi;p__Basidiomycota;c__Tremellomycetes;o__Tremellales;f__Incertae sedis;g__Cryptococcus;s__Cryptococcus huempii k__Fungi;p__Basidiomycota;c__Tremellomycetes;o__Tremellales;f__Incertae sedis;g__Cryptococcus;s__Cryptococcus laurentii k__Fungi;p__Basidiomycota;c__Tremellomycetes;o__Tremellales;f__Incertae sedis;g__Cryptococcus;s__Cryptococcus liquefaciens k__Fungi;p__Basidiomycota;c__Tremellomycetes;o__Tremellales;f__Incertae sedis;g__Cryptococcus;s__Cryptococcus magnus k__Fungi;p__Basidiomycota;c__Tremellomycetes;o__Tremellales;f__Incertae sedis;g__Cryptococcus;s__Cryptococcus oeirensis k__Fungi;p__Basidiomycota;c__Tremellomycetes;o__Tremellales;f__Incertae sedis;g__Cryptococcus;s__Cryptococcus paraflavus k__Fungi;p__Basidiomycota;c__Tremellomycetes;o__Tremellales;f__Incertae sedis;g__Cryptococcus;s__Cryptococcus phenolicus k__Fungi;p__Basidiomycota;c__Tremellomycetes;o__Tremellales;f__Incertae sedis;g__Cryptococcus;s__Cryptococcus psychrotolerans k__Fungi;p__Basidiomycota;c__Tremellomycetes;o__Tremellales;f__Incertae sedis;g__Cryptococcus;s__Cryptococcus randhawii k__Fungi;p__Basidiomycota;c__Tremellomycetes;o__Tremellales;f__Incertae sedis;g__Cryptococcus;s__Cryptococcus saitoi k__Fungi;p__Basidiomycota;c__Tremellomycetes;o__Tremellales;f__Incertae sedis;g__Cryptococcus;s__Cryptococcus shivajii k__Fungi;p__Basidiomycota;c__Tremellomycetes;o__Tremellales;f__Incertae sedis;g__Cryptococcus;s__Cryptococcus sp

| k__Fungi;p__ | Basidiomycota;c__ | Tremellomycetes;o__ | Tremellales;f__ | Incertae sedis;g__ | Cryptococcus;s__ | Cryptococcus sp AY_59 |
|---|---|---|---|---|---|---|
| k__Fungi;p__ | Basidiomycota;c__ | Tremellomycetes;o__ | Tremellales;f__ | Incertae sedis;g__ | Cryptococcus;s__ | Cryptococcus sp CBS 7890 |
| k__Fungi;p__ | Basidiomycota;c__ | Tremellomycetes;o__ | Tremellales;f__ | Incertae sedis;g__ | Cryptococcus;s__ | Cryptococcus sp D162_2 |
| k__Fungi;p__ | Basidiomycota;c__ | Tremellomycetes;o__ | Tremellales;f__ | Incertae sedis;g__ | Cryptococcus;s__ | Cryptococcus sp F6 |
| k__Fungi;p__ | Basidiomycota;c__ | Tremellomycetes;o__ | Tremellales;f__ | Incertae sedis;g__ | Cryptococcus;s__ | Cryptococcus sp FF_011314 |
| k__Fungi;p__ | Basidiomycota;c__ | Tremellomycetes;o__ | Tremellales;f__ | Incertae sedis;g__ | Cryptococcus;s__ | Cryptococcus sp JCM 11356 |
| k__Fungi;p__ | Basidiomycota;c__ | Tremellomycetes;o__ | Tremellales;f__ | Incertae sedis;g__ | Cryptococcus;s__ | Cryptococcus sp SA7L02 |
| k__Fungi;p__ | Basidiomycota;c__ | Tremellomycetes;o__ | Tremellales;f__ | Incertae sedis;g__ | Cryptococcus;s__ | Cryptococcus sp SM13L02 |
| k__Fungi;p__ | Basidiomycota;c__ | Tremellomycetes;o__ | Tremellales;f__ | Incertae sedis;g__ | Cryptococcus;s__ | Cryptococcus sp TC2_092 |
| k__Fungi;p__ | Basidiomycota;c__ | Tremellomycetes;o__ | Tremellales;f__ | Incertae sedis;g__ | Cryptococcus;s__ | Cryptococcus terreus |
| k__Fungi;p__ | Basidiomycota;c__ | Tremellomycetes;o__ | Tremellales;f__ | Incertae sedis;g__ | Cryptococcus;s__ | Cryptococcus terricola |
| k__Fungi;p__ | Basidiomycota;c__ | Tremellomycetes;o__ | Tremellales;f__ | Incertae sedis;g__ | Cryptococcus;s__ | Cryptococcus uzbekistanensis |
| k__Fungi;p__ | Basidiomycota;c__ | Tremellomycetes;o__ | Tremellales;f__ | Incertae sedis;g__ | Cryptococcus;s__ | Cryptococcus victoriae |
| k__Fungi;p__ | Basidiomycota;c__ | Tremellomycetes;o__ | Tremellales;f__ | Incertae sedis;g__ | Cryptococcus;s__ | Cryptococcus wieringae |
| k__Fungi;p__ | Basidiomycota;c__ | Tremellomycetes;o__ | Tremellales;f__ | Incertae sedis;g__ | Dioszegia;s__ | Dioszegia hungarica |
| k__Fungi;p__ | Basidiomycota;c__ | Tremellomycetes;o__ | Tremellales;f__ | Incertae sedis;g__ | Dioszegia;s__ | Dioszegia sp |
| k__Fungi;p__ | Basidiomycota;c__ | Tremellomycetes;o__ | Tremellales;f__ | Incertae sedis;g__ | Dioszegia;s__ | Dioszegia sp TP_Snow_Y120 |
| k__Fungi;p__ | Basidiomycota;c__ | Tremellomycetes;o__ | Tremellales;f__ | Incertae sedis;g__ | Dioszegia;s__ | Dioszegia sp YM24626 |
| k__Fungi;p__ | Basidiomycota;c__ | Tremellomycetes;o__ | Tremellales;f__ | Incertae sedis;g__ | Fellomyces;s__ | Fellomyces mexicanus |
| k__Fungi;p__ | Basidiomycota;c__ | Tremellomycetes;o__ | Tremellales;f__ | Incertae sedis;g__ | Tremella;s__ | Tremella moriformis |
| k__Fungi;p__ | Basidiomycota;c__ | Tremellomycetes;o__ | Tremellales;f__ | Incertae sedis;g__ | unidentified;s__ | Tremellales sp |
| k__Fungi;p__ | Basidiomycota;c__ | Tremellomycetes;o__ | Tremellales;f__ | unidentified;g__ | unidentified;s__ | Tremellales sp |
| k__Fungi;p__ | Basidiomycota;c__ | Tremellomycetes;o__ | Trichosporonales;f__ | Trichosporonaceae;g__ | Trichosporon;s__ | Trichosporon asahii |
| k__Fungi;p__ | Basidiomycota;c__ | Tremellomycetes;o__ | Trichosporonales;f__ | Trichosporonaceae;g__ | Trichosporon;s__ | Trichosporon asteroides |
| k__Fungi;p__ | Basidiomycota;c__ | Tremellomycetes;o__ | Trichosporonales;f__ | Trichosporonaceae;g__ | Trichosporon;s__ | Trichosporon moniliiforme |
| k__Fungi;p__ | Basidiomycota;c__ | Tremellomycetes;o__ | unidentified;f__ | unidentified;g__ | unidentified;s__ | Tremellomycetes sp |
| k__Fungi;p__ | Basidiomycota;c__ | Wallemiomycetes;o__ | Geminibasidiales;f__ | Geminibasidiaceae;g__ | Geminibasidium;s__ | Geminibasidium hirsutum |
| k__Fungi;p__ | Basidiomycota;c__ | Wallemiomycetes;o__ | Geminibasidiales;f__ | Geminibasidiaceae;g__ | Geminibasidium;s__ | Geminibasidium sp |
| k__Fungi;p__ | Basidiomycota;c__ | Wallemiomycetes;o__ | Wallemiales;f__ | Wallemiaceae;g__ | Wallemia;s__ | Wallemia muriae |
| k__Fungi;p__ | Basidiomycota;c__ | Wallemiomycetes;o__ | Wallemiales;f__ | Wallemiaceae;g__ | Wallemia;s__ | Wallemia sebi |
| k__Fungi;p__ | Basidiomycota;c__ | Wallemiomycetes;o__ | unidentified;f__ | unidentified;g__ | unidentified;s__ | Wallemiomycetes sp |
| k__Fungi;p__ | Basidiomycota;c__ | unidentified;o__ | unidentified;f__ | unidentified;g__ | unidentified;s__ | Basidiomycota sp |
| k__Fungi;p__ | Basidiomycota;c__ | unidentified;o__ | unidentified;f__ | unidentified;g__ | unidentified;s__ | Basidiomycota sp CC_15_08 |
| k__Fungi;p__ | Basidiomycota;c__ | unidentified;o__ | unidentified;f__ | unidentified;g__ | unidentified;s__ | Basidiomycota sp Chiang 2499 |
| k__Fungi;p__ | Basidiomycota;c__ | unidentified;o__ | unidentified;f__ | unidentified;g__ | unidentified;s__ | uncultured Basidiomycota |
| k__Fungi;p__ | Blastocladiomycota;c__ | unidentified;o__ | unidentified;f__ | unidentified;g__ | unidentified;s__ | uncultured Blastocladiomycota |
| k__Fungi;p__ | Chytridiomycota;c__ | Chytridiomycetes;o__ | Olpidiales;f__ | Olpidiaceae;g__ | Olpidium;s__ | Olpidium brassicae |
| k__Fungi;p__ | Chytridiomycota;c__ | Monoblepharidomycetes;o__ | Monoblepharidales;f__ | unidentified;g__ | unidentified;s__ | uncultured Hyaloraphidium |
| k__Fungi;p__ | Chytridiomycota;c__ | Monoblepharidomycetes;o__ | unidentified;f__ | unidentified;g__ | unidentified;s__ | Monoblepharidomycetes sp | k__Fungi;p__Glomeromycota;c__Glomeromycetes;o__Diversisporales;f__Acaulosporaceae;g__Entrophospora;s__Entrophospora sp k__Fungi;p__Glomeromycota;c__Glomeromycetes;o__Glomerales;f__Claroideoglomeraceae;g__Claroideoglomus;s__Claroideoglomus sp k__Fungi;p__Glomeromycota;c__Glomeromycetes;o__Glomerales;f__unidentified;g__unidentified;s__Glomerales sp k__Fungi;p__Glomeromycota;c__Glomeromycetes;o__Paraglomerales;f__Paraglomeraceae;g__Paraglomus;s__Paraglomus sp k__Fungi;p__Glomeromycota;c__Glomeromycetes;o__Paraglomerales;f__unidentified;g__unidentified;s__Paraglomerales sp k__Fungi;p__Glomeromycota;c__unidentified;o__unidentified;f__unidentified;g__unidentified;s__uncultured Glomeromycota k__Fungi;p__Rozellomycota;c__unidentified;o__unidentified;f__unidentified;g__unidentified;s__Rozellomycota sp k__Fungi;p__Zygomycota;c__Incertae sedis;o__Endogonales;f__unidentified;g__unidentified;s__Endogonales sp k__Fungi;p__Zygomycota;c__Incertae sedis;o__Kickxellales;f__Kickxellaceae;g__Ramicandelaber;s__Ramicandelaber sp k__Fungi;p__Zygomycota;c__Incertae sedis;o__Kickxellales;f__Kickxellaceae;g__Ramicandelaber;s__Ramicandelaber sp HMH_2010b k__Fungi;p__Zygomycota;c__Incertae sedis;o__Mortierellales;f__Mortierellaceae;g__Mortierella;s__Mortierella alpina k__Fungi;p__Zygomycota;c__Incertae sedis;o__Mortierellales;f__Mortierellaceae;g__Mortierella;s__Mortierella amoeboidea k__Fungi;p__Zygomycota;c__Incertae sedis;o__Mortierellales;f__Mortierellaceae;g__Mortierella;s__Mortierella angusta k__Fungi;p__Zygomycota;c__Incertae sedis;o__Mortierellales;f__Mortierellaceae;g__Mortierella;s__Mortierella bainieri k__Fungi;p__Zygomycota;c__Incertae sedis;o__Mortierellales;f__Mortierellaceae;g__Mortierella;s__Mortierella bisporalis k__Fungi;p__Zygomycota;c__Incertae sedis;o__Mortierellales;f__Mortierellaceae;g__Mortierella;s__Mortierella camargensis k__Fungi;p__Zygomycota;c__Incertae sedis;o__Mortierellales;f__Mortierellaceae;g__Mortierella;s__Mortierella capitata k__Fungi;p__Zygomycota;c__Incertae sedis;o__Mortierellales;f__Mortierellaceae;g__Mortierella;s__Mortierella chlamydospora k__Fungi;p__Zygomycota;c__Incertae sedis;o__Mortierellales;f__Mortierellaceae;g__Mortierella;s__Mortierella cystojenkinii k__Fungi;p__Zygomycota;c__Incertae sedis;o__Mortierellales;f__Mortierellaceae;g__Mortierella;s__Mortierella dichotoma k__Fungi;p__Zygomycota;c__Incertae sedis;o__Mortierellales;f__Mortierellaceae;g__Mortierella;s__Mortierella elongata k__Fungi;p__Zygomycota;c__Incertae sedis;o__Mortierellales;f__Mortierellaceae;g__Mortierella;s__Mortierella elongatula k__Fungi;p__Zygomycota;c__Incertae sedis;o__Mortierellales;f__Mortierellaceae;g__Mortierella;s__Mortierella exigua k__Fungi;p__Zygomycota;c__Incertae sedis;o__Mortierellales;f__Mortierellaceae;g__Mortierella;s__Mortierella gemmifera k__Fungi;p__Zygomycota;c__Incertae sedis;o__Mortierellales;f__Mortierellaceae;g__Mortierella;s__Mortierella horticola k__Fungi;p__Zygomycota;c__Incertae sedis;o__Mortierellales;f__Mortierellaceae;g__Mortierella;s__Mortierella humilis k__Fungi;p__Zygomycota;c__Incertae sedis;o__Mortierellales;f__Mortierellaceae;g__Mortierella;s__Mortierella lignicola k__Fungi;p__Zygomycota;c__Incertae sedis;o__Mortierellales;f__Mortierellaceae;g__Mortierella;s__Mortierella microzygospora k__Fungi;p__Zygomycota;c__Incertae sedis;o__Mortierellales;f__Mortierellaceae;g__Mortierella;s__Mortierella oligospora k__Fungi;p__Zygomycota;c__Incertae sedis;o__Mortierellales;f__Mortierellaceae;g__Mortierella;s__Mortierella paraensis k__Fungi;p__Zygomycota;c__Incertae sedis;o__Mortierellales;f__Mortierellaceae;g__Mortierella;s__Mortierella reticulata k__Fungi;p__Zygomycota;c__Incertae sedis;o__Mortierellales;f__Mortierellaceae;g__Mortierella;s__Mortierella rishikesha k__Fungi;p__Zygomycota;c__Incertae sedis;o__Mortierellales;f__Mortierellaceae;g__Mortierella;s__Mortierella schmuckeri k__Fungi;p__Zygomycota;c__Incertae sedis;o__Mortierellales;f__Mortierellaceae;g__Mortierella;s__Mortierella sp k__Fungi;p__Zygomycota;c__Incertae sedis;o__Mortierellales;f__Mortierellaceae;g__Mortierella;s__Mortierella sp 04M 158 k__Fungi;p__Zygomycota;c__Incertae sedis;o__Mortierellales;f__Mortierellaceae;g__Mortierella;s__Mortierella sp bc_besc_211a k__Fungi;p__Zygomycota;c__Incertae sedis;o__Mortierellales;f__Mortierellaceae;g__Mortierella;s__Mortierella stylospora k__Fungi;p__Zygomycota;c__Incertae sedis;o__Mortierellales;f__Mortierellaceae;g__Mortierella;s__Mortierella umbellata k__Fungi;p__Zygomycota;c__Incertae sedis;o__Mortierellales;f__Mortierellaceae;g__Mortierella;s__Mortierella wolfii

| k__Fungi;p__ | Zygomycota;c__ | Incertae sedis;o__ | Mortierellales;f__ | Mortierellaceae;g__ | Mortierella;s__ | Mortierella zonata |
|---|---|---|---|---|---|---|
| k__Fungi;p__ | Zygomycota;c__ | Incertae sedis;o__ | Mortierellales;f__ | Mortierellaceae;g__ | unidentified;s__ | Mortierellaceae sp |
| k__Fungi;p__ | Zygomycota;c__ | Incertae sedis;o__ | Mortierellales;f__ | unidentified;g__ | unidentified;s__ | Mortierellales sp |
| k__Fungi;p__ | Zygomycota;c__ | Incertae sedis;o__ | Mucorales;f__ | Cunninghamellaceae;g__ | Absidia;s__ | Absidia glauca |
| k__Fungi;p__ | Zygomycota;c__ | Incertae sedis;o__ | Mucorales;f__ | Cunninghamellaceae;g__ | Absidia;s__ | Absidia repens |
| k__Fungi;p__ | Zygomycota;c__ | Incertae sedis;o__ | Mucorales;f__ | Cunninghamellaceae;g__ | Absidia;s__ | Absidia sp |
| k__Fungi;p__ | Zygomycota;c__ | Incertae sedis;o__ | Mucorales;f__ | Cunninghamellaceae;g__ | Absidia;s__ | Absidia sp NEFU16 |
| k__Fungi;p__ | Zygomycota;c__ | Incertae sedis;o__ | Mucorales;f__ | Cunninghamellaceae;g__ | Absidia;s__ | Absidia spinosa |
| k__Fungi;p__ | Zygomycota;c__ | Incertae sedis;o__ | Mucorales;f__ | Cunninghamellaceae;g__ | Absidia;s__ | Absidia spinosa var spinosa |
| k__Fungi;p__ | Zygomycota;c__ | Incertae sedis;o__ | Mucorales;f__ | Cunninghamellaceae;g__ | Cunninghamella;s__ | Cunninghamella bertholletiae |
| k__Fungi;p__ | Zygomycota;c__ | Incertae sedis;o__ | Mucorales;f__ | Cunninghamellaceae;g__ | Cunninghamella;s__ | Cunninghamella echinulata |
| k__Fungi;p__ | Zygomycota;c__ | Incertae sedis;o__ | Mucorales;f__ | Cunninghamellaceae;g__ | Cunninghamella;s__ | Cunninghamella sp DF12098 |
| k__Fungi;p__ | Zygomycota;c__ | Incertae sedis;o__ | Mucorales;f__ | Cunninghamellaceae;g__ | Gongronella;s__ | Gongronella butleri |
| k__Fungi;p__ | Zygomycota;c__ | Incertae sedis;o__ | Mucorales;f__ | Cunninghamellaceae;g__ | Gongronella;s__ | Gongronella sp |
| k__Fungi;p__ | Zygomycota;c__ | Incertae sedis;o__ | Mucorales;f__ | Cunninghamellaceae;g__ | Gongronella;s__ | Gongronella sp CCMI 1101 |
| k__Fungi;p__ | Zygomycota;c__ | Incertae sedis;o__ | Mucorales;f__ | Cunninghamellaceae;g__ | Gongronella;s__ | Gongronella sp TL_2013 |
| k__Fungi;p__ | Zygomycota;c__ | Incertae sedis;o__ | Mucorales;f__ | Cunninghamellaceae;g__ | unidentified;s__ | Cunninghamellaceae sp |
| k__Fungi;p__ | Zygomycota;c__ | Incertae sedis;o__ | Mucorales;f__ | Mucoraceae;g__ | Actinomucor;s__ | Actinomucor elegans |
| k__Fungi;p__ | Zygomycota;c__ | Incertae sedis;o__ | Mucorales;f__ | Mucoraceae;g__ | Mucor;s__ | Mucor bainieri |
| k__Fungi;p__ | Zygomycota;c__ | Incertae sedis;o__ | Mucorales;f__ | Mucoraceae;g__ | Mucor;s__ | Mucor circinelloides f. circinelloides |
| k__Fungi;p__ | Zygomycota;c__ | Incertae sedis;o__ | Mucorales;f__ | Mucoraceae;g__ | Mucor;s__ | Mucor circinelloides f. griseocyanus |
| k__Fungi;p__ | Zygomycota;c__ | Incertae sedis;o__ | Mucorales;f__ | Mucoraceae;g__ | Mucor;s__ | Mucor ctenidius |
| k__Fungi;p__ | Zygomycota;c__ | Incertae sedis;o__ | Mucorales;f__ | Mucoraceae;g__ | Mucor;s__ | Mucor hiemalis |
| k__Fungi;p__ | Zygomycota;c__ | Incertae sedis;o__ | Mucorales;f__ | Mucoraceae;g__ | Mucor;s__ | Mucor lanceolatus |
| k__Fungi;p__ | Zygomycota;c__ | Incertae sedis;o__ | Mucorales;f__ | Mucoraceae;g__ | Mucor;s__ | Mucor moelleri |
| k__Fungi;p__ | Zygomycota;c__ | Incertae sedis;o__ | Mucorales;f__ | Mucoraceae;g__ | Mucor;s__ | Mucor mucedo |
| k__Fungi;p__ | Zygomycota;c__ | Incertae sedis;o__ | Mucorales;f__ | Mucoraceae;g__ | Mucor;s__ | Mucor racemosus f. racemosus |
| k__Fungi;p__ | Zygomycota;c__ | Incertae sedis;o__ | Mucorales;f__ | Mucoraceae;g__ | Mucor;s__ | Mucor zychae var. zychae |
| k__Fungi;p__ | Zygomycota;c__ | Incertae sedis;o__ | Mucorales;f__ | Mucoraceae;g__ | unidentified;s__ | Mucoraceae sp SM_1 |
| k__Fungi;p__ | Zygomycota;c__ | Incertae sedis;o__ | Mucorales;f__ | Rhizopodaceae;g__ | Rhizopus;s__ | Rhizopus arrhizus var. arrhizus |
| k__Fungi;p__ | Zygomycota;c__ | Incertae sedis;o__ | Mucorales;f__ | Rhizopodaceae;g__ | Rhizopus;s__ | Rhizopus lyococcus |
| k__Fungi;p__ | Zygomycota;c__ | Incertae sedis;o__ | Mucorales;f__ | Rhizopodaceae;g__ | Rhizopus;s__ | Rhizopus microsporus var. microsporus |
| k__Fungi;p__ | Zygomycota;c__ | Incertae sedis;o__ | Mucorales;f__ | Rhizopodaceae;g__ | Rhizopus;s__ | Rhizopus microsporus var. oligosporus |
| k__Fungi;p__ | Zygomycota;c__ | Incertae sedis;o__ | Mucorales;f__ | Syncephalastraceae;g__ | Circinella;s__ | Circinella chinensis |
| k__Fungi;p__ | Zygomycota;c__ | Incertae sedis;o__ | Mucorales;f__ | Syncephalastraceae;g__ | Circinella;s__ | Circinella muscae |
| k__Fungi;p__ | Zygomycota;c__ | Incertae sedis;o__ | Mucorales;f__ | Syncephalastraceae;g__ | Syncephalastrum;s__ | Syncephalastrum racemosum |
| k__Fungi;p__ | Zygomycota;c__ | Incertae sedis;o__ | Mucorales;f__ | Umbelopsidaceae;g__ | Umbelopsis;s__ | Umbelopsis angularis |
| k__Fungi;p__ | Zygomycota;c__ | Incertae sedis;o__ | Mucorales;f__ | Umbelopsidaceae;g__ | Umbelopsis;s__ | Umbelopsis dimorpha |
| k__Fungi;p__ | Zygomycota;c__ | Incertae sedis;o__ | Mucorales;f__ | Umbelopsidaceae;g__ | Umbelopsis;s__ | Umbelopsis ramanniana |

| | | | | | | |
|---|---|---|---|---|---|---|
| k_Fungi;p_ | Zygomycota;c_ | Incertae sedis;o_ | Mucorales;f_ | Umbelopsidaceae;g_ | Umbelopsis;s_ | Umbelopsis sp |
| k_Fungi;p_ | unidentified;c_ | unidentified;o_ | unidentified;f_ | unidentified;g_ | unidentified;s_ | Basal lineages |
| k_Fungi;p_ | unidentified;c_ | unidentified;o_ | unidentified;f_ | unidentified;g_ | unidentified;s_ | Calluna vulgaris root associated fungus |
| k_Fungi;p_ | unidentified;c_ | unidentified;o_ | unidentified;f_ | unidentified;g_ | unidentified;s_ | Fungi sp |
| k_Fungi;p_ | unidentified;c_ | unidentified;o_ | unidentified;f_ | unidentified;g_ | unidentified;s_ | fungal endophyte |
| k_Fungi;p_ | unidentified;c_ | unidentified;o_ | unidentified;f_ | unidentified;g_ | unidentified;s_ | fungal endophyte sp SS_179 |
| k_Fungi;p_ | unidentified;c_ | unidentified;o_ | unidentified;f_ | unidentified;g_ | unidentified;s_ | fungal endophyte sp SS_743 |
| k_Fungi;p_ | unidentified;c_ | unidentified;o_ | unidentified;f_ | unidentified;g_ | unidentified;s_ | fungal sp 2 GP_2013 |
| k_Fungi;p_ | unidentified;c_ | unidentified;o_ | unidentified;f_ | unidentified;g_ | unidentified;s_ | fungal sp 38 CC 06 28 |
| k_Fungi;p_ | unidentified;c_ | unidentified;o_ | unidentified;f_ | unidentified;g_ | unidentified;s_ | fungal sp ANTELF6 |
| k_Fungi;p_ | unidentified;c_ | unidentified;o_ | unidentified;f_ | unidentified;g_ | unidentified;s_ | fungal sp EXP0528F |
| k_Fungi;p_ | unidentified;c_ | unidentified;o_ | unidentified;f_ | unidentified;g_ | unidentified;s_ | fungal sp KRP27 |
| k_Fungi;p_ | unidentified;c_ | unidentified;o_ | unidentified;f_ | unidentified;g_ | unidentified;s_ | fungal sp P1S14 |
| k_Fungi;p_ | unidentified;c_ | unidentified;o_ | unidentified;f_ | unidentified;g_ | unidentified;s_ | fungal sp T2513 |
| k_Fungi;p_ | unidentified;c_ | unidentified;o_ | unidentified;f_ | unidentified;g_ | unidentified;s_ | fungal sp TRN254 |
| k_Fungi;p_ | unidentified;c_ | unidentified;o_ | unidentified;f_ | unidentified;g_ | unidentified;s_ | fungal sp TRN287 |
| k_Fungi;p_ | unidentified;c_ | unidentified;o_ | unidentified;f_ | unidentified;g_ | unidentified;s_ | fungal sp TRN436 |
| k_Fungi;p_ | unidentified;c_ | unidentified;o_ | unidentified;f_ | unidentified;g_ | unidentified;s_ | fungal sp TRN441 |
| k_Fungi;p_ | unidentified;c_ | unidentified;o_ | unidentified;f_ | unidentified;g_ | unidentified;s_ | fungal sp TRN499 |
| k_Fungi;p_ | unidentified;c_ | unidentified;o_ | unidentified;f_ | unidentified;g_ | unidentified;s_ | fungal sp acwVHS6_4 |
| k_Fungi;p_ | unidentified;c_ | unidentified;o_ | unidentified;f_ | unidentified;g_ | unidentified;s_ | fungal sp acwVHT66_5 |
| k_Fungi;p_ | unidentified;c_ | unidentified;o_ | unidentified;f_ | unidentified;g_ | unidentified;s_ | soil fungal sp ANG55 |
| k_Fungi;p_ | unidentified;c_ | unidentified;o_ | unidentified;f_ | unidentified;g_ | unidentified;s_ | uncultured ectomycorrhizal fungus |
| k_Fungi;p_ | unidentified;c_ | unidentified;o_ | unidentified;f_ | unidentified;g_ | unidentified;s_ | uncultured endophytic fungus |
| k_Fungi;p_ | unidentified;c_ | unidentified;o_ | unidentified;f_ | unidentified;g_ | unidentified;s_ | uncultured fungus |
| k_Fungi;p_ | unidentified;c_ | unidentified;o_ | unidentified;f_ | unidentified;g_ | unidentified;s_ | uncultured root_associated fungus |
| k_Fungi;p_ | unidentified;c_ | unidentified;o_ | unidentified;f_ | unidentified;g_ | unidentified;s_ | uncultured soil fungus |
| k_Fungi;p_ | unidentified;c_ | unidentified;o_ | unidentified;f_ | unidentified;g_ | unidentified;s_ | uncultured zygomycete |
| k_Protista;p_ | Cercozoa;c_ | unidentified;o_ | unidentified;f_ | unidentified;g_ | unidentified;s_ | Cercozoa sp |
| k_Protista;p_ | unidentified;c_ | unidentified;o_ | unidentified;f_ | unidentified;g_ | unidentified;s_ | Ichtyosporea |

APPENDIX C

The following list shows the current list of Micro-Wine-Makers species (fermentative species relevant in winemaking process) detected in samples.

Bacteria species index D0_kingdom D1_phylum D2_class D3_order D4_family D5_genus Species 1      Bacteria    Proteobacteria   Alphaproteobacteria Rhodospirillales Acetobacteraceae Acetobacter Acetobacter aceti 2      Bacteria    Proteobacteria   Alphaproteobacteria Rhodospirillales Acetobacteraceae Acetobacter Acetobacter cerevisiae 3      Bacteria    Proteobacteria   Alphaproteobacteria Rhodospirillales Acetobacteraceae Acetobacter Acetobacter estuniensis 4      Bacteria    Proteobacteria   Alphaproteobacteria Rhodospirillales Acetobacteraceae Acetobacter Acetobacter lovaniensis 5      Bacteria    Proteobacteria   Alphaproteobacteria Rhodospirillales Acetobacteraceae Acetobacter Acetobacter malorum 6      Bacteria    Proteobacteria   Alphaproteobacteria Rhodospirillales Acetobacteraceae Acetobacter Acetobacter oeni 7      Bacteria    Proteobacteria   Alphaproteobacteria Rhodospirillales Acetobacteraceae Acetobacter Acetobacter orleanensis

| | | |
|---|---|---|
| 8 | Bacteria | Proteobacteria Alphaproteobacteria Rhodospirillales Acetobacteraceae Acetobacter Acetobacter pasteurianus |
| 9 | Bacteria | Proteobacteria Alphaproteobacteria Rhodospirillales Acetobacteraceae Acetobacter Acetobacter peroxydans |
| 10 | Bacteria | Proteobacteria Alphaproteobacteria Rhodospirillales Acetobacteraceae Acetobacter Acetobacter tropicalis |
| 11 | Bacteria | Proteobacteria Gammaproteobacteria Pseudomonadales Moraxellaceae Acinetobacter Acinetobacter |
| 12 | Bacteria | Firmicutes Bacilli Bacillales Bacillaceae Bacillus Bacillus subtilis |
| 13 | Bacteria | Proteobacteria Betaproteobacteria Burkholderiales Comamonadaceae Comamonas Comamonas |
| 14 | Bacteria | Firmicutes Clostridia Clostridiales Family XI Finegoldia Finegoldia |
| 15 | Bacteria | Proteobacteria Alphaproteobacteria Rhodospirillales Acetobacteraceae Gluconacetobacter Gluconacetobacter entanii |
| 16 | Bacteria | Proteobacteria Alphaproteobacteria Rhodospirillales Acetobacteraceae Gluconacetobacter Gluconacetobacter europaeus |
| 17 | Bacteria | Proteobacteria Alphaproteobacteria Rhodospirillales Acetobacteraceae Gluconacetobacter Gluconacetobacter hansenii |
| 18 | Bacteria | Proteobacteria Alphaproteobacteria Rhodospirillales Acetobacteraceae Gluconacetobacter Gluconacetobacter intermedius |

| | |
|---|---|
| 19 | Bacteria Proteobacteria Alphaproteobacteria Rhodospirillales Acetobacteraceae Gluconacetobacter Gluconacetobacter johannae |
| 20 | Bacteria Proteobacteria Alphaproteobacteria Rhodospirillales Acetobacteraceae Gluconacetobacter Gluconacetobacter liquefaciens |
| 21 | Bacteria Proteobacteria Alphaproteobacteria Rhodospirillales Acetobacteraceae Gluconacetobacter Gluconacetobacter oboediens |
| 22 | Bacteria Proteobacteria Alphaproteobacteria Rhodospirillales Acetobacteraceae Gluconacetobacter Gluconacetobacter xylinus |
| 23 | Bacteria Proteobacteria Alphaproteobacteria Rhodospirillales Acetobacteraceae Gluconobacter Gluconobacter oxydans |
| 24 | Bacteria Firmicutes Bacilli Lactobacillales Lactobacillaceae Lactobacillus Lactobacillus brevis |
| 25 | Bacteria Firmicutes Bacilli Lactobacillales Lactobacillaceae Lactobacillus Lactobacillus buchneri |
| 26 | Bacteria Firmicutes Bacilli Lactobacillales Lactobacillaceae Lactobacillus Lactobacillus casei |
| 27 | Bacteria Firmicutes Bacilli Lactobacillales Lactobacillaceae Lactobacillus Lactobacillus curvatus |
| 28 | Bacteria Firmicutes Bacilli Lactobacillales Lactobacillaceae Lactobacillus Lactobacillus delbrueckii |
| 29 | Bacteria Firmicutes Bacilli Lactobacillales Lactobacillaceae Lactobacillus Lactobacillus diolivorans |
| 30 | Bacteria Firmicutes Bacilli Lactobacillales Lactobacillaceae Lactobacillus Lactobacillus fructivorans |

| | | |
|---|---|---|
| 31 | Bacteria Firmicutes Bacilli Lactobacillaceae Lactobacillus | Lactobacillales Lactobacillus hilgardii |
| 32 | Bacteria Firmicutes Bacilli Lactobacillaceae Lactobacillus | Lactobacillales Lactobacillus jensenii |
| 33 | Bacteria Firmicutes Bacilli Lactobacillaceae Lactobacillus | Lactobacillales Lactobacillus liechmannii |
| 34 | Bacteria Firmicutes Bacilli Lactobacillaceae Lactobacillus | Lactobacillales Lactobacillus mali |
| 35 | Bacteria Firmicutes Bacilli Lactobacillaceae Lactobacillus | Lactobacillales Lactobacillus paracasei |
| 36 | Bacteria Firmicutes Bacilli Lactobacillaceae Lactobacillus | Lactobacillales Lactobacillus nagelii |
| 37 | Bacteria Firmicutes Bacilli Lactobacillaceae Lactobacillus | Lactobacillales Lactobacillus kunkeei |
| 38 | Bacteria Firmicutes Bacilli Lactobacillaceae Lactobacillus | Lactobacillales Lactobacillus plantarum |
| 39 | Bacteria Firmicutes Bacilli Lactobacillaceae Lactobacillus | Lactobacillales Lactobacillus vini |
| 40 | Bacteria Firmicutes Bacilli Leuconostocaceae Leuconostoc | Lactobacillales Leuconostoc |
| 41 | Bacteria Firmicutes Bacilli Leuconostocaceae Oenococcus Oenococcus oeni | Lactobacillales |
| 43 | Bacteria Firmicutes Bacilli Lactobacillaceae Pediococcus | Lactobacillales Pediococcus damnosus |
| 44 | Bacteria Firmicutes Bacilli Lactobacillaceae Pediococcus | Lactobacillales Pediococcus inopinatus |
| 45 | Bacteria Firmicutes Bacilli Lactobacillaceae Pediococcus | Lactobacillales Pediococcus parvulus |

| | | | | | | |
|---|---|---|---|---|---|---|
| 46 | Bacteria | Firmicutes | Bacilli | Lactobacillales | Lactobacillaceae | Pediococcus | Pediococcus pentosaceus |
| 47 | Bacteria | Firmicutes | Bacilli | Bacillales | Staphylococcaceae | Staphylococcus | Staphylococcus |
| 48 | Bacteria | Firmicutes | Negativicutes | Selenomonadales | Veillonellaceae | Veillonella | Veillonella |
| 49 | Bacteria | Firmicutes | Bacilli | Bacillales | Listeriaceae | Listeria | Listeria seeligeri |

Funghi species

| index | D0_kingdom | Species |
|---|---|---|
| 1 | Fungi | Acremonium sp.(Cephalosporium) |
| 2 | Fungi | Acrostalagmus luteoalbus |
| 3 | Fungi | Actinomucor elegans |
| 4 | Fungi | Alternaria arbusti |
| 5 | Fungi | Alternaria japonica |
| 6 | Fungi | Alternaria longipes |
| 7 | Fungi | Alternaria radicina |
| 8 | Fungi | Alternaria alternate |
| 9 | Fungi | Arcyria cinerea |
| 10 | Fungi | Aspergillus ssp. |
| 11 | Fungi | Aspergillus caesiellus |
| 12 | Fungi | Aspergillus fumigatus |
| 13 | Fungi | Aspergillus sclerotiorum |

| 14 | Fungi | Aspergillus tubingensis |
| 15 | Fungi | Aureobasidium pullulans |
| 16 | Fungi | Bionectria ochroleuca |
| 17 | Fungi | Boeremia exigua |
| 18 | Fungi | Botryotinia fuckeliana |
| 19 | Fungi | Botryotinia porri |
| 20 | Fungi | Botrytis cinerea |
| 21 | Fungi | Botrytis elliptica |
| 22 | Fungi | Brettanomyces bruxellensis |
| 23 | Fungi | Candida tropicalis |
| 24 | Fungi | Candida railenensis |
| 25 | Fungi | Candida zeylanoides |
| 26 | Fungi | Candida glabrata |
| 27 | Fungi | Candida intermedia |
| 28 | Fungi | Candida krusei |
| 29 | Fungi | Candida oleophila |
| 30 | Fungi | Candida parapsilosis |
| 31 | Fungi | Candida stellata |
| 32 | Fungi | Candida vini |
| 33 | Fungi | Candida zemplinina |
| 34 | Fungi | Chaetomium globosum |
| 35 | Fungi | Chrysonilia sp. |

| 36 | Fungi | Ciborinia camelliae |
| 37 | Fungi | Cladosporium cladosporioides |
| 38 | Fungi | Cladosporium sphaerosperumum |
| 39 | Fungi | Clitocybe subditopoda |
| 40 | Fungi | Coniella petrakii |
| 41 | Fungi | Coniophora puteana |
| 42 | Fungi | Cosmospora gigas |
| 43 | Fungi | Cosmospora vilior |
| 44 | Fungi | Cryptococcus albidus |
| 45 | Fungi | Cryptococcus adeliensis |
| 46 | Fungi | Cryptococcus laurentii |
| 47 | Fungi | Cyberlindnera jadinii |
| 48 | Fungi | Cylindrocarpon didymum |
| 49 | Fungi | Cystofilobasidium capitatum |
| 50 | Fungi | Davidiella macrospora |
| 51 | Fungi | Davidiella tassiana |
| 52 | Fungi | Debaryomyces hansenii |
| 53 | Fungi | Dekkera anomala |
| 54 | Fungi | Diplodia seriata |
| 55 | Fungi | Elsinoe ampelina |
| 56 | Fungi | Embellisia allii |
| 57 | Fungi | Emericellopsis maritima |

| 58 | Fungi | Epicoccum nigrum |
| 59 | Fungi | Erysiphe necator |
| 60 | Fungi | Eurotium repens |
| 61 | Fungi | Exophiala spinifera |
| 62 | Fungi | Fusarium equiseti |
| 63 | Fungi | Fusarium oxysporum |
| 64 | Fungi | Fusarium redolens |
| 65 | Fungi | Fusarium sporotrichioides |
| 66 | Fungi | Geomyces pannorum |
| 67 | Fungi | Geotrichum sp. |
| 68 | Fungi | Gibberella avenacea |
| 69 | Fungi | Gliocladium sp. |
| 70 | Fungi | Guignardia bidwellii |
| 71 | Fungi | Hanseniaspora guilliermondii |
| 72 | Fungi | Hanseniaspora uvarum |
| 73 | Fungi | Hansenula anomala |
| 74 | Fungi | Humicola fuscoatra |
| 75 | Fungi | Ilyonectria liriodendri |
| 76 | Fungi | Ilyonectria macrodidyma |
| 77 | Fungi | Issatchenkia terricola |
| 78 | Fungi | Issatchenkia orientalis |
| 79 | Fungi | Isoetes melanopoda |

| | | |
|---|---|---|
| 80 | Fungi | Kabatiella microsticta |
| 81 | Fungi | Kluyveromyces marxianus |
| 82 | Fungi | Kluyveromyces thermotolerans |
| 83 | Fungi | Leucostoma niveum |
| 84 | Fungi | Lewia infectoria |
| 85 | Fungi | Macrophomina phaseolina |
| 86 | Fungi | Malassezia restricta |
| 87 | Fungi | Metarhizium anisopliae |
| 88 | Fungi | Metschnikowia pulcherrima |
| 89 | Fungi | Meyerozyma guilliermondii |
| 90 | Fungi | Monilinia laxa |
| 91 | Fungi | Mortierella alpina |
| 92 | Fungi | Mortierella hyalina |
| 93 | Fungi | Mucor sp. |
| 94 | Fungi | Mycosphaerella brassicicola |
| 95 | Fungi | Penicillium aculeatum |
| 96 | Fungi | Penicillium brevicompactum |
| 97 | Fungi | Penicillium canescens |
| 98 | Fungi | Penicillium commune |
| 99 | Fungi | Penicillium glabrum |
| 100 | Fungi | Penicillium roqueforti |
| 101 | Fungi | Penicillium sclerotigenum |

| 102 | Fungi | Penicillium spinulosum |
| 103 | Fungi | Penicillium expansum |
| 104 | Fungi | Penicillium paneum |
| 105 | Fungi | Penicillium corylophilum |
| 106 | Fungi | Peniophora incarnata |
| 107 | Fungi | Peyronellaea glomerata |
| 108 | Fungi | Peyronellaea pinodella |
| 109 | Fungi | Phoma multirostrata |
| 110 | Fungi | Phoma herbarum |
| 111 | Fungi | Phoma eupyrena |
| 112 | Fungi | Phoma tracheiphila |
| 113 | Fungi | Phomopsis viticola |
| 114 | Fungi | Pichia fermentans |
| 115 | Fungi | Pichia guilloermondi |
| 116 | Fungi | Pichia kudriavzevii |
| 117 | Fungi | Pichia membranifaciens |
| 118 | Fungi | Pichia Subpelliculosa |
| 119 | Fungi | Plasmopara viticola |
| 120 | Fungi | Plectosphaerella cucumerina |
| 121 | Fungi | Pleurotus eryngii |
| 122 | Fungi | Pseudopezicula tracheiphila |
| 123 | Fungi | Preussia intermedia |

| | | |
|---|---|---|
| 124 | Fungi | Rhizopus oryzae |
| 125 | Fungi | Rhizopus stolonifer |
| 126 | Fungi | Rhodotorula glutinis |
| 127 | Fungi | Rhodotorula mucilaginosa |
| 128 | Fungi | Rhodosporidium babjevae |
| 129 | Fungi | Saccharomyces bayanus |
| 130 | Fungi | Saccharomyces cerevisiae |
| 131 | Fungi | Saccharomyces exiguous |
| 132 | Fungi | Saccharomyces kudriavzevii |
| 133 | Fungi | Saccharomyces mikatae |
| 134 | Fungi | Saccharomyces paradoxus |
| 135 | Fungi | Saccharomyces uvarum |
| 136 | Fungi | Sarocladium strictum |
| 137 | Fungi | Sordaria lappae |
| 138 | Fungi | Sporobolomyces coprosmae |
| 139 | Fungi | Sporobolomyces roseus |
| 140 | Fungi | Stachybotrys chlorohalonata |
| 141 | Fungi | Tetracladium maxilliforme |
| 142 | Fungi | Tetracladium setigerum |
| 143 | Fungi | Tetracladium marchalianum |
| 144 | Fungi | Torulaspora delbrueckii |
| 145 | Fungi | Trichothecium roseum |

| | | |
|---|---|---|
| 146 | Fungi | Tsuchiyaea wingfieldii |
| 147 | Fungi | Ulocladium consortiale |
| 148 | Fungi | Ulocladium oudemansii |
| 149 | Fungi | Wallemia sebi |
| 150 | Fungi | Wickerhamomyces anomalus |
| 151 | Fungi | Zygosaccharomyces bailii |

The invention claimed is:

1. A method, comprising:
receiving a set of samples comprising agricultural material associated with a process;
extracting nucleic acid material from each of the set of samples, with use of 1,3-Propanediol, 2-amino-2-(hydroxymethyl)-, hydrochloride, and Tris HCl 2-Amino-2-(hydroxymethyl)-1,3-propanediol;
barcoding said nucleic acid material with a double-index barcoding process implementing tagging with a first class of Hamming codes and a second class of Golay codes configured to correct sequencing errors and detect multi-bit errors and increase sequencing depth performance;
amplifying said nucleic acid material in coordination with said barcoding, in order to generate a 16S library and an internal transcribed spacer (ITS) library from said nucleic acid material;
pooling material of the 16S library with material of the ITS library to generate a pooled library;
sequencing the pooled library within a single run of a high-throughput sequencer, thereby obtaining a set of nucleic acid sequence reads of 16S and ITS genes of microorganisms represented in the set of samples; and
generating one or more clusters upon clustering reads of the set of nucleic acid sequence reads; and
selecting a representative sequence from each of the one or more clusters to return a characterization of bacterial and fungal microorganism quantity and identity.

2. The method of claim 1, wherein the process comprises one of an agricultural process and a fermentation process.

3. The method of claim 1, wherein the characterization of bacterial and fungal microorganisms characterizes microorganisms from the group consisting essentially of: a single-celled organism, a bacteria, an archaea, a protozoan, a unicellular fungus and a protist.

4. The method of claim 3, wherein characterization of bacterial and fungal microorganisms characterizes microorganisms from the group consisting essentially of:
Proteobacteria consisting of any one of: *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas;*
Firmicutes consisting of at least one of: *Bacillus, Paenibacillus, Lactobacillus, Mycoplasma*, and *Acetobacterium;*
Actinobacteria consisting of at least one of: *Streptomyces, Rhodococcus, Microbacterium*, and *Curtobacterium;*
Ascomycota consisting of at least one of: *Trichoderma, Ampelomyces, Coniothyrium, Paecoelomyces, Penicillium, Cladosporium, Hypocrea, Beauveria, Metarhizium, Verticullium, Cordyceps, Pichea*, and *Candida;*
Basidiomycota consisting of at least one of: *Coprinus, Corticium*, and *Agaricus*; and
Oomycota consisting of at least one of: *Pythium, Mucor*, and *Mortierella.*

5. A method comprising:
receiving a set of samples;
extracting nucleic acid material from each of the set of samples;
barcoding said nucleic acid material with a double-index barcoding process prior to amplification of said nucleic acid material, the double-index barcoding process implementing tagging with a first class of Hamming codes and a second class of Golay codes configured to correct sequencing errors and detect multi-bit errors and increase sequencing depth performance;
generating a 16S library and an internal transcribed spacer (ITS) library from said nucleic acid material;
performing a sequencing operation with material of the 16S library and the ITS library, thereby obtaining a set of nucleic acid sequence reads of 16S and ITS genes of from at least one microorganisms represented in the set of samples;
returning an analysis of bacterial and fungal microorganism quantity and identity upon clustering reads of the set of nucleic acid sequence reads;
generating a microbiome profile based upon the analysis; and
performing bioremediation in relation to a process associated with said agricultural material.

6. The method of claim 5, extracting nucleic acid material from each of the set of samples comprises extracting with 1,3-Propanediol, 2-amino-2-(hydroxymethyl)-, hydrochloride, and Tris HCl 2-Amino-2-(hydroxymethyl)-1,3-propaneiol.

7. The method of claim 5, wherein the set of samples comprises samples taken during fermentation process.

8. The method of claim 5, further comprising extracting and sequencing material of a single-copy marker gene from the set of samples, and wherein the single-copy marker gene comprises a metal-dependent protease with chaperone activity.

9. The method of claim 5, further comprising:
pooling the 16S library and the ITS library; and
providing one or more primers for sequencing said 16S library pooled with said ITS library in a single sequencing run.

10. The method of claim 5, wherein generating the microbiome profile comprises generating the microbiome profile based on 800 or fewer microbes.

11. The method of claim 5, wherein clustering reads of the set of nucleic acid sequence reads comprises clustering sequences exhibiting 97% similarity, and selecting a representative sequence for each cluster for taxonomic assignment and phylogenetic tree construction.

12. The method of claim 5, wherein performing the sequencing operation comprises employing a long read sequencing platform.

* * * * *